(12) United States Patent
Scharenberg et al.

(10) Patent No.: US 11,959,073 B2
(45) Date of Patent: *Apr. 16, 2024

(54) COUPLING ENDONUCLEASES WITH END-PROCESSING ENZYMES DRIVES HIGH EFFICIENCY GENE DISRUPTION

(71) Applicant: SEATTLE CHILDREN'S HOSPITAL, Seattle, WA (US)

(72) Inventors: Andrew M. Scharenberg, Seattle, WA (US); Michael T. Certo, Seattle, WA (US); Kamila Sabina Gwiazda, Seattle, WA (US)

(73) Assignee: SEATTLE CHILDREN'S RESEARCH INSTITUTE, Seattle, WA (US)

( * ) Notice: Subject to any disclaimer, the term of this patent is extended or adjusted under 35 U.S.C. 154(b) by 249 days.

This patent is subject to a terminal disclaimer.

(21) Appl. No.: 17/244,180

(22) Filed: Apr. 29, 2021

(65) Prior Publication Data
US 2021/0254043 A1 Aug. 19, 2021

Related U.S. Application Data

(60) Continuation of application No. 15/215,405, filed on Jul. 20, 2016, now Pat. No. 11,008,565, which is a continuation of application No. 14/949,744, filed on Nov. 23, 2015, now Pat. No. 10,995,332, which is a division of application No. 14/173,705, filed on Feb. 5, 2014, now abandoned, which is a division of application No. 13/405,183, filed on Feb. 24, 2012, now Pat. No. 8,673,557.

(60) Provisional application No. 61/447,672, filed on Feb. 28, 2011.

(51) Int. Cl.
| | | |
|---|---|---|
| *C12N 15/62* | (2006.01) | |
| *A61K 9/00* | (2006.01) | |
| *A61K 35/28* | (2015.01) | |
| *A61K 38/45* | (2006.01) | |
| *A61K 38/46* | (2006.01) | |
| *A61K 38/52* | (2006.01) | |
| *C12N 9/12* | (2006.01) | |
| *C12N 9/16* | (2006.01) | |
| *C12N 9/22* | (2006.01) | |
| *C12N 9/90* | (2006.01) | |
| *C12N 15/10* | (2006.01) | |
| *A61K 35/12* | (2015.01) | |

(52) U.S. Cl.
CPC .......... *C12N 15/102* (2013.01); *A61K 9/0019* (2013.01); *A61K 35/28* (2013.01); *A61K 38/45* (2013.01); *A61K 38/465* (2013.01); *A61K 38/52* (2013.01); *C12N 9/1252* (2013.01); *C12N 9/22* (2013.01); *C12N 9/90* (2013.01); *C12N 15/62* (2013.01); *A61K 2035/124* (2013.01); *C07K 2319/60* (2013.01); *C12N 2800/80* (2013.01); *C12N 2840/203* (2013.01)

(58) Field of Classification Search
CPC ... C12N 9/12; C12N 9/90; C12N 9/22; C12N 9/16; C12N 15/62; C12N 15/10; A61K 38/45; A61K 38/46; A61K 35/28
See application file for complete search history.

(56) References Cited

U.S. PATENT DOCUMENTS

| | | |
|---|---|---|
| 8,673,557 B2 | 3/2014 | Scharenberg |
| 2004/0180352 A1 | 9/2004 | Padgett et al. |
| 2006/0206949 A1 | 9/2006 | Arnould et al. |
| 2008/0271166 A1 | 10/2008 | Epinat et al. |
| 2012/0244131 A1 | 9/2012 | Delacote et al. |

FOREIGN PATENT DOCUMENTS

| | | |
|---|---|---|
| CA | 2815512 A1 | 5/2012 |
| EP | 2 412 806 A1 | 2/2012 |
| WO | 2012058458 A2 | 5/2012 |
| WO | 2013009525 A1 | 1/2013 |

OTHER PUBLICATIONS

Communication pursuant to Rule 69 EPC issued for European patent application No. 19183306.0 dated Feb. 10, 2020, 9 pages.
Perrino, F. W., et al., "The Human TREX2 3'-5'-Exonuclease Structure Suggests a Mechanism for Efficient Nonprocessive DNA Catalysis," The Journal of Biological Chemistry, 280(15), 2005, pp. 15212-15218.
Stoddard, B. L., "Homing Endonucleases: From Microbial Genetic Invaders to Reagents for Targeted DNA Modification," Structure (19), 2011, pp. 7-15.
Decision on Motions 37 CFR 41.125(a), *Seattle Children's Research Institute v. Cellectis*, Interference No. 106,052, filed Apr. 27, 2017, 55 pages.
Decision on Priority 37 CFR 41.125(a), *Cellectis v. Seattle Children's Research Institute*, Interference No. 106,052, filed Aug. 30, 2018, 44 pages.
Smith et al., A combinatorial approach to create artificial homing endonucleases cleaving chosen sequences, Nov. 27, 2006, Nucleic Acid Research vol. 34, No. 22 e149, 1-12.
United States Patent and Trademark Office Patent Trial and Appeal Board, Judgment, in Patent Interference No. 106,052, Aug. 30, 2018, pp. 1-4.
United States Patent and Trademark Office Patent Trial and Appeal Board, Decision on Motions, in Patent Interference No. 106,052, Apr. 27, 2017, pp. 1-55.
Office Action in corresponding Canadian application No. 2828303, dated Dec. 14, 2017.

(Continued)

*Primary Examiner* — Maryam Monshipouri
(74) *Attorney, Agent, or Firm* — Rothwell, Figg, Ernst & Manbeck, P.C.

(57) ABSTRACT

The present disclosure relates to the co-expression of an endonuclease with an end-processing enzyme for the purpose of enhanced processing of the polynucleotide ends generated by endonuclease cleavage.

20 Claims, 39 Drawing Sheets

Specification includes a Sequence Listing.

(56) References Cited

OTHER PUBLICATIONS

Communication dated Apr. 10, 2017 in the European Patent Application No. 12751744.9 filed Sep. 26, 2013.
Ahn, Byungchan et al., "Regulation of WRN Helicase Activity in Human Base Excision Repair" The Journal of Biological Chemistry, Dec. 17, 2004, pp. 53465-53474, vol. 279, No. 51.
Ashworth, Justin et al., "Computational redesign of endonuclease DNA binding and cleavage specificity" Nature, Jun. 1, 2006, pp. 656-659, vol. 441.
Balasubramanian, Nandakumar et al., "Physical Interaction between the Herpes Simplex Virus Type 1 Exonuclease, UL12, and the DNA Double-Strand Break-Sensing MRN Complex" Journal of Virology, Dec. 2010, pp. 12504-12514, vol. 84, No. 24.
Bennardo, N., and J.M. Stark, "ATM Limits Incorrect End Utilization During Non-Homologous End Joining of Multiple Chromosome Breaks," PLoS Genetics 6(11):1-11, Nov. 2010.
Bennardo, N., et al., "Limiting the Persistence of a Chromosome Break Diminishes Its Mutagenic Potential," PLoS Genetics 5(10):1-14, Oct. 2009.
Boch, Jens et al., "Breaking the Code of DNA Binding Specificity of TAL-Type III Effectors" Science, Dec. 11, 2009, pp. 1509-1512, vol. 326.
Chevalier, Brett S. et al., "Design, Activity, and Structure of a Highly Specific Artificial Endonuclease" Molecular Cell, Oct. 2002, pp. 895-905, vol. 10.
Coates, Brad S., et al., "A Helitron-Like Transposon Superfamily from Lepidoptera Disrupts (GAAA)n Microsatellites and is Responsible for Flanking Sequence Similarity within a Microsatellite Family," J. Mol. Evol. 70:275-288, 2010.
Dahlroth, Sue-Li et al., "Crystal structure of the shutoff and exonuclease protein from the oncogenic Kaposi's sarcoma-associated herpesvirus" FEBS Journal, 2009, pp. 6636-6645, vol. 276.
EP communication received in application No. 12751744.9, dated Mar. 18, 2015.
Epinat, Jean-Charles et al., "A novel engineered meganuclease induces homologous recombination in yeast and mammalian cells" Nucleic Acids Research, 2003, pp. 2952-2962, vol. 31, No. 11.
Farjardo-Sanchez, E., "Computer Design of Obligate Heterodimer Meganucleases Allows Efficient Cutting of Custom DNA Sequences," Nucleic Acids Res. 36(7):2164-2173, 2008.
Gammon, Don B. et al., "The 3'-to-5' Exonuclease Activity of Vaccinia Virus DNA Polymerase Is Essential and Plays a Role in Promoting Virus Genetic Recombination" Journal of Virology, May 2009, Paaes 4236-4250, vol. 83, No. 9.
Garcia, Valerie et al., "Bidirectional resection of DNA double-strand breaks by Mre11 and Exo1" Nature, Nov. 10, 2011, pp. 241-244, vol. 479.
Glaunsinger, Britt et al., "The Exonuclease and Host Shutoff Functions of the SOX Protein of Kaposi's Sarcoma-Associated Herpesvirus Are Genetically Separable" Journal of Virology, Jun. 2005, pp. 7396-7401, vol. 79, No. 12.
Gunn, A., et al., Correct End Use During End Joining of Multiple Chromosomal Double Strand Breaks Is Influenced by Repair Protein RAD50, DNA-Dependent Protein Kinase DNA-PKcs, and Transcription Context J. Biol. Chem. 286(49):42470-42482 Dec. 9, 2011.
International Search Report and Written Opinion dated Jun. 7, 2012, received in connection with PCT/US12/26653.
Ishchenko, Alexander A., et al., "The 3'→5' Exonuclease of Apn1 Provides an Alternative Pathway to Repair 7,8-Dihydro-8-0xodeoxyguanosine in *Saccharomyces cerevisiae*," Molecular and Cellular Biology, oo. 6380-6390, Aug. 2005.
Jagannathan, Indu et al., "Activity of FEN1 Endonuclease on Nucleosome Substrates Is Dependent upon DNA Sequence but Not Flap Orientation" The Journal of Biological Chemistry, May 20, 2011, Paaes 17521-17529, vol. 286, No. 20.

Kratz, Katja, et al., "Deficiency of FANCD2-Associated Nuclease KIAA1018/FAN1 Sensitizes Cells to Interstrand Crosslinking Agents," Cell 142, 77-99, Jul. 9, 2010.
Kurosawa, Ava et al., "Functions and Regulation of Artemis: A Goddess in the Maintenance of Genome Integrity" J. Radiat. Res., 2010, pp. 503-509, vol. 51.
Lee, Byung-In et al., "The RAD2 Domain of Human Exonuclease 1 Exhibits 5' to 3' Exonuclease and Flap Structure-specific Endonuclease Activities" The Journal of Biological Chemistry, Dec. 31, 1999, pp. 37763-37769, vol. 274, No. 53.
Lenain, Christelle et al., "The Apollo 5' Exonuclease Functions Together with TRF2 to Protect Telomeres from DNA Repair" Current Biology, Jul. 11, 2006, pp. 1303-1310, vol. 16.
Mahajan, Kiran N. et al., "Association of terminal deoxynucleotidyl transferase with Ku" PNAS, Nov. 23, 1999 pp. 13926-13931, vol. 96, No. 24.
Marcaida, Maria J. et al. (2010) Homing endonucleases: from basics to therapeutic applications, Cell. Mol. Life Sci., 67:727-748.
Mashimo, Tomoji et al., "Efficient gene targeting by TAL effector nucleases coinjected with exonucleases in zygotes" Scientific Reports, Feb. 13, 2013 vol. 3, Article No. 1253.
Mazur, Dan J et al., "Excision of 3' Termini by the Trex1 and TREX2 3'→5' Exonucleases—Characterization of the Recombinant Proteins" The Journal of Biological Chemistry, May 18, 2001, Paaes 17022-17029, vol. 276, No. 20.
Monteilhet, Claude et al. (1990) Purification and characterization of the in vitro activity of I-Sce I, a novel and highly specific endonuclease encoded by a group I intron, Nucleic Acids Research, 18(6):1407-1413.
Moscou, Matthew J. et al., "A Simple Cipher Governs DNA Recognition by TAL Effectors" Science, Dec. 11, 2009, p. 1501, vol. 326.
Nicoletie, M.L., et al., "Mre11-Rad50-Xrs2 and Sae2 Promote 5' Strand Resection of DNA Double-Strand Breaks," Nat. Struct. Mot. Biol. 17(12):1478-1485, Dec. 2010.
Nimonkar, Amitabh V. et al., "BLM-DNA2-RPA-MRN and EX01-BLM-RPA-MRN constitute two DNA end resection machineries for human DNA break repair" Genes & Development, 2011, pp. 350-362, vol. 25.
Orans, Jillian et al., "Structures of Human Exonuclease 1 DNA Complexes Suggest a Unified Mechanism for Nuclease Family" Cell, Apr. 15, 2011, pp. 212-223, vol. 145.
Paques, Frédéric et al., "Meganucleases and DNA Double-Strand Break-Induced Recombination: Perspectives for Gene Therapy" Current Gene Therapy, 2007, pp. 49-66, vol. 7.
Porteus, M.H. and Baltimore D., "Chimeric Nucleases stimulate Gene Targeting in Human Cells," Science 300(5620):763, May 2003.
Reuven, Nina Bacher et al., "The Herpes Simplex Virus Type 1 Alkaline Nuclease and Single-Stranded DNA Binding Protein Mediate Strand Exchange in Vitro" Journal of Virology, Jul. 2003, pp. 7245-7433 vol. 77 No. 13.
Smith, J., et al., "A Combinatorial Approach to Create Artificial Homing Endonucleases Cleaving Chosen Sequences," Nucleic Acids Res. 34(22):1-12, 2006.
Tsutakawa, Susan E. et al., "Human Flap Endonuclease Structures, DNA Double-Base Flipping, and a Unified Understanding of the FEN1 Superfamily" Cell, Apr. 15, 2011, pp. 198-211, vol. 145.
Vallur, et al., Complementary Roles for Exonuclease 1 and Flap Endonuclease 1 in Maintenance of Triplet Repeats, The Journal of Biological Chemistry 285(37):28514-28519, Sep. 10, 2010.
Yoon, Jung-Hoon et al., "Characterization of the 3'→5' Exonuclease Activity Found in Human Nucleoside Diphosphate Kinase 1 (NDK1) and Several of Its Homologues" Biochemistry, 2005, pp. 15774-15786 vol. 44.
Zhang, Jinjin et al., "Crystal Structure of *E. coli* RecE Protein Reveals a Toroidal Tetramer for Processing Double-Stranded DNA Breaks" Structure, May 13, 2009, pp. 690-702, vol. 17.
Zhang, Jinjin et al., "Crystal structures of λ exonuclease in complex with DNA suggest an electrostatic ratchet mechanism for processivity" PNAS, Jul. 19, 2011, pp. 11872-11877, vol. 108, No. 29.

Sce

| SEQ ID NO | |
|---|---|
| 10 | TAGGTCAGGGTTCACACTAGT▓▓▓▓▓▓▓▓▓▓▓▓▓▓▓▓▓ACCTGCAGGTTGCCGGTGGTGCA |
| 11 | TAGGTCAGGGTTCACACTAGTAGG----------GTAATACCTGCAGGTTGCCGGTGGTGCA |
| 12 | TAGGTCAGGGTTCACACTAGTTAGGGATAACAGGGTAATACCTGCAGGTTGCCGGTGGTGCA |
| 13 | TAGGTCAGGGTTCACACTAGTTAGGGATAACAGGGTAATACCTGCAGGTTGCCGGTGGTGCA |
| 14 | TAGGTCAGGGTTCACACTAGTTAGGGATAACAGGGTAATACCTGCAGGTTGCCGGTGGTGCA |
| 15 | TAGGTCAGGGTTCACACTAGTTAGGGATAACAGGGTAATACCTGCAGGTTGCCGGTGGTGCA |
| 16 | TAGGTCAGGGTTCACACTAGTTAGGGATAACAGGGTAATACCTGCAGGTTGCCGGTGGTGCA |
| 17 | TAGGTCAGGGTTCACACTAG------ATAACAGGGTAATACCTGCAGGTTGCCGGTGGTGCA |
| 18 | TAGGTCAGGGTTCACACTAGTTAGGGATA-CAGGGTAATACCTGCAGGTTGCCGGTGGTGCA |
| 19 | TAGGTCAGGGTTCACACTAGTTAGGGATAACAGGGTAATACCTGCAGGTTGCCGGTGGTGCA |
| 20 | TAGGTCAGGGTTCACACTAGTTAGG---------GTAATACCTGCAAGTTGCCGGTGGTGCA |
| 21 | TAGGTCAGGGTTCACACTAGTTAGGGA----------------TGCAGGTTGCCGGTGGTGCA |
| 22 | TAGGTCAGGGTTCACACTAGTTAGGGATAACAGGGTAATACCTGCAGGTTGCCGGTGGTGCA |
| 23 | TAGGTCAGGGTTCACACTA---------------------TACCTGCAGGTTGCCGGTGGTGCA |
| 24 | TAGGTCAGGGTTCACACTAGTTAGGGATAACAGGGTAATACCTGCAGGTTGCCGGTGGTGCA |
| 25 | TAGGTCAGGGTTCACACTAGTTAGGGATAACAGGGTAATACCTGCAGGTTGCCGGTGGTGCA |
| 26 | TAGGTCAGGGTTCACACTAGTTAGGGATAACAGGGTAATACCTGCAGGTTGCCGGTGGTGCA |
| 27 | TAGGTCAGGGTTCACACTAGGTAGGTA-----GGGCAA--CCTGCAGGTTGCCGGTGGTGCA |
| 28 | TAGGTCAGGGTTCACACTAGTTAGGGATAACAGGGTAATACCTGCAGGTTGCCGGTGGTGCA |
| 29 | TAGGTCAGGGTTCACACTAGTTAGGGATAACAGGGTAATACCTGCAGGTTGCCGGTGGTGCA |
| 30 | TAGGTCAGGGTTCACACTAGTTAGGGATAACAGGGTAATACCTGCAGGTTGCCGGTGGTGCA |
| 31 | TAGGTCAGGGTTCACACTAGTTAGGGATAACAGGGTAATACCTGCAGGTTGCCGGTGGTGCA |
| 32 | TAGGTCAGGGTTCACACTAGTTAGGGATAACAGGGTAATACCTGCAGGTTGCCGGTGGTGCA |
| 33 | TAGGTCAGGGTTCACACTAGTTAGG---------GTAATACCTGCAGGTTGCCGGTGGTGCA |
| 34 | TAGGTCAGGGTTCACACTAGTTAGGGATAACAGGGTAATACCTGCAGGTTGCCGGTGGTGCA |
| 35 | TAGGTCAGGGTTCACACTAGTTAGGGATAACAGGGTAATACCTGCAGGTTGCCGGTGGTGCA |
| 36 | TAGGTCAGGGTTCACACTAGTTAGGGATAACAGGGTAATACCTGCAGGTTGCCGGTGGTGCA |
| 37 | TAGGTCAGGGTTCACACTAGTTAGGGATAACAGGGTAATACCTGCAGGTTGCCGGTGGTGCA |
| 38 | TAGGTCAGGGTTCACACTAGTTAGGGATAAC---------TACCTGCAGGTTGCCGGTGGTGCA |
| 39 | TAGGTCAGGGTTCACACTAGTTAGGGATAACAGGGTAATACCTGCAGGTTGCCGGTGGTGCA |
| 40 | TAGGTCAGGGTTCACACTA--------ATAACAGGGTAATACCTGCAGGTTGCCGGTGGTGCA |
| 41 | TAGGTCAGGGTTCACACTAGTTAGGGATAACAGGGTAATACCTGCTGGTTGCCGGTGGTGCA |
| 42 | TAGGTCAGGGTTCACACTAGTTAGGGATAACAGGGTAATACCTGCAGGTTGCCGGTGGTGCA |
| 43 | TAGGTCAGGGTTCACACTAGTTAGGGATAACAGGGTAATACCTGCAGGTTGCCGGTGGTGCA |
| 44 | TAGGTCAGGGTTCACACTAGTTAGG---------GTAATACCTGCAAGTTGCCGGTGGTGCC |
| 45 | TAGGTCAGGGTTCACACTAGTTAGGGATAACAGGGTAATACCTGCAGGTTGCCGGTGGTGCA |
| 46 | TAGGTCAGGGTTCACACTAGTTAGG-ATAACAGGGTAATACCTGCAGGTTGCCGGTGGTGCA |
| 47 | TAGGTCAGGGTTCACACTAGTTAGG-ATAACAGGGTAATACCTGCAGGTTGCCGGTGGTGCA |
| 48 | TAGGTCAGGGTTCACACTAGTTAGGGATAACAGGGTAATACCTGCAGGTTGCCGGTGGTGCA |
| 49 | TAGGTCAGGGTTCACACTAGTTAGGGATAACAGGGTAATACCTGCAGGTTGCCGGTGGTGCA |
| 50 | TAGGTCAGGGTTCACACTAGTTAGGGATAACAGGGTAATACCTGCAGGTTGCCGGTGGTGCA |
| 51 | TAGGTCAGGGTTCACACTAGTTAGG-ATAACAGGGTAATACCTGCAGGTTGCCGGTGGTGCA |
| 52 | TAGGTCAGGGTTCACACTAG------ATAACAGGGTAATACCTGCAGGTTGCCGGTGGTGCA |
| 53 | TAGGTCAGGGTTCACACTAGTTAGGGATAACAGGGTAATACCTGCAGGTTACCGGTGGTGCA |
| 54 | TAGGTCAGGGTTCACACTAGTTAGGGATAACAGGGTAATACCTGCAGGTTGCCGGTGGTGCA |
| 55 | TAGGTCAGGGTTCACACTAGTTAGGGATAACAGGGTAATACATGCAGGTTGCCGGTGGTGCA |
| 56 | TAGGTCAGGGTTCACACTAGTTAGGGATAACAGGGTAATACCTGCAGGTTGCCGGTGGTGCA |
| 57 | TAGGTCAGGGTTCACACTAGTTAGGGATAACAGGGTAATACCTGCAGGTTGCCGGTGGTGCA |

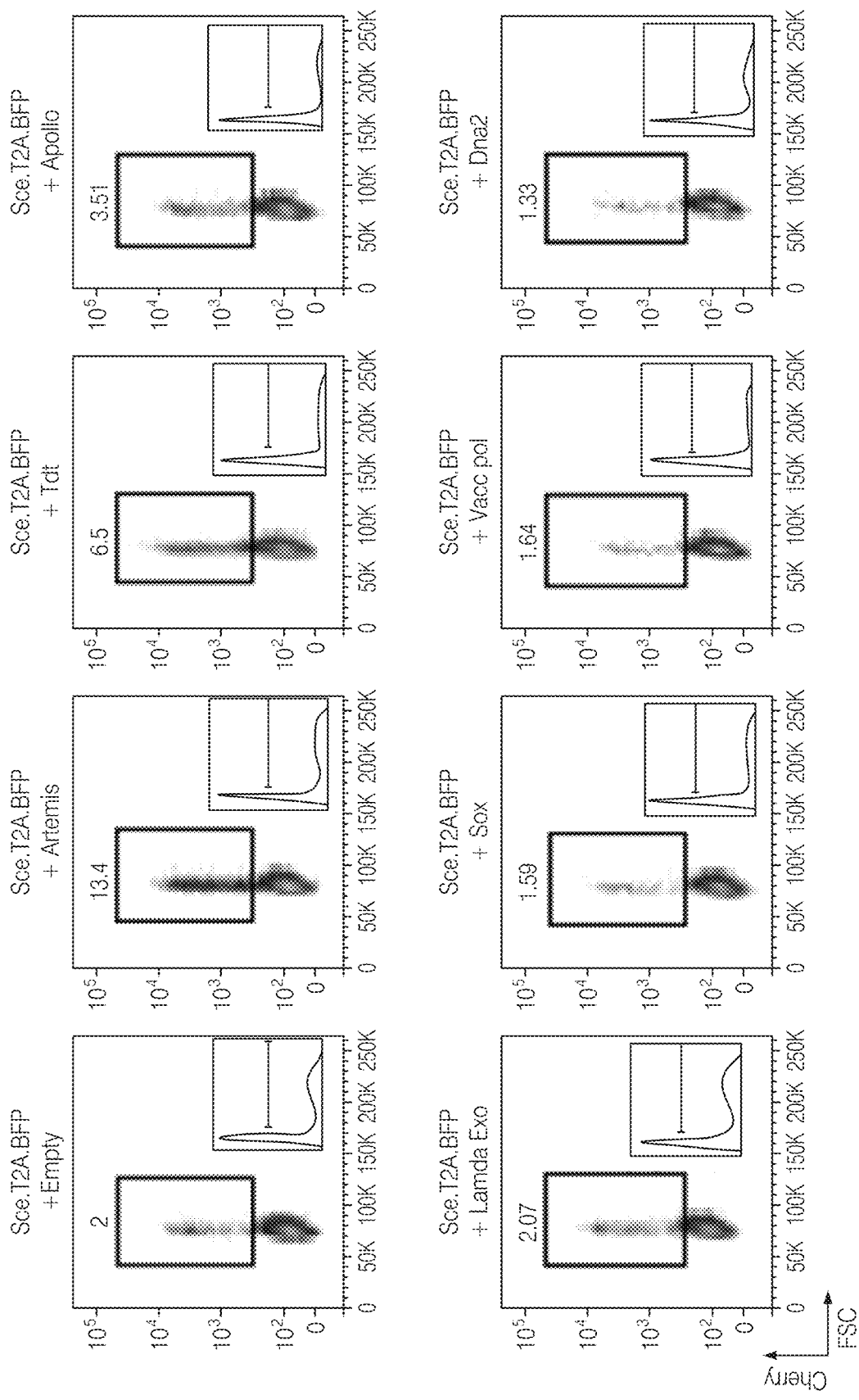
FIG. 17A₁

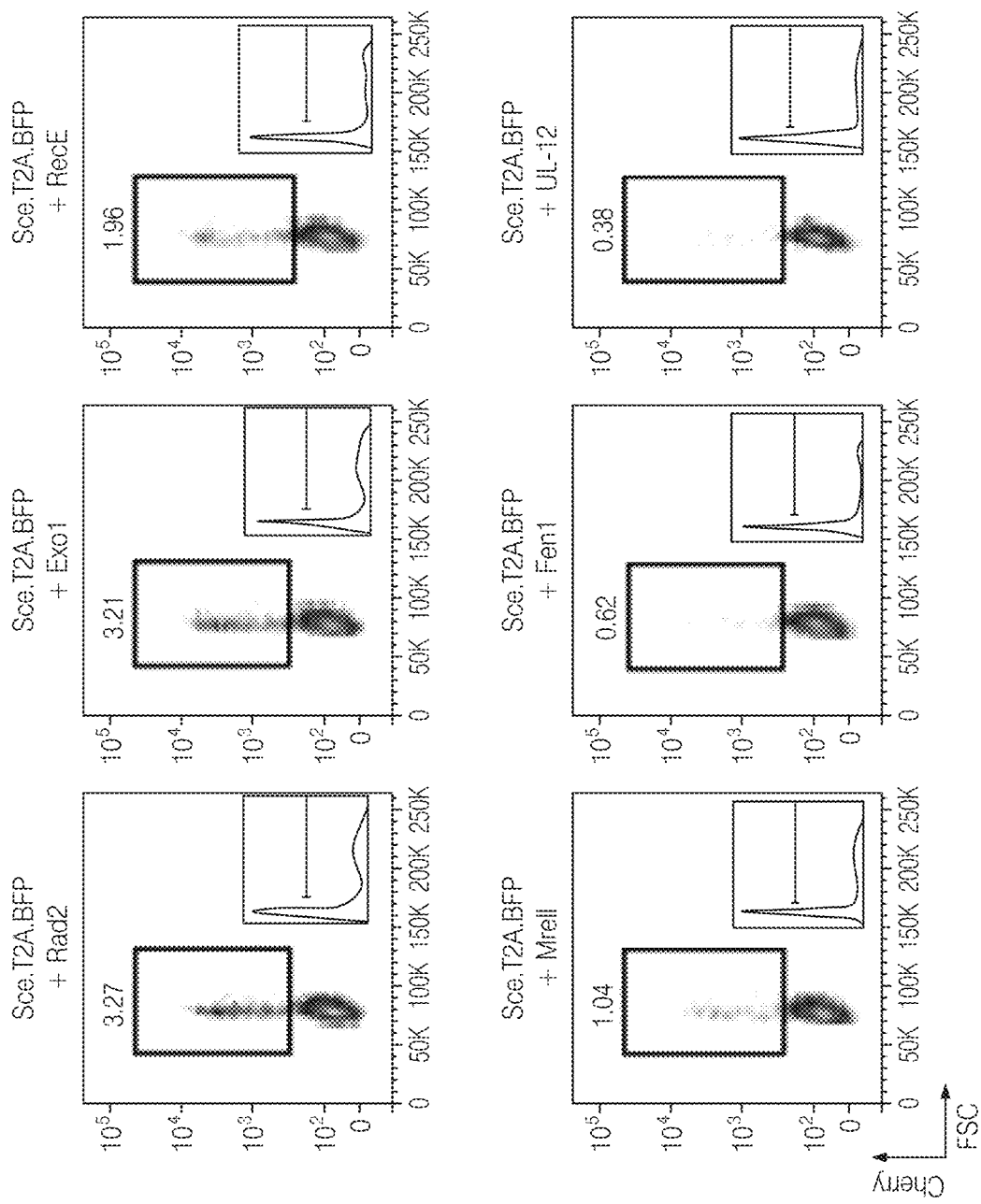
FIG. 17A₂

COUPLING ENDONUCLEASES WITH END-PROCESSING ENZYMES DRIVES HIGH EFFICIENCY GENE DISRUPTION

RELATED APPLICATION

The present application is a continuation application of U.S. application Ser. No. 15/215,405, filed Jul. 20, 2016, which is a continuation application of U.S. application Ser. No. 14/949,744, filed Nov. 23, 2015, which is a divisional application of U.S. application Ser. No. 14/173,705, filed on Feb. 5, 2014, which is a divisional application of U.S. application Ser. No. 13/405,183, filed on Feb. 24, 2012, now issued as U.S. Pat. No. 8,673,557, which in turn claims the benefit of priority to U.S. Provisional Patent Application No. 61/447,672, filed Feb. 28, 2011, and the disclosures for each of these related applications are incorporated herein by reference in their entireties.

STATEMENT REGARDING FEDERALLY SPONSORED R&D

This invention was made with government support under grant numbers CA133832, GM007270, DE019582, HL075453, HL092557, HL092553, HL092554, and AI096111 awarded by the National Institutes of Health. The government has certain rights in the invention.

REFERENCE TO SEQUENCE LISTING

The present application refers to a Sequence Listing in electronic format that was provided in parent U.S. application Ser. No. 15/215,405, filed Jul. 20, 2016, as a file entitled SCRI-025D1_SUBSTITUTE.TXT, created Feb. 5, 2014, which is 350 kb III Size. The information in the electronic format of the Sequence Listing filed in the parent application is incorporated herein by reference in its entirety.

FIELD

The present disclosure relates to molecular and cellular biology. Some embodiments relate to genome engineering and the introduction of targeted, site-specific DNA breaks mediated by endonucleases to achieve gene disruption or site-specific recombination. Several embodiments relate to compositions and methods for partial or complete inactivation of a target gene. Some embodiments relate to inactivation of a targeted gene for therapeutic purposes and/or to produce cell lines in which a target gene is inactivated.

BACKGROUND

Targeted gene disruption has wide applicability for research, therapeutic, agricultural, and industrial uses. One strategy for producing targeted gene disruption is through the generation of double-strand DNA breaks caused by site-specific endonucleases. Endonucleases are most often used for targeted gene disruption in organisms that have traditionally been refractive to more conventional gene targeting methods, such as algae, plants, and large animal models, including humans. For example, there are currently human clinical trials underway involving zinc finger nucleases for the treatment and prevention of HIV infection. Additionally, endonuclease engineering is currently being used in attempts to disrupt genes that produce undesirable phenotypes in crops.

The homing endonucleases, also known as meganucleases, are sequence specific endonucleases that generate double strand breaks in genomic DNA with a high degree of specificity due to their large (e.g., >14 bp) cleavage sites. While the specificity of the homing endonucleases for their target sites allows for precise targeting of the induced DNA breaks, homing endonuclease cleavage sites are rare and the probability of finding a naturally occurring cleavage site in a targeted gene is low.

One class of artificial endonucleases is the zinc finger endonucleases. Zinc finger endonucleases combine a non-specific cleavage domain, typically that of FokI endonuclease, with zinc finger protein domains that are engineered to bind to specific DNA sequences. The modular structure of the zinc finger endonucleases makes them a versatile platform for delivering site-specific double-strand breaks to the genome. One limitation of the zinc finger endonucleases is that low specificity for a target site or the presence of multiple target sites in a genome can result in off-target cleavage events. As Fok1 endonuclease cleaves as a dimer, one strategy to prevent off-target cleavage events has been to design zinc finger domains that bind at adjacent 9 base pair sites.

Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease.

The mutagenicity of the double strand DNA breaks generated by both the naturally occurring and artificial endonucleases depend upon the precision of DNA repair. The double strand breaks caused by endonucleases are commonly repaired through non-homologous end joining (NHEJ), which is the major DNA double-strand break repair pathway for many organisms. NHEJ is referred to as "non-homologous" because the break ends are ligated directly without the need for a homologous template, in contrast to homologous recombination, which utilizes a homologous sequence to guide repair. Imprecise repair through this pathway can result in mutations at the break site, such as DNA base deletions and insertions as well as translocations and telomere fusion. When the mutations are made within the coding sequence of a gene, they can render the gene and its subsequent protein product non-functional, creating a targeted gene disruption or "knockout" of the gene.

Double strand DNA break repair through the NHEJ pathway is often not mutagenic. The majority of endonuclease-induced breaks repaired by the NHEJ pathway involve precise re-ligation, resulting in the restoration of the original DNA sequence. This is especially true of the types of DNA breaks created by the current endonuclease platforms available for engineering site-specificity, namely homing endonucleases (meganucleases) and zinc finger nucleases. Both of these types of enzymes leave compatible base pair overhangs that do not require processing prior to re-ligation by the NHEJ pathway. When the overhangs are compatible, NHEJ repairs the break with a high degree of accuracy. Thus, from a genome engineering standpoint, many of the cleavage events generated by the current site-specific endonuclease platforms are unproductive.

The need for additional solutions to these problems is manifest.

SUMMARY

Mutagenesis of cellular DNA can occur when a DNA cleavage event is followed by imprecise end joining during DNA repair. As disclosed herein, one strategy for increasing the frequency of imprecise DNA repair events is by modifying compatible overhangs generated at double-strand DNA breaks with an end-processing enzyme. The methods and compositions described herein are broadly applicable and may involve any agent of interest which generates either blunt ends or compatible overhangs upon cleaving double stranded DNA, for example, nucleases, ionizing radiation, such as x-rays and gamma rays, as well as drugs such as bleomycin, cisplatin, and mitomycin C. Several embodiments disclosed herein relate to methods for coupling the generation of double-strand DNA breaks to modification of compatible overhangs generated at the cleavage site with a DNA end-processing enzyme. Several embodiments disclosed herein relate to methods for coupling the generation of double-strand DNA breaks to modification of blunt ends generated at the cleavage site with an end-processing enzyme. Some embodiments disclosed herein relate to methods for coupling the generation of double-strand DNA breaks to cleavage of the exposed phosphodiester bonds at the DNA break site by an exonuclease. Some embodiments disclosed herein relate to methods for coupling the generation of double-strand DNA breaks to the addition of DNA bases to an exposed DNA end by a non-template polymerase.

In yet another aspect, the methods and compositions described herein are broadly applicable and may involve any agent of interest which generates breaks in a polynucleotide. Several embodiments disclosed herein relate to methods for coupling the generation of polynucleotide breaks to modification of polynucleotide ends generated at the cleavage site with an end-processing enzyme. In some embodiments, the polynucleotide may be double stranded DNA, single stranded DNA, stranded RNA, single stranded RNA, double stranded DNA/RNA hybrids and synthetic polynucleotides.

Several embodiments disclosed herein relate to a strategy for increasing the frequency of imprecise DNA repair events by modifying compatible overhangs generated at exonuclease-induced DNA breaks with a DNA end-processing enzyme. Several embodiments disclosed herein relate to methods for coupling site-specific cleavage of a targeted DNA sequence to modification of compatible overhangs generated at the cleavage site with a DNA end-processing enzyme. Several embodiments disclosed herein relate to methods for coupling site-specific cleavage of a targeted DNA sequence to modification of blunt DNA ends generated at the cleavage site with a DNA end-processing enzyme. Some embodiments disclosed herein relate to methods for coupling site-specific cleavage of a targeted DNA sequence by an endonuclease to cleavage of the exposed phosphodiester bonds at the DNA cleavage site by an exonuclease. Some embodiments disclosed herein relate to methods for coupling site-specific cleavage of a targeted DNA sequence by an endonuclease to the addition of DNA bases to an exposed DNA end by a non-template polymerase. Some embodiments disclosed herein relate to methods for coupling site-specific cleavage of a targeted DNA sequence by an endonuclease to removal of a 5'phosphate at the DNA cleavage site by a 5'-phosphatase. Some embodiments disclosed herein relate to methods for coupling site-specific cleavage of a targeted DNA sequence by an endonuclease to removal of a 3'phosphate at the DNA cleavage site by a 3'phosphatase. Further disclosed herein are fusion proteins, comprising one or more site-specific endonuclease domains tethered to one or more DNA end-processing domains.

Non-limiting examples of endonucleases include homing endonucleases (meganucleases), zinc finger nucleases and TAL effector nucleases. The endonucleases may comprise heterologous DNA-binding and cleavage domains (e.g., zinc finger nucleases; homing endonuclease DNA-binding domains with heterologous cleavage domains or TAL-effector domain nuclease fusions) or, alternatively, the DNA-binding domain of a naturally-occurring nuclease may be altered to bind to a selected target site (e.g., a homing endonuclease that has been engineered to bind to site different than the cognate binding site or a TAL-effector domain nuclease fusion).

Non-limiting examples of DNA end-processing enzymes include 5-3'exonucleases, 3-5'exonucleases, 5-3' alkaline exonucleases, 5' flap endonucleases, helicases, phosphatases, hydrolases and template-independent DNA polymerases. The exonucleases may comprise heterologous DNA-binding and end-processing domains (e.g., a zinc finger and an exonuclease domain).

Several embodiments relate to co-expression of one or more endonucleases (enzymes that incise DNA at a specific internal target site) with one or more end-processing enzymes, in order to achieve enhanced processing of the polynucleotide ends produced by endonuclease-mediated polynucleotide cleavage. Several embodiments relate to co-expression of one or more endonucleases with one or more exonucleases (enzymes that catalyzes the removal of polynucleotide bases from an exposed polynucleotide end) in order to achieve enhanced processing of the polynucleotide ends produced by endonuclease-mediated polynucleotide cleavage. Several embodiments relate to co-expression of one or more endonucleases with one or more non-templative polymerases (enzymes that catalyze the addition of DNA bases to an exposed DNA end) in order to achieve enhanced processing of the DNA ends produced by endonuclease-mediated DNA cleavage. Several embodiments relate to co-expression of one or more endonucleases with one or more phosphatases that catalyze the removal of a 5' phosphate in order to achieve enhanced processing of the polynucleotide ends produced by endonuclease-mediated polynucleotide cleavage. Several embodiments relate to co-expression of one or more endonucleases with one or more phosphatases that catalyze the removal of a 3' phosphate in order to achieve enhanced processing of the polynucleotide ends produced by endonuclease-mediated polynucleotide cleavage. In some embodiments, an endonuclease is coupled to an end-processing enzyme.

Several embodiments relate to co-expression of one or more endonucleases (enzymes that incise DNA at a specific internal target site) with one or more DNA end-processing enzymes, in order to achieve enhanced processing of the DNA ends produced by endonuclease-mediated DNA cleavage. Several embodiments relate to co-expression of one or more endonucleases with one or more exonucleases (enzymes that catalyzes the removal of DNA bases from an exposed DNA end) in order to achieve enhanced processing of the DNA ends produced by endonuclease-mediated DNA cleavage. Several embodiments relate to co-expression of one or more endonucleases with one or more non-templative polymerases (enzymes that catalyze the addition of DNA bases to an exposed DNA end) in order to achieve enhanced processing of the DNA ends produced by endonuclease-mediated DNA cleavage. Several embodiments relate to co-expression of one or more endonucleases with one or more phosphatases that catalyze the removal of a 5' phosphate in order to achieve enhanced processing of the DNA ends produced by endonuclease-mediated DNA cleavage. Several embodiments relate to co-expression of one or more endonucleases with one or more phosphatases that catalyze the removal of a 3' phosphate in order to achieve enhanced processing of the DNA ends produced by endonuclease-mediated DNA cleavage. In some embodiments, an endonuclease is coupled to a DNA end-processing enzyme.

In one aspect, a method for improving the mutation frequency associated with endonuclease mediated cleavage of cellular DNA in a region of interest (e.g., a method for targeted disruption of genomic sequences) is provided, the method comprising: (a) selecting a sequence in the region of interest; (b) selecting a site-specific endonuclease which cleaves the sequence within the region of interest; and (c) delivering one or more fusion proteins to the cell, the fusion protein(s) comprising one or more site-specific endonuclease domains and one or more DNA end-processing domains; wherein the endonuclease domain cleaves the DNA in the region of interest. In some embodiments, a fusion protein can be delivered to a cell by delivering a polynucleotide encoding the fusion protein to a cell. In some embodiments the polynucleotide is DNA. In other embodiments, the polynucleotide is RNA. In some embodiments, a fusion protein can be expressed in a cell by delivering a DNA vector encoding the fusion protein to a cell, wherein the DNA vector is transcribed and the mRNA transcription product is translated to generate the fusion protein. In some embodiments, a fusion protein can be expressed in a cell by delivering an RNA molecule encoding the fusion protein to the cell wherein the RNA molecule is translated to generate the fusion protein. In some embodiments, a fusion protein may be delivered directly to the cell.

In another aspect, a method for improving the mutation frequency associated with endonuclease mediated cleavage of cellular DNA in a region of interest (e.g., a method for targeted disruption of genomic sequences) is provided, the method comprising: (a) selecting a sequence in the region of interest; (b) selecting one or more site-specific endonucleases which cleaves the sequence within the region of interest; and (c) co-expressing the one or more selected endonuclease and one or more end-processing enzyme in the cell; wherein the endonuclease cleaves the DNA in the region of interest and the end-processing enzyme modifies the DNA ends exposed by the endonuclease. The nucleases and end-processing enzymes can be expressed in a cell, e.g., by delivering the proteins to the cell or by delivering one or more polynucleotides encoding the nucleases to a cell. In some embodiments, a single polynucleotide encodes both the one or more endonucleases and the one or more end-processing enzymes under the control of a single promoter. In some embodiments, one or more endonucleases and one or more end-processing enzymes are coupled by one or more T2A "skip" peptide motifs. In some embodiments, one or more endonucleases and one or more end-processing enzymes are encoded by separate polynucleotides. In some embodiments, expression of the DNA end-processing enzyme precedes that of the endonuclease.

In yet another aspect, a method for improving the mutation frequency associated with endonuclease mediated cleavage of cellular DNA in multiple regions of interest (e.g., a method for targeted disruption of multiple genomic sequences) is provided, the method comprising: (a) selecting a first sequence in a first region of interest; (b) selecting a first site-specific endonuclease which cleaves the first sequence within the first region of interest; (c) selecting a second sequence in a second region of interest; (d) selecting a second site-specific endonuclease which cleaves the second sequence within the second region of interest and (c) co-expressing the selected endonucleases and one or more end-processing enzymes in the cell; wherein the first endonuclease cleaves the DNA in the first region of interest, the second endonuclease cleaves the DNA in the second region of interest and the one or more end-processing enzymes modify the exposed DNA ends. The nucleases and end-processing enzyme(s) can be expressed in a cell, e.g., by delivering the proteins to the cell or by delivering one or more polynucleotides encoding the nucleases and end-processing enzyme(s) to a cell. In some embodiments, a single polynucleotide encodes both the first and second endonucleases and the one or more end-processing enzyme under the control of a single promoter. In some embodiments, the endonucleases and the end-processing enzyme(s) are coupled by one or more T2A "skip" peptide motifs. In some embodiments, the first and second regions of interest are in the same gene. In other embodiments, the first and second regions of interest are in different genes. In some embodiments the method further comprises co-expression of a third, fourth, fifth, sixth, seventh, eighth, ninth, and/or tenth endonuclease in the cell.

In yet another aspect, the disclosure provides a method for treating or preventing, or inhibiting HIV infection or ameliorating a condition associated with HIV in a subject, the method comprising: (a) introducing, into a cell, a first nucleic acid encoding a first polypeptide, wherein the first polypeptide comprises: (i) a zinc finger DNA-binding domain that is engineered to bind to a first target site in the CCR5 gene; and (ii) a cleavage domain; and (iii) an end-processing domain under conditions such that the polypeptide is expressed in the cell, whereby the polypeptide binds to the target site and cleaves the CCR5 gene and end-processing enzyme domain modifies the endonuclease cleavage site; and (b) introducing the cell into the subject. In certain embodiments, the cell is selected from the group consisting of a hematopoietic stem cell, a T-cell, a macrophage, a dendritic cell, and an antigen-presenting cell.

In yet another aspect, the disclosure provides a method for treating or preventing or inhibiting HIV infection or ameliorating a condition associated with HIV in a subject, the method comprising: (a) introducing, into a cell, a first nucleic acid encoding a first polypeptide and a second polypeptide, wherein the first polypeptide comprises: (i) a zinc finger DNA-binding domain that is engineered to bind to a first target site in the CCR5 gene; and (ii) a cleavage domain; and the second polypeptide comprises a end-processing enzyme under conditions such that the polypeptides are co-expressed in the cell, whereby the first polypeptide binds to the target site and cleaves the CCR5 gene and the end-processing enzyme modifies the exposed DNA ends created at the endonuclease cleavage site; and (b) introducing the cell into the subject. In certain embodiments, the cell is selected from the group consisting of a hematopoietic stem cell, a T-cell, a macrophage, a dendritic cell and an antigen-presenting cell.

In another aspect, the disclosure provides a method for treating or preventing or inhibiting HIV infection or ameliorating a condition associated with HIV in a subject, the method comprising: (a) introducing, into a cell, a nucleic acid encoding a polypeptide, wherein the polypeptide comprises: (i) a homing endonuclease domain that is engineered to bind to a first target site in the CCR5 gene; and (ii) a end-processing domain under conditions such that the polypeptide is expressed in the cell, whereby the polypeptide binds to the target site and cleaves the CCR5 gene and modifies the exposed DNA ends created at the cleavage site; and (b) introducing the cell into the subject. In certain embodiments, the DNA end-processing domain comprises an exonuclease.

In another aspect, the disclosure provides a method for treating or preventing or inhibiting HIV infection or ameliorating a condition associated with HIV in a subject, the method comprising: (a) introducing, into a cell, a nucleic acid encoding a first polypeptide and a second polypeptide, wherein the first polypeptide comprises a homing endonuclease that is engineered to bind to a target site in the CCR5 gene; and the second polypeptide comprises a end-processing enzyme under conditions such that the polypeptides are co-expressed in the cell, whereby the first polypeptide binds to the target site and cleaves the CCR5 gene and the end-processing enzyme modifies the exposed DNA ends created at the endonuclease cleavage site; and (b) introducing the cell into the subject. In certain embodiments, the end-processing enzyme comprises an exonuclease. In some embodiments, the homing endonuclease and the end-processing enzyme are coupled by one or more T2A "skip" peptide motifs.

In yet another aspect, the disclosure provides a method for treating or preventing or inhibiting HIV infection or ameliorating a condition associated with HIV in a subject, the method comprising: (a) introducing, into a cell, a first nucleic acid encoding a first polypeptide, wherein the first polypeptide comprises: a homing endonuclease that is engineered to bind to a first target site in the CCR5 gene; and (b) introducing, into the cell, a second nucleic acid encoding a second polypeptide, wherein the second polypeptide comprises: a end-processing enzyme; under conditions such that the polypeptides are expressed in the cell, whereby the homing endonuclease binds to the target site and cleaves the CCR5 gene and the end-processing enzyme modifies the exposed DNA ends created at the endonuclease cleavage site; and (b) introducing the cell into the subject. In certain embodiments, the end-processing enzyme comprises an exonuclease. In some embodiments, expression of the end-processing enzyme precedes that of the endonuclease.

In another aspect, the disclosure provides a method for treating or preventing or inhibiting hyper IGE syndrome or ameliorating a condition associated with hyper IGE syndrome a subject, the method comprising: (a) introducing, into one or more cells, a nucleic acid encoding a polypeptide, wherein the polypeptide comprises: (i) a homing endonuclease domain that is engineered to bind to a first target site in the Stat3 gene; and (ii) a end-processing domain under conditions such that the polypeptide is expressed in the cell, whereby the polypeptide binds to the target site and cleaves the Stat3 gene and modifies the exposed DNA ends created at the endonuclease cleavage site. In certain embodiments, the end-processing enzyme domain comprises an exonuclease.

In yet another aspect, the disclosure provides a method for treating or preventing or inhibiting hyper IGE syndrome or ameliorating a condition associated with hyper IGE syndrome a subject, the method comprising: (a) introducing, into a cell, a first nucleic acid encoding a first polypeptide, wherein the first polypeptide comprises: a homing endonuclease that is engineered to bind to a first target site in the STAT3 gene; and (b) introducing, into the cell, a second nucleic acid encoding a second polypeptide, wherein the second polypeptide comprises: a end-processing enzyme; under conditions such that the polypeptides are expressed in the cell, whereby the homing endonuclease binds to the target site and cleaves the STAT3 gene and the end-processing enzyme modifies the exposed DNA ends created at the endonuclease cleavage site. In certain embodiments, the end-processing enzyme comprises an exonuclease. In some embodiments, the expression of the end-processing enzyme precedes that of the endonuclease.

In yet another aspect, the disclosure provides a method for treating or preventing or inhibiting hyper IGE syndrome or ameliorating a condition associated with hyper IGE syndrome a subject, the method comprising: (a) introducing, into a cell, a nucleic acid encoding a first polypeptide and a second polypeptide, wherein the first polypeptide comprises a homing endonuclease that is engineered to bind to a first target site in the STAT3 gene and the second polypeptide comprises a end-processing enzyme; under conditions such that the polypeptides are co-expressed in the cell, whereby the homing endonuclease binds to the target site and cleaves the STAT3 gene and the end-processing enzyme modifies the exposed DNA ends created at the endonuclease cleavage site. In certain embodiments, the end-processing enzyme comprises an exonuclease. In some embodiments, the homing endonuclease and the end-processing enzyme are coupled by one or more T2A "skip" peptide motifs.

BRIEF DESCRIPTION OF THE DRAWINGS

FIGS. 6A and 6B shows the results of DNA sequencing of amplicons surrounding the I-SceI target site in HEK293 Traffic Light Reporter cells treated with I-SceI-IRES-BFP or I-SceI-T2A-Trex2-IRES-BFP.

FIG. $17A_1$ and FIG. $17A_2$ show representative flow plots of HEK293 Traffic Light Reporter cells following co-transfection of I-SceI-IRES-BFP and an expression plasmid coding for the indicated end-processing enzyme.

DETAILED DESCRIPTION

Definitions

Figure 1A:
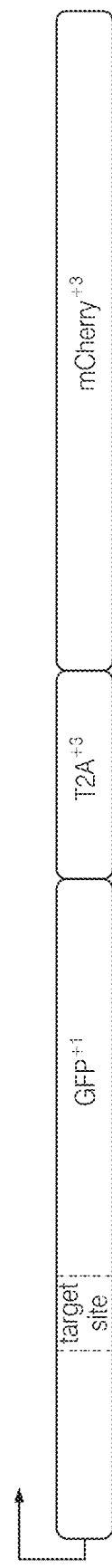
FIG. 1A shows a schematic of the Traffic Light Reporter system (TLR) for measuring the effectiveness of exonuclease induced gene disruption. mCherry positive cells represent a proportion of the total cells that have undergone gene disruption.
Figure 1B:
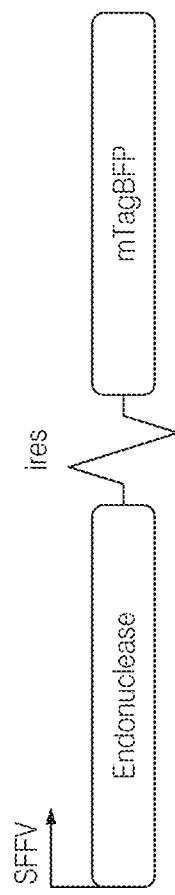
FIGS. 1B-1H show schematic representations of expression vectors for delivery of endonucleases and DNA end-processing enzymes.
Figure 1C:
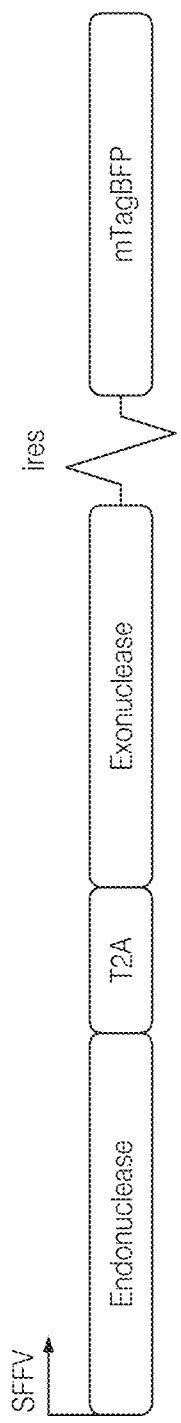
Figure 1D:
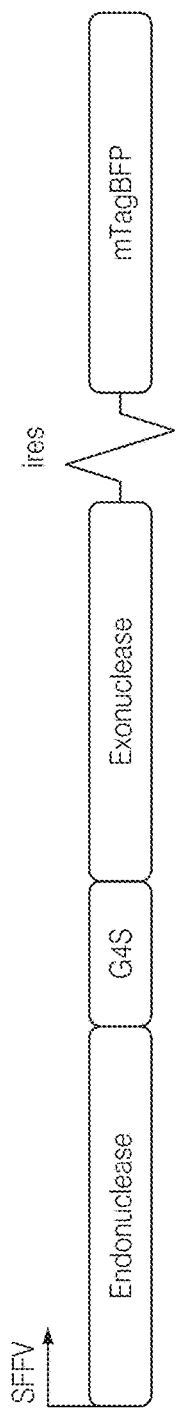
Figure 1E:
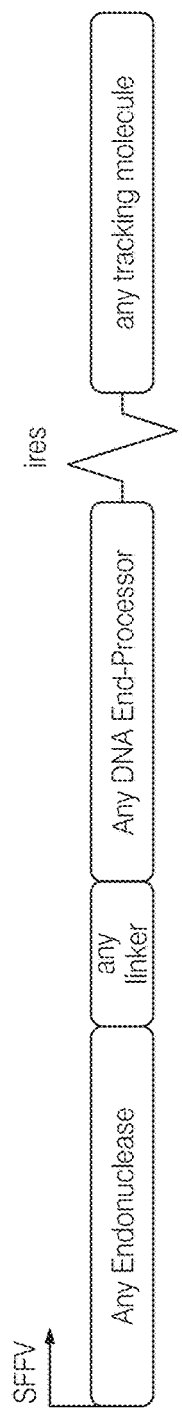
Figure 1F:
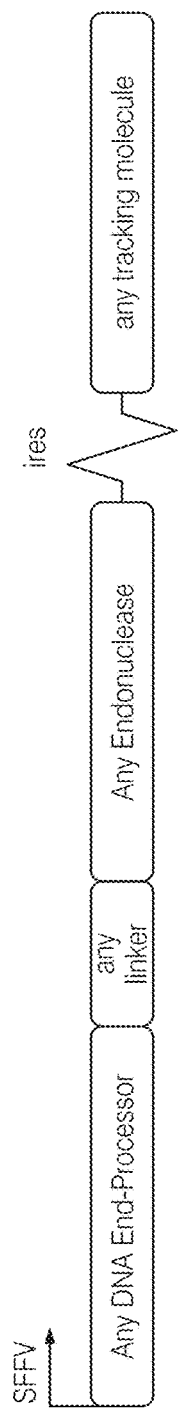
Figure 1G:
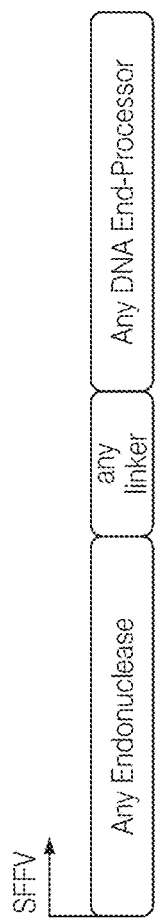
Figure 1H:
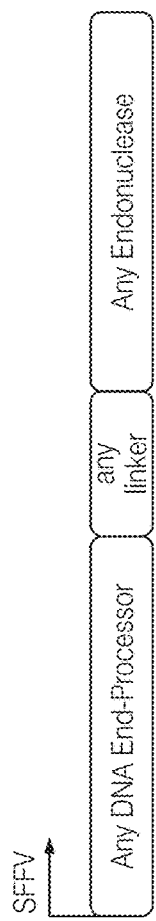

In the description that follows, a number of terms are used extensively. The following definitions are provided to facilitate understanding of the present embodiments.

As used herein, "a" or "an" may mean one or more than one.

As used herein, the term "about" indicates that a value includes the inherent variation of error for the method being employed to determine a value, or the variation that exists among experiments.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (e.g., GAU and GAC triplets each encode Asp). It will be understood that, as a result of the degeneracy of the genetic code, a multitude of nucleotide sequences encoding a given protein such as an endonuclease, end-processing enzyme, or endonuclease/end-processing enzyme fusion protein of the present embodiments may be produced.

The term "complementary to" means that the complementary sequence is homologous to all or a portion of a reference polynucleotide sequence. For illustration, the nucleotide sequence "CATTAG" corresponds to a reference sequence "CATTAG" and is complementary to a reference sequence "GTAATC."

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another non-limiting example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art may also use the term "cDNA" to refer to a double-stranded DNA molecule consisting of such a single-stranded DNA molecule and its complementary DNA strand. The term "cDNA" may also refer to a clone of a cDNA molecule synthesized from an RNA template.

A "promoter" is a nucleotide sequence that directs the transcription of a structural gene. In some embodiments, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). As used herein, a promoter may be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (e.g., endogenous DNA) so long as that host DNA is combined with non-host DNA (e.g., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptide components, such as carbohydrate groups. Carbohydrates and other non-peptide substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present embodiments, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, plastome, or bacteriophage that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transduced with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, "transient transfection" refers to the introduction of exogenous nucleic acid(s) into a host cell by a method that does not generally result in the integration of the exogenous nucleic into the genome of the transiently transfected host cell.

By the term "host cell" is meant a cell that contains one or more nucleases, for example endonucleases, end-processing enzymes, and/or endonuclease/end-processing enzyme fusion proteins encompassed by the present embodiments or a vector encoding the same that supports the replication, and/or transcription or transcription and translation (expression) of one or more nucleases, for example endonucleases, end-processing enzymes, and/or endonuclease/end-processing enzyme fusion proteins. Host cells for use in the present invention can be prokaryotic cells or eukaryotic cells. Examples of prokaryotic host cells include, but are not limited to, E. coli, nitrogen fixing bacteria, Staphylococcus aureus, Staphylococcus albus, Lactobacillus acidophilus, Bacillus anthracis, Bacillus subtilis, Bacillus thuringiensis, Clostridium tetani, Clostridium botulinum, Streptococcus mutans, Streptococcus pneumoniae, mycoplasmas, and cyanobacteria. Examples of eukaryotic host cells include, but are not limited to, protozoa, fungi, algae, plant, insect, amphibian, avian and mammalian cells.

"Integrative transformants" are recombinant host cells, in which heterologous DNA has become integrated into the genomic DNA of the cells.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, e.g., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers, or alternatively glycosylated or derivative forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "gene expression" refers to the biosynthesis of a gene product. For example, in the case of a structural gene, gene expression involves transcription of the structural gene into mRNA and the translation of mRNA into one or more polypeptides.

The term "endonuclease" refers to enzymes that cleave the phosphodiester bond within a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An endonuclease may cut a polynucleotide symmetrically, leaving "blunt" ends, or in positions that are not directly opposing, creating overhangs, which may be referred to as "sticky ends." The methods and compositions described herein may be applied to cleavage sites generated by endonucleases.

The term "homing endonuclease" refers to double stranded DNases that have large, asymmetric recognition sites (12-40 base pairs). Homing endonuclease recognition sites are extremely rare. For example, an 18 base pair recognition sequence will occur only once in every $7 \times 10^{10}$ base pairs of random sequence. This is equivalent to only one site in 20 mammalian-sized genomes. Unlike standard restriction endonucleases, however, homing endonucleases tolerate some sequence degeneracy within their recognition sequence. As a result, their observed sequence specificity is typically in the range of 10-12 base pairs. Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. Examples of homing endonucleases include, but are not limited to, I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII. Their recognition sequences are known. The specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66. The methods and compositions described herein may be applied to cleavage sites generated by homing endonucleases.

The term "TAL effector nuclease" (TALEN) refers to a nuclease comprising a TAL-effector domain fused to a nuclease domain. TAL-effector DNA binding domains, isolated from the plant pathogen *Xanthomonas* have been described (see Boch et al., (2009) Science 29 Oct. 2009 (10.1126/science.117881) and Moscou and Bogdanove, (2009) Science 29 Oct. 2009 (10.1126/science.1178817)). These DNA binding domains may be engineered to bind to a desired target and fused to a nuclease domain, such as the FokI nuclease domain, to derive a TAL effector domain-nuclease fusion protein. The methods and compositions described herein may be applied to cleavage sites generated by TAL effector nucleases.

The term "Zinc-finger nuclease" (ZFN) refers to artificial restriction enzymes generated by fusing a zinc finger DNA-binding domain to a DNA-cleavage domain. Zinc finger domains can be engineered to bind to a desired target site. In some embodiments, the cleavage domain comprises the non-specific cleavage domain of FokI. In other embodiments, the cleavage domain comprises all or an active portion of another nuclease. In some embodiments, the cleavage domain may comprise Trex2 or an active fragment thereof. The methods and compositions described herein may be applied to cleavage sites generated by zinc-finger nucleases The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. A end-processing enzyme may modify may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group. Non-limiting examples of types of DNA end-processing enzymes include 5-3' exonucleases, 5-3' alkaline exonucleases, 3-5' exonucleases, 5' flap endonucleases, helicases, phosphatases, hydrolases and template-independent DNA polymerases. Examples of DNA end-processing enzymes include, but are not limited to, Trex2, Trex1, Trex1 without transmembrane domain, Apollo, Artemis, DNA2, Exo1, ExoT, ExoIII, FenI, FanI, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phosphatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. Many DNA end-processing enzymes are highly conserved throughout evolution, and thus likely to function in several different species. Further, homologues of DNA end-processing enzymes may be readily identifiable in organisms of biotechnological interest, including plants, animals, and algae. Contemplated herein are methods of modifying DNA end-processing enzymes to optimize activity or processivity.

The term "exonuclease" refers to enzymes that cleave phosphodiester bonds at the end of a polynucleotide chain via a hydrolyzing reaction that breaks phosphodiester bonds at either the 3' or 5' end. The polynucleotide may be double-stranded DNA (dsDNA), single-stranded DNA (ssDNA), RNA, double-stranded hybrids of DNA and RNA, and synthetic DNA (for example, containing bases other than A, C, G, and T). The term "5' exonuclease" refers to exonucleases that cleave the phosphodiester bond at the 5' end. The term "3' exonuclease" refers to exonucleases that cleave the phosphodiester bond at the 3' end. Exonucleases may cleave the phosphodiester bonds at the end of a polynucleotide chain at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. Exonucleases may cleave the phosphodiester bonds at blunt ends or sticky ends. *E. coli* exonuclease I and exonuclease III are two commonly used 3'-exonucleases that have 3'-exonucleolytic single-strand degradation activity. Other examples of 3'-exonucleases include Nucleoside diphosphate kinases (NDKs), NDK1 (NM23-H1), NDK5, NDK7, and NDK8 (Yoon J-H, et al., Characterization of the 3' to 5' exonuclease activity found in human nucleoside diphosphate kinase 1 (NDK1) and several of its homologues. *Biochemistry* 2005: 44(48):15774-15786.), WRN (Ahn, B., et al., Regulation of WRN helicase activity in human base excision repair. *J. Biol. Chem.* 2004, 279:53465-53474) and Three prime repair exonuclease 2 (Trex2) (Mazur, D. J., Perrino, F. W., Excision of 3' termini by the Trex1 and TREX2 3'→5' exonucleases. Characterization of the recombinant proteins. J. Biol. Chem. 2001, 276:17022-17029.). *E. coli* exonuclease VII and T7-exonuclease Gene 6 are two commonly used 5'-3' exonucleases that have 5% exonucleolytic single-strand degradation activity. The exonuclease can be originated from prokaryotes, such as *E. coli* exonucleases, or eukaryotes, such as yeast, worm, murine, or human exonucleases.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

The terms "target site" or "target sequence" refers to a nucleic acid sequence that defines a portion of a nucleic acid to which a binding molecule will bind, provided sufficient conditions for binding exist. For example, the target sites for several homing endonucleases are shown in Table 1.

TABLE 1

Examples of Homing Endonucleases and their Target Sites.

| Homing Endonucleases | Target |
|---|---|
| I-SceI | TAGGGATAACAGGGTAAT (SEQ ID No. 1) |
| I-LtrI | AATGCTCCTATACGACGTTTAG (SEQ ID No. 2) |
| I-GpiI | TTTTCCTGTATATGACTTAAAT (SEQ ID No. 3) |
| I-GzeI | GCCCCTCATAACCCGTATCAAG (SEQ ID No. 4) |
| I-xMpeMI | TAGATAACCATAAGTGCTAAT (SEQ ID No.5) |
| I-PanMI | GCTCCTCATAATCCTTATCAAG (SEQ ID No. 6) |
| I-CreI | TCAAAACGTCGTGAGACAGTTTGG (SEQ ID No. 7) |
| I-OnuI | TTTCCACTTATTCAACCTTTTA (SEQ ID No. 8) |
| I-HjeMI | TTGAGGAGGTTTCTCTGTTAAT (SEQ ID No. 9) |
| I-AniI | TGAGGAGGTTTCTCTGTAAA (SEQ ID No. 10) |

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a host cell as a single protein. A fusion protein can comprise at least part of one polypeptide fused with another polypeptide. In some embodiments, a fusion protein can comprise at least a part of one polypeptide fused with at least a part of the same polypeptide. One example of a fusion protein is monomorized Trex2 (at least a part of Trex2 fused to at least a part of Trex2).

The term "endonuclease/end-processing enzyme fusion protein" or "fusion protein having endonuclease and end-processing activity" refers to an enzyme, which has an endonuclease catalytic domain and an end-processing catalytic domain and exhibits endonuclease and end-processing activity.

A "domain" of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., an endonuclease domain, a polynucleotide binding domain, such as a DNA-binding domain, or an end-processing domain).

"Prokaryotic" cells lack a true nuclease. Examples of prokaryotic cells are bacteria (e.g., cyanobacteria, *Lactobacillus acidophilus*, Nitrogen-Fixing Bacteria, *Helicobacter pylori*, *Bifidobacterium*, *Staphylococcus aureus*, *Bacillus anthrax*, *Clostridium tetani*, *Streptococcus pyogenes*, *Staphylococcus pneumoniae*, *Klebsiella pneumoniae* and *Escherichia coli*) and archaea (e.g., Crenarchaeota, Euryarchaeota, and Korarchaeota).

"Eukaryotic" cells include, but are not limited to, algae cells, fungal cells (such as yeast), plant cells, animal cells, mammalian cells, and human cells (e.g., T-cells).

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

"Algae" are predominantly aquatic organisms that carry out oxygen-evolving photosynthesis but lack specialized water-conducting and food-conducting tissues. Algae may be unicellular or multicellular. Algae may be adapted to live in salt water, fresh water and on land. Example of algae include, but are not limited to, diatoms, chlorophyta (for example, volvox, spirogyra), euglenophyta, dinoflagellata, chrysophyta, phaephyta (for example, fucus, kelp, sargassum), and rhodophyta (for example, lemanae).

The term "subject" as used herein includes all members of the animal kingdom including non-human primates and humans.

Overview

Several embodiments described herein relate to a method of improving the rate of gene disruptions caused by imprecise repair of DNA double-strand breaks. In some embodiments, DNA end-processing enzymes are provided to enhance the rate of gene disruption. Some aspects of the present embodiments include, without limitation, enhanced rates of DNA end-processing enzyme-mediated processing of DNA ends at the site of a double-strand break.

Targeted DNA double-strand breaks introduced by rare-cleaving endonucleases can be harnessed for gene disruption applications in diverse cell types by engaging non-homologous end joining DNA repair pathways. However, endonucleases create chemically clean breaks that are often subject to precise repair, limiting the efficiency of targeted gene disruption. Several embodiments described herein relate to a method of improving the rate of targeted gene disruptions caused by imprecise repair of endonuclease-induced site-specific DNA double-strand breaks. In some embodiments, site specific endonucleases are coupled with end-processing enzymes to enhance the rate of targeted gene disruption. Coupling may be, for example, physical, spatial, and/or temporal.

Some aspects of the present embodiments include, without limitation, enhanced rates of end-processing enzyme-mediated processing of endonuclease-produced DNA ends, leading to enhanced targeted gene disruption at the genomic target site. Using this strategy, embodiments described herein show over 25 fold increased endonuclease-induced disruption rates. Certain embodiments described herein can achieve complete knockout of a target gene within a population. This technology further has the potential to dramatically increase the utility of rare-cleaving endonucleases for genetic knockout applications. Improving the mutation rate associated with endonucleases facilitates endonuclease engineering, as enzymes with different levels of activity can be utilized. In some embodiments, endo-end-processor coupling is used modify DNA ends for endonuclease-induced genome engineering. In some embodiments, expression of exonucleases capable of processive 5' end resection coupled with manipulation of the DNA repair environment can be used to enhance homologous recombination-mediated gene targeting.

Not to be bound by any particular theory, the resolution of a double-strand DNA breaks by "error-prone" non-homologous end-joining (NHEJ) can be harnessed to create targeted disruptions and genetic knockouts, as the NHEJ process can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, and ligates ends back together with minimal processing. As the DNA breaks created by designer endonuclease platforms (zinc-finger nucleases (ZFNs), TAL effector nucleases (TALENs), and homing endonucleases (HEs)) all leave chemically clean, compatible overhang breaks that do not require processing prior to ligation, they are excellent substrates for precise repair by the cNHEJ pathway. In the absence or failure of the classical NHEJ pathway to resolve a break, alternative NHEJ pathways (altNHEJ) can substitute: however, these pathways are considerably more mutagenic.

Not to be bound by any particular theory, modification of DNA double-strand breaks by end-processing enzymes may bias repair towards an altNHEJ pathway. Further, different subsets of end-processing enzymes may enhance disruption by different mechanisms. For example, Trex2, an exonuclease that specifically hydrolyzes the phosphodiester bonds which are exposed at 3' overhangs, biases repair at break sites toward mutagenic deletion. By contrast, terminal deoxynucleotidyl transferase (TdT), a non-templative polymerase, is expected to bias repair at break sites toward mutagenic insertions by promoting the addition of nucleotide bases to alter DNA ends prior to ligation. Accordingly, one of skill in the art may use end-processing enzymes with different activities to provide for a desired engineering outcome. Further one of skill in the art may use synergy between different end-processing enzymes to achieve maximal or unique types of knockout effects.

Several embodiments described herein couple DNA breaks created by endonucleases with end-processing enzymes is a robust way to improve the rates of targeted disruption in a variety of cell types and species, without associated toxicity to the host. This is an important advance at least because: 1) Double-strand breaks (DSBs) trigger cell cycle checkpoints to arrest division until the break has been resolved; in the case of a "persistent break" (a repetitive cycle of cleaving and precise repair), cells may arrest indefinitely, leading to apoptosis. 2) Engineering applications often utilize transient delivery of an endonuclease, providing only a short window in which enzyme concentration is sufficient to achieve breaks. 3) Persistent breaks can be a source of translocations. Coupling endonucleases to end-processing enzymes prevents the establishment of a persistent break and reduces the incidence of gross chromosomal rearrangements, thereby potentially improving the safety of endonuclease-induced targeted disruption. 4) Multiple changes in a single round of mutagenesis may be achieved, for use for example, in multi-allelic knockouts and multiplexing, as data described herein suggests that coupling endonucleases to end-processing enzymes improves the mutagenic rate of two given endonucleases 5-fold at their respective targets, a 25-fold improvement may be realized in disrupting both targets simultaneously.

Any suitable method may be used to provide endonucleases, end-processing enzymes, and/or fusion proteins having endonuclease and end-processing activity to host cells. In some embodiments one or more polypeptides having endonuclease and/or end-processing activity may be provided directly to cells. In some embodiments, expression of endonucleases, end-processing enzymes and/or fusion proteins having endonuclease and end-processing activity in a host cell can result from delivery of one or more polynucleotides encoding one or more endonucleases, end-processing enzymes, and/or fusion proteins having endonuclease and end-processing activity to the host cell. In some embodiments, one or more polynucleotides is a DNA expression vector. In some embodiments, one or more polynucleotides is an RNA expression vector. In some embodiments, trans-splicing, polypeptide cleavage and/or polypeptide ligation can be involved in expression of one or more proteins in a cell. Methods for polynucleotide and polypeptide delivery to cells are well known in the art.

The compositions and methods described herein are useful for generating targeted disruptions of the coding sequences of genes and in some embodiments, creating gene knockouts. Targeted cleavage by the compositions and methods described herein can also be used to alter non-coding sequences (e.g., regulatory sequences such as promoters, enhancers, initiators, terminators, splice sites) to alter the levels of expression of a gene product. Such methods can be used, for example, for biological research, for biotechnology applications such as crop modification, for therapeutic purposes, functional genomics, and/or target validation studies.

Targeted mutations resulting from the methods and compositions described herein include, but are not limited to, point mutations (e.g., conversion of a single base pair to a different base pair), substitutions (e.g., conversion of a plurality of base pairs to a different sequence of identical length), insertions of one or more base pairs, deletions of one or more base pairs and any combination of the aforementioned sequence alterations.

Some embodiments relate to coupling the activity of one or more site-specific endonucleases with one or more end-processing enzymes. In some embodiments, the endonucleases and end-processing enzymes are provided as separate proteins. In some embodiments, the endonucleases and end-processing enzymes are co-expressed in a cell. If expression of the separate endonucleases and end-processing enzymes is by polynucleotide delivery, each of the endonucleases and end-processing enzymes can be encoded by separate polynucleotides, or by a single polynucleotide. In some embodiments, the endonucleases and end-processing enzymes are encoded by a single polynucleotide and expressed by a single promoter. In some embodiments, an endonuclease and end-processing enzymes are linked by a T2A sequence which allows for two separate proteins to be produced from a single translation. In some embodiments, a different linker sequence can be used. In other embodiments a single polynucleotide encodes the endonucleases and end-processing enzymes separated by an Internal Ribosome Entry Sequence (IRES).

Several embodiments relate to coupling the activity of one or more site-specific endonucleases selected from the group consisting of: homing endonucleases (meganucleases) (including engineered homing endonucleases), zinc finger nucleases, and TAL effector nucleases with one or more end-processing enzymes. The endonucleases may comprise heterologous DNA-binding and cleavage domains (e.g., zinc finger nucleases; homing endonuclease DNA-binding domains with heterologous cleavage domains or TAL-effector domain nuclease fusions) or, alternatively, the DNA-binding domain of a naturally-occurring nuclease may be altered to bind to a selected target site (e.g., a homing endonuclease that has been engineered to bind to site different than the cognate binding site or a TAL-effector domain nuclease fusion). In some embodiments, the endonucleases and end-processing enzymes are provided as a fusion protein. In some embodiments, the endonucleases and end-processing enzymes are provided as separate proteins. In some embodiments, the endonucleases and end-processing enzymes are co-expressed in a cell.

Several embodiments relate to coupling the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII with one or more DNA end-processing enzymes selected from the group consisting of: Trex2, Trex1, Trex1 without transmembrane domain, Apollo, Artemis, DNA2, Exo1, ExoT, ExoIII, FenI, FanI, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phosphatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

Several embodiments relate to coupling the activity of one or more ZFNs with one or more DNA end-processing enzymes selected from the group consisting of: Trex2, Trex1, Trex1 without transmembrane domain, Apollo, Artemis, DNA2, Exo1, ExoT, ExoIII, FenI, FanI, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phosphatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. In some embodiments, the ZFNs and DNA end-processing enzymes are provided as a fusion protein. In some embodiments, the ZFNs and DNA end-processing enzymes are provided as separate proteins. In some embodiments, the ZFNs and DNA end-processing enzymes are co-expressed in a host cell.

Several embodiments relate to coupling the activity of one or more TALENs with one or more DNA end-processing enzymes selected from the group consisting of: Trex2, Trex1, Trex1 without transmembrane domain, Apollo, Artemis, DNA2, Exo1, ExoT, ExoIII, FenI, FanI, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phosphatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and UL-12. In some embodiments, the TALENs and DNA end-processing enzymes are provided as a fusion protein. In some embodiments, the TALENs and DNA end-processing enzymes are provided as separate proteins. In some embodiments, the TALENs and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Apollo, Artemis, Dna2, Exo1, MreII, Rad2, RecE, Lambda exonuclease, Sox, exonuclease VII, T7-exonuclease Gene 6 and UL-12. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Sox and UL-12. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of one or more DNA end-processing enzymes selected from the group consisting of: Trex2, Vaccinia DNA polymerase, MreII, exonuclease I, exonuclease III, NDK1, NDK5, NDK7, NDK8, and WRN. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of FenI. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

In several embodiments, the activity of one or more site-specific homing endonucleases selected from the group consisting of: I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-TevI, I-TevII, and I-TevIII is coupled with the activity of TdT. In some embodiments, the homing endonucleases and DNA end-processing enzymes are provided as a fusion protein. In some embodiments, the endonucleases and DNA end-processing enzymes are provided as separate proteins. In some embodiments, the endonucleases and DNA end-processing enzymes are co-expressed in a host cell.

Some embodiments relate to coupling the activity of multiple site-specific endonucleases with the activity of one or more end-processing enzymes. The site specific endonucleases may cleave target sites within the same gene or in different genes. In some embodiments, 1, 2, 3, 4, 5, 6, 7, 8, 9, or 10 site-specific endonucleases may be provided to a cell along with one or more end-processing enzymes. In some embodiments, a combination of homing endonucleases, zinc finger endonucleases, and/or TAL effector endonucleases may be provided to a cell with one or more end-processing enzymes. In some embodiments, the end-processing enzyme is an exonuclease. In some embodiments, a 5' and a 3' exonuclease may be provided. If expression of the multiple endonucleases and one or more exonucleases is by polynucleotide delivery, each of the endonucleases and exonucleases can be encoded by separate polynucleotides, or by a single polynucleotide. In some embodiments, the endonucleases and exonucleases are encoded by a single polynucleotide and expressed by a single promoter. In some embodiments, the endonucleases and exonucleases are linked by a T2A sequence which allows for separate proteins to be produced from a single translation. In some embodiments, different linker sequences can be used. In other embodiments, a single polynucleotide encodes the endonucleases and exonucleases separated by IRESs.

Several embodiments relate to a heterologous fusion protein, which comprises an endonuclease domain and an end-processing domain or portions thereof. Several embodiments relate to a heterologous fusion construct, which encodes a fusion protein having endonuclease and end-processing activity. The present embodiments also relate to vectors and host cells comprising the heterologous fusion construct as well as methods for producing a fusion protein having endonuclease and end-processing activity and compositions thereof. In one embodiment, the endonuclease domain is coupled to the end-processing domain by recombinant means (e.g., the fusion protein is generated by translation of a nucleic acid in which a polynucleotide encoding all or a portion of a endonuclease is joined in-frame with a polynucleotide encoding all or a portion of a end-processing enzyme). In other embodiments, the endonuclease domain and end-processing domain of a fusion protein may be linked chemically. This chemical linkage can be carried out, for example, by using bifunctional linker molecules, such as, BS3 (Bis[sulfosuccinimidyl] suberate).

Some embodiments relate to a fusion protein comprising an endonuclease domain and exonuclease domain. In some embodiments the fusion protein comprises at least a fragment or variant of a homing endonuclease and at least a fragment or variant of an exonuclease, for example a 3' exonuclease, which are associated with one another by genetic or chemical conjugation to one another. In several embodiments, the 3' exonuclease is a Trex2 monomer, dimer, or a variant thereof. In other embodiments, the fusion protein comprises at least a fragment or variant of a zinc finger endonuclease and at least a fragment or variant of a 5' exonuclease, which are associated with one another, by genetic fusion or chemical conjugation to one another. The endonuclease and exonuclease, once part of the fusion protein, may be referred to as a "portion", "region," "domain" or "moiety" of the endo/exo-nuclease fusion protein.

In some embodiments, an end-processing enzyme (or fragment or variant thereof) is fused directly to an endonuclease (or fragment or variant thereof). The end-processing enzyme (or fragment or variant thereof) may be fused to the amino terminus or the carboxyl terminus of the endonuclease (or fragment or variant thereof).

An endonuclease/end-processing enzyme fusion protein may optionally include a linker peptide between the endonuclease and end-processing enzyme domains to provide greater physical separation between the moieties and thus maximize the accessibility of the endonuclease portion, for instance, for binding to its target sequence. The linker peptide may consist of amino acids selected to make it more flexible or more rigid depending on the relevant function. The linker sequence may be cleavable by a protease or cleavable chemically to yield separate endonuclease and end-processing enzyme moieties. Examples of enzymatic cleavage sites in the linker include sites for cleavage by a proteolytic enzyme, such as enterokinase, Factor Xa, trypsin, collagenase, and thrombin. In some embodiments, the protease is one which is produced naturally by the host or it is exogenously introduced. Alternatively, the cleavage site in the linker may be a site capable of being cleaved upon exposure to a selected chemical, e.g., cyanogen bromide, hydroxylamine, or low pH. The optional linker sequence may serve a purpose other than the provision of a cleavage site. The linker sequence should allow effective positioning of the endonuclease moiety with respect to the end-processing enzyme moiety so that the endonuclease domain can recognize and cleave its target sequence and the end-processing domain can modify the DNA ends exposed at the cleavage site. The linker may also be a simple amino acid sequence of a sufficient length to prevent any steric hindrance between the endonuclease domain and the end-processing domain. In addition, the linker sequence may provide for post-translational modification including, but not limited to, e.g., phosphorylation sites, biotinylation sites, sulfation sites, γ-carboxylation sites, and the like.

In some embodiments the linker sequence comprises from about 4 to 30 amino acids, more preferably from about 8 to 22 amino acids. That is, the linker sequence can be any number of amino acids from about 4 to 30, such as at least or equal to 4, 5, 6, 7, 8, 9, 10, 11, 12, 13, 14, 15, 16, 17, 18, 19, 20, 21, 22, 23, 24, 25, 26, 27, 28, 29, or 30 amino acids. In some embodiments, the linker sequence is flexible so as not hold the biologically active peptide in a single undesired conformation. The linker may be predominantly comprised of amino acids with small side chains, such as glycine, alanine, and serine, to provide for flexibility. In some embodiments about 80 or 90 percent or greater of the linker sequence comprises glycine, alanine, or serine residues, particularly glycine and serine residues. In several embodiments, a G4S linker peptide separates the end-processing and endonuclease domains of the fusion protein. In other embodiments, a T2A linker sequence allows for two separate proteins to be produced from a single translation. Suitable linker sequences can be readily identified empirically. Additionally, suitable size and sequences of linker sequences also can be determined by conventional computer modeling techniques.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are well known in the art.

A variety of DNA molecules encoding the above-described endonucleases, end-processing enzymes and fusion proteins may be constructed for providing the selected proteins or peptides to a cell. The DNA molecules encoding the endonucleases, end-processing enzyme, and fusion proteins may be modified to contain different codons to optimize expression in a selected host cell, as is known in the art.

A variety of RNA molecules encoding the above-described endonucleases, end-processing enzymes and fusion proteins may be constructed for providing the selected proteins or peptides to a cell. The RNA molecules encoding the endonucleases, end-processing enzyme, and fusion proteins may be modified to contain different codons to optimize expression in a selected host cell, as is known in the art.

Several embodiments relate to the prevention of precise cNHEJ mediated repair of endonuclease-induced double strand breaks by simultaneous expression of end-processing enzymes capable of recognizing the post-endonuclease break structure, resulting in the modification of DNA ends prior to ligation, promoting a mutagenic outcome. Some embodiments relate to the simultaneous expression exonucleases capable of recognizing the post-endonuclease break structure, resulting in the trimming of DNA ends prior to ligation, promoting a mutagenic outcome. Simultaneous expression of a site-specific endonuclease and an end-processing enzyme improves the efficiency of targeted gene disruption by up to ~70 fold, essentially fixing a mutagenic outcome in 100% of a population of cells containing the target site in less than 72 hours.

In some embodiments, effective amounts of endonucleases and end-processing enzymes or an effective amount of a fusion protein are delivered to a cell either directly by contacting the cell will the protein(s) or by transient expression from an expression construct. In such embodiments, cell division reduces the concentration of the nucleases to sub-active levels within a few cell divisions.

Several embodiments relate to a method of conferring site specificity on a DNA end-processing enzyme by physically tethering an end-processing enzyme domain to a site specific DNA binding domain. In some embodiments, the end-processing enzyme domain is tethered to a DNA binding domain through a linker peptide. The composition and structure of the linker peptide is not especially limited and in some embodiments the linker may be chemically or enzymatically cleavable. The linker peptide may be flexible or rigid and may comprise from about 4 to 30 amino acids. In other embodiments, the end-processing enzyme domain is chemically fused to a DNA binding domain. Not wishing to be bound by a particular theory, imparting site specificity to a end-processing enzyme through tethering the end-processing enzyme to a site specific DNA binding domain decreases toxicity associated with indiscriminate end-processing activity, such as exonuclease activity, and reduces the effective amount of end-processing enzyme required for efficient modification of the exposed double stranded DNA break caused by endonuclease activity compared to untethered end-processing enzyme. In some embodiments, the end-processing enzyme is tethered to a homing endonuclease. In other embodiments, the end-processing enzyme is tethered to zinc finger endonuclease. In some embodiments, an end-processing enzyme domain is tethered to a zinc finger DNA binding domain which binds to a DNA sequence adjacent to the cleavage site of a homing endonuclease or zinc finger endonuclease.

Figure 11A:
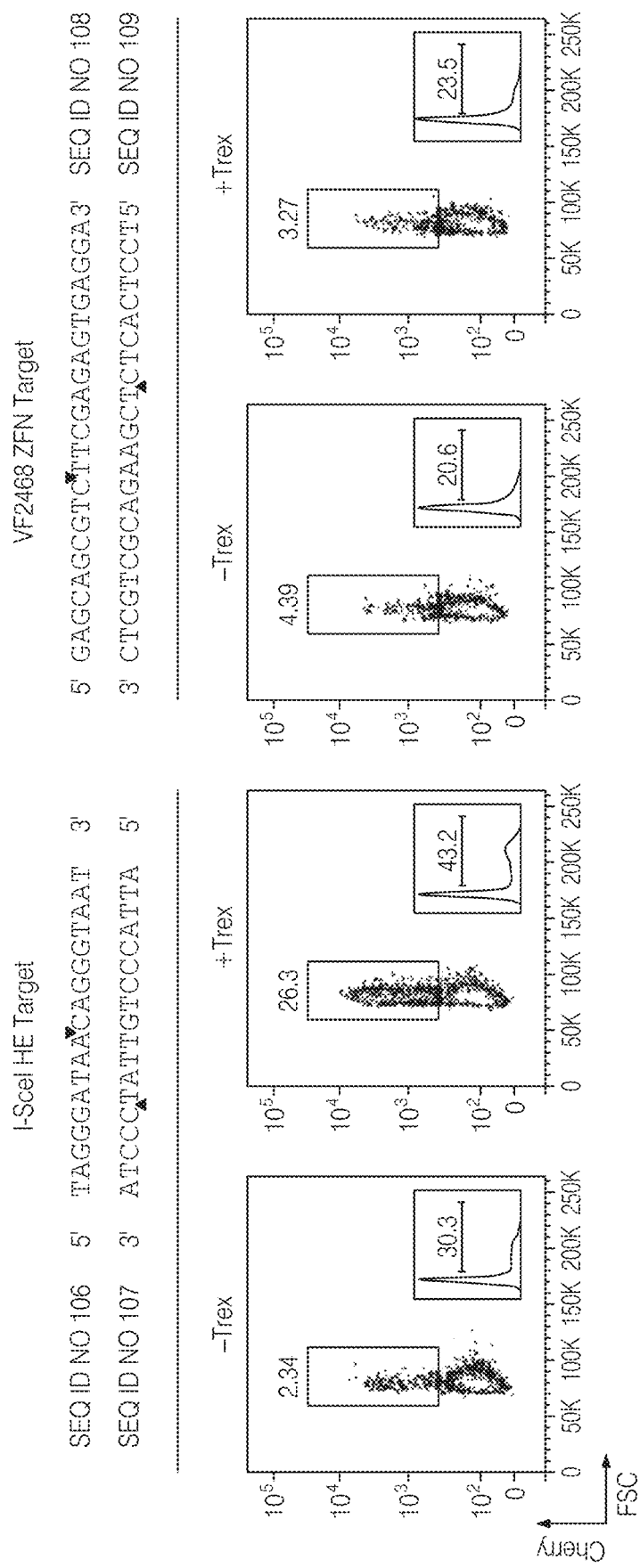
FIG. 11A shows representative flow plots and targets sites of HEK293 Traffic Light Reporter cells following transfection with a homing endonuclease with and without Trex2 and a zinc finger nuclease with and without Trex2.
Figure 11C:
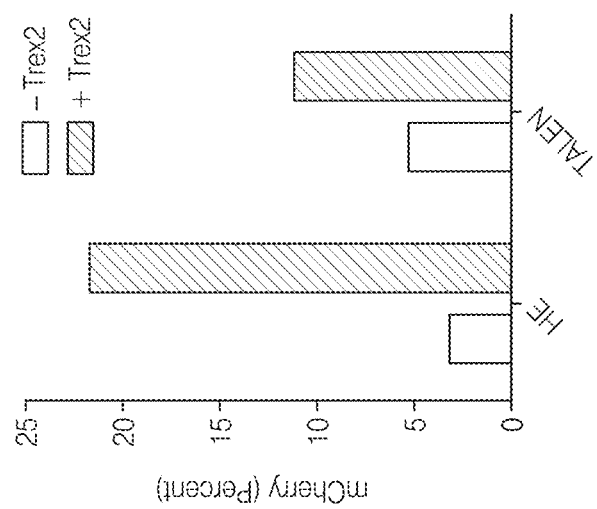
FIG. 11C shows a graph of HEK293 Traffic Light Reporter cells following co-transfection of an HE with Trex2 or a TALEN with Trex2.
Figure 11B:
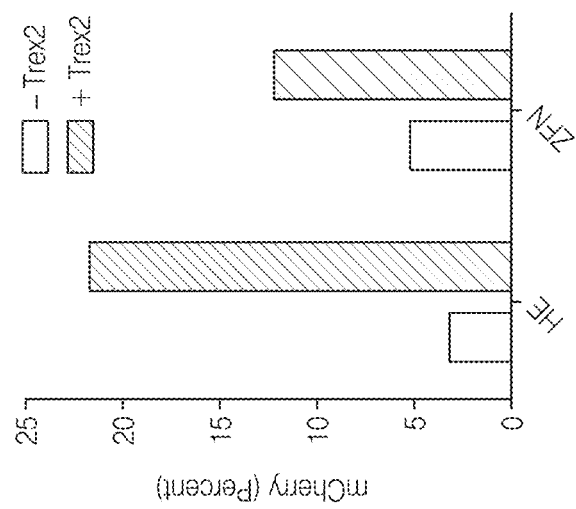
FIG. 11B shows a graph of an independent experiment examining cleavage site mutation for I-SceI and Zinc Finger Nuclease in the presence and absence of Trex2.

Several embodiments relate to coupling the activity of one or more site-specific endonucleases with Trex2. Trex2 may be provided as a monomer or dimer. The Trex2 enzyme specifically hydrolyzes the phosphodiester bonds which are exposed at 3' overhangs. While the homing endonucleases generate 3' overhangs which are susceptible to Trex2 exonuclease activity, the zinc finger nucleases, which utilize the FokI cleavage domain, generate double strand DNA breaks with 5' overhangs. The homing endonucleases and zinc finger nucleases generate mutations at their cleavage sites at a baseline rate. Co-expression of Trex2 with homing endonucleases increased the mutation rate ~70 fold. Co-expression of Trex2 with zinc finger endonucleases was also observed to effect on the rate of mutation. See FIGS. 11A and 11B. Accordingly, several embodiments described herein relate to improving the mutation rate associated zinc finger endonuclease targeted cleavage events by coupling zinc finger endonuclease to exonucleases which cleave 5' overhangs. Some embodiments relate to coupling 3' exonucleases to zinc finger endonucleases wherein the nuclease domain of the zinc finger endonuclease generates 3' overhangs.

Some embodiments relate to the co-expression of a homing endonuclease and the exonuclease, Trex2, via a single promoter linked by a T2A sequence that enables separate polypeptides to be produced from a single translation event. In this way, the endonuclease and exonuclease are provided in a 1 to 1 ratio. Higher rates of modification are achieved using T2A linked expression of the homing endonuclease, I-SceI, and Trex2 than is achieved through co-transduction of separate I-SceI, and Trex2 expression constructs. In some embodiments, a fusion protein comprising one or more endonuclease domains and one or more Trex2 domains may be provided.

In another aspect, methods of co-expressing an end-processing enzyme with a zinc finger endonuclease capable of mutating the CCR-5 gene and/or inactivating CCR-5 function in a cell or cell line are provided. In some embodiments, a method for improving the inactivation of a CCR-5 gene in a human cell is provided, the method comprising administering to the cell any site specific endonuclease having a target site in a CCR5 coupled to an end-processing enzyme. In some embodiments, a method for improving the inactivation of a CCR-5 gene in a human cell is provided, the method comprising administering to the cell any site specific endonuclease having a target site in a CCR5 coupled to an exonuclease capable of cleaving the phosphodiester bonds created at the site of endonuclease cleavage. In some embodiments, a method for improving the inactivation of a CCR-5 gene in a human cell is provided, the method comprising administering to the cell any site specific endonuclease having a target site in a CCR5 and contemporaneously administering an exonuclease capable of cleaving the phosphodiester bonds created at the site of endonuclease cleavage. Examples of suitable endonucleases include engineered homing endonucleases and meganucleases, which have very long recognition sequences, some of which are likely to be present, on a statistical basis, once in a human-sized genome. Any such nuclease having a unique target site in a CCR5 gene can be used instead of, or in addition to, a zinc finger nuclease, in conjunction with an exonuclease for targeted cleavage in a CCR5 gene. Some embodiments relate to administration of a fusion protein comprising a CCR5-site-specific endonuclease and an exonuclease capable of cleaving the phosphodiester bonds created at the site of endonuclease cleavage.

Expression Vectors

Expression constructs can be readily designed using methods known in the art. Examples of nucleic acid expression vectors include, but are not limited to: recombinant viruses, lentiviruses, adenoviruses, plasmids, bacterial artificial chromosomes, yeast artificial chromosomes, human artificial chromosomes, minicircle DNA, episomes, cDNA, RNA, and PCR products. In some embodiments, nucleic acid expression vectors encode a single peptide (e.g., an endonuclease, an end-processing enzyme, or a fusion protein having endonuclease and end-processing activity). In some embodiments, nucleic acid expression vectors encode one or more endonucleases and one or more end-processing enzymes in a single, polycistronic expression cassette. In some embodiments, one or more endonucleases and one or more end-processing enzymes are linked to each other by a 2A peptide sequence or equivalent "autocleavage" sequence. In some embodiments, a polycistronic expression cassette may incorporate one or more internal ribosomal entry site (IRES) sequences between open reading frames. In some embodiments, the nucleic acid expression vectors are DNA expression vectors. In some embodiments, the nucleic acid expression vectors are RNA expression vectors.

In some embodiments, a nucleic acid expression vector may further comprise one or more selection markers that facilitate identification or selection of host cells that have received and express the endonuclease(s), end-processing enzyme(s), and/or fusion protein(s) having endonuclease and end-processing activity along with the selection marker. Examples of selection markers include, but are not limited to, genes encoding fluorescent proteins, e.g., EGFP, DS-Red, YFP, and CFP; genes encoding proteins conferring resistance to a selection agent, e.g., $Puro^R$ gene, $Zeo^R$ gene, $Hygro^R$ gene, $neo^R$ gene, and the blasticidin resistance gene. In some cases, the selection marker comprises a fluorescent reporter and a selection marker.

In some embodiments, a DNA expression vector may comprise a promoter capable of driving expression of one or more endonuclease(s), end-processing enzyme(s), and/or fusion protein(s) having endonuclease and end-processing activity. Examples of promoters include, but are not limited to, retroviral LTR elements; constitutive promoters such as CMV, HSV1-TK, SV40, EF-1α, β-actin; inducible promoters, such as those containing Tet-operator elements; and tissue specific promoters. Suitable bacterial and eukaryotic promoters are well known in the art and described, e.g., in Sambrook et al., Molecular Cloning, A Laboratory Manual (2nd ed. 2001); Kriegler, Gene Transfer and Expression: A Laboratory Manual (1990); and Current Protocols in Molecular Biology (2010). Non-limiting examples of plant promoters include promoter sequences derived from *A. thaliana* ubiquitin-3 (ubi-3).

In some embodiments, a nucleic acid encoding one or more endonucleases, end-processing enzymes, and/or fusion proteins having endonuclease and end-processing activity can be cloned into a vector for transformation into prokaryotic or eukaryotic cells. In some embodiments, nucleic acids encoding different endonucleases and end-processing enzymes are cloned into the same vector. In such cases, the nucleic acids encoding different endonucleases and end-processing enzymes may optionally be separated by T2A or IRES sequences. Vectors can be prokaryotic vectors, e.g., plasmids, or shuttle vectors, insect vectors, or eukaryotic vectors, including plant vectors described herein. Expression of the nucleases and fusion proteins may be under the control of a constitutive promoter or an inducible promoter.

Introduction of polypeptides having endonuclease and/or end-processing activity and/or polynucleotides encoding polypeptides having endonuclease and/or end-processing activity into host cells may use any suitable methods for nucleic acid or protein delivery as described herein or as would be known to one of ordinary skill in the art. The polypeptides and polynucleotides described herein can be delivered into cultured cells in vitro, as well as in situ into tissues and whole organisms. Introduction of the polypeptides and polynucleotides of the present embodiments into a host cell can be accomplished chemically, biologically, or mechanically. This may include, but is not limited to, electroporation, sonoporation, use of a gene gun, lipotransfection, calcium phosphate transfection, use of dendrimers, microinjection, polybrene, protoplast fusion, the use of viral vectors including adenoviral, AAV, and retroviral vectors, and group II ribozymes.

Organisms

The present invention is applicable to any prokaryotic or eukaryotic organism in which it is desired to create a targeted genetic mutation. Examples of eukaryotic organisms include, but are not limited to, algae, plants, animals (e.g., mammals such as mice, rats, primates, pigs, cows, sheep, rabbits, etc.), fish, and insects. In some embodiments, isolated cells from the organism can be genetically modified as described herein. In some embodiments, the modified cells can develop into reproductively mature organisms. Eukaryotic (e.g., algae, yeast, plant, fungal, piscine, avian, and mammalian cells) cells can be used. Cells from organisms containing one or more additional genetic modifications can also be used.

Examples of mammalian cells include any cell or cell line of the organism of interest, for example oocytes, somatic cells, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells and myeloma cells like SP2 or NS0. Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, muscle stem cells, skin stem cells, and neuronal stem cells.

Examples of target plants and plant cells include, but are not limited to, monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus,*

*Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*. The term plant cells include isolated plant cells as well as whole plants or portions of whole plants such as seeds, callus, leaves, roots, etc. The present disclosure also encompasses seeds of the plants described above. The present disclosure further encompasses the progeny, clones, cell lines, or cells of the plants described.

Generating Homozygously Modified Organisms

Cells in which one or more endonucleases are co-expressed with one or more end-processing enzyme(s) and/or cells in which one or more fusion proteins having endonuclease and end-processing activity are expressed are then assayed for the presence of mutations at the endonuclease cleavage site(s). Such modified cells can be identified using any suitable method known to the skilled artisan, including sequencing, PCR analysis, southern blotting, and the like. In some embodiments, an amplicon spanning the endonuclease target site is generated by PCR. The amplicon is then exposed to the endonuclease and the ability of the endonuclease to cut the amplicon is assessed. Mutation of the target site is indicated by the absence of endonuclease generated cleavage products.

Subsequently, cells containing the mutated target site(s) are cultured or otherwise treated such that they generate a whole organism with the mutated target site. For example, traditional methods of pro-nuclear injection or oocyte injection can be used to generate animals with the mutated target site. Likewise, plant cells containing the mutated target site(s) can be cultured to regenerate a whole plant which possesses the mutant genotype and thus the desired phenotype. Regeneration can also be obtained from plant callus, explants, organs, pollens, embryos, or parts thereof. Once the heterozygous organisms containing the mutated target site(s) reach reproductive maturity, they can be crossed to each other, or in some instances, spores may be grown into haploids. Of the resulting progeny from crosses, approximately 25% will be homozygous mutant/mutant at the target locus.

Pharmaceutical Compositions and Administration

Endonucleases, end-processing enzymes and fusion proteins having endonuclease and end-processing activity and expression vectors encoding endonucleases, end-processing enzymes and fusion proteins having endonuclease and end-processing activity can be administered directly to a patient for targeted cleavage of a DNA sequence and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia and the like. In some embodiments, the compositions described herein (e.g., endonucleases, end-processing enzymes and fusion proteins having endonuclease and end-processing activity and expression vectors encoding endonucleases, end-processing enzymes and fusion proteins having endonuclease and end-processing activity) can be used in methods of treating, preventing, or inhibiting a disease (e.g., cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia) or ameliorating a disease condition or symptom associated with a disease, such as, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hyper IGE syndrome, hemophilia. In some embodiments endonucleases, end-processing enzymes and fusion proteins having endonuclease and end-processing activity and expression vectors encoding endonucleases, end-processing enzymes and fusion proteins having endonuclease and end-processing activity are administered to treat, prevent, or inhibit an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, and neurofibromatosis or ameliorate a disease condition or symptom associated with an autosomal dominant disease, such as achondroplasia, pseudoachondroplasia, the multiple epiphyseal dysplasias, chondrodysplasias, osteogenesis imperfecta, Marfan syndrome, polydactyly, hereditary motor sensory neuropathies I and II (Charcot-Marie-Tooth disease), myotonic dystrophy, and neurofibromatosis. In some embodiments endonucleases, end-processing enzymes and fusion proteins having endonuclease and end-processing activity and expression vectors encoding endonucleases, end-processing enzymes and fusion proteins having endonuclease and end-processing activity are administered to treat, prevent, or inhibit a disease caused by misregulation of genes. In some embodiments endonucleases, end-processing enzymes and fusion proteins having endonuclease and end-processing activity and expression vectors encoding endonucleases, end-processing enzymes and fusion proteins having endonuclease and end-processing activity are administered to treat, prevent, or inhibit a cancer, such as BCL-2, Bcl-XI, and FLIP, or ameliorate a disease condition or symptom associated with a cancer, such as BCL-2, Bcl-XI, and FLIP, by, for example, increasing the mutation rate of genes with anti-apoptotic activity.

Examples of microorganisms that can be inhibited (e.g., inhibiting the growth or infection) by provision of endonucleases, end-processing enzymes and fusion proteins having endonuclease and end-processing activity include pathogenic bacteria, e.g., *chlamydia*, rickettsial bacteria, mycobacteria, staphylococci, streptococci, pneumococci, meningococci and conococci, *klebsiella, proteus, serratia, pseudomonas, legionella, diphtheria, salmonella,* bacilli, cholera, tetanus, botulism, anthrax, plague, leptospirosis, and Lyme disease bacteria; infectious fungus, e.g., *Aspergillus, Candida* species; protozoa such as sporozoa (e.g., Plasmodia), rhizopods (e.g., *Entamoeba*) and *flagellates* (*Trypanosoma, Leishmania, Trichomonas, Giardia,* etc.); viral diseases, e.g., hepatitis (A, B, or C), herpes virus (e.g., VZV, HSV-1, HSV-6, HSV-II, CMV, and EBV), HIV, Ebola, adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing homing endonucleases or zinc finger endonucleases into ultimate contact with the tissue to be treated. The endonucleases, end-processing enzymes and fusion proteins having endonuclease and end-processing activity are administered in any suitable manner, and in some embodiments with pharmaceutically acceptable carriers. Suitable methods of administering such proteins or polynucleotides are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington's Pharmaceutical Sciences).

The endonucleases, end-processing enzymes and fusion proteins having endonuclease and end-processing activity or vectors encoding endonucleases, end-processing enzymes and fusion proteins having endonuclease and end-processing activity, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Kits

Also provided are kits for performing any of the above methods. The kits typically contain one or more endonucleases, end-processing enzymes and/or fusion proteins having endonuclease and end-processing activity or expression vectors encoding endonucleases, end-processing enzymes and/or fusion proteins having endonuclease and end-processing activity as described herein. The kits may also contain a reporter construct, such as the mCherry+ reporter construct described herein, containing a cloning site for insertion of the target site for a selected endonuclease of interest. In some embodiments, kits may contain one or more plasmids according to SEQ ID NOs: 110-145. For example, kits for screening mutagenesis produced by coupled endonuclease and end-processing activity and/or fusion proteins with activity to a particular gene are provided with one or more reporter constructs containing the desired target site(s). Similarly, kits for enriching cells for a population of cells having a endonuclease-mediated genomic modification may comprise a reporter construct comprising a target site present in the genome of the cells and one or more endonuclease specific to the target site of interest and one or more selected end-processing enzymes and/or one or more fusion proteins specific to the target site of interest.

The kits can also contain cells, buffers for transformation of cells, culture media for cells, and/or buffers for performing assays. Typically, the kits also contain a label, which includes any material such as instructions, packaging or advertising leaflet that is attached to or otherwise accompanies the other components of the kit.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The present embodiments should therefore not be limited by the above described embodiment, method, and examples, but by all embodiments and methods within the scope and spirit of the present embodiments.

The following Examples are presented for the purposes of illustration and should not be construed as limitations.

Example 1

Co-Expression of the Homing Endonuclease, I-SceI, and Trex2 Exonuclease Increases the Rate at which I-SceI Induces Mutations To determine if coupling an exonuclease with a site-specific endonuclease could enhance targeted gene disruption efficiency, we assessed the effect of Trex2 on the mutagenic repair of DSBs generated by I-SceI. To ensure that Trex2 would be co-expressed with I-SceI, we developed expression vectors that drive coupled expression of both an endonuclease and an end-processing enzyme from a single promoter via a T2A "skip" peptide motif. We also included mTagBFP fluorescent protein co-expression by an internal ribosomal entry site (IRES) for tracking transfection efficiency.

To measure the rate of nuclease-induced targeted disruption, a mutNHEJ reporter construct (Traffic Light Reporter (TLR)) was constructed by placing the I-SceI target site, SEQ ID NO: 146 5'-AGTTACGCTAGGGA-TAACAGGGTAATATAG-3', in front of the mCherry fluorescent protein ORF in the +3 reading frame. See FIG. 1A. When an endonuclease-induced DNA cleavage event results in a frameshift into the +3 reading frame, the mCherry fluorescent protein is placed in frame and correctly translated, resulting in red fluorescent cells that may be easily detected by flow cytometry. HEK cell lines harboring the TLR were generated by plating $0.1 \times 10^6$ HEK293 cells 24 hrs prior to transduction in a 24 well plate. mutNHEJ (TLR) reporter cell lines were made by transducing HEK293 cells at limiting titer (~5%) with ~25 ngs of an integrating lentivirus containing the reporter construct with 4 ug/ml polybrene. Media was changed 24 hrs after transduction.

Expression vectors comprising the homing endonuclease, I-SceI, a fluorescent protein (BFP), and optionally Trex2 with either a T2A or G4S linker peptide were constructed according to the schematics provided in FIGS. 1B-H.

$0.1 \times 10^{\wedge}6$ HEK293 cells containing a genomically-integrated mutNHEJ (TLR) reporter cassette were plated 24 hrs prior to transfection in a 24 well plate. The HEK 293 cells were transfected with expression constructs comprising the I-SceI mutant D44A alone, the I-SceI mutant D44A coupled to Trex2 via a T2A linker, I-SceI alone or I-SceI coupled to Trex2 via a T2A linker using Fugene transfection reagent according to manufacture's protocol. 72 hours following transduction of the cell line with the expression vectors, the cells were analyzed by flow cytometry on a BD LSRII or BD FACS ARIAII. The mCherry fluorophore was excited using a 561 nm laser and acquired with a 610/20 filter. The mTagBFP fluorophore was excited on a 405 nm laser with a 450/50 filter. Data was analyzed using FlowJo software (FlowJo, Ashland Oreg.).

Figure 2A:
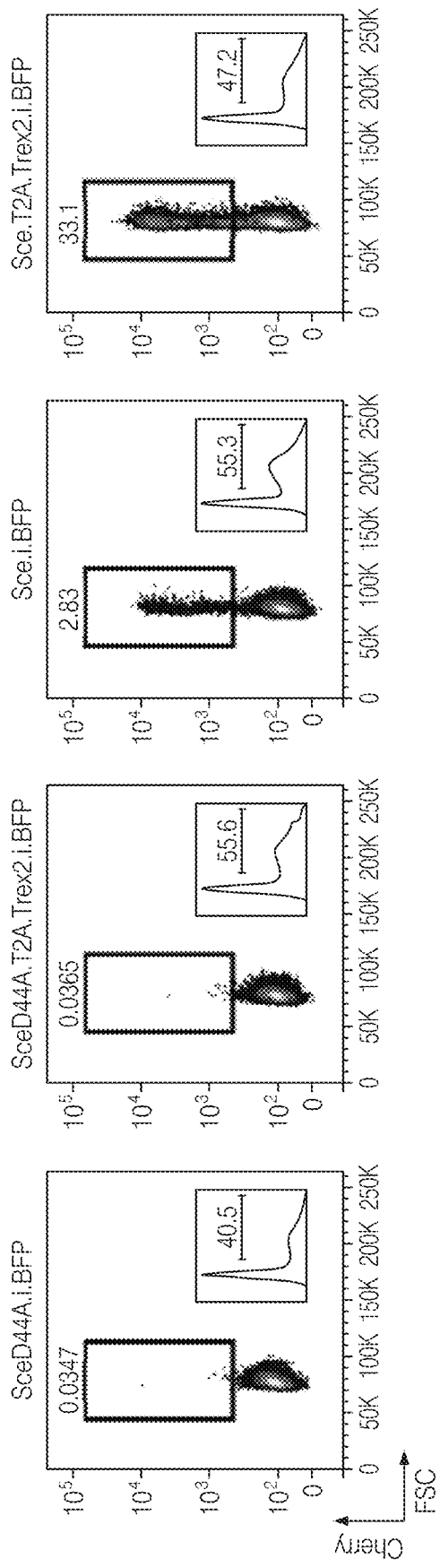
FIG. 2A shows representative flow plots of HEK293 cells harboring Traffic light Reporter transfected with expression vectors encoding SceD44A-IRES-BFP, SceD44A-T2A-Trex2-IRES-BFP, I-SceI-IRES-BFP, and I-SceI-T2A-Trex2-IRES-BFP. SceD44A corresponds to an inactive mutant form of I-SceI.
Figure 2B:
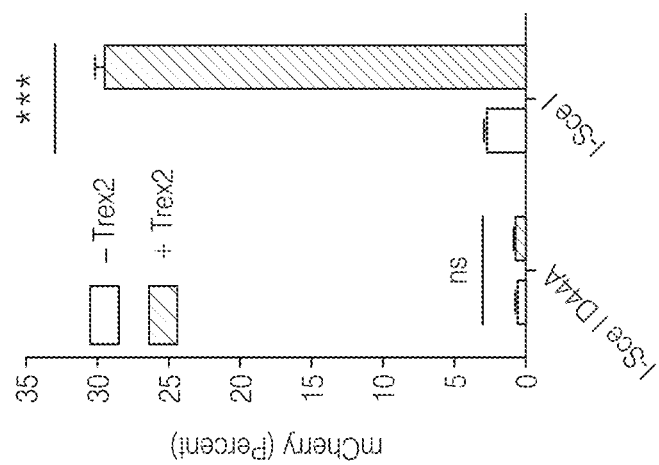
FIG. 2B shows quantification of gene disruption in three independent transfections of the vectors indicated in FIG. 2A. Error bars represent standard error of the mean (SEM), and p-values (with * representing $p<0.05$, $p<0.005$, and *$p<0.0005$) were calculated using the Student's two-tailed unpaired t-test to compare the samples indicated in this and all subsequent figures.

The plot shown in FIG. 2A demonstrates that I-SceI expression induced mutagenic NHEJ events as visualized by mCherry+ expression and that the rate of mutagenic NHEJ events (mCherry+) was significantly increased following co-expression of I-SceI with the exonuclease Trex2. See FIG. 2A. While neither I-SceI D44A (catalytically inactive) nor I-SceI D44A coupled to Trex2 was able to induce any measurable gene disruption, I-SceI coupled to Trex2 via T2A linkage exhibited a substantial increase in mCherry positive cells compared to I-SceI alone. See FIG. 2A.

Figure 6B:
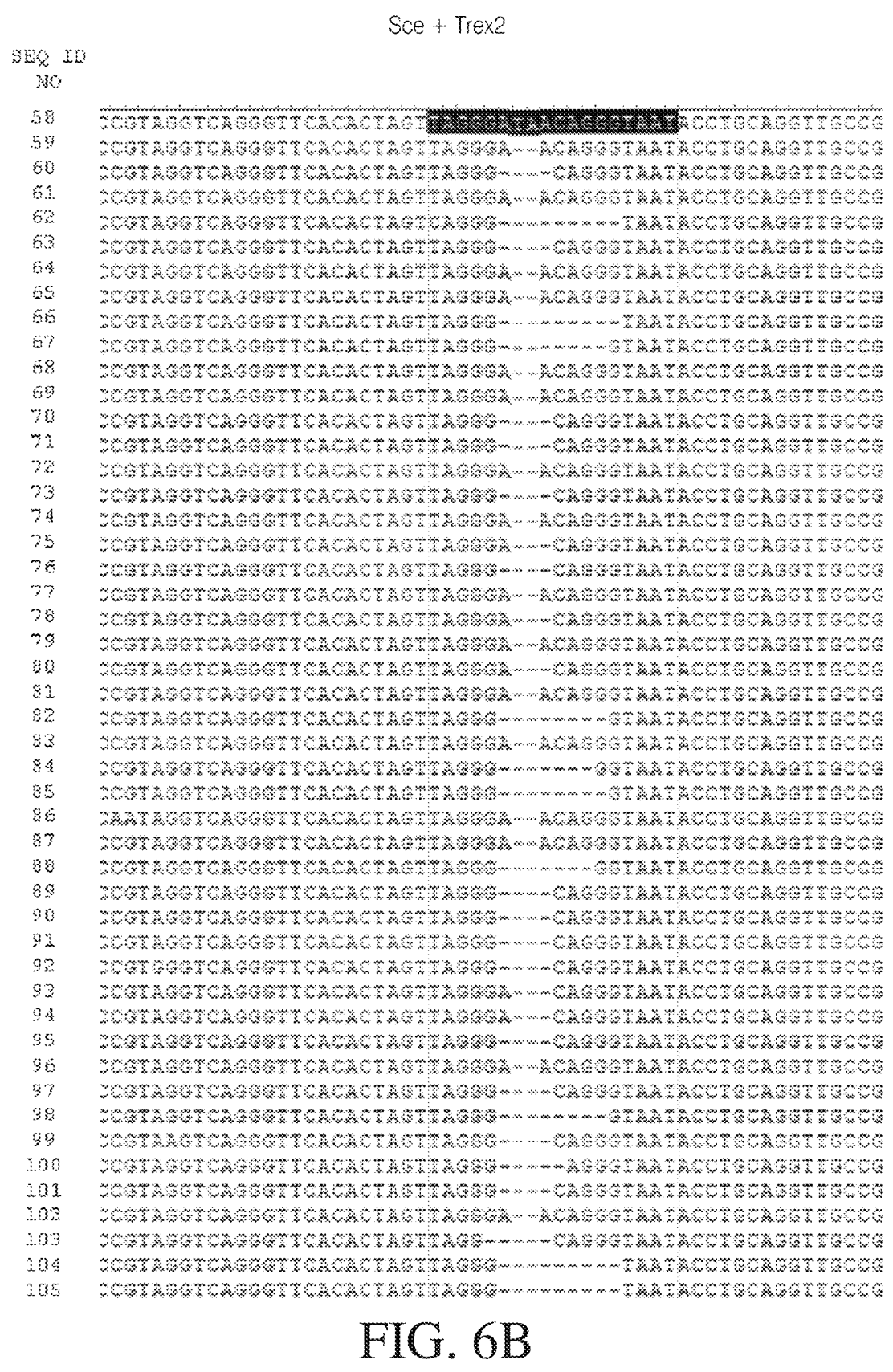

Following co-expression of I-SceI endonuclease and Trex2 exonuclease, genomic DNA was extracted from the HEK 293 reporter cells using Qiagen's DNA easy kit. Amplicons spanning the I-SceI target site were generated by PCR, cloned into a shuttle vector and subjected to DNA sequencing of the I-SceI target site. The sequencing demonstrated that essentially every cell in the population contains a mutated I-SceI target site, as predicted by the reporter readout. See FIGS. 6A and 6B.

Figure 21A:
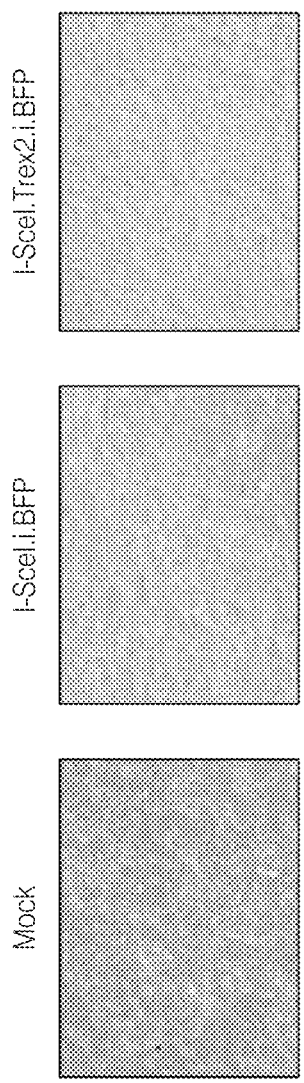
FIG. 21A shows live cell image of cells 72 hrs post mock transfection or transfection with an expression vectors encoding I-SceI-IRES-BFP or I-SceI-T2A-Trex2-IRES-BFP.
Figure 21B:
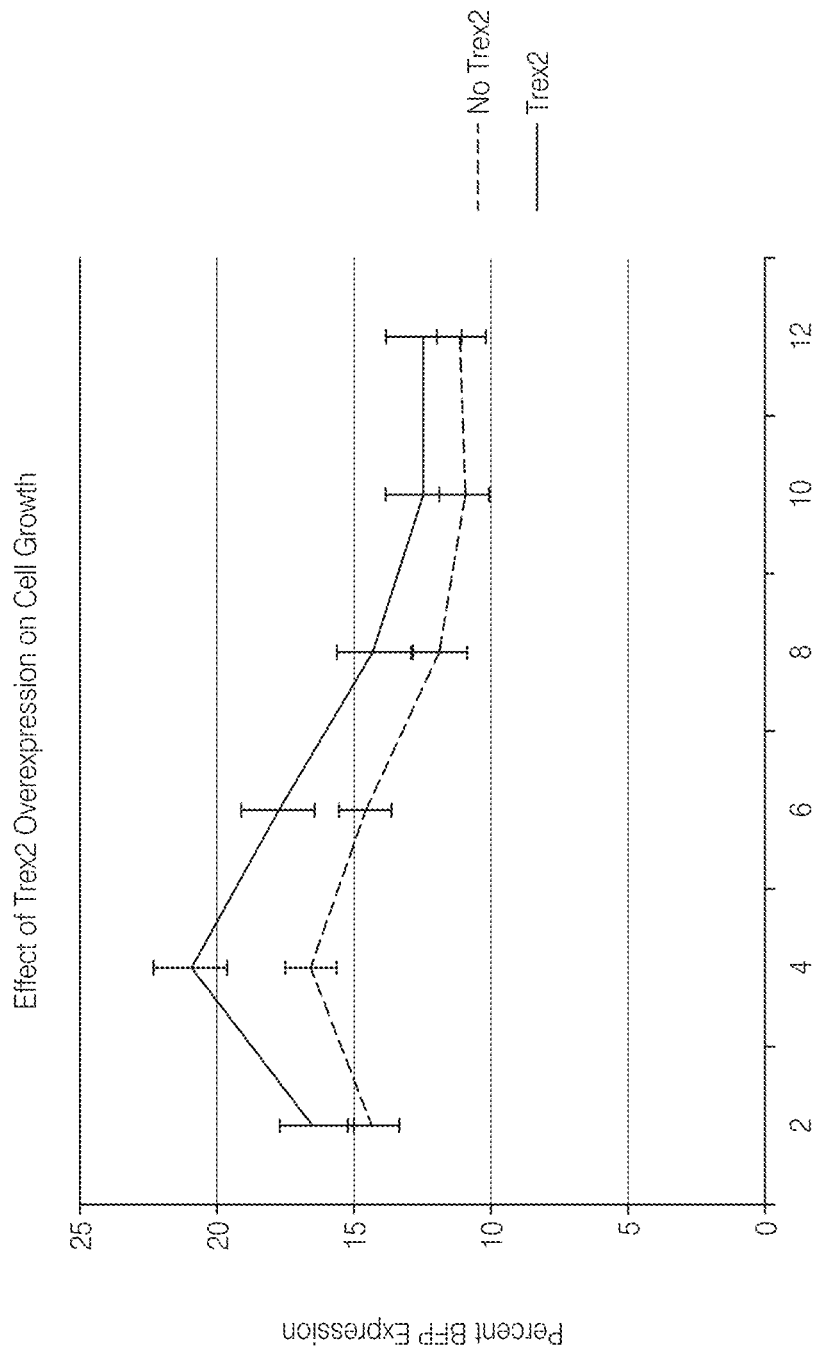
FIG. 21B shows a graph depicting maintenance of BFP expression in cells transduced with an integrating lentivirus containing BFP alone (no Trex2) or Trex2-BFP.

HEK 293 cells were transduced with expression constructs comprising the I-SceI mutant D44A alone, I-SceI alone or I-SceI coupled to Trex2 via a T2A linker. Following transduction of the cell line with the expression vectors, the cells were analyzed by visual inspection daily. Live cell images were taken 72 hours post transduction with the expression vectors. The cells treated in each manner appeared indistinguishable, and there is no overt toxicity associated with Trex2 co-expression. See FIG. 21B.

Figure 4A:
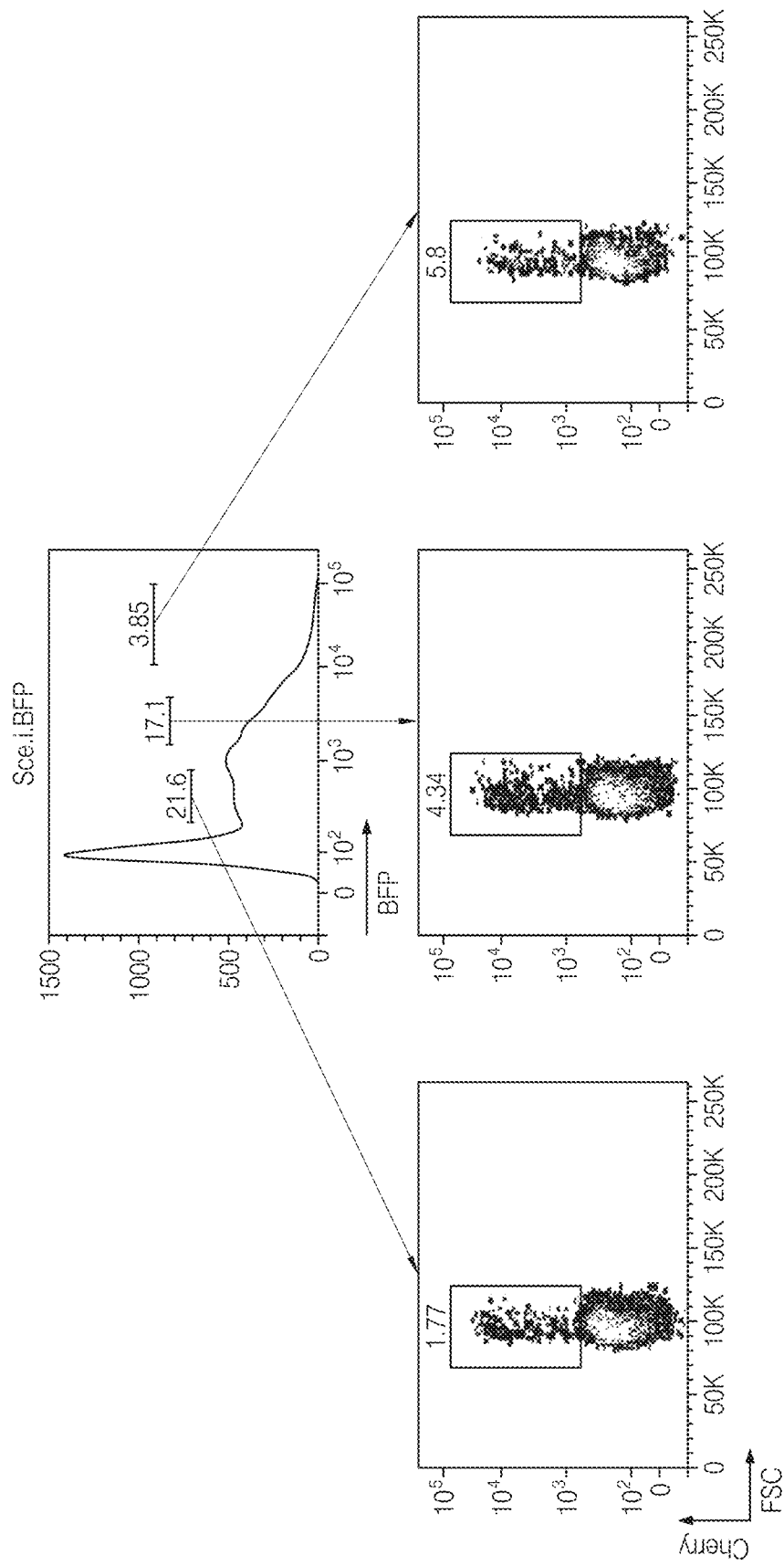
FIG. 4A shows gating analysis of HEK293 cells harboring Traffic Light Reporter transfected with I-SceI-IRES-BFP.
Figure 4B:
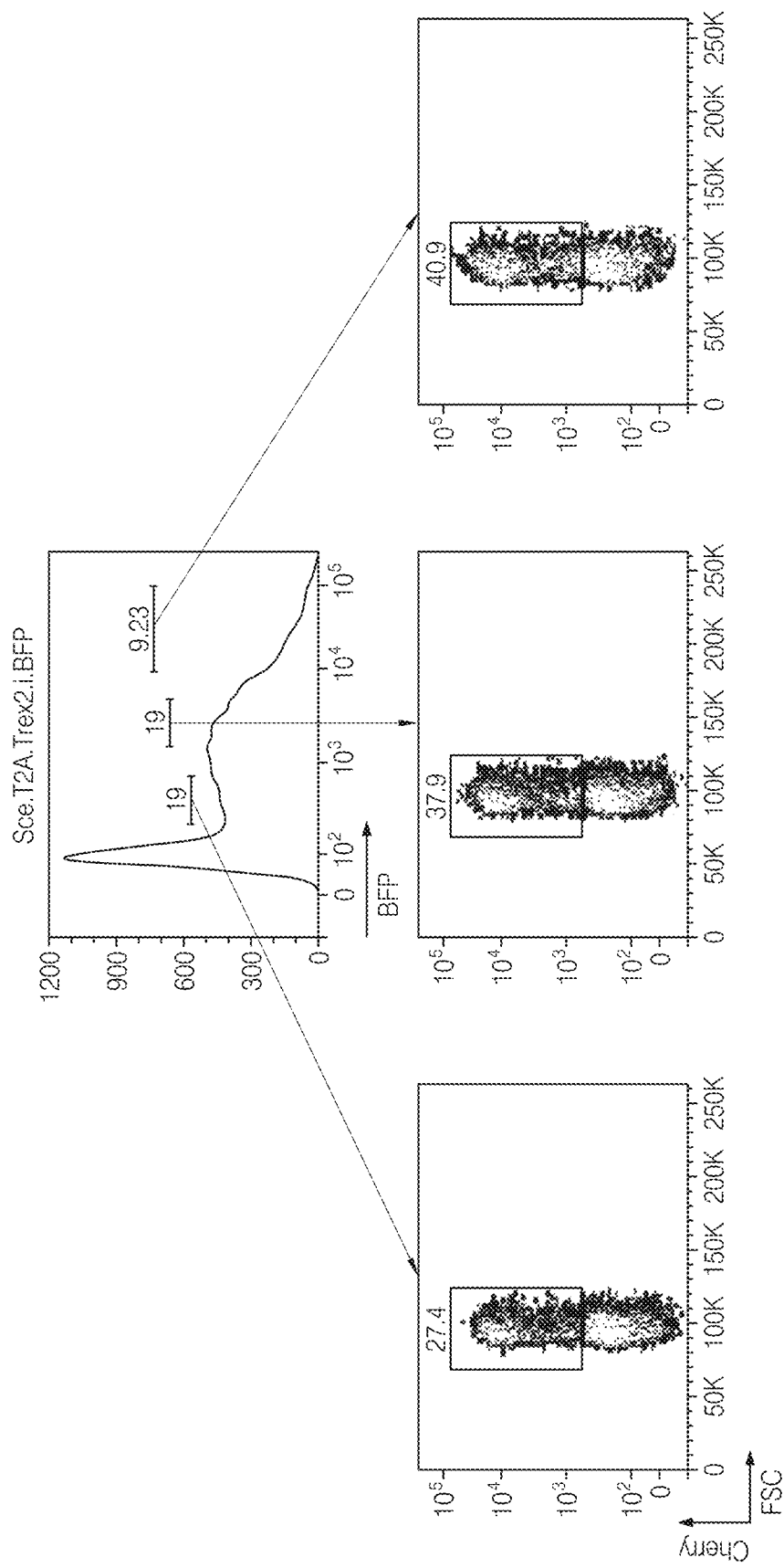
FIG. 4B shows a gating analysis of HEK293 cells harboring Traffic Light Reporter transfected with I-SceI-T2A-Trex2-IRES-BFP expression vectors.

To assess the total gene disruption rate, I-SceI and I-SceI-T2A-Trex2 transfected cells were sorted based on varying BFP expression levels. HEK 293 cells containing a genomically-integrated cassette corresponding to the targeted disruption reporter illustrated in FIG. 1A (TLR) were transduced with expression constructs comprising I-SceI-IRES-BFP (blue fluorescent protein) or I-SceI-T2A-Trex2-IRES-BFP. Expression of I-SceI-IRES-BFP and I-SceI-T2A-Trex2-IRES-BFP was measured in the transduced cells by a gating analysis of flow cytometry plots of BFP activity. Cells with low, low-medium, medium and high levels of BFP expression (corresponding to different levels of I-SceI endonuclease or I-SceI endonuclease/Trex2 exonuclease expression) were then assayed for induced mutagenic NHEJ events as visualized by mCherry+ expression. The data demonstrated that low levels of I-SceI alone resulted in lower mutation levels, while expression of I-SceI in combination with Trex2 result in high modification rates even at low levels of expression from the I-SceI-T2A-Trex2-IRES-BFP construct. See FIGS. 4A and 4B.

Figure 5A:
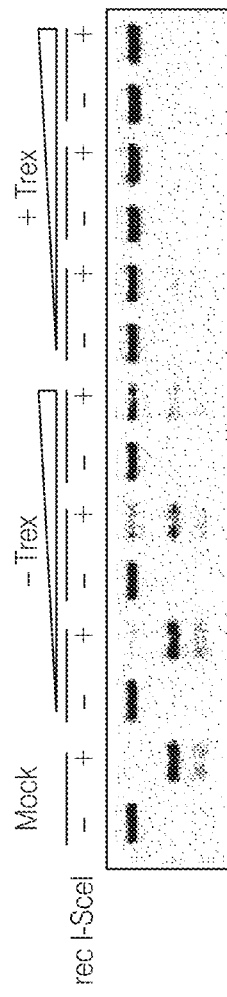
FIG. 5A shows an I-SceI restriction digest of amplicons flanking the I-SceI target site from HEK293 cells harboring traffic light reporter sorted by BFP expression levels follow transfection with expression constructs as indicated in FIG. 4A and FIG. 4B.
Figure 5B:
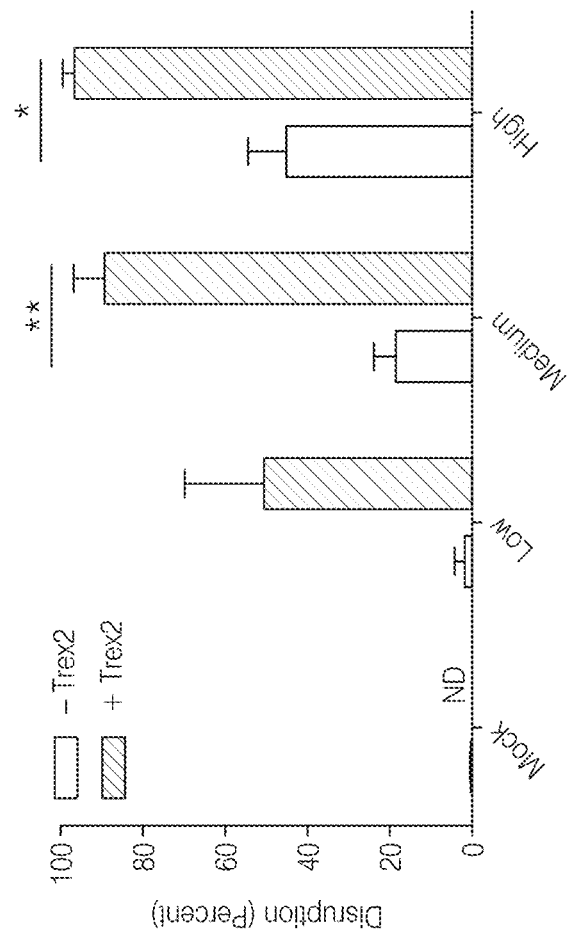
FIG. 5B shows quantification of three independent experiments as described in FIG. 5A.

After the I-SceI and I-SceI-T2A-Trex2 transfected cells were sorted based on varying BFP expression levels, the area flanking the I-SceI target was amplified from each of the populations by PCR. 100 ng of each PCR product was digested in vitro with recombinant I-SceI (New England Biolabs) for 6 hours at 37° C. DNA was separated using a 1% agarose gel stained with ethidium bromide to look for a resistant band, indicative of a mutagenic event at the locus that destroyed the I-SceI target site. See FIG. 5A. Percent disruption was calculated by quantifying band intensity using Image J software, and dividing the intensity of the undigested band by the total. At low endonuclease expression levels, a 25-fold increase in total gene disruption between I-SceI and I-SceI coupled to Trex2 (2.2 to 50.2% respectively) was observed, and nearly 100% of targets were disrupted in the medium and high expression gates of I-SceI T2A Trex2 (90.3, and 97.1% respectively) See FIG. 5B.

Figure 7:
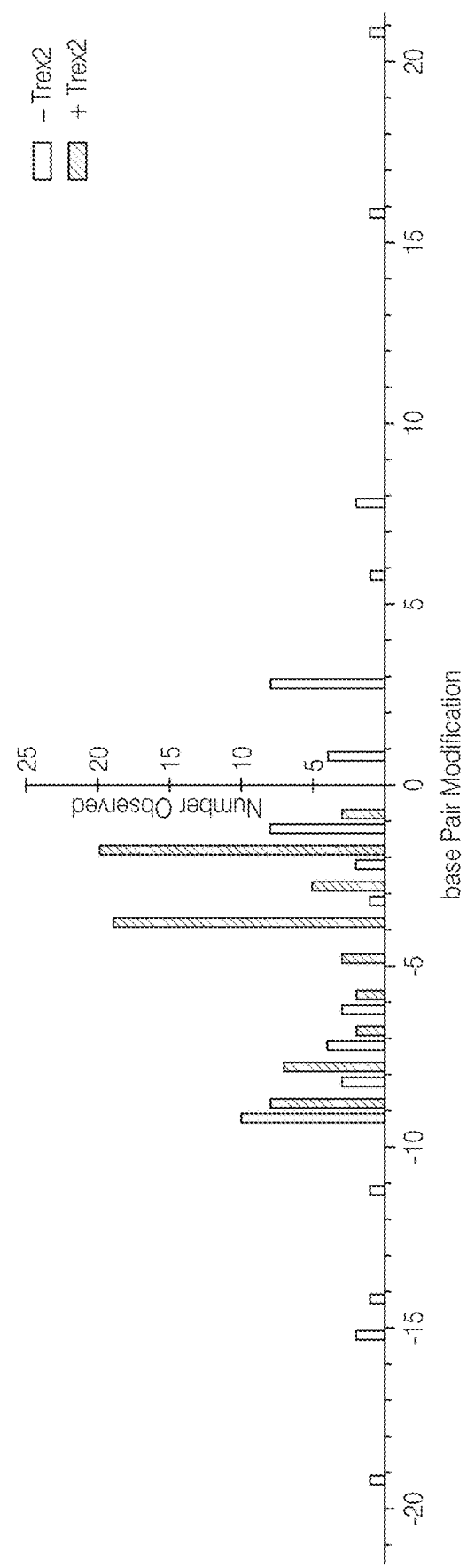
FIG. 7 shows a graph scoring observed mutations (deletions are negative, insertions are positive) at the I-SceI target site following transfection of HEK293 Traffic Light Reporter cells with I-SceI-IRES-BFP or I-SceI-T2A-Trex2-IRES-BFP as described in FIG. 5.
Figure 8A:
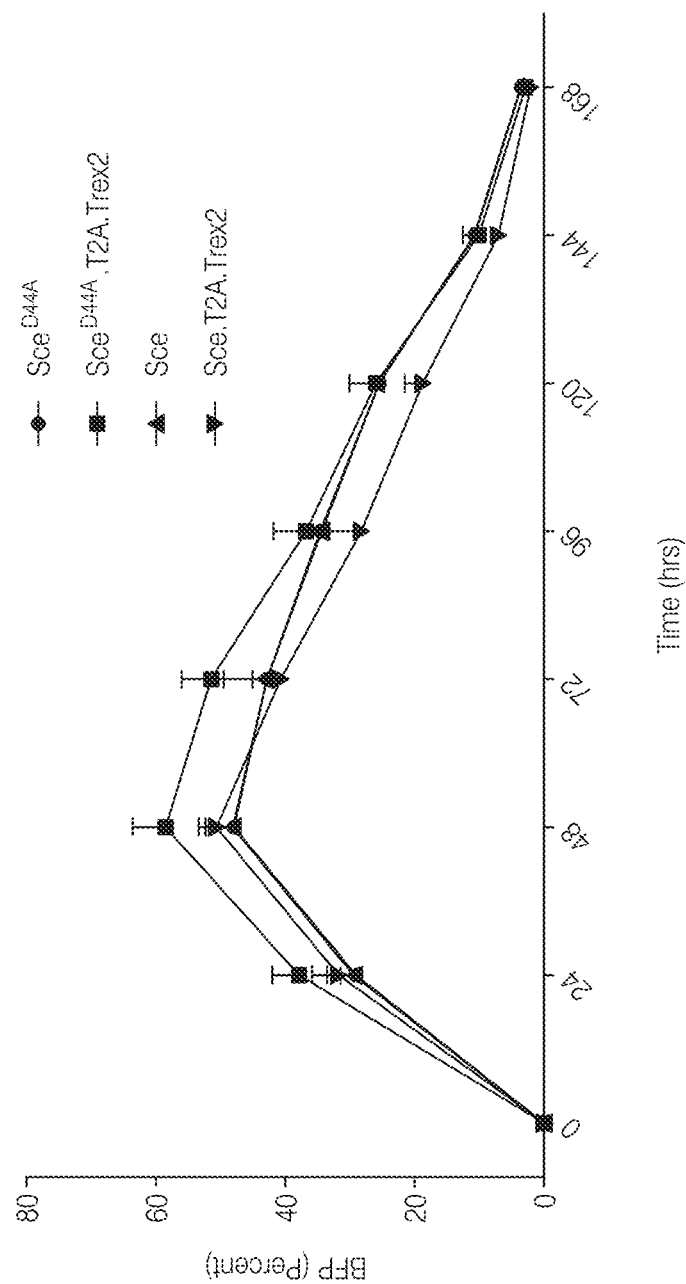
FIG. 8A shows a kinetic time course analysis demonstrating transient expression of I-SceI-T2A-Trex2-IRES-BFP after transfection into HEK293 cells harboring Traffic Light Reporter. The constructs shown are tagged to BFP by an IRES sequence downstream of either I-SceI or Trex2.
Figure 8B:
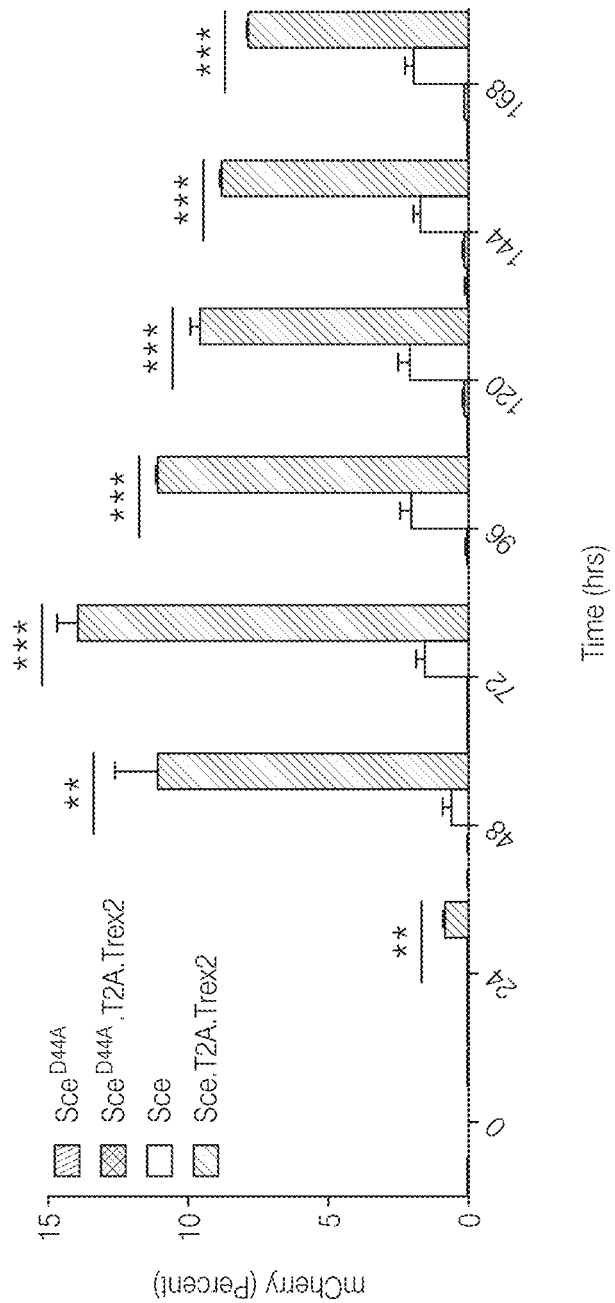
FIG. 8B shows a graph quantifying 3 experiments of HEK293T cells transfected with the vectors indicated in FIG. 8A, analyzed at the indicated time-points. Cherry indicates gene disruption rates observed in transfected cells.

These experiments indicate that while I-SceI exhibits a dose dependent increase in gene disruption, I-SceI coupled to Trex2 quickly becomes saturated. Sequence analysis of the I-SceI target site in high expressing cells confirmed that 100% of cells were modified in the I-SceI-T2A-Trex2 treated cells. See FIGS. 6A and 6B. Comparison of the mutation spectra between I-SceI alone and I-SceI.T2A.Trex2 showed a trend towards small deletion events in the exonuclease treated cells. See FIGS. 6A, 6B and 7. In a kinetic analysis, while all constructs exhibited similar expression patterns, Trex2 expression coincided with the appearance of disruption events at earlier time-points. See FIGS. 8A and 8B. In sum, coupling of endonucleases to Trex2 expression in a single open reading frame resulted in up to 25-fold enhancement in the efficiency of targeted gene disruption in cells from multiple species and in primary cell types, and is able to drive targeted knockout rates to near completion within 72 hrs.

Example 2

Trex2 Exonuclease Increases the Mutation Rate of a Variety of Homing Endonucleases The applicability of Trex2-enhanced disruption to multiple different nuclease scaffolds was evaluated. Targeted disruption reporter cassettes (mutNHEJ reporter cassettes) with target cleavage sites for I-Ltr, I-Gpi, I-Gze, I-MpeMI, I-PanMI, I-Cre, I-OnuI, I-HjeMI, and I-AniI (See Table 1) were generated by placing the endonuclease target site of interest placed in front of the mCherry fluorescent protein ORF in the +3 reading frame. HEK293T Reporter cell lines containing genomically-integrated I-Ltr, I-Gpi, I-Gze, I-MpeMI, I-PanMI, I-Cre, I-OnuI, I-HjeMI, and I-AniI TLR reporter cassettes were then generated. Each cell line was transfected with an expression construct for its respective enzyme with or without co-transfection of an expression construct encoding Trex2, and disruption rates were measured.

Figure 10:
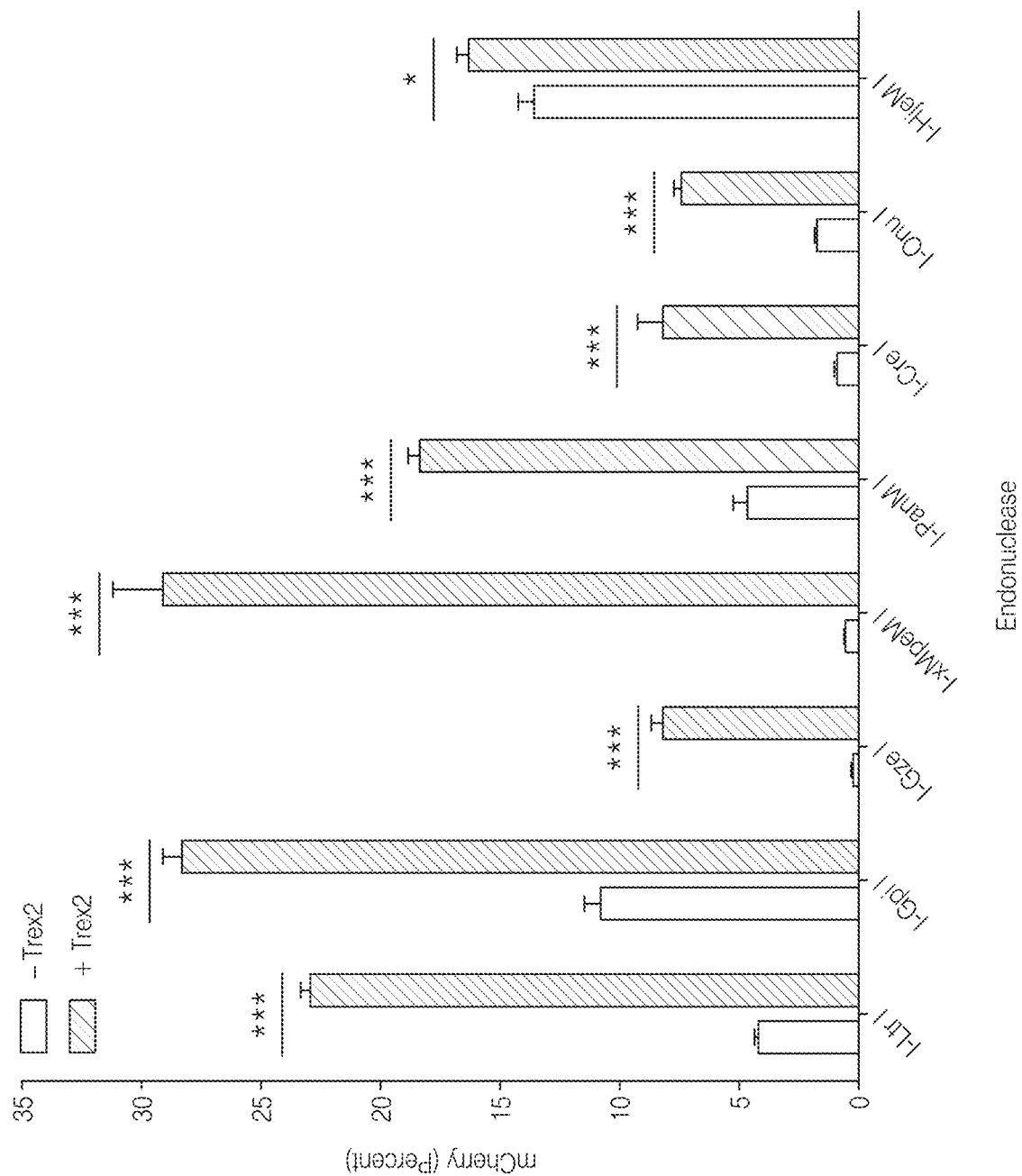
FIG. 10 shows a graph quantifying gene disruption rates of several different homing endonucleases with and without Trex2 exonuclease as measured by HEK293 cells harboring Traffic Light Reporters with respective target sites for the indicated homing endonucleases.

The effect of Trex2 co-expression with each of I-Ltr, I-Gpi, I-Gze, I-MpeMI, I-PanMI, I-Cre, I-OnuI, I-HjeMI, and I-AniI homing endonucleases was analyzed by flow cytometry. For each of the different Homing Endonucleases tested, disruption rates increased when coupled to Trex2, demonstrating that the Trex2 exonuclease can facilitate gene disruption from breaks generated by a variety of different homing endonucleases, which leave different 3' 4 bp overhangs and possess varying enzyme kinetics. See FIG. 10. This data demonstrates that Trex2 expression increases the mutagenesis rates associated with targeted DNA cleavage by a variety of homing endonucleases. Further, co-expression of Trex2 with I-Gze increased mCherry+ expression significantly over the background levels observed with I-Gze expression alone. See FIG. 10.

Homing Endonucleases in the panel having very low activity were rescued by coupling to Trex2. See FIG. 10. This suggests that Homing Endonucleases that appear inactive may be generating breaks at an undetectable rate, and that addition of Trex2 reveals these breaks by catalyzing end processing prior to break ligation. This is consistent with the observation that Trex2 can increase disruption rates of a higher activity enzyme, such as I-SceI, even at very low expression levels.

Figure 12A:
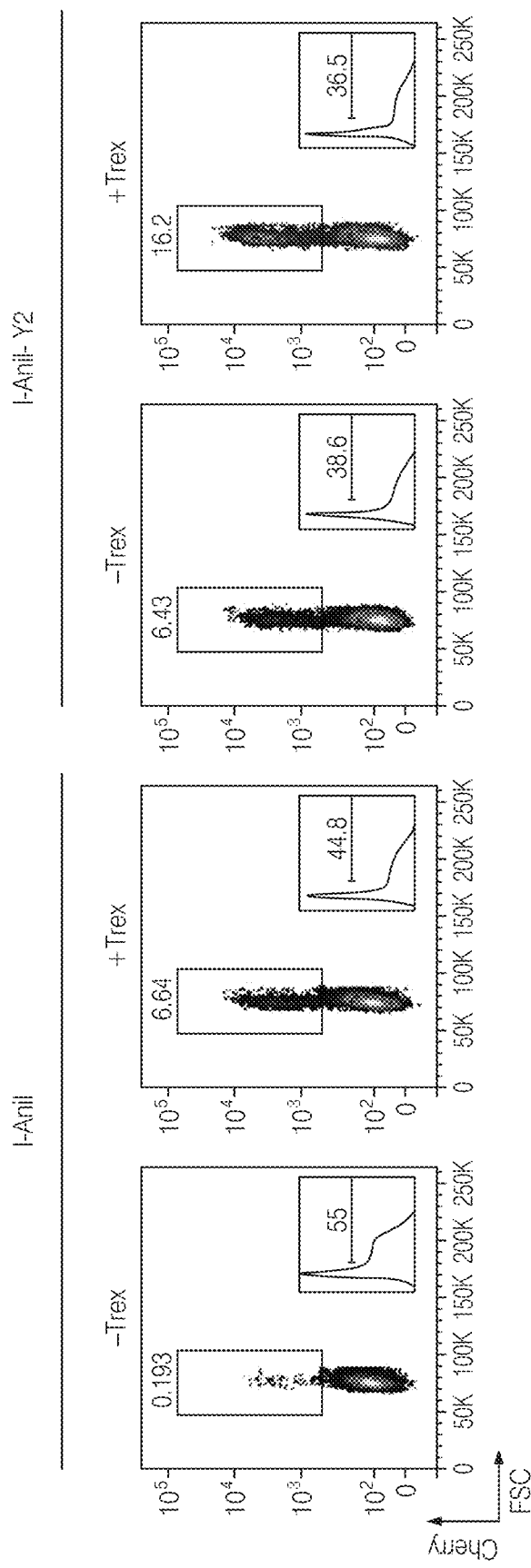
FIG. 12A shows representative flow plots of HEK293 cells harboring Traffic Light Reporters with an I-AniI target site following transfection with either I-AniI-IRES-BFP, I-AniI-T2A-Trex2-IRES-BFP, I-AniIY2-IRES-BFP, I-AniIY2-T2A-Trex2-IRES-BFP.
Figure 12B:
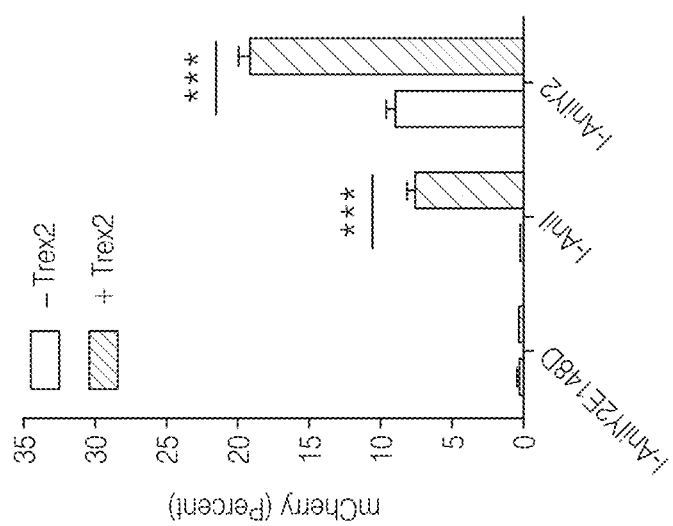
FIG. 12B shows a graph quantitating 3 independent experiments as performed in FIG. 12A.
Figure 13:
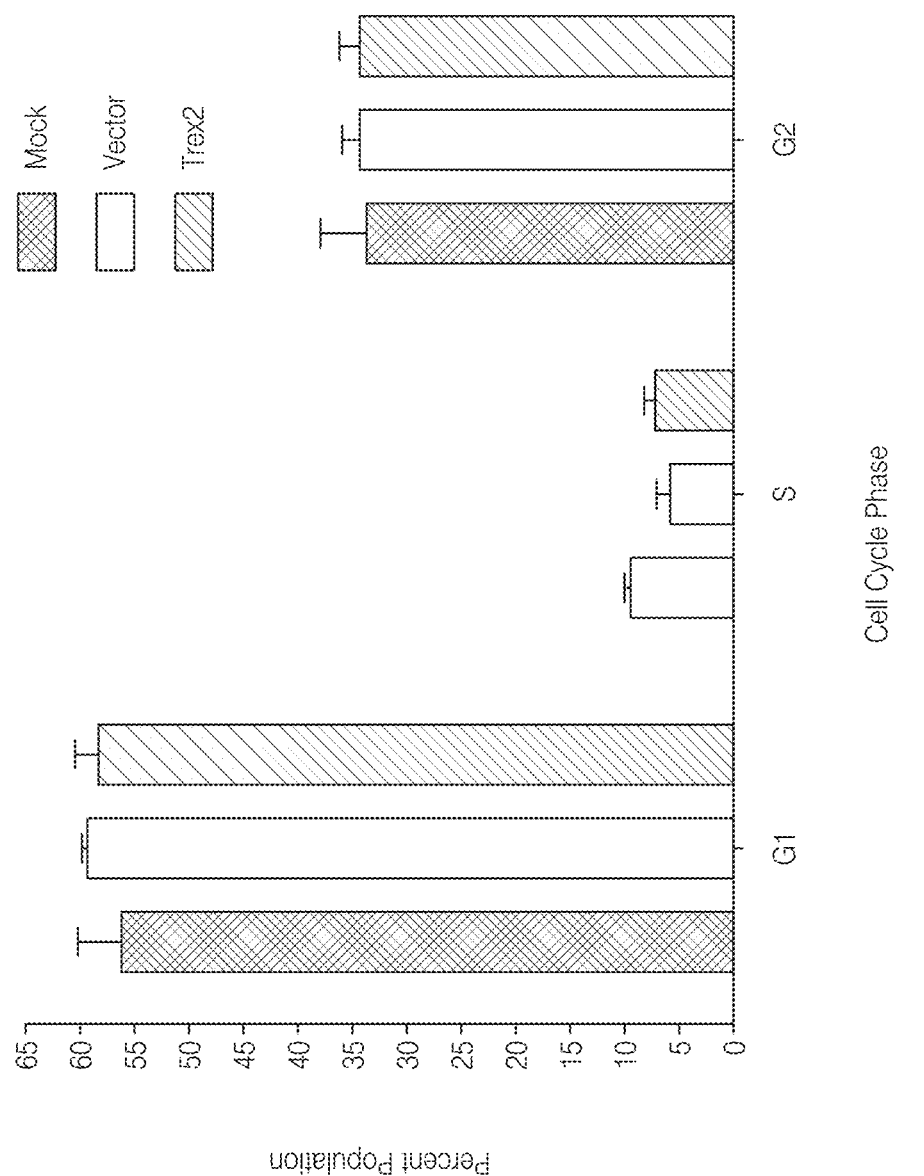
FIG. 13 shows graph depicting cell cycle analysis of murine embryonic fibroblasts transduced with Mock, I-SceI-IRES-BFP, or I-SceI-T2A-Trex2-IRES-BFP viruses.
Figure 14:
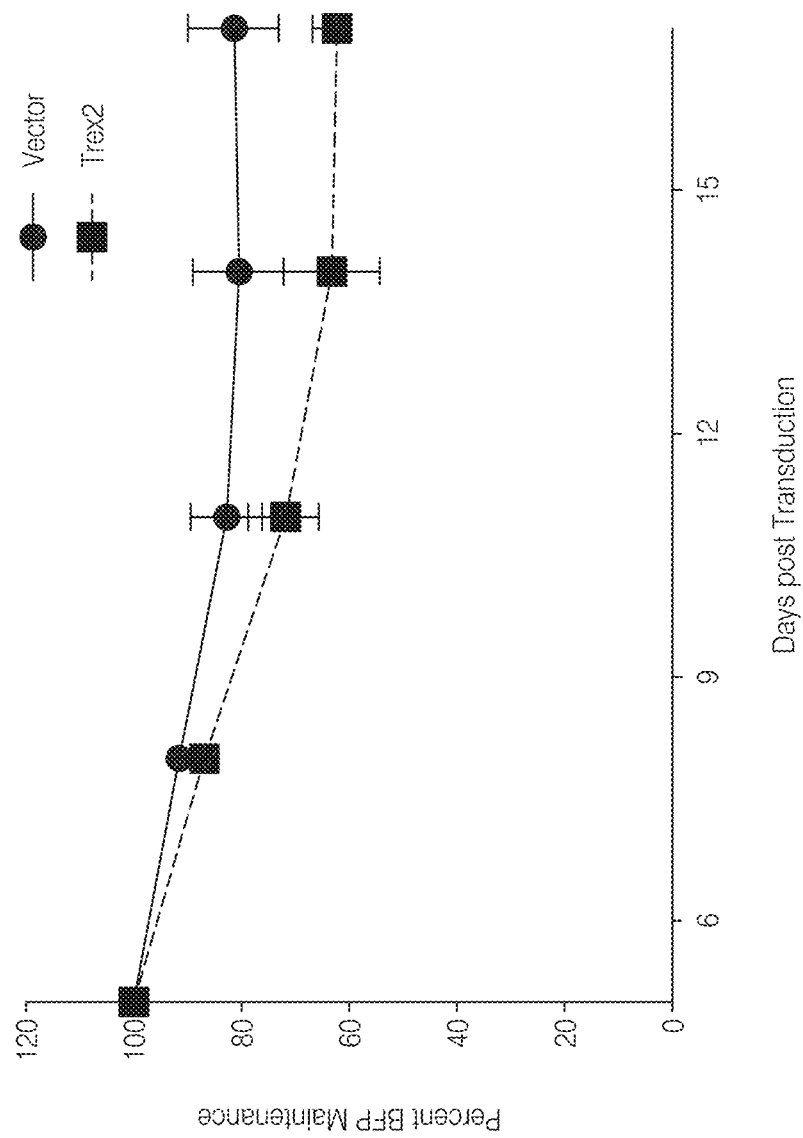
FIG. 14 shows a graph depicting maintenance of BFP expression in cells transduced with an integrating lentivirus containing I-SceID44A-IRES-BFP or I-SceID44A-T2A-Trex2-IRES-BFP.
Figure 15A:
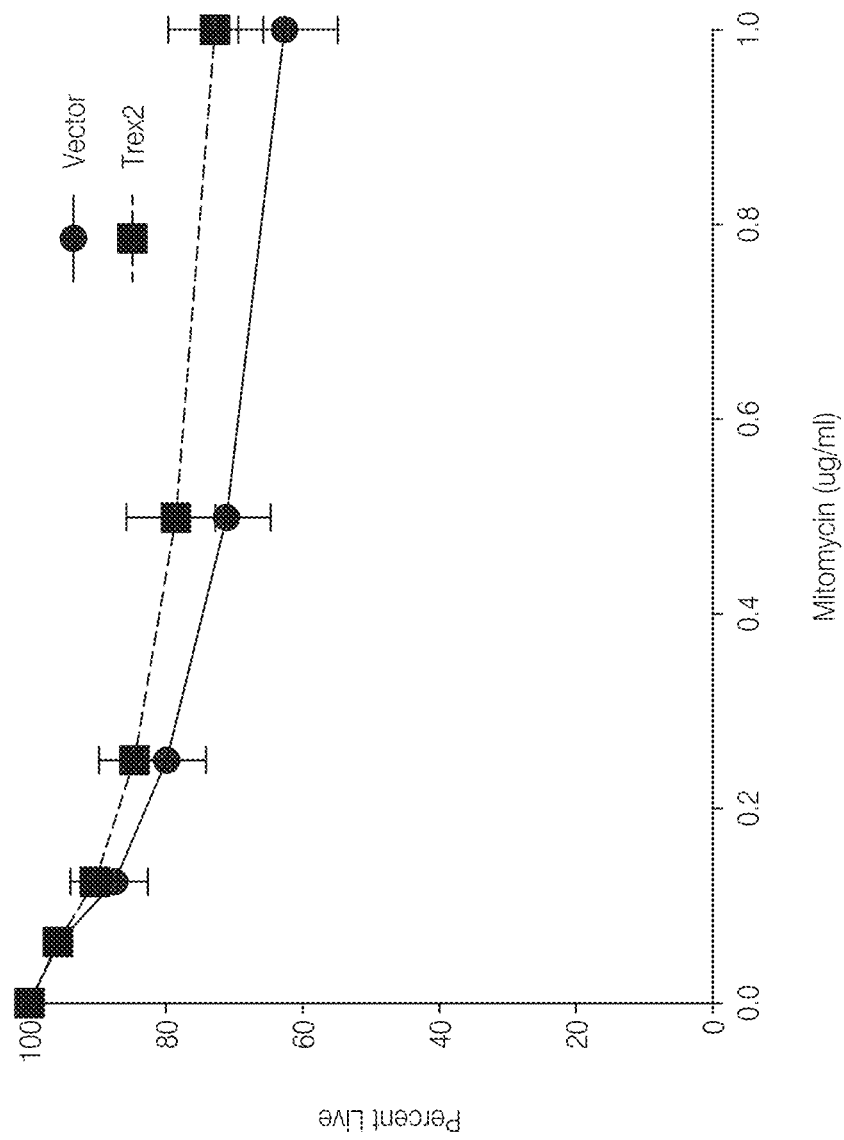
FIG. 15A shows a graph measuring human CD34+ hematopietic stem cell survival when transduced with I-SceID44A-IRES-BFP or I-SceID44A-T2A-Trex2-IRES-BFP and challenged with Mitomycin C.
Figure 15B:
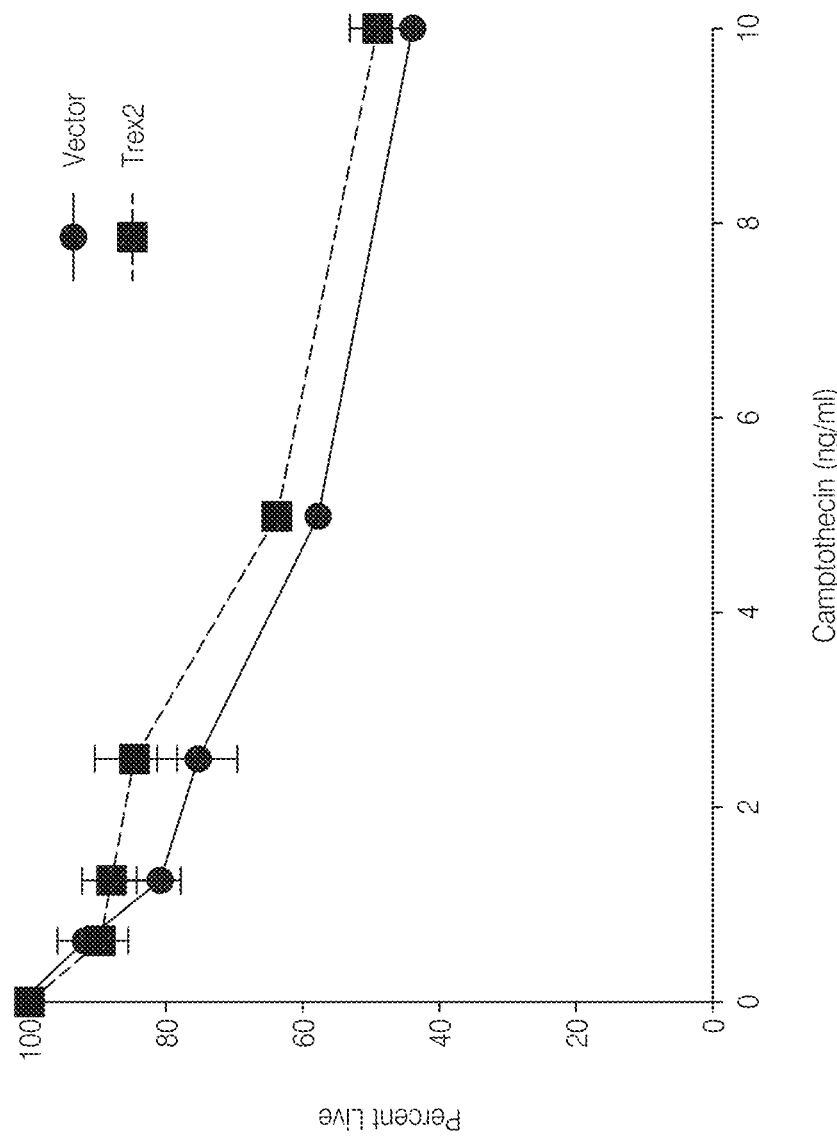
FIG. 15B shows a graph measuring human CD34+ hematopietic stem cell survival when transduced with I-SceID44A-IRES-BFP or I-SceID44A-T2A-Trex2-IRES-BFP and challenged with camptothecin.
Figure 15C:
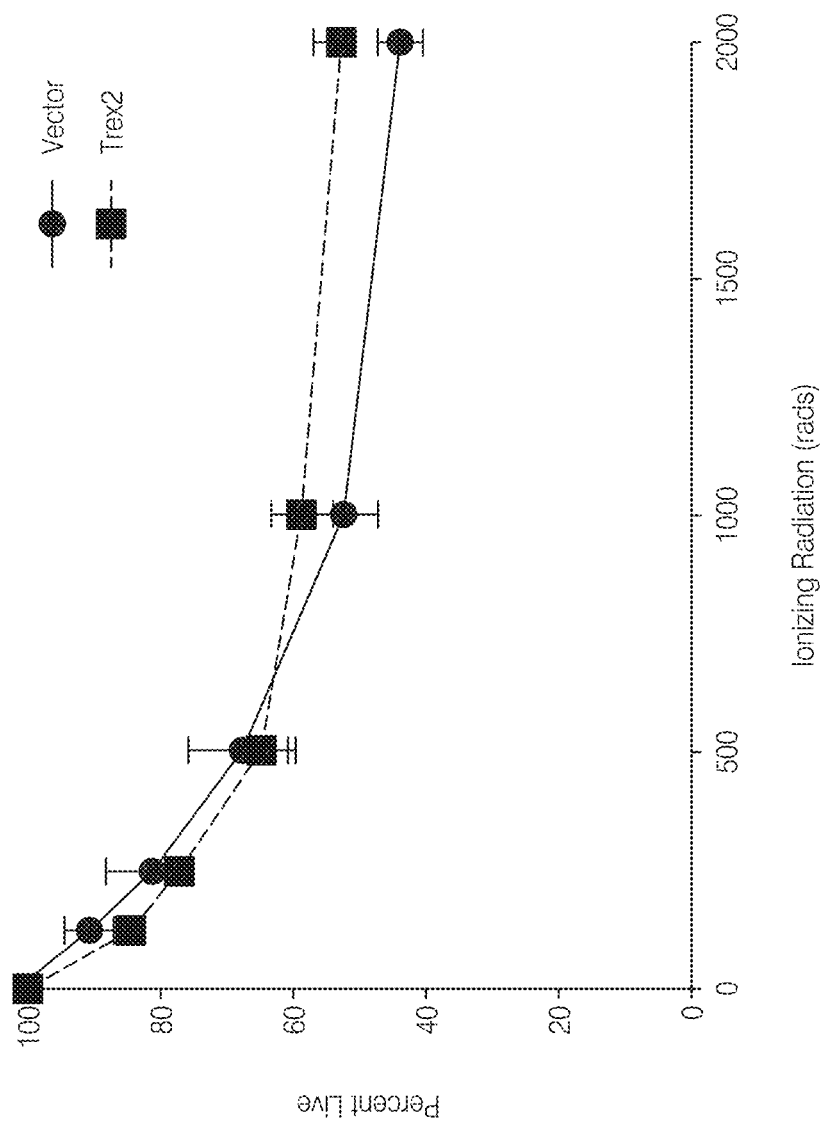
FIG. 15C shows a graph measuring human CD34+ hematopietic stem cell survival when transduced with I-SceID44A-IRES-BFP or I-SceID44A-T2A-Trex2-IRES-BFP and challenged with ionizing radiation.
Figure 16A:
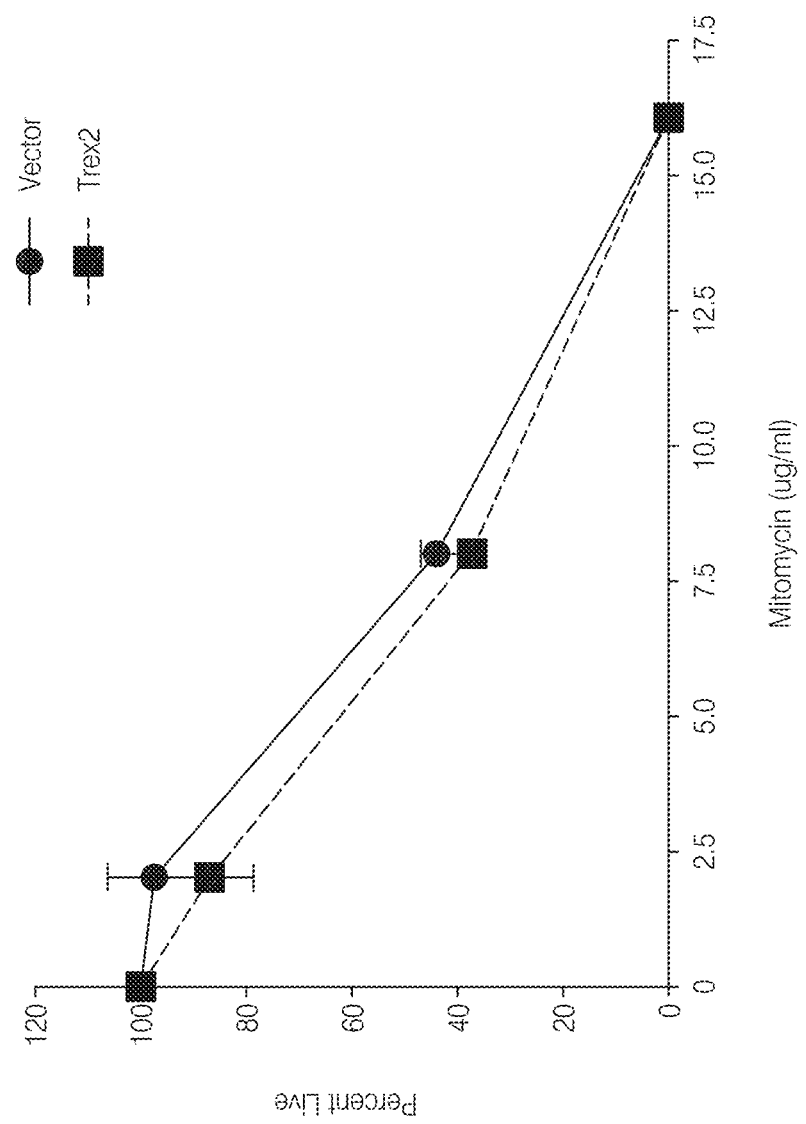
FIG. 16A shows a graph measuring murine embryonic fibroblast cell survival when transduced with I-SceID44A-IRES-BFP or I-SceID44A-T2A-Trex2-IRES-BFP and challenged with Mitomycin C.
Figure 16B:
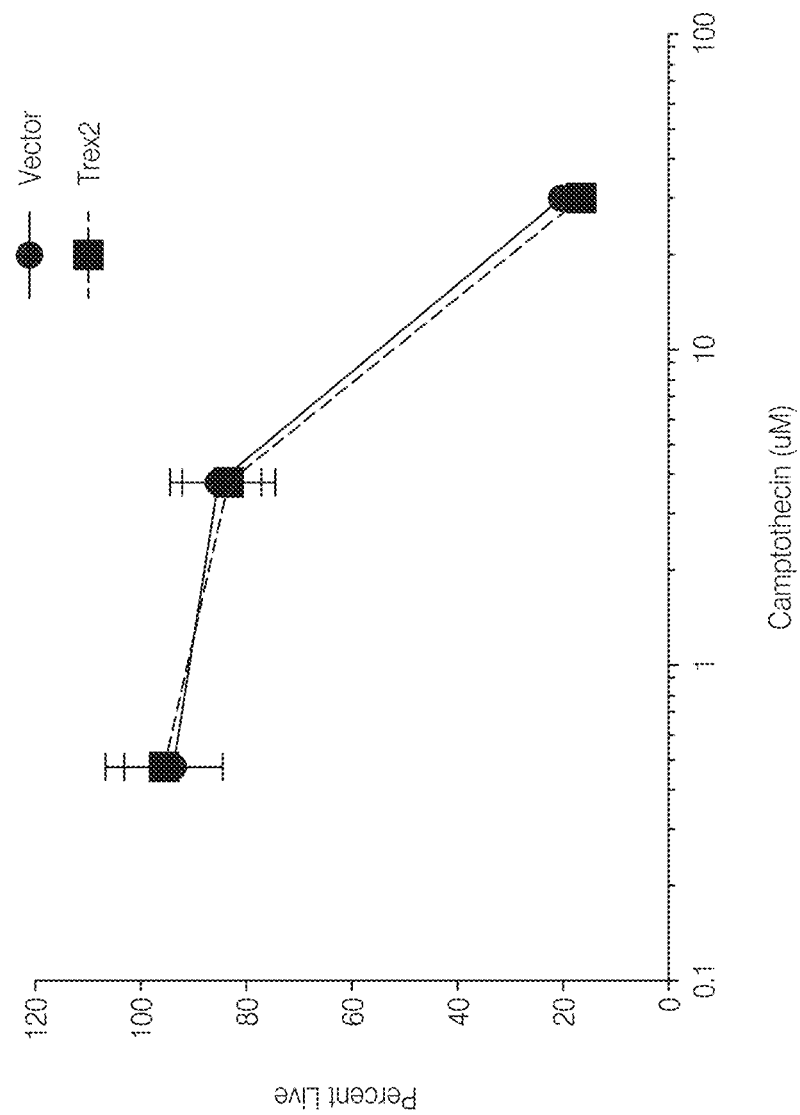
FIG. 16B shows a graph measuring murine embryonic fibroblast cell survival when transduced with I-SceID44A-IRES-BFP or I-SceID44A-T2A-Trex2-IRES-BFP and challenged with camptothecin.

To test the ability of Trex2 to reveal breaks caused by Homing Endonucleases having very low activity, the effect of coupling Trex2 on the gene disruption rate of the I-AniI Homing Endonucleases was analyzed by flow cytometry. WT I-AniI exhibits very little activity in cells and expression of WT I-AniI alone does not exhibit targeted disruption activity. See FIGS. 12A and 12B. Coupling of Trex2 to WT I-AniI increases its gene disruption capacity to that of the highly active I-AniI variant, I-AniI Y2. See FIGS. 12A and 12B. I-AniI Y2 was subjected to several rounds of directed evolution to improve its activity. Coupling of Trex2 to an inactive form of I-AniI, I-AniI E148D, shows no increase in reporter expression. This data demonstrates that Trex2 expression increases the mutagenesis rates associated with targeted DNA cleavage by sub-active homing endonucleases.

Together, these results show that Trex2 can increase disruption rates for a variety of homing endonucleases and rescue low-activity endonucleases, effectively lowering the engineering bar for enzymes designed to produce gene disruption at novel target sites.

Example 3

Co-Expression of Trex2 Exonuclease Affects the Mutation Rate Associated with FokI Zinc Finger Nuclease Mediated Breaks A reporter cell line was generated that harbors a 5' ACC ATC TTC ttcaag GAC GAC GGC 3' (SEQ ID NO. 147) target site for a corresponding zinc finger nuclease containing a FokI nuclease domain. Expression vectors encoding the zinc finger nuclease were transduced into reporter cell lines harboring the TLR-FokI reporter cassette with and without Trex2. Co-expression of Trex2 with the zinc finger nuclease results in an increased mutation rate. See FIG. 11B.

Example 4

The Chimeric I-SceI-G4s-Trex2 Endo/Exo-Nuclease Fusion Protein Improves the Rate of Targeted Disruption Expression vectors comprising HA-I-SceI-BFP, (HA-I-SceI)-T2A-Trex2-BFP or (HA-I-SceI)-G4S-Trex2-BFP were constructed as described in Example 1. The I-SceI gene used to construct the expression vectors further encoded an N-terminal HA epitope tag. The (HA-I-SceI)-T2A-(HA-Trex2-BFP) expression vector expresses HA-I-SceI and Trex2 in a 1 to 1 ratio from a single promoter, but the T2A linker sequence allows for two separate proteins to be produced from a single translation. The (HA-I-SceI)-G4S-(HA-Trex2)-BFP expression vector produces an endo/exo-nuclease fusion protein where HA-I-SceI and Trex2 proteins are coupled together by a G4S linker peptide. The HA-I-SceI-BFP, (HA-I-SceI)-T2A-Trex2-BFP and (HA-I-SceI)-G4S-Trex2-BFP expression vectors were transduced into HEK293 cells containing a genomically-integrated cassette corresponding to the targeted disruption reporter illustrated in FIG. 1A.

Figure 3A:
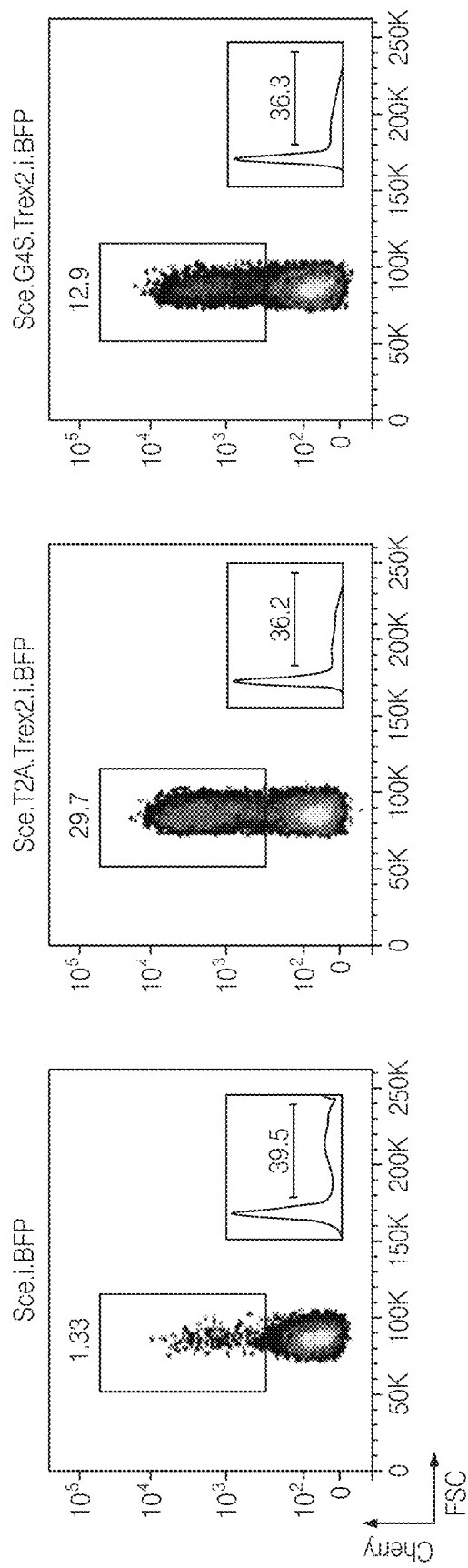
FIG. 3A shows representative flow plots of HEK293 cells harboring Traffic light Reporter transfected with expression vectors encoding I-SceI-IRES-BFP, I-SceI-T2A-Trex2-BFP, or I-SceI-G4S-Trex2-IRES BFP.

Following transduction of the cell line with the expression vectors, the cells were analyzed for mCherry+ expression by flow cytometry. The plot shown in FIG. 3A demonstrated that I-SceI-G4S-Trex2 endo/exo fusion proteins are active and increase targeted disruption rates over provision of I-SceI alone. See FIGS. 3A-C.

However, Sce-G4S-Trex2, despite stable fusion protein expression, was inferior at inducing gene disruption compared to Sce-T2A-Trex2, possibly due to steric hindrance. See FIG. 3A.

Figure 3C:
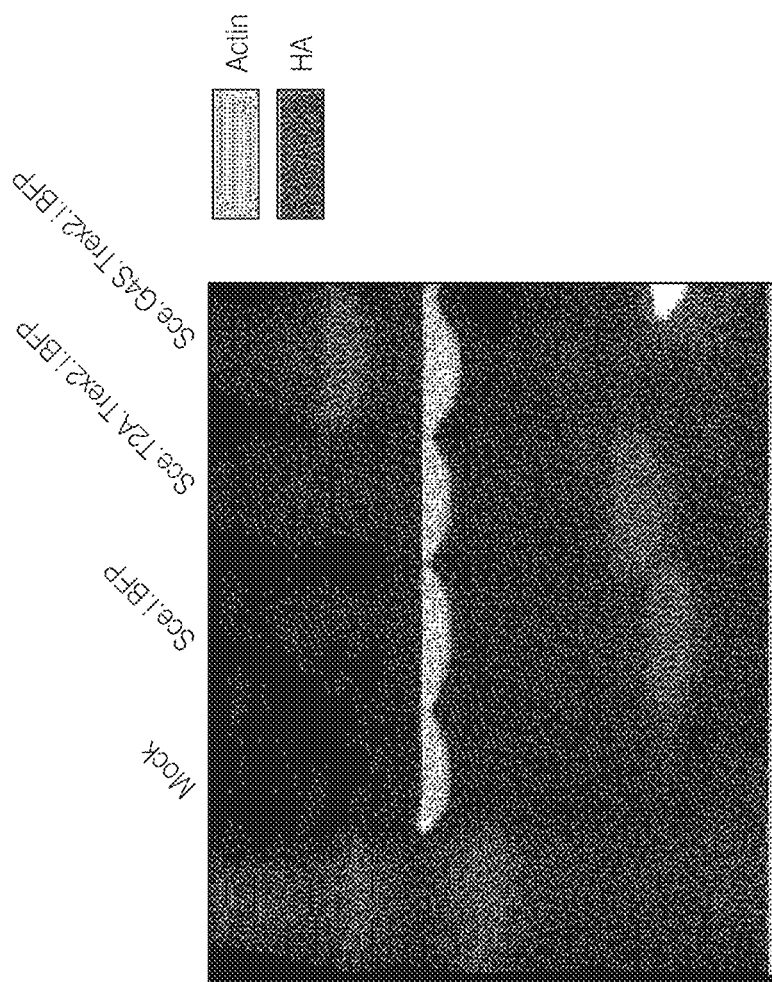
FIG. 3C is a licor western blot showing size and stability of the HA-tagged I-SceI in indicated HEK293T lysates.
Figure 3B:
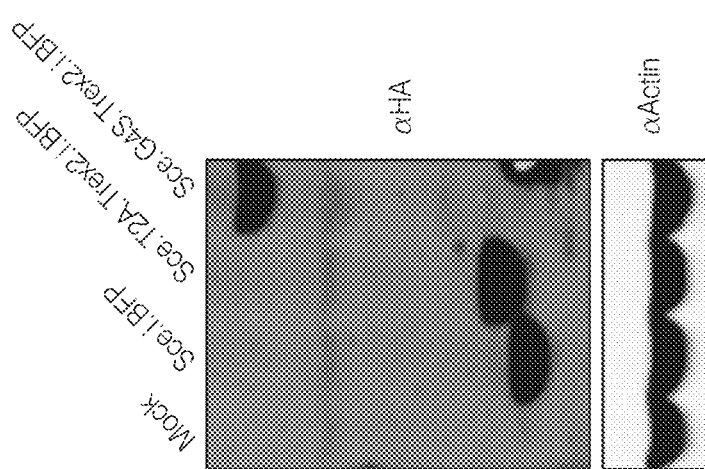
FIG. 3B shows an anti-HA western blot demonstrating equal expression of endonucleases, and stability of the (HA-)I-SceI, (HA-)I-SceI-T2A and (HA-)I-SceI-G4S-Trex2 proteins from FIG. 3A.

An anti-HA western blot was performed to assess the stability of the HA-I-SceI, HA-I-SceI-T2A and (HA-I-SceI)-G4S-Trex2 proteins in the expressing cells. As shown in FIGS. 3B and 3C, the chimeric (HA-I-SceI)-G4S-Trex2 endo-exo fusion protein was expressed at the same levels as I-SceI alone, or I-SceI containing a residual T2A tag peptide.

Example 5

Co-Expression of I-SceI and Trex2 Exonuclease Increases the Rate of I-SceI-Induced Mutations in Primary Cells To determine if Trex2 would increase gene disruption rates in primary cells, primary murine embryonic fibroblasts (MEFs) were isolated from a mouse with an I-SceI site "knocked into" the Interleukin-2 receptor subunit gamma (IL2RG) locus ("Sce-SCID" mouse, unpublished data, G.C., D.J.R., A.M.S). MEFs were isolated from Sce-SCID embryos at 12-14 days gestation. Briefly, individual embryos were removed from the uterus and washed with PBS. The head and red tissue were removed from the embryo, and the remaining tissue was minced. The tissue was incubated with trypsin-EDTA for 10 minutes at 37° C., followed by centrifugation at 10,000×G for 5 minutes. The pellet was re-suspended in MEF media and plated at 37° C. MEF cells were cultured in glutamine-free Dulbecco's modified Eagle's medium supplemented with 2 mM L-glutamine, 10% Fetal Bovine Serum (FBS) and 1% penicillin/streptomycin.

Figure 9A:
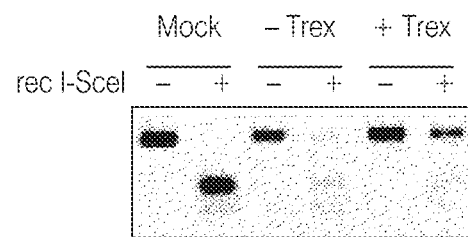
FIG. 9A shows an I-SceI restriction digest of amplicons from primary murine embryonic fibroblasts spanning an I-SceI target site 72 hours post transduction with I-SceI-IRES BFP or I-SceI-T2A-Trex2-IRES-BFP.
Figure 9B:
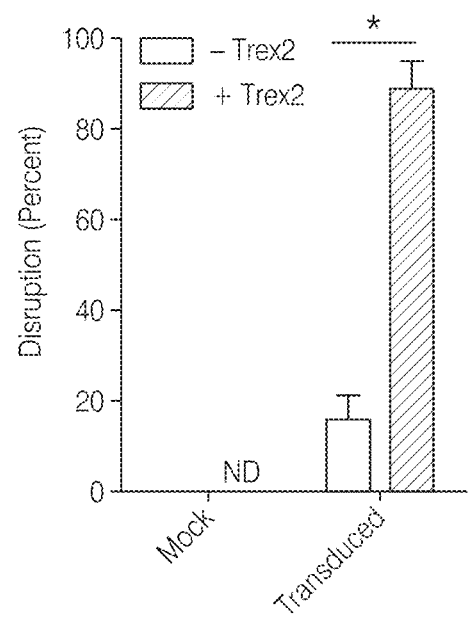
FIG. 9B shows a graph quantifying cleavage site disruption in 2 independent experiments.
Figure 9C:
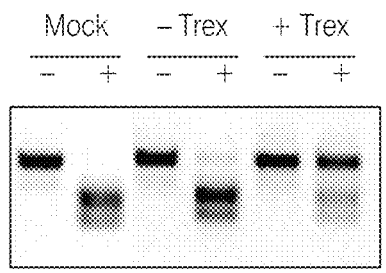
FIG. 9C shows an I-SceI restriction digest of amplicons from lineage depleted bone marrow spanning an I-SceI target site 72 hours post transduction with I-SceI-IRES BFP or I-SceI-T2A-Trex2-IRES-BFP.
Figure 9D:
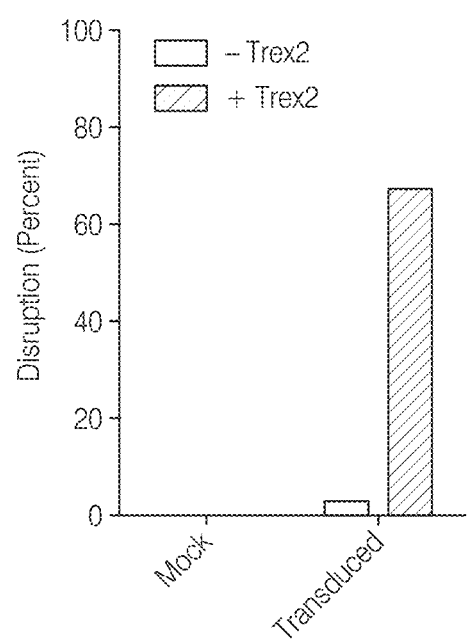
FIG. 9D shows quantification of bands from FIG. 9C.

$1.0 \times 10^5$ Sce-SCID MEF cells were seeded in a 24-well plate 24 hours prior to transduction with I-SceI or I-SceI.T2A.Trex2 expressing recombinant lentiviral vectors (LV). 0.5 µg DNA was used for each expression vector, and transfected using Fugene6 or XtremeGene9 (Roche) according to the manufacture's protocol. Cells were passaged 24 hours later and analyzed 72 hours post transduction. Total gene disruption at the I-SceI target site was assayed using the digestion assay described in Example 1. A 6-fold increase in disruption at the common gamma chain locus was observed with I-SceI coupled to Trex2 (I-SceI=15.8, I-SceI.T2A.Trex2=88.7). See FIGS. 9A and 9B. Additionally, since IL2RG is only expressed in a subset of differentiated hematopoietic cells, these experiments demonstrate Trex2 can facilitate high frequency disruption at unexpressed loci.

Example 6

Effect of Exonuclease Over-Expression on Repair of Endogenous DNA Damage

To determine if exonuclease over-expression alters the cells ability to repair other types of endogenous DNA damage, Trex2 expressing cells are treated with model DNA damage inducing agents. $1.0 \times 10^6$ Sce-SCID MEFs were seeded in a 10 cm dish 24 hours before transduction. 500 µL of 10×LV (pCVL.SFFV.sceD44A.IRES.BFP or T2A.TREX2.IRES.BFP) was added to the culture with 4 µg/mL polybrene. 24 hours post-transduction, cells were passaged to 15 cm plates. 72 hours post-transduction, $1.0 \times 10^5$ Sce-SCID MEFs were seeded in a 12-well plate with 1 mL media and treated as indicated with DNA damage inducing agents: Mitomycin C (Sigma Aldrich, St. Louis), Camptothecin (Sigma Aldrich, St. Louis), or ionizing radiation. 48 hours after exposure, cells were incubated in 0.5 µg/mL PI as above and analyzed by flow cytometry. For CD34+ cells, 72 hours post-transduction with Trex2 expressing LV, 2.0×10⁵ CD34+ HSCs were seeded in a 96-well plate in 200 μL of media, DNA damaging agents were added to the media, and plates analyzed as above. Over-expression of Trex2 had no adverse effect on cell cycle or sensitivity to model DNA damaging agents, suggesting cells maintain high fidelity DNA repair at lesions occurring independently of those created by the endonuclease. See FIGS. 13, 14, 15A, 15B, 15C, 16A and 16B.

Example 7

Co-Expression of I-SceI and End-Processing Enzymes Increases the Rate of I-SceI-Induced Mutations To determine if the results of coupling homing endonucleases with Trex2 could be extended to other DNA modifying enzymes, a library of 13 candidate enzymes possessing an array of biochemical end-processing activities derived from mammalian, bacterial or viral species was generated. See Table 2. The library of DNA end-processing enzymes was cloned into the pExodus vector with genes synthesized by Genscript (Piscataway, N.J.) as cDNA codon-optimized for human expression. See SEQ ID NOs. 110-145.

Figure 17B:
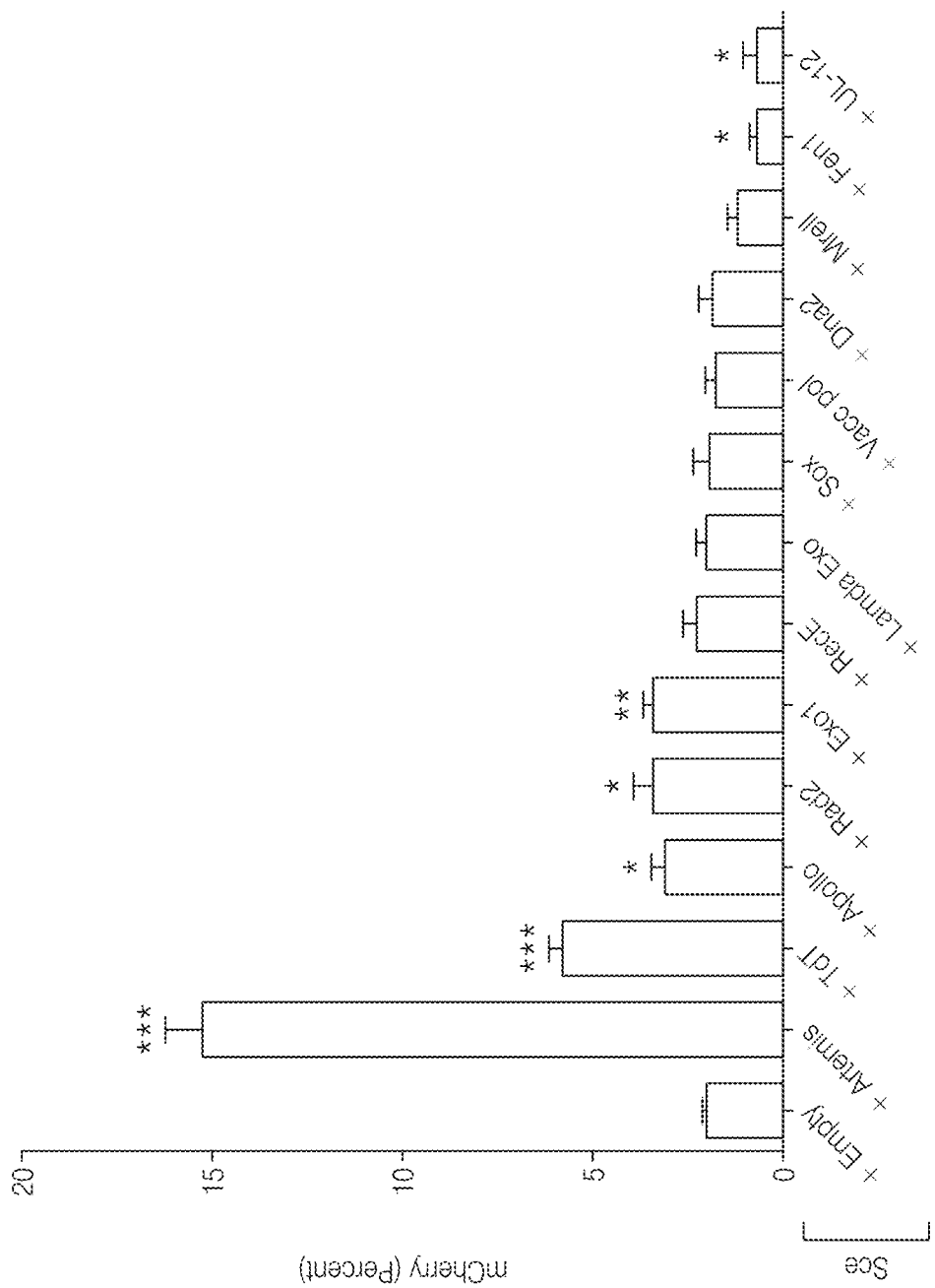
FIG. 17B shows a graph quantifying 3 independent experiments as performed in FIG. $17A_1$ and FIG. $17A_2$.
Figure 18A:
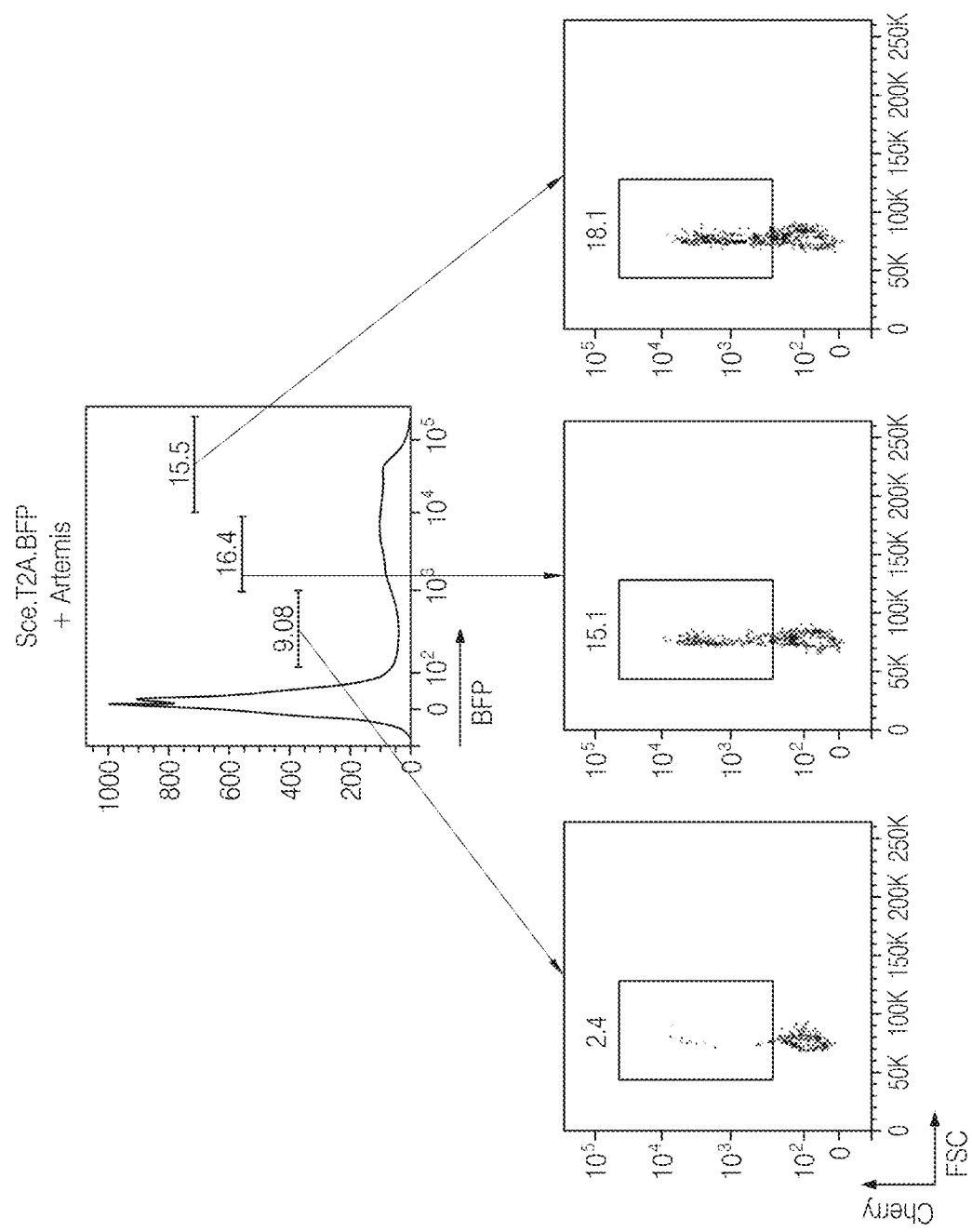
FIG. 18A shows representative flow plots of a gating analysis of I-SceI-IRES-BFP co-transfected with ARTEMIS expression plasmid as indicated in FIG. $17A_1$ and FIG. $17A_2$.
Figure 18B:
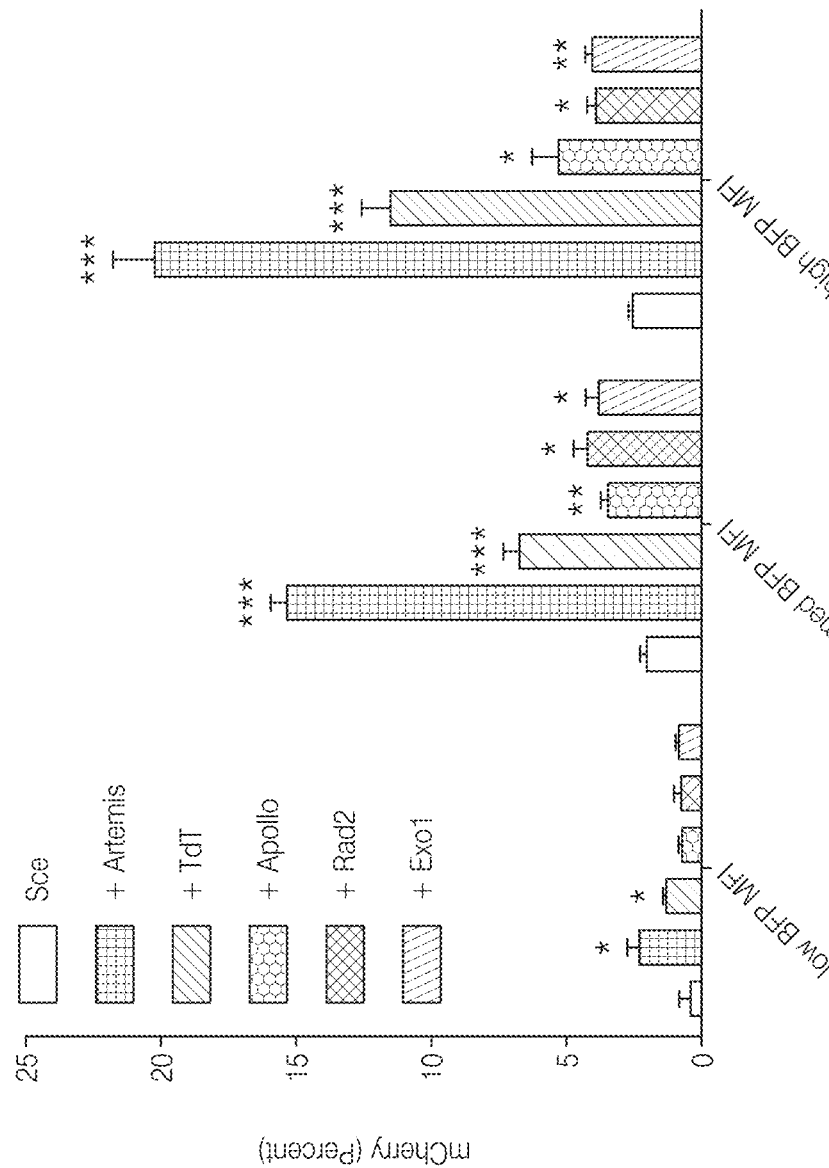
FIG. 18B shows a graph quantifying gating analysis of several end-processing enzymes from 3 independent experiments as indicated in FIG. $17A_1$ and FIG. $17A_2$.
Figure 19A:
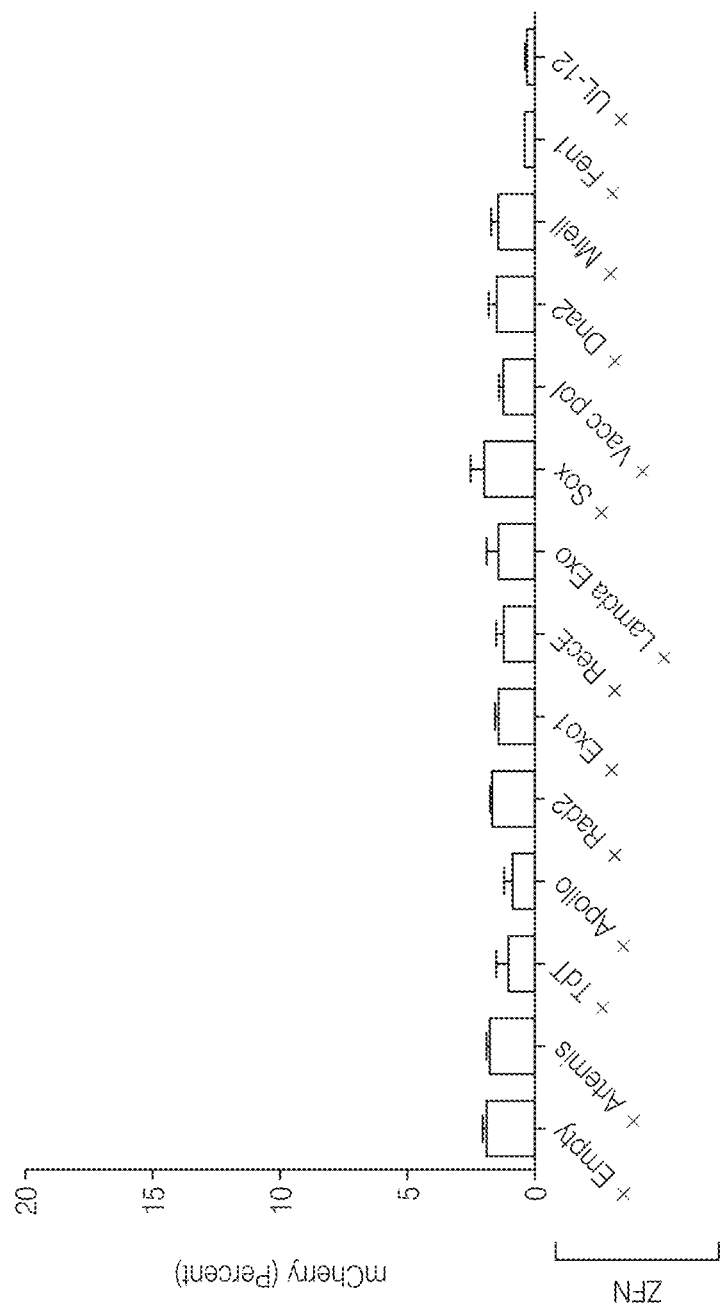
FIG. 19A shows a graph of HEK293 Traffic Light Reporter cells following co-transfection with a zinc finger nuclease and the indicated end-processing enzyme expression plasmid.

The library of DNA end-processing enzymes was screened by co-expressing each enzyme with either the homing endonuclease, I-SceI, or the Zinc Finger Nuclease, VF2468, in the respective HEK293T TLR cells. See FIGS. 17A$_1$, 17A$_2$, 17B, 18A, 19A and 19B. Five of DNA end-processing enzymes (Artemis, Tdt, Apollo, Rad2, and Exo1) robustly increased the gene disruption efficiency of I-SceI. See FIGS. 17A$_1$, 17A$_2$ and 17B. Additionally, the gene disruption activity of these five enzymes was analyzed at three levels of I-SceI expression (quantified by the mean fluorescence intensity, MFI, of the BFP fluorophore). Coexpression of these enzymes with I-SceI increased I-SceI's mutagenic efficiency, even at low levels of endonuclease expression. See FIGS. 18A and 18B. In contrast, although several of the DNA end-processing enzymes possess 5' exonuclease activity, a significant effect of any enzyme on increasing the gene disruption efficiency of the VF2468 ZFN was not observed. See FIG. 19A.

Figure 19B:
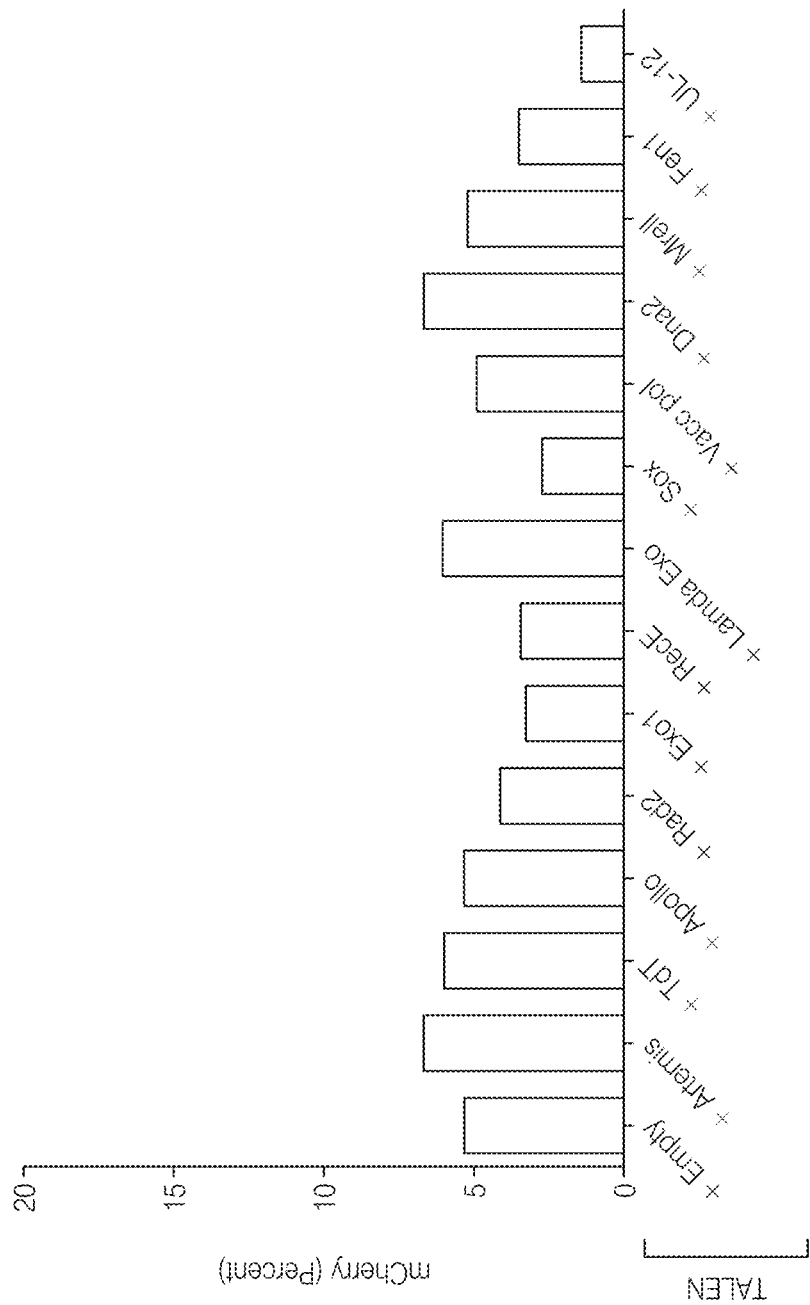
FIG. 19B shows a graph of HEK293 Traffic Light Reporter cells following co-transfection with a TALEN and the indicated end-processing enzyme expression plasmid.
Figure 20A:
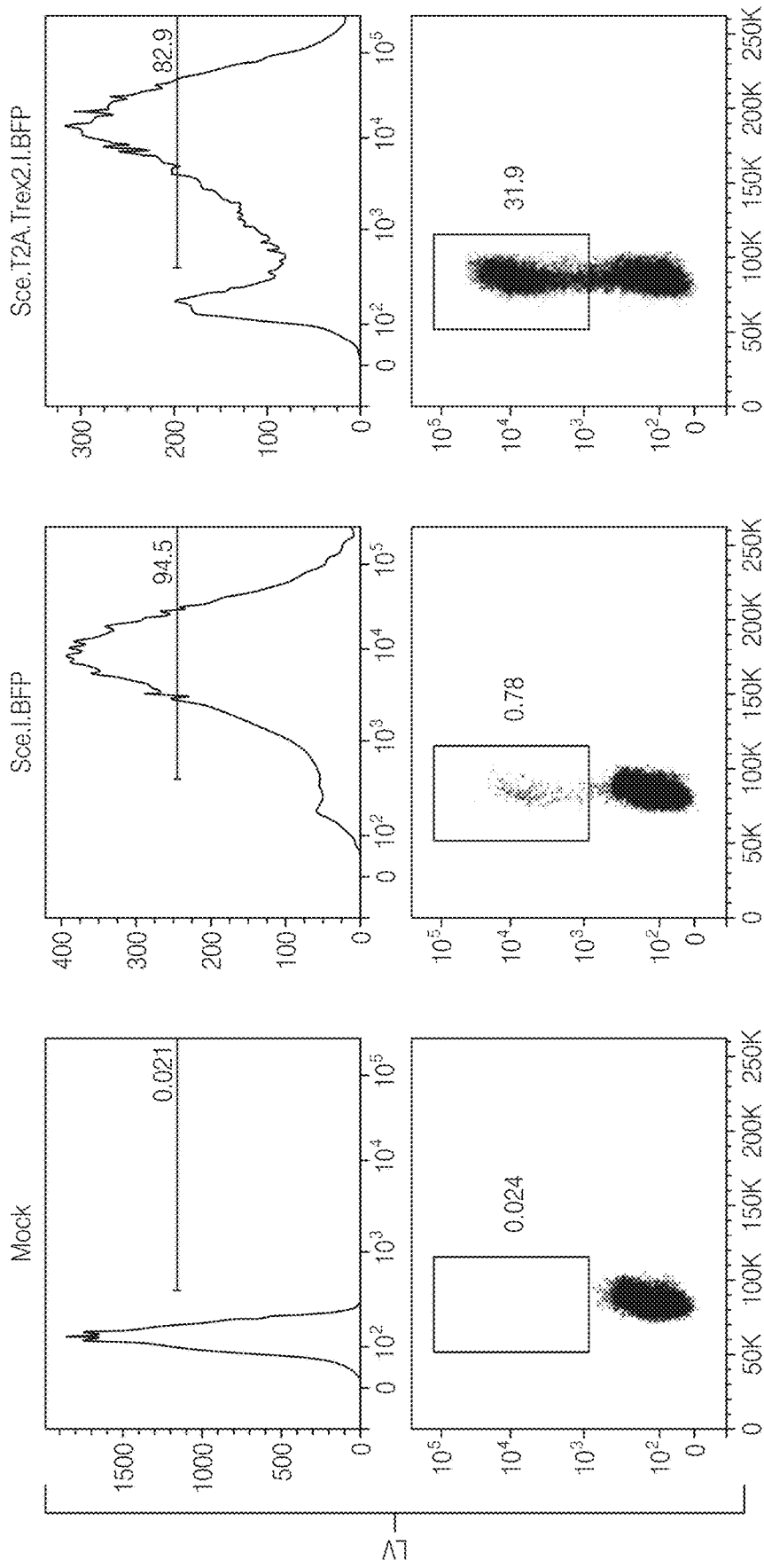
FIGS. 20A and 20B show a comparison of expression levels and gene disruption rates between integrating lentivirus and integrase deficient lentivirus from I-SceI with and without exonuclease coupling on HEK293 Traffic Light reporter cells.
Figure 20B:
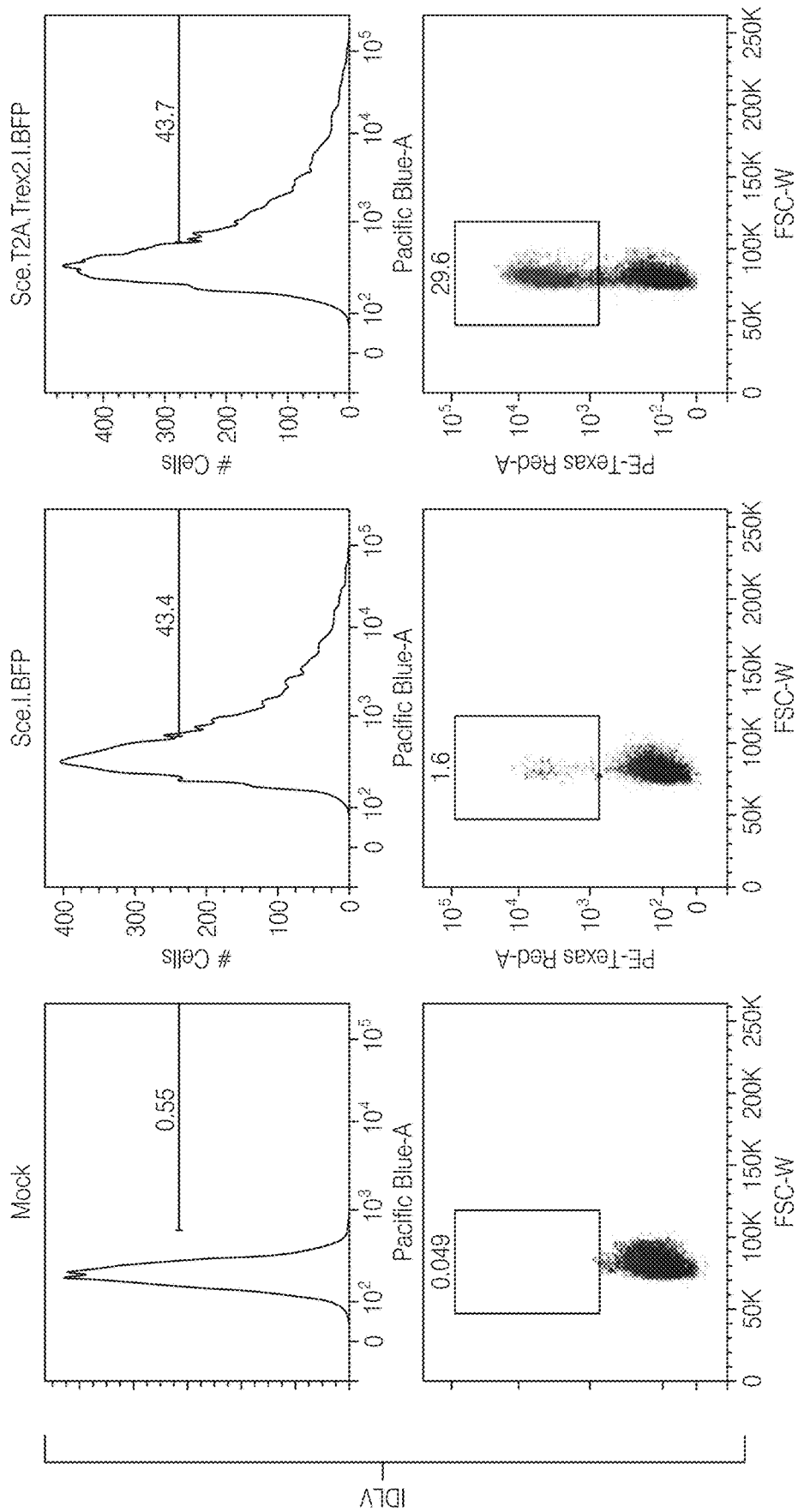

In addition, the library of DNA end-processing enzymes was screened by co-expressing each enzyme with TALEN. See FIG. 19B.

TABLE 2

Library of DNA End-Processing Enzymes.

| Enzyme | Gene name | Activity | Species of origin | NLS added | Reference |
|---|---|---|---|---|---|
| Apollo | SNM1B | 5-3' exonuclease | Human | No | Lenain, C. et al., The Apollo 5' exonuclease functions together with TRF2 to protect telomeresfrom DNA repair. *Curr. Biol.* 16, 1303-1310 (2006). |
| Artemis | Artemis | 5-3' exonuclease | Human | No | Kurosawa, A., and Adachi, N. Functions and regulation of Artemis: a goddess in the maintenance ofgenome integrity. *J Radiat. Res. (Tokyo)* 51, 503-509 (2010). |
| Dna2 | DNA2 | 5-3' exonuclease, helicase | Human | No | Nimonkar, A. V., et al. BLM-DNA2-RPA-MRN and EXO1-BLM-RPA-MRN constitute two DNA end resection machineries for human DNA break repair. *Genes Dev* 25, 350-362 (2011). |
| Exo1 | EXO1 | 5-3' exonuclease | Human | No | Nimonkar, A. V. et al. BLM-DNA2-RPA-MRN and EXO1-BLM-RPA-MRN constitute two DNA end resection machineries for human DNA break repair. *Genes Dev* 25, 350-362 (2011). Orans, J., et al. |

TABLE 2-continued

Library of DNA End-Processing Enzymes.

| Enzyme | Gene name | Activity | Species of origin | NLS added | Reference |
|---|---|---|---|---|---|
| | | | | | Structures of human exonuclease 1 DNA complexes suggest a unified mechanism for nuclease family. *Cell* 145, 212-223 (2011). |
| Fen1 | FEN1 | 5' flap endonuclease | Human | No | Jagannathan, I., Pepenella, S. Hayes, J. J. Activity of FEN1 endonuclease on nucleosome substrates is dependent upon DNA sequence but not flap orientation. *J. Biol. Chem.* 286, 17521-17529 (2011). Tsutakawa, S. E., et al., Human flap endonuclease structures, DNA double-base flipping, and a unified understanding of the FEN1 superfamily. *Cell* 145, 198-211 (2011). |
| Mre11 | MRE11 | 5-3' and 3-5' exonuclease | Human | No | Garcia, V., Phelps, S. E., Gray, S., and Neale, M. J. Bidirectional resection of DNA double-strand breaks by Mre11 and Exo1. *Nature* 479, 241-244 (2011). |
| Rad2 | n/a (catalytic domain of Exo1) | 5-3' exonuclease (Exo1 catalytic domain) | Human | No | Lee, B. I., and Wilson, D. M., 3rd The RAD2 domain of human exonuclease 1 exhibits 5' to 3' exonuclease and flap structure-specific endonuclease activities. *J Bio.l Chem.* 274, 37763-37769 (1999). |
| TdT (terminal deoxynucleotidyl transferase) | TdT | Single-stranded Template independent DNA polymerase | Human | No | Mahajan, K. N., et al., Association of terminal deoxynucleotidyl transferase with Ku. *Proc. Natl. Acad. Sci. USA* 96, 13926-13931 (1999). |
| RecE | RecE | 5-3' exonuclease | *E. coli* | Yes | Zhang, J., Xing, X., Herr, A. B., and Bell, C. E. Crystal structure of E. coli RecE protein reveals a toroidal tetramer for processing double-stranded DNA breaks. *Structure* 17, 690-702 (2009). |
| Lambda exonuclease | λ exonuclease | 5-3' exonuclease | Bacteriophage λ | Yes | Zhang, J., McCabe, K. A., and Bell, C. E. Crystal structures of lambda exonuclease in complex withDNA suggest an electrostatic ratchet |

TABLE 2-continued

Library of DNA End-Processing Enzymes.

| Enzyme | Gene name | Activity | Species of origin | NLS added | Reference |
|---|---|---|---|---|---|
| | | | | | mechanism for processivity. *Proc. Natl. Acad. Sci. USA* 108, 11872-11877 (2011). |
| Sox (T24I mutation) | SOX | 5-3' alkaline exonuclease | Kaposi's sarcoma associated herpes virus | Yes | Glaunsinger, B., Chavez, L., and Ganem, D., The exonuclease and host shutoff functions of the SOX protein of Kaposi's sarcoma-associated herpesvirus are genetically separable. *J Virol.* 79, 7396-7401 (2005). Dahlroth, S. L., et al., Crystal structure of the shutoff and exonuclease protein from the oncogenic Kaposi's sarcoma-associated herpes virus. *FEBS J* 276, 6636-6645 (2009). |
| Vaccinia DNA polymerase | E9L | 3-5' exonuclease | Vaccinia poxvirus | Yes | Gammon, D. B., and Evans, D. H., The 3'-to-5' exonuclease activity of vaccinia virus DNA polymerase is essential and plays a role in promoting virus genetic recombination. *J. Virol.* 83, 4236-4250 (2009). |
| UL-12 | UL12 | 5-3' alkaline exonuclease | Herpes simplex virus (HSV)-1 | Yes | Reuven, N. B., et al. The herpes simplex virus type 1 alkaline nuclease and single-stranded DNA binding protein mediate strand exchange in vitro. *J. Virol.* 77, 7425-7433 (2003). Balasubramanian, N., et al. Physical interaction between the herpes simplex virus type 1 exonuclease, UL12, and the DNA double-strand break-sensing MRN complex. *J. Virol.* 84, 12504-12514 (2010). |

Example 8

Exonuclease Screen

An expression library containing both 3' and 5' specific exonucleases is screened by expressing the exonucleases in cells containing a targeted disruption reporter harboring a homing endonuclease target site, for example an I-SceI target site. The exonucleases are co-expressed in the reporter cells with a homing endonuclease, for example I-Sce-I, which generates 3' overhangs upon cleaving its target site. Exonucleases which increase the rate of disruption, as visualized by mCherry+ expression, of the homing endonuclease target site over expression of the homing endonuclease alone are then identified.

An expression library containing both 3' and 5' specific exonucleases is additionally screened by expressing the exonucleases in cells containing a targeted disruption reporter harboring a zinc finger endonuclease target site. The exonucleases are co-expressed in the reporter cells with a zinc finger endonuclease, which generates 5' overhangs upon cleaving its target site with Fok1. Exonucleases which increase the rate of disruption, as visualized by mCherry+ expression, of the zinc finger endonuclease target site over expression of the zinc finger endonuclease alone are identified.

Example 9

Trex-Multiplex

Increasing disruption rates for individual nucleases by coupling endonuclease activity with exonuclease activity, enables multiple simultaneous changes to a genome (multiplexing).

Three homing endonuclease are designed to knock out three different genes (x, y, and z). In the absence of exonuclease co-expression, the efficiency of producing a disruptive mutation, knockout, for each gene individually is 10%, which means that the chance of successfully producing all three disruptive mutations in a single cell with a single round of endonuclease expression is 0.1%. An exonuclease, for example Trex2, is co-expressed with the three homing endonucleases to increase the rate of mutagenesis induced by the homing endonucleases. A 5-fold increase in the mutagenesis rate, to 50% for each individual gene, improves the chance of disrupting all three in a single cell, in a single round to 12.5%, a 125-fold difference.

Example 10

Reduction of Chromosomal Abnormalities During Endonuclease Mediated Targeted Disruption Endonucleases, such as homing endonucleases, zinc finger nucleases, and TAL effector nucleases, induce indiscriminate chromosomal abnormalities, such as translocations. To test the ability of co-expression of an exonuclease that facilitates disruption of an endonuclease target site to decrease the incidence of indiscriminate chromosomal abnormalities, an endonuclease, or a series of endonucleases are expressed in the presence and absence of Trex2. Karyotyping analysis or GCH array analysis is performed to determine if the incidence of genomic abnormalities induced by the endonucleases is reduced.

Example 11

Imparting Site-Specificity to Exonucleases

An exonuclease of interest, for example Trex2, is directly fused or coupled through a linker peptide to an endonuclease or to a DNA binding domain which specifically binds to a target site adjacent to the site where exonuclease activity is desired.

Example 12

Method of Treating, Preventing, or Inhibiting HIV Infection in a Human Patient Hematopoetic stem cells are isolated from bone marrow obtained from a human subject. The isolated stem cells are contacted with an effective amount of a zinc finger nuclease (ZFN) having target sites in the human CCR-5 gene and contemporaneously contacted with a 5' exonuclease. The contacted cells are allowed to recover in media for 72 hrs and then screened for targeted disruption of the CCR-5 gene. Cells containing a targeted disruption in CCR-5 are then propagated under appropriate conditions. The subject is given a daily intervenous (i.v.) injection of about 20 million cells containing the targeted disruption in the CCR-5 gene. This dosage can be adjusted based on the results received and the judgment of the attending physician. The protocol is preferably continued for at least about 1 or 2 weeks, preferably at least about 1 or 2 months, and may be continued on a chronic basis.

Example 13

Method of Treating, Preventing, or Inhibiting HIV Infection in a Human Patient Hematopoetic stem cells are isolated from bone marrow obtained from a human subject. The isolated stem cells are contacted with an effective amount of a homing endonuclease engineered to cleave a target site in the human CCR-5 gene and contemporaneously contacted with Trex2 exonuclease. The contacted cells are allowed to recover in media for 72 hrs and then screened for targeted disruption of the CCR-5 gene. Cells containing a targeted disruption in CCR-5 are then propagated under appropriate conditions. The subject is given a daily intervenous (i.v.) injection of about 20 million cells containing the targeted disruption in the CCR-5 gene. This dosage can be adjusted based on the results of the treatment and the judgment of the attending physician. The protocol is preferably continued for at least about 1 or 2 weeks, preferably at least about 1 or 2 months, and may be continued on a chronic basis.

Example 14

Method of Treating, Preventing, or Inhibiting HIV Infection in a Human Patient Hematopoetic stem cells are isolated from bone marrow obtained from a human subject. The isolated stem cells are contacted with an effective amount of a fusion protein comprising an endonuclease domain linked to an exonuclease domain wherein the endonuclease domain comprises a homing endonuclease engineered to cleave a target site in the human CCR-5 gene or fragment thereof and wherein the exonuclease domain comprises Trex2 exonuclease or a fragment thereof. The contacted cells are allowed to recover in media for 72 hrs and then screened for targeted disruption of the CCR-5 gene. Cells containing a targeted disruption in CCR-5 are then propagated under appropriate conditions. The subject is given a daily intervenous (i.v.) injection of about 20 million cells containing the targeted disruption in the CCR-5 gene. This dosage can be adjusted based on the results of the treatment and the judgment of the attending physician. The protocol is preferably continued for at least about 1 or 2 weeks, preferably at least about 1 or 2 months, and may be continued on a chronic basis.

Example 15

End-Modifying Enzyme Screen

An expression library containing end-modifying enzymes is screened by expressing the end-modifying enzymes in cells containing a targeted disruption reporter harboring a homing endonuclease target site, for example an I-SceI target site. The end-modifying enzymes are co-expressed in the reporter cells with a homing endonuclease, for example I-Sce-I, which generates 3' overhangs upon cleaving its target site. End-modifying enzymes which increase the rate of disruption, as visualized by mCherry+ expression, of the homing endonuclease target site over expression of the homing endonuclease alone are then identified.

An expression library containing end-modifying enzymes is additionally screened by expressing the exonucleases in cells containing a targeted disruption reporter harboring a zinc finger endonuclease target site. The end-modifying enzymes are co-expressed in the reporter cells with a zinc finger endonuclease, which generates 5' overhangs upon cleaving its target site with FokI. End-modifying enzymes which increase the rate of disruption, as visualized by mCherry+ expression, of the zinc finger endonuclease target site over expression of the zinc finger endonuclease alone are identified.

Example 16

Method of Treating, Preventing, or Inhibiting Cancer in a Human Patient

A patient having cancer is identified. The isolated an effective amount of an endonuclease targeting a site within the regulatory or coding sequence of an anti-apoptotic gene is administered in combination with an end processing enzyme. The patient is monitored for increased apoptosis and or decreased malignant cell proliferation. In some embodiments, tumor growth is monitored. The protocol may be administered on a periodic or chronic basis.

What is claimed is:

1. A method of increasing mutagenesis at a double-strand DNA (dsDNA) break at a selected dsDNA target site in a eukaryotic cell comprising:
   a) selecting a dsDNA target site for mutagenesis; and
   b) introducing into the eukaryotic cell a polynucleotide sequence encoding a homing endonuclease that binds and cleaves the selected dsDNA target site, and an exonuclease; wherein the exonuclease exhibits exonuclease activity at the cleaved dsDNA target site, resulting in increased mutagenesis at the selected dsDNA target site as compared to mutagenesis that occurs in the absence of exonuclease activity.

2. The method of claim 1, wherein the homing endonuclease is a LAGLIDADG homing endonuclease.

3. The method of claim 2, wherein the homing endonuclease is I-OnuI.

4. The method of claim 1, wherein the homing endonuclease is engineered to bind and cleave the selected dsDNA target site.

5. The method of claim 1, wherein the eukaryotic cell is a human cell.

6. The method of claim 1, wherein the mutagenesis is an insertion or deletion at the selected dsDNA target site.

7. The method of claim 1, wherein the exonuclease exhibits 3' to 5' exonuclease activity.

8. The method of claim 2, wherein the exonuclease exhibits 3' to 5' exonuclease activity.

9. The method of claim 3, wherein the exonuclease exhibits 3' to 5' exonuclease activity.

10. The method of claim 1, wherein the exonuclease is Trex2 or a biologically active fragment thereof.

11. The method of claim 2, wherein the exonuclease is Trex2 or a biologically active fragment thereof.

12. The method of claim 3, wherein the exonuclease is Trex2 or a biologically active fragment thereof.

13. The method of claim 1, wherein the exonuclease is Trex2.

14. The method of claim 2, wherein the exonuclease is Trex2.

15. The method of claim 3, wherein the exonuclease is Trex2.

16. The method of claim 1, wherein the homing endonuclease and the exonuclease are encoded by a single polynucleotide.

17. The method of claim 16, wherein the homing endonuclease is coupled to the exonuclease by a linker domain.

18. The method of claim 17, wherein the linker domain is a peptide linker comprising 4 to 30 amino acids.

19. The method of claim 17, wherein the linker domain is a G4S linker.

20. The method of claim 17, wherein the linker domain is a T2A linker.

* * * * *

SEQUENCE LISTING

```
<160> NUMBER OF SEQ ID NOS: 147

<210> SEQ ID NO 1
<211> LENGTH: 18
<212> TYPE: DNA
<213> ORGANISM: Artificial Sequence
<220> FEATURE:
<223> OTHER INFORMATION: Sequence of the I-SceI target site

<400> SEQUENCE: 1
tagggataac agggtaat                                                        18

<210> SEQ ID NO 2
<211> LENGTH: 22
<212> TYPE: DNA
<213> ORGANISM: Artificial Sequence
<220> FEATURE:
<223> OTHER INFORMATION: Sequence of the I-LtrI target site

<400> SEQUENCE: 2
aatgctccta tacgacgttt ag                                                   22

<210> SEQ ID NO 3
<211> LENGTH: 22
<212> TYPE: DNA
<213> ORGANISM: Artificial Sequence
<220> FEATURE:
<223> OTHER INFORMATION: Sequence of the I-GpiI target site

<400> SEQUENCE: 3
ttttcctgta tatgacttaa at                                                   22

<210> SEQ ID NO 4
<211> LENGTH: 22
<212> TYPE: DNA
<213> ORGANISM: Artificial Sequence
<220> FEATURE:
<223> OTHER INFORMATION: Sequence of the I-GzeI target site

<400> SEQUENCE: 4
gcccctcata acccgtatca ag                                                   22

<210> SEQ ID NO 5
<211> LENGTH: 21
<212> TYPE: DNA
<213> ORGANISM: Artificial Sequence
<220> FEATURE:
<223> OTHER INFORMATION: Sequence of the I-xMpeMI target site
```

```
<400> SEQUENCE: 5
tagataacca taagtgctaa t                                              21

<210> SEQ ID NO 6
<211> LENGTH: 22
<212> TYPE: DNA
<213> ORGANISM: Artificial Sequence
<220> FEATURE:
<223> OTHER INFORMATION: Sequence of the I-PanMI target site

<400> SEQUENCE: 6
gctcctcata atccttatca ag                                             22

<210> SEQ ID NO 7
<211> LENGTH: 24
<212> TYPE: DNA
<213> ORGANISM: Artificial Sequence
<220> FEATURE:
<223> OTHER INFORMATION: Sequence of the I-CreI target site

<400> SEQUENCE: 7
tcaaaacgtc gtgagacagt ttgg                                           24

<210> SEQ ID NO 8
<211> LENGTH: 22
<212> TYPE: DNA
<213> ORGANISM: Artificial Sequence
<220> FEATURE:
<223> OTHER INFORMATION: Sequence of the I-OnuI target site

<400> SEQUENCE: 8
tttccactta ttcaaccttt ta                                             22

<210> SEQ ID NO 9
<211> LENGTH: 22
<212> TYPE: DNA
<213> ORGANISM: Artificial Sequence
<220> FEATURE:
<223> OTHER INFORMATION: Sequence of the I-HjeMI target site

<400> SEQUENCE: 9
ttgaggaggt ttctctgtta at                                             22

<210> SEQ ID NO 10
<211> LENGTH: 20
<212> TYPE: DNA
<213> ORGANISM: Artificial Sequence
<220> FEATURE:
<223> OTHER INFORMATION: Sequence of the I-AniI target site

<400> SEQUENCE: 10
tgaggaggtt tctctgtaaa                                                20

<210> SEQ ID NO 11
<211> LENGTH: 53
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 11
taggtcaggg ttcacactag ttagggtaat acctgcaggt tgccggtggt gca           53
```

```
<210> SEQ ID NO 12
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 12
taggtcaggg ttcacactag ttagggataa cagggtaata cctgcaggtt gccggtggtg    60
ca                                                                  62

<210> SEQ ID NO 13
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 13
taggtcaggg ttcacactag ttagggataa cagggtaata cctgcaggtt gccggtggtg    60
ca                                                                  62

<210> SEQ ID NO 14
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 14
taggtcaggg ttcacactag ttagggataa cagggtaata cctgcaggtt gccggtggtg    60
ca                                                                  62

<210> SEQ ID NO 15
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 15
taggtcaggg ttcacactag ttagggataa cagggtaata cctgcaggtt gccggtggtg    60
ca                                                                  62

<210> SEQ ID NO 16
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 16
taggtcaggg ttcacactag ttagggataa cagggtaata cctgcaggtt gccggtggtg    60
ca                                                                  62

<210> SEQ ID NO 17
<211> LENGTH: 56
<212> TYPE: DNA
<213> ORGANISM: Artificial Sequence
```

```
<220> FEATURE:
<223> OTHER INFORMATION: Sequence of amplicon surrounding the I-SceI
      target site treated with I-SceI.

<400> SEQUENCE: 17
taggtcaggg ttcacactag ataacagggt aatacctgca ggttgccggt ggtgca        56

<210> SEQ ID NO 18
<211> LENGTH: 61
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 18
taggtcaggg ttcacactag ttagggatac agggtaatac ctgcaggttg ccggtggtgc   60
a                                                                   61

<210> SEQ ID NO 19
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 19
taggtcaggg ttcacactag ttagggataa cagggtaata cctgcaggtt gccggtggtg   60
ca                                                                  62

<210> SEQ ID NO 20
<211> LENGTH: 53
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 20
taggtcaggg ttcacactag ttagggtaat acctgcaggt tgccggtggt gca           53

<210> SEQ ID NO 21
<211> LENGTH: 47
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 21
taggtcaggg ttcacactag ttagggatgc aggttgccgg tggtgca                  47

<210> SEQ ID NO 22
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 22
taggtcaggg ttcacactag ttagggataa cagggtaata cctgcaggtt gccggtggtg   60
ca                                                                  62
```

<210> SEQ ID NO 23
<211> LENGTH: 43
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 23
taggtcaggg ttcacactat acctgcaggt tgccggtggt gca                    43

<210> SEQ ID NO 24
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 24
taggtcaggg ttcacactag ttagggataa cagggtaata cctgcaggtt gccggtggtg    60
ca                                                                  62

<210> SEQ ID NO 25
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 25
taggtcaggg ttcacactag ttagggataa cagggtaata cctgcaggtt gccggtggtg    60
ca                                                                  62

<210> SEQ ID NO 26
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 26
taggtcaggg ttcacactag ttagggataa cagggtaata cctgcaggtt gccggtggtg    60
ca                                                                  62

<210> SEQ ID NO 27
<211> LENGTH: 55
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 27
taggtcaggg ttcacactag ttaggtaggg caacctgcag gttgccggtg gtgca          55

<210> SEQ ID NO 28
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 28
taggtcaggg ttcacactag ttagggataa cagggtaata cctgcaggtt gccggtggtg    60
ca                                                                  62

<210> SEQ ID NO 29
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 29
taggtcaggg ttcacactag ttagggataa cagggtaata cctgcaggtt gccggtggtg    60
ca                                                                  62

<210> SEQ ID NO 30
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 30
taggtcaggg ttcacactag ttagggataa cagggtaata cctgcaggtt gccggtggtg    60
ca                                                                  62

<210> SEQ ID NO 31
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 31
taggtcaggg ttcacactag ttagggataa cagggtaata cctgcaggtt gccggtggtg    60
ca                                                                  62

<210> SEQ ID NO 32
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 32
taggtcaggg ttcacactag ttagggataa cagggtaata cctgcaggtt gccggtggtg    60
ca                                                                  62

<210> SEQ ID NO 33
<211> LENGTH: 53
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 33
taggtcaggg ttcacactag ttagggtaat acctgcaggt tgccggtggt gca           53

<210> SEQ ID NO 34
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 34
taggtcaggg ttcacactag ttagggataa cagggtaata cctgcaggtt gccggtggtg      60
ca                                                                    62

<210> SEQ ID NO 35
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 35
taggtcaggg ttcacactag ttagggataa cagggtaata cctgcaggtt gccggtggtg      60
ca                                                                    62

<210> SEQ ID NO 36
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 36
taggtcaggg ttcacactag ttagggataa cagggtaata cctgcaggtt gccggtggtg      60
ca                                                                    62

<210> SEQ ID NO 37
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 37
taggtcaggg ttcacactag ttagggataa cagggtaata cctgcaggtt gccggtggtg      60
ca                                                                    62

<210> SEQ ID NO 38
<211> LENGTH: 55
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 38
taggtcaggg ttcacactag ttagggataa ctacctgcag gttgccggtg gtgca           55

<210> SEQ ID NO 39
<211> LENGTH: 62
<212> TYPE: DNA
<213> ORGANISM: Artificial Sequence -continued
<220> FEATURE:
<223> OTHER INFORMATION: Sequence of amplicon surrounding the I-SceI
      target site treated with I-SceI.

<400> SEQUENCE: 39
taggtcaggg ttcacactag ttagggataa cagggtaata cctgcaggtt gccggtggtg    60
ca                                                                   62

<210> SEQ ID NO 40
<211> LENGTH: 55
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 40
taggtcaggg ttcacactaa taacagggta atacctgcag gttgccggtg gtgca         55

<210> SEQ ID NO 41
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 41
taggtcaggg ttcacactag ttagggataa cagggtaata cctgctggtt gccggtggtg    60
ca                                                                   62

<210> SEQ ID NO 42
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 42
taggtcaggg ttcacactag ttagggataa cagggtaata cctgcaggtt gccggtggtg    60
ca                                                                   62

<210> SEQ ID NO 43
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 43
taggtcaggg ttcacactag ttagggataa cagggtaata cctgcaggtt gccggtggtg    60
ca                                                                   62

<210> SEQ ID NO 44
<211> LENGTH: 53
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 44
taggtcaggg ttcacactag ttagggtaat acctgcaagt tgccggtggt gcc       53

<210> SEQ ID NO 45
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 45
taggtcaggg ttcacactag ttagggataa cagggtaata cctgcaggtt gccggtggtg    60
ca                                                                  62

<210> SEQ ID NO 46
<211> LENGTH: 61
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 46
taggtcaggg ttcacactag ttaggataac agggtaatac ctgcaggttg ccggtggtgc    60
a                                                                   61

<210> SEQ ID NO 47
<211> LENGTH: 61
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 47
taggtcaggg ttcacactag ttaggataac agggtaatac ctgcaggttg ccggtggtgc    60
a                                                                   61

<210> SEQ ID NO 48
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 48
taggtcaggg ttcacactag ttagggataa cagggtaata cctgcaggtt gccggtggtg    60
ca                                                                  62

<210> SEQ ID NO 49
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 49
taggtcaggg ttcacactag ttagggataa cagggtaata cctgcaggtt gccggtggtg    60
ca                                                                  62

<210> SEQ ID NO 50

```
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 50
taggtcaggg ttcacactag ttagggataa cagggtaata cctgcaggtt gccggtggtg    60
ca                                                                  62

<210> SEQ ID NO 51
<211> LENGTH: 61
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 51
taggtcaggg ttcacactag ttaggataac agggtaatac ctgcaggttg ccggtggtgc    60
a                                                                   61

<210> SEQ ID NO 52
<211> LENGTH: 56
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 52
taggtcaggg ttcacactag ataacagggt aatacctgca ggttgccggt ggtgca        56

<210> SEQ ID NO 53
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 53
taggtcaggg ttcacactag ttagggataa cagggtaata cctgcaggtt accggtggtg    60
ca                                                                  62

<210> SEQ ID NO 54
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 54
taggtcaggg ttcacactag ttagggataa cagggtaata cctgcaggtt gccggtggtg    60
ca                                                                  62

<210> SEQ ID NO 55
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.
```

<400> SEQUENCE: 55
taggtcaggg ttcacactag ttagggataa cagggtaata catgcaggtt gccggtggtg      60
ca                                                                    62

<210> SEQ ID NO 56
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 56
taggtcaggg ttcacactag ttagggataa cagggtaata cctgcaggtt gccggtggtg      60
ca                                                                    62

<210> SEQ ID NO 57
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI.

<400> SEQUENCE: 57
taggtcaggg ttcacactag ttagggataa cagggtaata cctgcaggtt gccggtggtg      60
ca                                                                    62

<210> SEQ ID NO 58
<211> LENGTH: 62
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 58
ccgtaggtca gggttcacac tagttaggga taacagggta atacctgcag gttgccggtg      60
gt                                                                    62

<210> SEQ ID NO 59
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 59
ccgtaggtca gggttcacac tagttaggga acagggtaat acctgcaggt tgccggtggt      60

<210> SEQ ID NO 60
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 60
ccgtaggtca gggttcacac tagttagggc agggtaatac ctgcaggttg ccggtggt       58

<210> SEQ ID NO 61
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 61
ccgtaggtca gggttcacac tagttaggga acagggtaat acctgcaggt tgccggtggt    60

<210> SEQ ID NO 62
<211> LENGTH: 53
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 62
ccgtaggtca gggttcacac tagtcagggt aatacctgca ggttgccggt ggt    53

<210> SEQ ID NO 63
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 63
ccgtaggtca gggttcacac tagttagggc agggtaatac ctgcaggttg ccggtggt    58

<210> SEQ ID NO 64
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 64
ccgtaggtca gggttcacac tagttaggga acagggtaat acctgcaggt tgccggtggt    60

<210> SEQ ID NO 65
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 65
ccgtaggtca gggttcacac tagttaggga acagggtaat acctgcaggt tgccggtggt    60

<210> SEQ ID NO 66
<211> LENGTH: 53
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 66
ccgtaggtca gggttcacac tagttagggt aatacctgca ggttgccggt ggt    53

<210> SEQ ID NO 67

```
<211> LENGTH: 54
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 67
ccgtaggtca gggttcacac tagttagggg taatacctgc aggttgccgg tggt              54

<210> SEQ ID NO 68
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 68
ccgtaggtca gggttcacac tagttaggga acagggtaat acctgcaggt tgccggtggt        60

<210> SEQ ID NO 69
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 69
ccgtaggtca gggttcacac tagttaggga acagggtaat acctgcaggt tgccggtggt        60

<210> SEQ ID NO 70
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 70
ccgtaggtca gggttcacac tagttagggc agggtaatac ctgcaggttg ccggtggt          58

<210> SEQ ID NO 71
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 71
ccgtaggtca gggttcacac tagttagggc agggtaatac ctgcaggttg ccggtggt          58

<210> SEQ ID NO 72
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 72
ccgtaggtca gggttcacac tagttaggga acagggtaat acctgcaggt tgccggtggt        60

<210> SEQ ID NO 73
<211> LENGTH: 58
```

```
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 73
ccgtaggtca gggttcacac tagttagggc agggtaatac ctgcaggttg ccggtggt         58

<210> SEQ ID NO 74
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 74
ccgtaggtca gggttcacac tagttaggga acagggtaat acctgcaggt tgccggtggt       60

<210> SEQ ID NO 75
<211> LENGTH: 59
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 75
ccgtaggtca gggttcacac tagttaggga cagggtaata cctgcaggtt gccggtggt        59

<210> SEQ ID NO 76
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 76
ccgtaggtca gggttcacac tagttagggc aggtaatacc tgcaggtttg ccggtggt         58

<210> SEQ ID NO 77
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 77
ccgtaggtca gggttcacac tagttaggga acagggtaat acctgcaggt tgccggtggt       60

<210> SEQ ID NO 78
<211> LENGTH: 59
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 78
ccgtaggtca gggttcacac tagttaggga cagggtaata cctgcaggtt gccggtggt        59

<210> SEQ ID NO 79
<211> LENGTH: 60
<212> TYPE: DNA
```

<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 79
ccgtaggtca gggttcacac tagttaggga acagggtaat acctgcaggt tgccggtggt    60

<210> SEQ ID NO 80
<211> LENGTH: 59
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 80
ccgtaggtca gggttcacac tagttaggga cagggtaata cctgcaggtt gccggtggt     59

<210> SEQ ID NO 81
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 81
ccgtaggtca gggttcacac tagttaggga acagggtaat acctgcaggt tgccggtggt    60

<210> SEQ ID NO 82
<211> LENGTH: 54
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 82
ccgtaggtca gggttcacac tagttagggg taatacctgc aggttgccgg tggt          54

<210> SEQ ID NO 83
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 83
ccgtaggtca gggttcacac tagttaggga acagggtaat acctgcaggt tgccggtggt    60

<210> SEQ ID NO 84
<211> LENGTH: 55
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 84
ccgtaggtca gggttcacac tagttagggg gtaatacctg caggttgccg gtggt         55

<210> SEQ ID NO 85
<211> LENGTH: 54
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 85
ccgtaggtca gggttcacac tagttagggg taatacctgc aggttgccgg tggt          54

<210> SEQ ID NO 86
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 86
caataggtca gggttcacac tagttaggga acagggtaat acctgcaggt tgccggtggt    60

<210> SEQ ID NO 87
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 87
ccgtaggtca gggttcacac tagttaggga acagggtaat acctgcaggt tgccggtggt    60

<210> SEQ ID NO 88
<211> LENGTH: 55
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 88
ccgtaggtca gggttcacac tagttagggg gtaatacctg caggttgccg gtggt         55

<210> SEQ ID NO 89
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 89
ccgtaggtca gggttcacac tagttagggc agggtaatac ctgcaggttg ccgtggt       58

<210> SEQ ID NO 90
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 90
ccgtaggtca gggttcacac tagttagggc agggtaatac ctgcaggttg ccgtggt       58

<210> SEQ ID NO 91
<211> LENGTH: 58
<212> TYPE: DNA
<213> ORGANISM: Artificial Sequence
<220> FEATURE:

<223> OTHER INFORMATION: Sequence of amplicon surrounding the I-SceI
      target site treated with I-SceI and Trex2.

<400> SEQUENCE: 91
ccgtaggtca gggttcacac tagttagggc agggtaatac ctgcaggttg ccggtggt        58

<210> SEQ ID NO 92
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 92
ccgtgggtca gggttcacac tagttagggc agggtaatac ctgcaggttg ccggtggt        58

<210> SEQ ID NO 93
<211> LENGTH: 59
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 93
ccgtaggtca gggttcacac tagttaggga cagggtaata cctgcaggtt gccggtggt       59

<210> SEQ ID NO 94
<211> LENGTH: 59
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 94
ccgtaggtca gggttcacac tagttaggga cagggtaata cctgcaggtt gccggtggt       59

<210> SEQ ID NO 95
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 95
ccgtaggtca gggttcacac tagttagggc agggtaatac ctgcaggttg ccggtggt        58

<210> SEQ ID NO 96
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 96
ccgtaggtca gggttcacac tagttaggga acagggtaat acctgcaggt tgccggtggt      60

<210> SEQ ID NO 97
<211> LENGTH: 58
<212> TYPE: DNA
<213> ORGANISM: Artificial Sequence
<220> FEATURE:
<223> OTHER INFORMATION: Sequence of amplicon surrounding the I-SceI target site treated with I-SceI and Trex2.

<400> SEQUENCE: 97
cagggtaata cctgcaggtt gccggtggtc agggtaatac ctgcaggttg ccggtggt    58

<210> SEQ ID NO 98
<211> LENGTH: 54
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 98
cagggtaata cctgcaggtt gccggtggtg taatacctgc aggttgccgg tggt    54

<210> SEQ ID NO 99
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 99
cagggtaata cctgcaggtt gccggtggtc agggtaatac ctgcaggttg ccggtggt    58

<210> SEQ ID NO 100
<211> LENGTH: 57
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 100
ccgtaggtca gggttcacac tagttaggga gggtaatacc tgcaggttgc cggtggt    57

<210> SEQ ID NO 101
<211> LENGTH: 58
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 101
ccgtaggtca gggttcacac tagttagggc agggtaatac ctgcaggttg ccggtggt    58

<210> SEQ ID NO 102
<211> LENGTH: 60
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 102
ccgtaggtca gggttcacac tagttaggga acagggtaat acctgcaggt tgccggtggt    60

<210> SEQ ID NO 103
<211> LENGTH: 57
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 103
ccgtaggtca gggttcacac tagttaggca gggtaatacc tgcaggttgc cggtggt     57

<210> SEQ ID NO 104
<211> LENGTH: 53
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 104
ccgtaggtca gggttcacac tagttagggt aatacctgca ggttgccggt ggt     53

<210> SEQ ID NO 105
<211> LENGTH: 53
<212> TYPE: DNA
<213> ORGANISM: Artificial Sequence
<220> FEATURE:
<223> OTHER INFORMATION: Sequence of amplicon surrounding the I-SceI
      target site treated with I-SceI and Trex2.

<400> SEQUENCE: 105
ccgtaggtca gggttcacac tagttagggt aatacctgca ggttgccggt ggt     53

<210> SEQ ID NO 106
<211> LENGTH: 18
<212> TYPE: DNA
<213> ORGANISM: Artificial Sequence
<220> FEATURE:
<223> OTHER INFORMATION: I-SceI target site 5'-3'

<400> SEQUENCE: 106
tagggataac agggtaat     18

<210> SEQ ID NO 107
<211> LENGTH: 18
<212> TYPE: DNA
<213> ORGANISM: Artificial Sequence
<220> FEATURE:
<223> OTHER INFORMATION: I-SceI target site 3'-5'

<400> SEQUENCE: 107
attaccctgt tatcccta     18

<210> SEQ ID NO 108
<211> LENGTH: 24
<212> TYPE: DNA
<213> ORGANISM: Artificial Sequence
<220> FEATURE:
<223> OTHER INFORMATION: VF2468 target site 5'-3'

<400> SEQUENCE: 108
gagcagcgtc ttcgagagtg agga     24

<210> SEQ ID NO 109
<211> LENGTH: 24
<212> TYPE: DNA
<213> ORGANISM: Artificial Sequence
<220> FEATURE:
<223> OTHER INFORMATION: VF2468 target site 3'-5'

<400> SEQUENCE: 109
tcctcactct cgaagacgct gctc     24

<210> SEQ ID NO 110
<211> LENGTH: 7611
<212> TYPE: DNA
<213> ORGANISM: Artificial Sequence
<220> FEATURE:
<223> OTHER INFORMATION: Plasmid pCVL.SFFV.HA.NLS.SceOpt.IRES.mTagBFP

<400> SEQUENCE: 110

```
gacgtcaatg tagtcttatg caatactctt gtagtcttgc aacatggtaa cgatgagtta      60
gcaacatgcc ttacaaggag agaaaaagca ccgtgcatgc cgattggtgg aagtaaggtg     120
gtacgatcgt gccttattag gaaggcaaca gacgggtctg acatggattg gacgaaccac     180
tgaattgccg cattgcagag atattgtatt aagtgccta gctcgataca taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta aaggagaga tgggtgcg agagcgtcag tattaagcgg     600
gggagaatta gatcgcgatg ggaaaaaatt cggttaaggc caggggggaaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca agatagagga agagcaaaac     900
aaaagtaaga ccaccgcaca gcaagcggcc ctgatcttca gacctggagg aggagatatg     960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctgggaatt    1320
tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800
cggttaactt ttaaaagaaa aggggggatt ggggggtaca gtgcagggga agaatagta    1860
gacataatag caacagacat acaaactaaa gaattacaaa aacaaattac aaaaattcaa    1920
aattttatcg attacgcgtc acgtgctagc tgcagtaacg ccattttgca aggcatggaa    1980
aaataccaaa ccaagaatag agaagttcag atcaagggcg gtacatgaa aatagctaac    2040
gttgggccaa acaggatatc tgcggtgagc agtttcggcc ccggcccggg gccaagaaca    2100
```

```
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
gcttctgctt cccgagctct ataaaagagc tcacaacccc tcactcggcg cgccagtcct    2340
ccgacagact gagtcgcccg ctcgagccgc caccatggga tatccatacg atgtcccaga    2400
ttatgcgcca cctaagaaga aacgcaaagt cgaattcaag aacatcaaga agaaccaggt    2460
catgaacctg ggccccaaca gcaagctgct gaaggagtac aagagccagc tgatcgagct    2520
gaacatcgag cagttcgagg ccggcatcgg cctgatcctg gcgacgcct acatcaggag    2580 cagggacgag ggcaagacct actgcatgca gttcgagtgg aagaacaagg cctacatgga    2640
ccacgtgtgc ctgctgtacg accagtgggg gctgagcccc ccccacaaga aggagagggt    2700
gaaccacctg ggcaacctgg tcatcacctg gggcgcccag accttcaagc accaggcctt    2760
caacaagctg gccaacctgt tcatcgtgaa caacaagaag accatcccca caacctggt    2820 ggagaactac ctgaccccca tgagcctggc ctactggttc atggacgacg gcggcaagtg    2880
ggactacaac aagaacagca ccaacaagag catcgtgctg aacacccaga gcttcacctt    2940
cgaggaggtg gagtacctgg tgaagggcct gaggaacaag ttccagctga actgctacgt    3000
gaagatcaac aagaacaagc ccatcatcta catcgacagc atgagctacc tgatcttcta    3060
caacctgatc aagccctacc tgatccccca gatgatgtac aagctgccca caccatcag    3120 cagcgagacc ttcctgaagt gacctgcagg tcgagcatgc atctagggcg gccaattccg    3180
cccctctccc tccccccccc ctaacgttac tggccgaagc cgcttggaat aaggccggtg    3240
tgcgtttgtc tatatgtgat tttccaccat attgccgtct tttggcaatg tgagggcccg    3300
gaaacctggc cctgtcttct tgacgagcat tcctagggt ctttccctc tcgccaaagg    3360 aatgcaaggt ctgttgaatg tcgtgaagga agcagttcct ctggaagctt cttgaagaca    3420
aacaacgtct gtagcgaccc tttgcaggca gcggaacccc ccacctggcg acaggtgcct    3480
ctgcggccaa agccacgtg tataagatac acctgcaaag gcggcacaac cccagtgcca    3540
cgttgtgagt tggatagttg tggaaagagt caaatggctc tcctcaagcg tattcaacaa    3600
ggggctgaag gatgcccaga aggtaccca ttgtatggga tctgatctgg ggcctcggtg    3660
cacatgcttt acatgtgttt agtcgaggtt aaaaaaacgt ctaggccccc cgaaccacgg    3720
ggacgtggtt ttcctttgaa aaacacgatg ataagcttgc cacaacccct accggtcgcc    3780
accatgagcg agctgattaa ggagaacatg cacatgaagc tgtacatgga gggcaccgtg    3840
gacaaccatc acttcaagtg cacatccgag ggcgaaggca gccctacga gggcacccag    3900 accatgagaa tcaaggtggt cgagggcggc cctctcccct cgccttcga catcctggct    3960 actagcttcc tctacggcag caagaccttc atcaaccaca cccagggcat cccgacttc    4020 ttcaagcagt ccttccctga ggcttcaca tgggagagag tcaccacata cgaagacggg    4080
ggcgtgctga ccgctaccca ggacaccagc ctccaggacg gctgcctcat ctacaacgtc    4140
aagatcagag gggtgaactt cacatccaac ggccctgtga tgcagaagaa aacactcggc    4200
tgggaggcct tcaccgagac gctgtacccc gctgacggcg gcctgaagg cagaaacgac    4260 atggccctga agctcgtggg cgggagccat ctgatcgcaa acatcaagac cacatataga    4320
tccaagaaac ccgctaagaa cctcaagatg cctggcgtct actatgtgga ctacagactg    4380
gaaagaatca aggaggccaa caacgagacc tacgtcgagc agcacgaggt ggcagtggcc    4440
```

-continued

```
agatactgcg acctccctag caaactgggg cacaagctta attgattcta gagtcgaccg    4500
agcatcttac cgccatttat acccatattt gttctgtttt tcttgatttg ggtatacatt    4560
taaatgttaa tagaacaaaa tggtggggca atcatttaca ttttaggga tatgtaatta     4620
ctagttcagg tgtattgcca caagacaaac atgttaagaa actttcccgt tatttacgct    4680
ctgttcctgt taatcaacct ctggattaca aaatttgtga agattgact gatattctta     4740
actatgttgc tccttttacg ctgtgtggat atgctgcttt atagcctctg tatctagcta    4800
ttgcttcccg tacggctttc gttttctcct ccttgtataa atcctggttg ctgtctcttt    4860
tagaggagtt gtggcccgtt gtccgtcaac gtggcgtggt gtgctctgtg tttgctgacg    4920
caacccccac tggctggggc attgccacca cctgtcaact cctttctggg actttcgctt    4980
tccccctccc gatcgccacg gcagaactca tcgccgcctg ccttgcccgc tgctggacag    5040
gggctaggtt gctgggcact gataattccg tggtgttgtc atcggtacct ttttaaaaga    5100
aaaggggga ctggaagggc taattcactc ccaacgaaga caagatatca taacttcgta     5160
tagcatacat tatacgaagt tataatttat ttgtgaaatt tgtgatgcta ttgctttatt    5220
tgtaaccata tgtttatttg tgaaatttgt gatgctattg ctttatttgt aaccattgct    5280
ttttgcttgt actgggtctc tctggttaga ccagatctga gcctgggagc tctctggcta    5340
actagggaac ccactgctta agcctcaata aagcttgcct cgaccagcct cgactgtgcc    5400
ttctagttgc cagccatctg ttgtttgccc ctccccgtg ccttccttga ccctggaagg     5460
tgccactccc actgtccttt cctaataaaa tgaggaaatt gcatcgcatt gtctgagtag    5520
gtgtcattct attctggggg gtggggtggg gcaggacagc aaggggagg attgggaaga     5580
caatagcagg catgctgggg atgcggtggg ctctatggcc tgcagctgca ttaatgaatc    5640
ggccaacgcg cggggagagg cggtttgcgt attgggcgct cttccgcttc ctcgctcact    5700
gactcgctgc gctcggtcgt tcggctgcgg cgagcggtat cagctcactc aaaggcggta    5760
atacggttat ccacagaatc aggggataac gcaggaaaga acatgtgagc aaaaggccag    5820
caaaaggcca ggaaccgtaa aaaggccgcg ttgctggcgt ttttccatag gctccgcccc    5880
cctgacgagc atcacaaaaa tcgacgctca agtcagaggt ggcgaaaccc gacaggacta    5940
taaagatacc aggcgtttcc ccctggaagc tccctcgtgc gctctcctgt tccgaccctg    6000
ccgcttaccg gatacctgtc cgcctttctc ccttcgggaa gcgtggcgct ttctcatagc    6060
tcacgctgta ggtatctcag ttcggtgtag tcgttcgct ccaagctggg ctgtgtgcac     6120
gaaccccccg ttcagcccga ccgctgcgcc ttatccggta actatcgtct tgagtccaac    6180
ccggtaagac acgacttatc gccactggca gcagccactg gtaacaggat tagcagagcg    6240
aggtatgtag gcggtgctac agagttcttg aagtggtggc ctaactacgg ctacactaga    6300
aggacagtat ttggtatctg cgctctgctg aagccagtta ccttcggaaa aagagttggt    6360
agctcttgat ccggcaaaca aaccaccgct ggtagcggtg gtttttttgt ttgcaagcag    6420
cagattacgc gcagaaaaaa aggatctcaa gaagatcctt tgatctttt ctacgggtct     6480
gacgctcagt ggaacgaaaa ctcacgttaa gggattttgg tcatgagatt atcaaaaagg    6540
atcttcacct agatcctttt aaattaaaaa tgaagtttta aatcaatcta agtatatat     6600
gagtaaactt ggtctgacag ttaccaatgc ttaatcagtg aggcacctat ctcagcgatc    6660
tgtctatttc gttcatccat agttgcctga ctccccgtcg tgtagataac tacgatacgg    6720
gagggcttac catctggccc cagtgctgca atgataccgc gagacccacg ctcaccggct    6780
ccagatttat cagcaataaa ccagccagcc ggaagggccg agcgcagaag tggtcctgca    6840
```

```
actttatccg cctccatcca gtctattaat tgttgccggg aagctagagt aagtagttcg    6900
ccagttaata gtttgcgcaa cgttgttgcc attgctacag gcatcgtggt gtcacgctcg    6960
tcgtttggta tggcttcatt cagctccggt tcccaacgat caaggcgagt tacatgatcc    7020
cccatgttgt gcaaaaaagc ggttagctcc ttcggtcctc cgatcgttgt cagaagtaag    7080
ttggccgcag tgttatcact catggttatg gcagcactgc ataattctct tactgtcatg    7140
ccatccgtaa gatgcttttc tgtgactggt gagtactcaa ccaagtcatt ctgagaatag    7200
tgtatgcggc gaccgagttg ctcttgcccg gcgtcaatac gggataatac cgcgccacat    7260
agcagaactt taaaagtgct catcattgga aaacgttctt cggggcgaaa actctcaagg    7320
atcttaccgc tgttgagatc cagttcgatg taacccactc gtgcacccaa ctgatcttca    7380
gcatctttta ctttcaccag cgtttctggg tgagcaaaaa caggaaggca aaatgccgca    7440
aaaaagggaa taagggcgac acggaaatgt tgaatactca tactcttcct ttttcaatat    7500
tattgaagca tttatcaggg ttattgtctc atgagcggat acatatttga atgtatttag    7560
aaaaataaac aaataggggt tccgcgcaca tttccccgaa aagtgccacc t             7611

<210> SEQ ID NO 111
<211> LENGTH: 7611
<212> TYPE: DNA
<213> ORGANISM: Artificial Sequence
<220> FEATURE:
<223> OTHER INFORMATION: Plasmid
      pCVL.SFFV.HA.NLS.SceOptD44A.IRES.mTagBFP

<400> SEQUENCE: 111
gacgtcaatg tagtcttatg caatactctt gtagtcttgc aacatggtaa cgatgagtta      60
gcaacatgcc ttacaaggag agaaaaagca ccgtgcatgc cgattggtgg aagtaaggtg     120
gtacgatcgt gccttattag gaaggcaaca cgggtctg acatggattg gacgaaccac      180
tgaattgccg cattgcagag atattgtatt taagtgccta gctcgataca taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta aaggagaga tgggtgcg agagcgtcag tattaagcgg     600
gggagaatta gatcgcgatg ggaaaaaatt cggttaaggc caggggggaaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca agatagagga agagcaaaac     900
aaaagtaaga ccaccgcaca gcaagcggcc ctgatcttca gacctggagg aggagatatg     960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
acgctgacgg tacaggccag acaattattg tctggtatag tgcagcagca gaacaatttg    1200
ctgagggcta ttgaggcgca acagcatctg ttgcaactca cagtctgggg catcaagcag    1260
```

```
ctccaggcaa gaatcctggc tgtggaaaga tacctaaagg atcaacagct cctgggatt    1320 tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800
cggttaactt ttaaaagaaa aggggggatt ggggggtaca gtgcagggga agaatagta    1860 gacataatag caacagacat acaaactaaa gaattacaaa acaaattac aaaaattcaa    1920 aattttatcg attacgcgtc acgtgctagc tgcagtaacg ccattttgca aggcatggaa    1980
aaataccaaa ccaagaatag agaagttcag atcaagggcg ggtacatgaa aatagctaac    2040
gttgggccaa acaggatatc tgcggtgagc agtttcggcc ccggcccggg gccaagaaca    2100
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
gcttctgctt cccgagctct ataaaagagc tcacaacccc tcactcggcg cgccagtcct    2340
ccgacagact gagtcgcccg ctcgagccgc caccatggga tatccatacg atgtcccaga    2400
ttatgcgcca cctaagaaga acgcaaagt cgaattcaag aacatcaaga gaaccaggt     2460 catgaacctg ggccccaaca gcaagctgct gaaggagtac aagagccagc tgatcgagct    2520
gaacatcgag cagttcgagg ccggcatcgg cctgatcctg ggcgctgcct acatcaggag    2580
cagggacgag ggcaagacct actgcatgca gttcgagtgg aagaacaagg cctacatgga    2640
ccacgtgtgc ctgctgtacg accagtgggt gctgagcccc cccacaaga aggagagggt    2700 gaaccacctg ggcaacctgg tcatcacctg gggcgcccag accttcaagc accaggcctt    2760
caacaagctg gccaacctgt tcatcgtgaa caacaagaag accatcccca caacctggt    2820 ggagaactac ctgacccca tgagcctggc ctactggttc atggacgacg gcggcaagtg    2880
ggactacaac aagaacagca ccaacaagag catcgtgctg aacacccaga gcttcacctt    2940
cgaggaggtg gagtacctgg tgaagggcct gaggaacaag ttccagctga actgctacgt    3000
gaagatcaac aagaacaagc ccatcatcta catcgacagc atgagctacc tgatcttcta    3060
caacctgatc aagccctacc tgatccccca gatgatgtac aagctgccca acaccatcag    3120
cagcgagacc ttcctgaagt gacctgcagg tcgagcatgc atctagggcg gccaattccg    3180
cccctctccc tccccccccc ctaacgttac tggccgaagc cgcttggaat aaggccggtg    3240
tgcgtttgtc tatatgtgat tttccaccat attgccgtct tttggcaatg tgagggcccg    3300
gaaacctggc cctgtcttct tgacgagcat tcctaggggt cttttcccctc tcgccaaagg    3360 aatgcaaggt ctgttgaatg tcgtgaagga agcagttcct ctggaagctt cttgaagaca    3420
aacaacgtct gtagcgaccc tttgcaggca gcggaacccc ccacctggcg acaggtgcct    3480
ctgcggccaa aagccacgtg tataagatac acctgcaaag gcggcacaac cccagtgcca    3540
cgttgtgagt tggatagttg tggaaagagt caaatggctc tcctcaagcg tattcaacaa    3600
```

-continued

```
ggggctgaag gatgcccaga aggtacccca ttgtatggga tctgatctgg ggcctcggtg    3660
cacatgcttt acatgtgttt agtcgaggtt aaaaaaacgt ctaggccccc cgaaccacgg    3720
ggacgtggtt ttcctttgaa aaacacgatg ataagcttgc cacaacccett accggtcgcc    3780 accatgagcg agctgattaa ggagaacatg cacatgaagc tgtacatgga gggcaccgtg    3840
gacaaccatc acttcaagtg cacatccgag ggcgaaggca agccctacga gggcacccag    3900
accatgagaa tcaaggtggt cgagggcggc cctctcccct tcgccttcga catcctggct    3960
actagcttcc tctacggcag caagaccttc atcaaccaca cccagggcat ccccgacttc    4020
ttcaagcagt ccttccctga gggcttcaca tgggagagag tcaccacata cgaagacggg    4080
ggcgtgctga ccgctaccca ggacaccagc ctccaggacg gctgcctcat ctacaacgtc    4140
aagatcagag gggtgaactt cacatccaac ggccctgtga tgcagaagaa aacactcggc    4200
tgggaggcct tcaccgagac gctgtacccc gctgacggcg gcctggaagg cagaaacgac    4260
atggccctga gctcgtgggg cgggagccat ctgatcgcaa acatcaagac cacatataga    4320
tccaagaaac ccgctaagaa cctcaagatg cctggcgtct actatgtgga ctacagactg    4380
gaaagaatca aggaggccaa caacgagacc tacgtcgagc agcacgaggt ggcagtggcc    4440
agatactgcg acctccctag caaactgggg cacaagctta attgattcta gagtcgaccg    4500
agcatcttac cgccatttat acccatattt gttctgtttt tcttgatttg ggtatacatt    4560
taaatgttaa tagaacaaaa tggtggggca atcatttaca tttttaggga tatgtaatta    4620
ctagttcagg tgtattgcca caagacaaac atgttaagaa actttcccgt tatttacgct    4680
ctgttcctgt taatcaacct ctggattaca aaatttgtga agattgact gatattctta    4740 actatgttgc tccttttacg ctgtgtggat atgctgcttt atagcctctg tatctagcta    4800
ttgcttcccg tacggctttc gttttctcct ccttgtataa atcctggttg ctgtctcttt    4860
tagaggagtt gtggcccgtt gtccgtcaac gtggcgtggt gtgctctgtg tttgctgacg    4920
caacccccac tggctgggc attgccacca cctgtcaact cctttctggg actttcgctt    4980
tccccctccc gatcgccacg gcagaactca tcgccgcctg ccttgcccgc tgctggacag    5040
gggctaggtt gctgggcact gataattccg tggtgttgtc atcggtacct tttaaaaga    5100 aaggggggga ctggaagggc taattcactc ccaacgaaga caagatatca aacttcgta    5160 tagcatacat tatacgaagt tataaattta ttgtgaaatt tgtgatgcta ttgctttatt    5220
tgtaaccata tgtttatttg tgaaatttgt gatgctattg ctttatttgt aaccattgct    5280
ttttgcttgt actgggtctc tctggttaga ccagatctga gcctgggagc tctctggcta    5340
actagggaac ccactgctta agcctcaata aagcttgcct cgaccagcct cgactgtgcc    5400
ttctagttgc cagccatctg ttgtttgccc ctcccccgtg ccttccttga ccctggaagg    5460
tgccactccc actgtccttt cctaataaaa tgaggaaatt gcatcgcatt gtctgagtag    5520
gtgtcattct attctggggg gtggggtggg caggacagc aagggggagg attgggaaga    5580
caatagcagg catgctgggg atgcggtggg ctctatggcc tgcagctgca ttaatgaatc    5640
ggccaacgcg cggggagagg cggtttgcgt attgggcgct cttccgcttc ctcgctcact    5700
gactcgctgc gctcggtcgt tcggctgcgg cgagcggtat cagctcactc aaaggcggta    5760
atacggttat ccacagaatc aggggataac gcaggaaaga acatgtgagc aaaaggccag    5820
caaaaggcca ggaaccgtaa aaaggccgcg ttgctggcgt ttttccatag gctccgcccc    5880
cctgacgagc atcacaaaaa tcgacgctca agtcagaggt ggcgaaaccc gacaggacta    5940
taaagatacc aggcgtttcc ccctggaagc tccctcgtgc gctctcctgt tccgaccctg    6000
```

```
ccgcttaccg gatacctgtc cgcctttctc ccttcgggaa gcgtggcgct ttctcatagc      6060
tcacgctgta ggtatctcag ttcggtgtag gtcgttcgct ccaagctggg ctgtgtgcac      6120
gaaccccccg ttcagcccga ccgctgcgcc ttatccggta actatcgtct tgagtccaac      6180
ccggtaagac acgacttatc gccactggca gcagccactg gtaacaggat tagcagagcg      6240
aggtatgtag gcggtgctac agagttcttg aagtggtggc ctaactacgg ctacactaga      6300
aggacagtat ttggtatctg cgctctgctg aagccagtta ccttcggaaa aagagttggt      6360
agctcttgat ccggcaaaca aaccaccgct ggtagcggtg gtttttttgt ttgcaagcag      6420
cagattacgc gcagaaaaaa aggatctcaa gaagatcctt tgatcttttc tacggggtct      6480
gacgctcagt ggaacgaaaa ctcacgttaa gggattttgg tcatgagatt atcaaaaagg      6540
atcttcacct agatcctttt aaattaaaaa tgaagtttta aatcaatcta agtatatat       6600 gagtaaactt ggtctgacag ttaccaatgc ttaatcagtg aggcacctat ctcagcgatc      6660
tgtctatttc gttcatccat agttgcctga ctccccgtcg tgtagataac tacgatacgg      6720
gagggcttac catctggccc cagtgctgca atgataccgc gagacccacg ctcaccggct      6780
ccagatttat cagcaataaa ccagccagcc ggaagggccg agcgcagaag tggtcctgca      6840
actttatccg cctccatcca gtctattaat tgttgccggg aagctagagt aagtagttcg      6900
ccagttaata gtttgcgcaa cgttgttgcc attgctacag gcatcgtggt gtcacgctcg      6960
tcgtttggta tggcttcatt cagctccggt tcccaacgat caaggcgagt tacatgatcc      7020
cccatgttgt gcaaaaaagc ggttagctcc ttcggtcctc cgatcgttgt cagaagtaag      7080
ttggccgcag tgttatcact catggttatg gcagcactgc ataattctct tactgtcatg      7140
ccatccgtaa gatgcttttc tgtgactggt gagtactcaa ccaagtcatt ctgagaatag      7200
tgtatgcggc gaccgagttg ctcttgcccg gcgtcaatac gggataatac cgcgccacat      7260
agcagaactt taaaagtgct catcattgga aaacgttctt cggggcgaaa actctcaagg      7320
atcttaccgc tgttgagatc cagttcgatg taacccactc gtgcacccaa ctgatcttca      7380
gcatctttta ctttcaccag cgtttctggg tgagcaaaaa caggaaggca aaatgccgca      7440
aaaaagggaa taagggcgac acggaaatgt tgaatactca tactcttcct ttttcaatat      7500
tattgaagca tttatcaggg ttattgtctc atgagcggat acatatttga atgtatttag      7560
aaaaataaac aaatagggGt tccgcgcaca tttccccgaa aagtgccacc t               7611
```

<210> SEQ ID NO 112
<211> LENGTH: 8394
<212> TYPE: DNA
<213> ORGANISM: Artificial Sequence
<220> FEATURE:
<223> OTHER INFORMATION: Plasmid
    pCVL.SFFV.HA.NLS.Sce(Opt).T2A.Trex2.IRES.mTagBFP

<400> SEQUENCE: 112

```
gacgtcaatg tagtcttatg caatactctt gtagtcttgc aacatggtaa cgatgagtta      60
gcaacatgcc ttacaaggag agaaaaagca ccgtgcatgc cgattggtgg aagtaaggtg      120
gtacgatcgt gccttattag gaaggcaaca gacgggtctg acatggattg gacgaaccac      180
tgaattgccg cattgcagag atattgtatt taagtgccta gctcgataca taaacgggtc      240
tctctggtta gaccagatct gagcctggga gctctctggc taactaggga acccactgct      300
taagcctcaa taaagcttgc cttgagtgct tcaagtagtg tgtgcccgtc tgttgtgtga      360
ctctggtaac tagagatccc tcagaccctt ttagtcagtg tggaaaatct ctagcagtgg      420
```

```
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg     600
gggagaatta gatcgcgatg ggaaaaaatt cggttaaggc caggggggaaa gaaaaaatat   660 aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa agggggggatt gggggggtaca gtgcagggga agaatagta   1860 gacataatag caacagacat acaaactaaa gaattacaaa aacaaattac aaaaattcaa   1920
aattttatcg attacgcgtc acgtgctagc tgcagtaacg ccatttttgca aggcatggaa   1980 aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc    2280
gcttctgctt cccgagctct ataaaagagc tcacaacccc tcactcggcg cgccagtcct   2340
ccgacagact gagtcgcccg ctcgagccgc caccatggga tatccatacg atgtcccaga    2400
ttatgcgcca cctaagaaga aacgcaaagt cgaattcaag aacatcaaga agaaccaggt   2460
catgaacctg ggccccaaca gcaagctgct gaaggagtac aagagccagc tgatcgagct   2520
gaacatcgag cagttcgagg ccggcatcgg cctgatcctg gcgacgcct acatcaggag    2580 cagggacgag ggcaagacct actgcatgca gttcgagtgg aagaacaagg cctacatgga   2640
ccacgtgtgc ctgctgtacg accagtgggt gctgagcccc cccacaaga aggagagggt     2700 gaaccacctg ggcaacctgg tcatcacctg gggcgcccag accttcaagc accaggcctt   2760
```

```
caacaagctg gccaacctgt tcatcgtgaa caacaagaag accatcccca caacctggt     2820
ggagaactac ctgaccccca tgagcctggc ctactggttc atggacgacg cggcaagtg     2880
ggactacaac aagaacagca ccaacaagag catcgtgctg aacacccaga gcttcacctt     2940
cgaggaggtg gagtacctgg tgaagggcct gaggaacaag ttccagctga actgctacgt     3000
gaagatcaac aagaacaagc ccatcatcta catcgacagc atgagctacc tgatcttcta     3060
caacctgatc aagccctacc tgatccccca gatgatgtac aagctgccca acaccatcag     3120
cagcgagacc ttcctgaagg gcggcggcgg atccggtgag ggcagaggaa gtcttctaac     3180
atgcggtgac gtggaggaga atccgggccc ctccggatct gagccacctc gggctgagac     3240
cttttgtattc ctggacctag aagccactgg gctcccaaac atggaccctg agattgcaga     3300
gatatccctt tttgctgttc accgctcttc cctggagaac ccagaacggg atgattctgg     3360
ttccttggtg ctgccccgtg ttctggacaa gctcacactg tgcatgtgcc cggagcgccc     3420
cttttactgcc aaggccagtg agattactgg tttgagcagc gaaagccttga tgcactgcgg     3480
gaaggctggt ttcaatggcg ctgtggtaag gacactgcag ggcttcctaa gccgccagga     3540
gggcccatcc tgccttgtgg cccacaatgg cttcgattat gacttccac tgctgtgcac      3600
ggagctacaa cgtctgggtg cccatctgcc ccaagacact gtctgcctgg acacactgcc     3660
tgcattgcgg ggcctggacc gtgctcacag ccacggcacc agggctcaag gccgcaaaag     3720
ctacagcctg gccagtctct tccaccgcta cttccaggct gaacccagtg ctgcccattc     3780
agcagaaggt gatgtgcaca ccctgcttct gatcttcctg catcgtgctc ctgagctgct     3840
cgcctgggca gatgagcagg cccgcagctg ggctcatatt gagcccatgt acgtgccacc     3900
tgatggtcca agcctcgaag cctgacctgc aggtcgagca tgcatctagg gcggccaatt     3960
ccgcccctct ccctccccc cccctaacgt tactggccga agccgcttgg aataaggccg     4020
gtgtgcgttt gtctatatgt gattttccac catattgccg tcttttggca atgtgagggc     4080
ccggaaacct ggccctgtct tcttgacgag cattcctagg ggtctttccc ctctcgccaa     4140
aggaatgcaa ggtctgttga atgtcgtgaa ggaagcagtt cctctggaag cttcttgaag     4200
acaaacaacg tctgtagcga ccccttttgcag gcagcggaac cccccacctg cgacaggtg     4260
cctctgcggc caaaagccac gtgtataaga tacacctgca aaggcggcac aaccccagtg     4320
ccacgttgtg agttggatag ttgtggaaag agtcaaatgg ctctcctcaa gcgtattcaa     4380
caagggctg aaggatgccc agaaggtacc ccattgtatg ggatctgatc tggggcctcg     4440
gtgcacatgc tttacatgtg tttagtcgag gttaaaaaaa cgtctaggcc cccgaaacca     4500
cggggacgtg gttttccttt gaaaaacacg atgataagct tgccacaacc cttaccggtc     4560
gccaccatga gcgagctgat taaggagaac atgcacatga agctgtacat ggagggcacc     4620
gtggacaacc atcacttcaa gtgcacatcc gagggcgaag gcaagcccta cgagggcacc     4680
cagaccatga gaatcaaggt ggtcgagggc ggccctctcc ccttcgcctt cgacatcctg     4740
gctactagct tcctctacgg cagcaagacc ttcatcaacc acacccaggg catcccgac     4800
ttcttcaagc agtccttccc tgagggcttc acatgggaga gagtcaccac atacgaagac     4860
gggggcgtgc tgaccgctac ccaggacacc agcctccagg acggctgcct catctacaac     4920
gtcaagatca gaggggtgaa cttcacatcc aacggccctg tgatgcagaa gaaaacactc     4980
ggctgggagg ccttcaccga gacgctgtac cccgctgacg gcggcctgga aggcagaaac     5040
gacatggccc tgaagctcgt gggcgggagc catctgatcg caaacatcaa gaccacatat     5100
agatccaaga aacccgctaa gaacctcaag atgcctggcg tctactatgt ggactacaga     5160
```

```
ctggaaagaa tcaaggaggc caacaacgag acctacgtcg agcagcacga ggtggcagtg   5220
gccagatact gcgacctccc tagcaaactg gggcacaagc ttaattgatt ctagagtcga   5280
ccgagcatct taccgccatt tatacccata tttgttctgt ttttcttgat ttgggtatac   5340
atttaaatgt taatagaaca aaatggtggg gcaatcattt acattttag ggatatgtaa    5400 ttactagttc aggtgtattg ccacaagaca aacatgttaa gaaactttcc cgttatttac   5460
gctctgttcc tgttaatcaa cctctggatt acaaaatttg tgaaagattg actgatattc   5520
ttaactatgt tgctcctttt acgctgtgtg gatatgctgc tttatagcct ctgtatctag   5580
ctattgcttc ccgtacggct ttcgttttct cctccttgta taaatcctgg ttgctgtctc   5640
ttttagagga gttgtggccc gttgtccgtc aacgtggcgt ggtgtgctct gtgtttgctg   5700
acgcaacccc cactggctgg ggcattgcca ccacctgtca actcctttct gggactttcg   5760
ctttccccct cccgatcgcc acggcagaac tcatcgccgc ctgccttgcc cgctgctgga   5820
caggggctag gttgctgggc actgataatt ccgtggtgtt gtcatcggta ccttttttaaa  5880 agaaaagggg ggactggaag ggctaattca ctcccaacga agacaagata tcataacttc   5940
gtatagcata cattatacga agttataatt tatttgtgaa atttgtgatg ctattgcttt   6000
atttgtaacc atatgtttat ttgtgaaatt tgtgatgcta ttgctttatt tgtaaccatt   6060 gcttttgct tgtactgggt ctctctggtt agaccagatc tgagcctggg agctctctgg    6120
ctaactaggg aacccactgc ttaagcctca ataaagcttg cctcgaccag cctcgactgt   6180
gccttctagt tgccagccat ctgttgtttg cccctccccc gtgccttcct tgaccctgga   6240
aggtgccact cccactgtcc tttcctaata aaatgaggaa attgcatcgc attgtctgag   6300
taggtgtcat tctattctgg ggggtggggt ggggcaggac agcaagggg aggattggga    6360 agacaatagc aggcatgctg gggatgcggt gggctctatg gcctgcagct gcattaatga   6420
atcggccaac gcgcggggag aggcggtttg cgtattgggc gctcttccgc ttcctcgctc   6480
actgactcgc tgcgctcggt cgttcggctg cggcgagcgg tatcagctca ctcaaaggcg   6540
gtaatacggt tatccacaga atcagggga acgcaggaa agaacatgtg agcaaaaggc     6600
cagcaaaagg ccaggaaccg taaaaaggcc gcgttgctgg cgttttttcca taggctccgc   6660 ccccctgacg agcatcacaa aaatcgacgc tcaagtcaga ggtggcgaaa cccgacagga   6720
ctataaagat accaggcgtt tccccctgga agctccctcg tgcgctctcc tgttccgacc   6780
ctgccgctta ccggatacct gtccgccttt ctcccttcgg gaagcgtggc gctttctcat   6840
agctcacgct gtaggtatct cagttcggtg taggtcgttc gctccaagct gggctgtgtg   6900
cacgaacccc ccgttcagcc cgaccgctgc gccttatccg gtaactatcg tcttgagtcc   6960
aacccggtaa gacacgactt atcgccactg gcagcagcca ctggtaacag gattagcaga   7020
gcgaggtatg taggcggtgc tacagagttc ttgaagtggt ggcctaacta cggctacact   7080
agaaggacag tatttggtat ctgcgctctg ctgaagccag ttaccttcgg aaaaagagtt   7140
ggtagctctt gatccggcaa acaaaccacc gctggtagcg gtggtttttt tgtttgcaag   7200
cagcagatta cgcgcagaaa aaaggatct caagaagatc ctttgatctt ttctacgggg    7260
tctgacgctc agtggaacga aaactcacgt taagggattt tggtcatgag attatcaaaa   7320
aggatcttca cctagatcct tttaaattaa aaatgaagtt ttaaatcaat ctaaagtata   7380
tatgagtaaa cttggtctga cagttaccaa tgcttaatca gtgaggcacc tatctcagcg   7440
atctgtctat ttcgttcatc catagttgcc tgactccccg tcgtgtagat aactacgata   7500
```

|  |  |
|---|---|
| cgggagggct taccatctgg ccccagtgct gcaatgatac cgcgagaccc acgctcaccg | 7560 |
| gctccagatt tatcagcaat aaaccagcca gccggaaggg ccgagcgcag aagtggtcct | 7620 |
| gcaactttat ccgcctccat ccagtctatt aattgttgcc gggaagctag agtaagtagt | 7680 |
| tcgccagtta atagtttgcg caacgttgtt gccattgcta caggcatcgt ggtgtcacgc | 7740 |
| tcgtcgtttg gtatggcttc attcagctcc ggttcccaac gatcaaggcg agttacatga | 7800 |
| tcccccatgt tgtgcaaaaa agcggttagc tccttcggtc ctccgatcgt tgtcagaagt | 7860 |
| aagttggccg cagtgttatc actcatggtt atggcagcac tgcataattc tcttactgtc | 7920 |
| atgccatccg taagatgctt ttctgtgact ggtgagtact caaccaagtc attctgagaa | 7980 |
| tagtgtatgc ggcgaccgag ttgctcttgc ccggcgtcaa tacgggataa taccgcgcca | 8040 |
| catagcagaa ctttaaaagt gctcatcatt ggaaaacgtt cttcggggcg aaaactctca | 8100 |
| aggatcttac cgctgttgag atccagttcg atgtaaccca ctcgtgcacc caactgatct | 8160 |
| tcagcatctt ttactttcac cagcgtttct gggtgagcaa aaacaggaag gcaaaatgcc | 8220 |
| gcaaaaaagg gaataagggc gacacggaaa tgttgaatac tcatactctt cctttttcaa | 8280 |
| tattattgaa gcatttatca gggttattgt ctcatgagcg gatacatatt tgaatgtatt | 8340 |
| tagaaaaata aacaaatagg ggttccgcgc acatttcccc gaaaagtgcc acct | 8394 |

<210> SEQ ID NO 113
<211> LENGTH: 8394
<212> TYPE: DNA
<213> ORGANISM: Artificial Sequence
<220> FEATURE:
<223> OTHER INFORMATION: Plasmid
      pCVL.SFFV.HA.NLS.SceOptD44A.T2A.Trex2.IRES.mTagBFP

<400> SEQUENCE: 113

|  |  |
|---|---|
| gacgtcaatg tagtcttatg caatactctt gtagtcttgc aacatggtaa cgatgagtta | 60 |
| gcaacatgcc ttacaaggag agaaaaagca ccgtgcatgc cgattggtgg aagtaaggtg | 120 |
| gtacgatcgt gccttattag gaaggcaaca gacgggtctg acatggattg gacgaaccac | 180 |
| tgaattgccg cattgcagag atattgtatt taagtgccta gctcgataca taaacgggtc | 240 |
| tctctggtta gaccagatct gagcctggga gctctctggc taactaggga acccactgct | 300 |
| taagcctcaa taaagcttgc cttgagtgct tcaagtagtg tgtgcccgtc tgttgtgtga | 360 |
| ctctggtaac tagagatccc tcagaccctt ttagtcagtg tggaaaatct ctagcagtgg | 420 |
| cgcccgaaca gggacttgaa agcgaaaggg aaaccagagg agctctctcg acgcaggact | 480 |
| cggcttgctg aagcgcgcac ggcaagaggc gaggggcggc gactggtgag tacgccaaaa | 540 |
| attttgacta gcggaggcta aaggagaga gatgggtgcg agagcgtcag tattaagcgg | 600 |
| gggagaatta gatcgcgatg ggaaaaaatt cggttaaggc caggggggaaa gaaaaaatat | 660 |
| aaattaaaac atatagtatg ggcaagcagg gagctagaac gattcgcagt taatcctggc | 720 |
| ctgttagaaa catcagaagg ctgtagacaa atactgggac agctacaacc atcccttcag | 780 |
| acaggatcag aagaacttag atcattatat aatacagtag caaccctcta ttgtgtgcat | 840 |
| caaaggatag agataaaaga caccaaggaa gctttagaca agatagagga agagcaaaac | 900 |
| aaaagtaaga ccaccgcaca gcaagcggcc ctgatcttca gacctggagg aggagatatg | 960 |
| agggacaatt ggagaagtga attatataaa tataaagtag taaaaattga accattagga | 1020 |
| gtagcaccca ccaaggcaaa gagaagagtg gtgcagagag aaaaaagagc agtgggaata | 1080 |
| ggagctttgt tccttgggtt cttgggagca gcaggaagca ctatgggcgc agcgtcaatg | 1140 |

-continued

```
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctgggatt     1320
tgggggttgct ctggaaaact catttgcacc actgctgtgc cttggaatgc tagttggagt   1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800
cggttaactt ttaaaagaaa aggggggatt ggggggtaca gtgcagggga agaatagta     1860
gacataatag caacagacat acaaactaaa gaattacaaa acaaattac aaaaattcaa     1920
aattttatcg attacgcgtc acgtgctagc tgcagtaacg ccattttgca aggcatggaa    1980
aaataccaaa ccaagaatag agaagttcag atcaagggcg ggtacatgaa aatagctaac    2040
gttgggccaa acaggatatc tgcggtgagc agtttcggcc ccggcccggg gccaagaaca    2100
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
gcttctgctt cccgagctct ataaaagagc tcacaaccc ctcactcggcg cgccagtcct    2340
ccgacagact gagtcgcccg ctcgagccgc caccatggga tatccatacg atgtcccaga    2400
ttatgcgcca cctaagaaga acgcaaagt cgaattcaag aacatcaaga gaaccaggt     2460
catgaacctg gcccccaaca gcaagctgct gaaggagtac aagagccagc tgatcgagct    2520
gaacatcgag cagttcgagg ccggcatcgg cctgatcctg ggcgctgcct acatcaggag    2580
cagggacagg ggcaagacct actgcatgca gttcgagtgg aagaacaagg cctacatgga    2640
ccacgtgtgc ctgctgtacg accagtgggt gctgagcccc cccacaaga aggagagggt    2700
gaaccacctg ggcaacctgg tcatcacctg gggcgcccag accttcaagc accaggcctt    2760
caacaagctg gccaacctgt tcatcgtgaa caacaagaag accatcccca caacctggt     2820
ggagaactac ctgaccccca tgagcctggc ctactggttc atggacgacg cggcaagtg     2880
ggactacaac aagaacagca ccaacaagag catcgtgctg aacacccaga gcttcaccct    2940
cgaggaggtg gagtacctgg tgaagggcct gaggaacaag ttccagctga actgctacgt    3000
gaagatcaac aagaacaagc ccatcatcta catcgacagc atgagctacc tgatcttcta    3060
caacctgatc aagccctacc tgatccccca tgatgtgtac aagctgccca caccatcag    3120
cagcgagacc ttcctgaagg gcggcggcgg atccggtgag ggcagaggaa gtcttctaac    3180
atgcggtgac gtggaggaga atccgggccc ctccggatct gagccacctc gggctgagac    3240
ctttgtattc ctggacctag aagccactgg gctcccaaac atggaccctg agattgcaga    3300
gatatcccct tttgctgttc accgctcttc cctggagaac ccagaacggg atgattctgg    3360
ttccttggtg ctgccccgtg ttctggacaa gctcacactg tgcatgtgcc ggagcgccc    3420
ctttactgcc aaggccagtg agattactgg tttgagcagc gaaagcctga tgcactgcg    3480
gaaggctggt ttcaatggcg ctgtggtaag gacactgcag ggcttcctaa gccgccagga    3540
```

```
gggcccatc tgccttgtgg cccacaatgg cttcgattat gacttccac tgctgtgcac      3600 ggagctacaa cgtctgggtg cccatctgcc ccaagacact gtctgcctgg acacactgcc     3660
tgcattgcgg ggcctggacc gtgctcacag ccacggcacc agggctcaag gccgcaaaag     3720
ctacagcctg gccagtctct tccaccgcta cttccaggct gaacccagtg ctgcccattc     3780
agcagaaggt gatgtgcaca ccctgcttct gatcttcctg catcgtgctc ctgagctgct     3840
cgcctgggca gatgagcagg cccgcagctg ggctcatatt gagcccatgt acgtgccacc     3900
tgatggtcca agcctcgaag cctgacctgc aggtcgagca tgcatctagg gcggccaatt     3960
ccgcccctct ccctcccccc ccctaacgt tactggccga agccgcttgg aataaggccg      4020
gtgtgcgttt gtctatatgt gattttccac catattgccg tcttttggca atgtgagggc     4080
ccggaaacct ggccctgtct tcttgacgag cattcctagg ggtctttccc ctctcgccaa     4140
aggaatgcaa ggtctgttga atgtcgtgaa ggaagcagtt cctctggaag cttcttgaag     4200
acaaacaacg tctgtagcga ccctttgcag gcagcggaac ccccccactg gcgacaggtg     4260
cctctgcggc caaaagccac gtgtataaga tacacctgca aaggcggcac aaccccagtg     4320
ccacgttgtg agttggatag ttgtggaaag agtcaaatgg ctctcctcaa gcgtattcaa     4380 caagggctg aaggatgccc agaaggtacc ccattgtatg ggatctgatc tggggcctcg      4440
gtgcacatgc tttacatgtg tttagtcgag gttaaaaaaa cgtctaggcc cccgaacca      4500 cggggacgtg gttttccttt gaaaaacacg atgataagct tgccacaacc cttaccggtc     4560
gccaccatga gcgagctgat taaggagaac atgcacatga agctgtacat ggagggcacc     4620
gtggacaacc atcacttcaa gtgcacatcc gagggcgaag gcaagcccta cgagggcacc     4680
cagaccatga gaatcaaggt ggtcgagggc ggccctctcc ccttcgcctt cgacatcctg     4740
gctactagct tcctctacgg cagcaagacc ttcatcaacc acacccaggg catccccgac     4800
ttcttcaagc agtccttccc tgagggcttc acatgggaga gagtcaccac atacgaagac     4860
gggggcgtgc tgaccgctac ccaggacacc agcctccagg acggctgcct catctacaac     4920
gtcaagatca gagggtgaa cttcacatcc aacggccctg tgatgcagaa gaaaacactc      4980
ggctgggagg ccttcaccga gacgctgtac cccgctgacg gcggcctgga aggcagaaac     5040
gacatggccc tgaagctcgt gggcgggagc catctgatcg caaacatcaa gaccacatat     5100
agatccaaga aacccgctaa gaacctcaag atgcctggcg tctactatgt ggactacaga     5160
ctggaaagaa tcaaggaggc caacaacgag acctacgtcg agcagcacga ggtggcagtg     5220
gccagatact gcgacctccc tagcaaactg gggcacaagc ttaattgatt ctagagtcga     5280
ccgagcatct taccgccatt tatacccata tttgttctgt ttttcttgat ttgggtatac     5340
atttaaatgt taatagaaca aaatggtggg gcaatcattt acattttag ggatatgtaa      5400 ttactagttc aggtgtattg ccacaagaca aacatgttaa gaaactttcc cgttatttac     5460
gctctgttcc tgttaatcaa cctctggatt acaaaatttg tgaaagattg actgatattc     5520
ttaactatgt tgctcctttt acgctgtgtg gatatgctgc tttatagcct ctgtatctag     5580
ctattgcttc ccgtacggct ttcgttttct cctccttgta taaatcctgg ttgctgtctc     5640
ttttagagga gttgtggccc gttgtccgtc aacgtggcgt ggtgtgctct gtgtttgctg     5700
acgcaacccc cactggctgg ggcattgcca ccacctgtca actcctttct gggactttcg     5760
ctttccccct cccgatcgcc acggcagaac tcatcgccgc ctgccttgcc cgctgctgga     5820 cagggggctag gttgctgggc actgataatt ccgtggtgtt gtcatcggta ccttttaaa      5880
```

| | |
|---|---|
| agaaaaggggg ggactggaag ggctaattca ctcccaacga agacaagata tcataacttc | 5940 |
| gtatagcata cattatacga agttataatt tatttgtgaa atttgtgatg ctattgcttt | 6000 |
| atttgtaacc atatgtttat ttgtgaaatt tgtgatgcta ttgctttatt tgtaaccatt | 6060 |
| gcttttgct tgtactgggt ctctctggtt agaccagatc tgagcctggg agctctctgg | 6120 |
| ctaactaggg aacccactgc ttaagcctca ataaagcttg cctcgaccag cctcgactgt | 6180 |
| gccttctagt tgccagccat ctgttgtttg cccctccccc gtgccttcct tgaccctgga | 6240 |
| aggtgccact cccactgtcc tttcctaata aaatgaggaa attgcatcgc attgtctgag | 6300 |
| taggtgtcat tctattctgg ggggtggggt ggggcaggac agcaagggg aggattggga | 6360 |
| agacaatagc aggcatgctg gggatgcggt gggctctatg gcctgcagct gcattaatga | 6420 |
| atcggccaac gcgcgggag aggcggtttg cgtattgggc gctcttccgc ttcctcgctc | 6480 |
| actgactcgc tgcgctcggt cgttcggctg cggcgagcgg tatcagctca ctcaaaggcg | 6540 |
| gtaatacggt tatccacaga atcagggat aacgcaggaa agaacatgtg agcaaaaggc | 6600 |
| cagcaaaagg ccaggaaccg taaaaaggcc gcgttgctgg cgtttttcca taggctccgc | 6660 |
| ccccctgacg agcatcacaa aaatcgacgc tcaagtcaga ggtggcgaaa cccgacagga | 6720 |
| ctataaagat accaggcgtt tccccctgga agctccctcg tgcgctctcc tgttccgacc | 6780 |
| ctgccgctta ccggatacct gtccgccttt ctcccttcgg gaagcgtggc gctttctcat | 6840 |
| agctcacgct gtaggtatct cagttcggtg taggtcgttc gctccaagct gggctgtgtg | 6900 |
| cacgaacccc ccgttcagcc cgaccgctgc gccttatccg gtaactatcg tcttgagtcc | 6960 |
| aacccggtaa gacacgactt atcgccactg gcagcagcca ctggtaacag gattagcaga | 7020 |
| gcgaggtatg taggcggtgc tacagagttc ttgaagtggt ggcctaacta cggctacact | 7080 |
| agaaggacag tatttggtat ctgcgctctg ctgaagccag ttaccttcgg aaaaagagtt | 7140 |
| ggtagctctt gatccggcaa acaaaccacc gctggtagcg gtggtttttt tgtttgcaag | 7200 |
| cagcagatta cgcgcagaaa aaaggatctc aagaagatc ctttgatctt ttctacgggg | 7260 |
| tctgacgctc agtggaacga aaactcacgt taagggattt tggtcatgag attatcaaaa | 7320 |
| aggatcttca cctagatcct tttaaattaa aaatgaagtt ttaaatcaat ctaaagtata | 7380 |
| tatgagtaaa cttggtctga cagttaccaa tgcttaatca gtgaggcacc tatctcagcg | 7440 |
| atctgtctat ttcgttcatc catagttgcc tgactccccg tcgtgtagat aactacgata | 7500 |
| cgggagggct taccatctgg ccccagtgct gcaatgatac cgcgagaccc acgctcaccg | 7560 |
| gctccagatt tatcagcaat aaaccagcca gccggaaggg ccgagcgcag aagtggtcct | 7620 |
| gcaactttat ccgcctccat ccagtctatt aattgttgcc gggaagctag agtaagtagt | 7680 |
| tcgccagtta atagtttgcg caacgttgtt gccattgcta caggcatcgt ggtgtcacgc | 7740 |
| tcgtcgtttg gtatggcttc attcagctcc ggttcccaac gatcaaggcg agttacatga | 7800 |
| tcccccatgt tgtgcaaaaa agcggttagc tccttcggtc ctccgatcgt tgtcagaagt | 7860 |
| aagttggccg cagtgttatc actcatggtt atggcagcac tgcataattc tcttactgtc | 7920 |
| atgccatccg taagatgctt ttctgtgact ggtgagtact caaccaagtc attctgagaa | 7980 |
| tagtgtatgc ggcgaccgag ttgctcttgc ccggcgtcaa tacgggataa taccgcgcca | 8040 |
| catagcagaa ctttaaaagt gctcatcatt ggaaaacgtt cttcggggcg aaaactctca | 8100 |
| aggatcttac cgctgttgag atccagttcg atgtaaccca ctcgtgcacc caactgatct | 8160 |
| tcagcatctt ttactttcac cagcgtttct gggtgagcaa aaacaggaag gcaaaatgcc | 8220 |
| gcaaaaaagg gaataagggc gacacggaaa tgttgaatac tcatactctt cctttttcaa | 8280 |

| | | |
|---|---|---|
| tattattgaa gcatttatca gggttattgt ctcatgagcg gatacatatt tgaatgtatt | 8340 | |
| tagaaaaata aacaaatagg ggttccgcgc acatttcccc gaaaagtgcc acct | 8394 | |

<210> SEQ ID NO 114
<211> LENGTH: 7671
<212> TYPE: DNA
<213> ORGANISM: Artificial Sequence
<220> FEATURE:
<223> OTHER INFORMATION: Plasmid pCVL.SFFV.HA.NLS.I-Ani I.IRES.mTagBFP

<400> SEQUENCE: 114

| | |
|---|---|
| gacgtcaatg tagtcttatg caatactctt gtagtcttgc aacatggtaa cgatgagtta | 60 |
| gcaacatgcc ttacaaggag agaaaaagca ccgtgcatgc cgattggtgg aagtaaggtg | 120 |
| gtacgatcgt gccttattag gaaggcaaca gacgggtctg acatggattg gacgaaccac | 180 |
| tgaattgccg cattgcagag atattgtatt taagtgccta gctcgataca taaacgggtc | 240 |
| tctctggtta gaccagatct gagcctggga gctctctggc taactaggga acccactgct | 300 |
| taagcctcaa taaagcttgc cttgagtgct tcaagtagtg tgtgcccgtc tgttgtgtga | 360 |
| ctctggtaac tagagatccc tcagaccctt ttagtcagtg tggaaaatct ctagcagtgg | 420 |
| cgcccgaaca gggacttgaa agcgaaaggg aaaccagagg agctctctcg acgcaggact | 480 |
| cggcttgctg aagcgcgcac ggcaagaggc gaggggcggc gactggtgag tacgccaaaa | 540 |
| attttgacta gcggaggcta aaggagaga gatgggtgcg agagcgtcag tattaagcgg | 600 |
| gggagaatta gatcgcgatg ggaaaaaatt cggttaaggc cagggggaaa gaaaaaatat | 660 |
| aaattaaaac atatagtatg ggcaagcagg gagctagaac gattcgcagt taatcctggc | 720 |
| ctgttagaaa catcagaagg ctgtagacaa atactgggac agctacaacc atcccttcag | 780 |
| acaggatcag aagaacttag atcattatat aatacagtag caaccctcta ttgtgtgcat | 840 |
| caaaggatag agataaaaga caccaaggaa gctttagaca agatagagga gagcaaaac | 900 |
| aaaagtaaga ccaccgcaca gcaagcggcc ctgatcttca gacctggagg aggagatatg | 960 |
| agggacaatt ggagaagtga attatataaa tataaagtag taaaaattga accattagga | 1020 |
| gtagcaccca ccaaggcaaa gagaagagtg gtgcagagag aaaaaagagc agtgggaata | 1080 |
| ggagctttgt tccttgggtt cttgggagca gcaggaagca ctatgggcgc agcgtcaatg | 1140 |
| acgctgacgg tacaggccag acaattattg tctggtatag tgcagcagca gaacaatttg | 1200 |
| ctgagggcta ttgaggcgca acagcatctg ttgcaactca cagtctgggg catcaagcag | 1260 |
| ctccaggcaa gaatcctggc tgtggaaaga tacctaaagg atcaacagct cctggggatt | 1320 |
| tggggttgct ctggaaaact catttgcacc actgctgtgc cttggaatgc tagttggagt | 1380 |
| aatgaatctc tggaacagat ttggaatcac acgacctgga tggagtggga cagagaaatt | 1440 |
| aacaattaca caagcttaat acactcctta attgaagaat cgcaaaacca gcaagaaaag | 1500 |
| aatgaacaag aattattgga attagataaa tgggcaagtt tgtggaattg gtttaacata | 1560 |
| acaaattggc tgtggtatat aaaattattc ataatgatag taggaggctt ggtaggttta | 1620 |
| agaatagttt ttgctgtact ttctatagtg aatagagtta ggcagggata ttcaccatta | 1680 |
| tcgtttcaga cccacctccc aaccccgagg ggacccgaca ggcccgaagg aatagaagaa | 1740 |
| gaaggtggag agagagacag agacagatcc attcgattag tgaacggatc tcgacggtat | 1800 |
| cggttaactt ttaaagaaa agggggggatt ggggggtaca gtgcaggga aagaatagta | 1860 |
| gacataatag caacagacat acaaactaaa gaattacaaa aacaaattac aaaaattcaa | 1920 |

-continued

```
aattttatcg attacgcgtc acgtgctagc tgcagtaacg ccattttgca aggcatggaa      1980
aaataccaaa ccaagaatag agaagttcag atcaagggcg ggtacatgaa aatagctaac      2040
gttgggccaa acaggatatc tgcggtgagc agtttcggcc ccggcccggg gccaagaaca      2100
gatggtcacc gcagtttcgg ccccggcccg aggccaagaa cagatggtcc ccagatatgg      2160
cccaaccctc agcagtttct taagacccat cagatgtttc caggctcccc caaggacctg      2220
aaatgaccct gcgccttatt tgaattaacc aatcagcctg cttctcgctt ctgttcgcgc      2280
gcttctgctt cccgagctct ataaaagagc tcacaacccc tcactcggcg cgccagtcct      2340
ccgacagact gagtcgcccg ctcgagccgc caccatggga tatccatacg atgtcccaga      2400
ttatgcgcca cctaagaaga aacgcaaagt cgaattcggc agcgatctga cctacgccta      2460
tctggtgggc ctgttcgagg cgacggata  tttttccatc actaaaaagg caagtacct       2520 gacctatgag ctgggaattg aactgtctat caaggatgtg cagctgatct acaagatcaa      2580
gaagatcctg gggatcggca ttgtgagctt caggaagaga acgagattg  aaatggtggc      2640 cctgaggatc agggataaga atcacctgaa atctaagatt ctgcccatct tcgagaagta      2700
tcctatgttt agtaacaaac agtacgacta tctgaggttt agaaatgctc tgctgagcgg      2760
catcatctcc ctgaggatc  tgccagacta tacccggtcc gacgagcccc tgaacagcat      2820
cgaatccatc attaatacat cttacttcag tgcctggctg gtgggcttca tcgaggctga      2880
agggtgcttc tctgtgtaca aactgaacaa ggacgatgac tatctgattg ccagttttga      2940
tatcgctcag agggatggag acatcctgat tagcgccatc agaaagtacc tgtccttcac      3000
cacaaaggtg tatctggaca aaacaaattg tagcaaactg aaggtcacta gcgtgcgctc      3060
cgtggagaac atcattaagt tcctgcagaa tgctcctgtg aaactgctgg gcaacaaaaa      3120
gctgcagtac aaactgtggc tgaagcagct gcggaaaatc tctcgctaca gtgaaaaaat      3180
caagattcca tccaattatt aacctgcagg tcgagcatgc atctagggcg gccaattccg      3240
cccctctccc tcccccccc  ctaacgttac tggccgaagc cgcttggaat aaggccggtg      3300
tgcgtttgtc tatatgtgat tttccaccat attgccgtct tttggcaatg tgagggcccg      3360
gaaacctggc cctgtcttct tgacgagcat tcctaggggt cttccctc  tcgccaaagg      3420 aatgcaaggt ctgttgaatg tcgtgaagga agcagttcct ctggaagctt cttgaagaca      3480
aacaacgtct gtagcgaccc tttgcaggca gcggaacccc ccacctgcg  acaggtgcct      3540 ctgcggccaa aagccacgtg tataagatac acctgcaaag gcggcacaac cccagtgcca      3600
cgttgtgagt tggatagttg tggaaagagt caaatggctc tcctcaagcg tattcaacaa      3660
ggggctgaag gatgcccaga aggtacccca ttgtatggga tctgatctgg ggcctcggtg      3720
cacatgcttt acatgtgttt agtcgaggtt aaaaaaacgt ctaggccccc cgaaccacgg      3780
ggacgtggtt ttcctttgaa aaacacgatg ataagcttgc cacaacccttt accggtcgcc      3840 accatgagcg agctgattaa ggagaacatg cacatgaagc tgtacatgga gggcaccgtg      3900
gacaaccatc acttcaagtg cacatccgag ggcgaaggca gccctacga  gggcacccag      3960 accatgagaa tcaaggtggt cgagggcggc cctctcccct tcgccttcga catcctggct      4020
actagcttcc tctacggcag caagaccttc atcaaccaca cccagggcat ccccgacttc      4080
ttcaagcagt ccttccctga gggcttcaca tgggagagag tcaccacata cgaagacggg      4140
ggcgtgctga ccgctaccca ggacaccagc ctccaggacg gctgcctcat ctacaacgtc      4200
aagatcagag gggtgaactt cacatccaac ggccctgtga tgcagaagaa aacactcggc      4260
tgggaggcct tcaccgagac gctgtacccc gctgacggcg gcctggaagg cagaaacgac      4320
```

```
atggccctga agctcgtggg cgggagccat ctgatcgcaa acatcaagac cacatataga    4380
tccaagaaac ccgctaagaa cctcaagatg cctggcgtct actatgtgga ctacagactg    4440
gaaagaatca aggaggccaa caacgagacc tacgtcgagc agcacgaggt ggcagtggcc    4500
agatactgcg acctccctag caaactgggg cacaagctta attgattcta gagtcgaccg    4560
agcatcttac cgccatttat acccatattt gttctgtttt tcttgatttg ggtatacatt    4620
taaatgttaa tagaacaaaa tggtggggca atcatttaca ttttagggga tatgtaatta    4680
ctagttcagg tgtattgcca caagacaaac atgttaagaa actttcccgt tatttacgct    4740
ctgttcctgt taatcaacct ctggattaca aaatttgtga agattgact gatattctta     4800
actatgttgc tccttttacg ctgtgtggat atgctgcttt atagcctctg tatctagcta    4860
ttgcttcccg tacggctttc gttttctcct ccttgtataa atcctggttg ctgtctcttt    4920
tagaggagtt gtggcccgtt gtccgtcaac gtggcgtggt gtgctctgtg tttgctgacg    4980
caacccccac tggctggggc attgccacca cctgtcaact cctttctggg actttcgctt    5040
tccccctccc gatcgccacg gcagaactca tcgccgcctg ccttgcccgc tgctggacag    5100
gggctaggtt gctgggcact gataattccg tggtgttgtc atcggtacct ttttaaaaga    5160
aaaggggggga ctggaagggc taattcactc ccaacgaaga caagatatca taacttcgta   5220
tagcatacat tatacgaagt tataatttat ttgtgaaatt tgtgatgcta ttgctttatt    5280
tgtaaccata tgtttatttg tgaaatttgt gatgctattg ctttatttgt aaccattgct    5340
ttttgcttgt actgggtctc tctggttaga ccagatctga gcctgggagc tctctggcta    5400
actagggaac ccactgctta agcctcaata agcttgcct cgaccagcct cgactgtgcc     5460
ttctagttgc cagccatctg ttgtttgccc ctccccgtg ccttccttga ccctggaagg     5520
tgccactccc actgtccttt cctaataaaa tgaggaaatt gcatcgcatt gtctgagtag    5580
gtgtcattct attctggggg gtggggtggg caggacagc aagggggagg attgggaaga     5640
caatagcagg catgctgggg atgcggtggg ctctatggcc tgcagctgca ttaatgaatc    5700
ggccaacgcg cggggagagg cggtttgcgt attgggcgct cttccgcttc ctcgctcact    5760
gactcgctgc gctcggtcgt tcggctgcgg cgagcggtat cagctcactc aaaggcggta    5820
atacggttat ccacagaatc agggagataac gcaggaaaga acatgtgagc aaaaggccag    5880
caaaaggcca ggaaccgtaa aaaggccgcg ttgctggcgt ttttccatag gctccgcccc    5940
cctgacgagc atcacaaaaa tcgacgctca agtcagaggt ggcgaaaccc gacaggacta    6000
taaagatacc aggcgtttcc ccctggaagc tccctcgtgc gctctcctgt tccgaccctg    6060
ccgcttaccg gatacctgtc cgcctttctc ccttcgggaa gcgtggcgct ttctcatagc    6120
tcacgctgta ggtatctcag ttcggtgtag tcgttcgct ccaagctggg ctgtgtgcac     6180
gaaccccccg ttcagcccga ccgctgcgcc ttatccggta actatcgtct tgagtccaac    6240
ccggtaagac acgacttatc gccactggca gcagccactg gtaacaggat tagcagagcg    6300
aggtatgtag gcggtgctac agagttcttg aagtggtggc ctaactacgg ctacactaga    6360
aggacagtat ttggtatctg cgctctgctg aagccagtta ccttcggaaa aagagttggt    6420
agctcttgat ccggcaaaca aaccaccgct ggtagcggtg gtttttttgt ttgcaagcag    6480
cagattacgc gcagaaaaaa aggatctcaa gaagatcctt tgatcttttc tacggggtct    6540
gacgctcagt ggaacgaaaa ctcacgttaa gggattttgg tcatgagatt atcaaaaagg    6600
atcttcacct agatcctttt aaattaaaaa tgaagtttta atcaatcta aagtatatat     6660
```

| | | | | | |
|---|---|---|---|---|---|
| gagtaaactt | ggtctgacag | ttaccaatgc | ttaatcagtg | aggcacctat | ctcagcgatc | 6720 |
| tgtctatttc | gttcatccat | agttgcctga | ctccccgtcg | tgtagataac | tacgatacgg | 6780 |
| gagggcttac | catctggccc | cagtgctgca | atgataccgc | gagacccacg | ctcaccggct | 6840 |
| ccagatttat | cagcaataaa | ccagccagcc | ggaagggccg | agcgcagaag | tggtcctgca | 6900 |
| actttatccg | cctccatcca | gtctattaat | tgttgccggg | aagctagagt | aagtagttcg | 6960 |
| ccagttaata | gtttgcgcaa | cgttgttgcc | attgctacag | gcatcgtggt | gtcacgctcg | 7020 |
| tcgtttggta | tggcttcatt | cagctccggt | tcccaacgat | caaggcgagt | tacatgatcc | 7080 |
| cccatgttgt | gcaaaaaagc | ggttagctcc | ttcggtcctc | cgatcgttgt | cagaagtaag | 7140 |
| ttggccgcag | tgttatcact | catggttatg | gcagcactgc | ataattctct | tactgtcatg | 7200 |
| ccatccgtaa | gatgcttttc | tgtgactggt | gagtactcaa | ccaagtcatt | ctgagaatag | 7260 |
| tgtatgcggc | gaccgagttg | ctcttgcccg | gcgtcaatac | gggataatac | cgcgccacat | 7320 |
| agcagaactt | taaaagtgct | catcattgga | aaacgttctt | cggggcgaaa | actctcaagg | 7380 |
| atcttaccgc | tgttgagatc | cagttcgatg | taacccactc | gtgcacccaa | ctgatcttca | 7440 |
| gcatctttta | ctttcaccag | cgtttctggg | tgagcaaaaa | caggaaggca | aaatgccgca | 7500 |
| aaaaagggaa | taagggcgac | acggaaatgt | tgaatactca | tactcttcct | ttttcaatat | 7560 |
| tattgaagca | tttatcaggg | ttattgtctc | atgagcggat | acatatttga | atgtatttag | 7620 |
| aaaaataaac | aaataggggt | tccgcgcaca | tttccccgaa | aagtgccacc | t | 7671 |

<210> SEQ ID NO 115
<211> LENGTH: 8445
<212> TYPE: DNA
<213> ORGANISM: Artificial Sequence
<220> FEATURE:
<223> OTHER INFORMATION: Plasmid
    pCVL.SFFV.HA.NLS.IAni-I.T2A.Trex2.IRES.mTagBFP

<400> SEQUENCE: 115

| | | | | | |
|---|---|---|---|---|---|
| gacgtcaatg | tagtcttatg | caatactctt | gtagtcttgc | aacatggtaa | cgatgagtta | 60 |
| gcaacatgcc | ttacaaggag | agaaaaagca | ccgtgcatgc | cgattggtgg | aagtaaggtg | 120 |
| gtacgatcgt | gccttattag | gaaggcaaca | gacgggtctg | acatggattg | gacgaaccac | 180 |
| tgaattgccg | cattgcagag | atattgtatt | taagtgccta | gctcgataca | taaacgggtc | 240 |
| tctctggtta | gaccagatct | gagcctggga | gctctctggc | taactaggga | acccactgct | 300 |
| taagcctcaa | taaagcttgc | cttgagtgct | tcaagtagtg | tgtgcccgtc | tgttgtgtga | 360 |
| ctctggtaac | tagagatccc | tcagaccctt | ttagtcagtg | tggaaaatct | ctagcagtgg | 420 |
| cgcccgaaca | gggacttgaa | agcgaaaggg | aaaccagagg | agctctctcg | acgcaggact | 480 |
| cggcttgctg | aagcgcgcac | ggcaagaggc | gaggggcggc | gactggtgag | tacgccaaaa | 540 |
| attttgacta | gcggaggcta | gaaggagaga | gatgggtgcg | agagcgtcag | tattaagcgg | 600 |
| gggagaatta | gatcgcgatg | ggaaaaaatt | cggttaaggc | cagggggaaa | gaaaaaatat | 660 |
| aaattaaaac | atatagtatg | ggcaagcagg | gagctagaac | gattcgcagt | taatcctggc | 720 |
| ctgttagaaa | catcagaagg | ctgtagacaa | atactgggac | agctacaacc | atcccttcag | 780 |
| acaggatcag | aagaacttag | atcattatat | aatacagtag | caaccctcta | ttgtgtgcat | 840 |
| caaaggatag | agataaaaga | caccaaggaa | gctttagaca | agatagagga | agagcaaaac | 900 |
| aaaagtaaga | ccaccgcaca | gcaagcggcc | ctgatcttca | gacctggagg | aggagatatg | 960 |
| agggacaatt | ggagaagtga | attatataaa | tataaagtag | taaaaattga | accattagga | 1020 |

| | |
|---|---|
| gtagcaccca ccaaggcaaa gagaagagtg gtgcagagag aaaaaagagc agtgggaata | 1080 |
| ggagctttgt tccttgggtt cttgggagca gcaggaagca ctatgggcgc agcgtcaatg | 1140 |
| acgctgacgg tacaggccag acaattattg tctggtatag tgcagcagca gaacaatttg | 1200 |
| ctgagggcta ttgaggcgca acagcatctg ttgcaactca cagtctgggg catcaagcag | 1260 |
| ctccaggcaa gaatcctggc tgtggaaaga tacctaaagg atcaacagct cctggggatt | 1320 |
| tggggttgct ctggaaaact catttgcacc actgctgtgc cttggaatgc tagttggagt | 1380 |
| aatgaatctc tggaacagat tggaatcac acgacctgga tggagtggga cagagaaatt | 1440 |
| aacaattaca caagcttaat acactcctta attgaagaat cgcaaaacca gcaagaaaag | 1500 |
| aatgaacaag aattattgga attagataaa tgggcaagtt tgtggaattg gtttaacata | 1560 |
| acaaattggc tgtggtatat aaaattattc ataatgatag taggaggctt ggtaggttta | 1620 |
| agaatagttt ttgctgtact ttctatagtg aatagagtta ggcagggata ttcaccatta | 1680 |
| tcgtttcaga cccacctccc aaccccgagg ggacccgaca ggcccgaagg aatagaagaa | 1740 |
| gaaggtggag agagagacag agacagatcc attcgattag tgaacggatc tcgacggtat | 1800 |
| cggttaactt ttaaaagaaa aggggggatt ggggggtaca gtgcagggga agaatagta | 1860 |
| gacataatag caacagacat acaaactaaa gaattacaaa aacaaattac aaaaattcaa | 1920 |
| aattttatcg attacgcgtc acgtgctagc tgcagtaacg ccattttgca aggcatggaa | 1980 |
| aaataccaaa ccaagaatag agaagttcag atcaagggcg ggtacatgaa aatagctaac | 2040 |
| gttgggccaa acaggatatc tgcggtgagc agtttcggcc ccggcccggg gccaagaaca | 2100 |
| gatggtcacc gcagtttcgg ccccggcccg aggccaagaa cagatggtcc ccagatatgg | 2160 |
| cccaaccctc agcagtttct taagacccat cagatgtttc caggctcccc caaggacctg | 2220 |
| aaatgacccct gcgccttatt tgaattaacc aatcagcctg cttctcgctt ctgttcgcgc | 2280 |
| gcttctgctt cccgagctct ataaagagc tcacaacccc tcactcggcg cgccagtcct | 2340 |
| ccgacagact gagtcgcccg ctcgagccgc caccatggga tatccatacg atgtcccaga | 2400 |
| ttatgcgcca cctaagaaga acgcaaagt cgaattcggc agcgatctga cctacgccta | 2460 |
| tctggtgggc ctgttcgagg gcgacggata tttttccatc actaaaaagg gcaagtacct | 2520 |
| gacctatgag ctgggaattg aactgtctat caaggatgtg cagctgatct acaagatcaa | 2580 |
| gaagatcctg gggatcggca ttgtgagctt caggaagaga aacgagattg aaatggtggc | 2640 |
| cctgaggatc agggataaga atcacctgaa atctaagatt ctgcccatct tcgagaagta | 2700 |
| tcctatgttt agtaacaaac agtacgacta tctgagggttt agaaatgctc tgctgagcgg | 2760 |
| catcatctcc ctggaggatc tgccagacta tacccggtcc gacgagcccc tgaacagcat | 2820 |
| cgaatccatc attaatacat cttacttcag tgcctggctg gtgggcttca tcgaggctga | 2880 |
| aggtgcttc tctgtgtaca aactgaacaa ggacgatgac tatctgattg ccagttttga | 2940 |
| tatcgctcag agggatggag acatcctgat tagcgccatc agaaagtacc tgtccttcac | 3000 |
| cacaaaggtg tatctggaca aaacaaattg tagcaaactg aaggtcacta gcgtgcgctc | 3060 |
| cgtggagaac atcattaagt tcctgcagaa tgctcctgtg aaactgctgg gcaacaaaaa | 3120 |
| gctgcagtac aaaactgtggc tgaagcagct gcggaaaatc tctcgctaca gtgaaaaaat | 3180 |
| caagattcca tccaattatg gatccggtga gggcagagga agtcttctaa catgcggtga | 3240 |
| cgtggaggag aatccgggcc cctccggatc tgagccacct cgggctgaga cctttgtatt | 3300 |
| cctgacctta gaagccactg ggctcccaaa catggaccct gagattgcag agatatccct | 3360 |
| ttttgctgtt caccgctctt ccctggagaa cccagaacgg gatgattctg gttccttggt | 3420 |

```
gctgccccgt gttctggaca agctcacact gtgcatgtgc ccggagcgcc cctttactgc   3480
caaggccagt gagattactg gtttgagcag cgaaagcctg atgcactgcg ggaaggctgg   3540
tttcaatggc gctgtggtaa ggacactgca gggcttccta agccgccagg agggccccat   3600
ctgccttgtg gccacaatg gcttcgatta tgacttccca ctgctgtgca cggagctaca    3660
acgtctgggt gccatctgc cccaagacac tgtctgcctg acacactgc ctgcattgcg     3720 gggcctggac cgtgctcaca gccacggcac cagggctcaa ggccgcaaaa gctacagcct   3780
ggccagtctc ttccaccgct acttccaggc tgaacccagt gctgcccatt cagcagaagg   3840
tgatgtgcac accctgcttc tgatcttcct gcatcgtgct cctgagctgc tcgcctgggc   3900
agatgagcag gccgcagct gggctcatat tgagcccatg tacgtgccac ctgatggtcc    3960
aagcctcgaa gctgacctg caggtcgagc atgcatctag gcggccaat tccgcccctc     4020 tccctccccc ccccctaacg ttactggccg aagccgcttg aataaggcc ggtgtgcgtt    4080 tgtctatatg tgattttcca ccatattgcc gtcttttggc aatgtgaggg cccggaaacc   4140
tggccctgtc ttcttgacga gcattcctag gggtctttcc cctctcgcca aggaatgca    4200 aggtctgttg aatgtcgtga aggaagcagt tcctctggaa gcttcttgaa acaaacaac    4260 gtctgtagcg acccttttgca ggcagcggaa ccccccacct ggcgacaggt gcctctgcgg  4320
ccaaaagcca cgtgtataag atacacctgc aaaggcggca caaccccagt gccacgttgt   4380
gagttggata gttgtggaaa gagtcaaatg gctctcctca agcgtattca acaaggggct   4440
gaaggatgcc cagaaggtac cccattgtat gggatctgat ctggggcctc ggtgcacatg   4500
ctttacatgt gtttagtcga ggttaaaaaa acgtctaggc cccccgaacc acggggacgt    4560
ggttttcctt tgaaaaacac gatgataagc ttgccacaac ccttaccggt cgccaccatg   4620
agcgagctga ttaaggagaa catgcacatg aagctgtaca tggagggcac cgtggacaac   4680
catcacttca gtgcacatc cgagggcgaa ggcaagccct acgagggcac ccagaccatg    4740
agaatcaagg tggtcgaggg cggccctctc cccttcgcct tcgacatcct ggctactagc   4800
ttcctctacg gcagcaagac cttcatcaac cacacccagg gcatccccga cttcttcaag   4860
cagtccttcc ctgagggctt cacatgggag agagtcacca catacgaaga cggggcgtg    4920 ctgaccgcta cccaggacac cagcctccag gacggctgcc tcatctacaa cgtcaagatc   4980
agaggggtga acttcacatc caacggccct gtgatgcaga gaaaacact cggctggag    5040 gccttcaccg agacgctgta ccccgctgac ggcggcctgg aaggcagaaa cgacatggcc   5100
ctgaagctcg tgggcgggag ccatctgatc gcaaacatca agaccacata tagatccaag   5160
aaacccgcta agaacctcaa gatgcctggc gtctactatg tggactacag actggaaaga   5220
atcaaggagg ccaacaacga gacctacgtc gagcagcacg aggtggcagt ggccagatac   5280
tgcgacctcc ctagcaaact ggggcacaag cttaattgat tctagagtcg accgagcatc   5340
ttaccgccat ttatacccat atttgttctg ttttcttga tttgggtata catttaaatg     5400
ttaatagaac aaaatggtgg ggcaatcatt tacatttta gggatatgta attactagtt    5460
caggtgtatt gccacaagac aaacatgtta agaaactttc ccgttattta cgctctgttc   5520
ctgttaatca acctctggat tacaaaattt gtgaaagatt gactgatatt cttaactatg   5580
ttgctccttt tacgctgtgt ggatatgctg ctttatagcc tctgtatcta gctattgctt   5640
cccgtacggc tttcgttttc tcctccttgt ataaatcctg gttgctgtct cttttagagg   5700
agttgtggcc cgttgtccgt caacgtggcg tggtgtgctc tgtgtttgct gacgcaaccc   5760
```

|  |  |  |  |  |  |
|---|---|---|---|---|---|
| ccactggctg | gggcattgcc | accacctgtc | aactcctttc | tgggactttc | gctttccccc | 5820 |
| tcccgatcgc | cacggcagaa | ctcatcgccg | cctgccttgc | ccgctgctgg | acagggcta | 5880 |
| ggttgctggg | cactgataat | tccgtggtgt | tgtcatcggt | accttttaa | aagaaaaggg | 5940 |
| gggactggaa | gggctaattc | actcccaacg | aagacaagat | atcataactt | cgtatagcat | 6000 |
| acattatacg | aagttataat | ttatttgtga | aatttgtgat | gctattgctt | tatttgtaac | 6060 |
| catatgttta | tttgtgaaat | ttgtgatgct | attgctttat | ttgtaaccat | tgcttttgc | 6120 |
| ttgtactggg | tctctctggt | tagaccagat | ctgagcctgg | gagctctctg | gctaactagg | 6180 |
| gaacccactg | cttaagcctc | aataaagctt | gcctcgacca | gctcgactg | tgccttctag | 6240 |
| ttgccagcca | tctgttgttt | gcccctcccc | cgtgccttcc | ttgaccctgg | aaggtgccac | 6300 |
| tcccactgtc | ctttcctaat | aaaatgagga | aattgcatcg | cattgtctga | gtaggtgtca | 6360 |
| ttctattctg | ggggtgggg | tggggcagga | cagcaagggg | gaggattggg | aagacaatag | 6420 |
| caggcatgct | ggggatgcgg | tgggctctat | ggcctgcagc | tgcattaatg | aatcggccaa | 6480 |
| cgcgcggga | gaggcggttt | gcgtattggg | cgctcttccg | cttcctcgct | cactgactcg | 6540 |
| ctgcgctcgg | tcgttcggct | gcggcgagcg | gtatcagctc | actcaaaggc | ggtaatacgg | 6600 |
| ttatccacag | aatcaggga | taacgcagga | aagaacatgt | gagcaaaagg | ccagcaaaag | 6660 |
| gccaggaacc | gtaaaaaggc | cgcgttgctg | gcgtttttcc | ataggctccg | cccccctgac | 6720 |
| gagcatcaca | aaaatcgacg | ctcaagtcag | aggtggcgaa | acccgacagg | actataaaga | 6780 |
| taccaggcgt | ttccccctgg | aagctccctc | gtgcgctctc | ctgttccgac | cctgccgctt | 6840 |
| accggatacc | tgtccgcctt | tctcccttcg | ggaagcgtgg | cgctttctca | tagctcacgc | 6900 |
| tgtaggtatc | tcagttcggt | gtaggtcgtt | cgctccaagc | tgggctgtgt | gcacgaaccc | 6960 |
| cccgttcagc | ccgaccgctg | cgccttatcc | ggtaactatc | gtcttgagtc | caacccggta | 7020 |
| agacacgact | tatcgccact | ggcagcagcc | actggtaaca | ggattagcag | agcgaggtat | 7080 |
| gtaggcggtg | ctacagagtt | cttgaagtgg | tggcctaact | acggctacac | tagaaggaca | 7140 |
| gtatttggta | tctgcgctct | gctgaagcca | gttaccttcg | gaaaaagagt | tggtagctct | 7200 |
| tgatccggca | aacaaaccac | cgctggtagc | ggtggttttt | ttgtttgcaa | gcagcagatt | 7260 |
| acgcgcagaa | aaaaggatc | tcaagaagat | cctttgatct | tttctacggg | gtctgacgct | 7320 |
| cagtggaacg | aaaactcacg | ttaagggatt | ttggtcatga | gattatcaaa | aaggatcttc | 7380 |
| acctagatcc | tttaaatta | aaatgaagt | tttaaatcaa | tctaaagtat | atatgagtaa | 7440 |
| acttggtctg | acagttacca | atgcttaatc | agtgaggcac | ctatctcagc | gatctgtcta | 7500 |
| tttcgttcat | ccatagttgc | ctgactcccc | gtcgtgtaga | taactacgat | acgggagggc | 7560 |
| ttaccatctg | gccccagtgc | tgcaatgata | ccgcgagacc | cacgctcacc | ggctccagat | 7620 |
| ttatcagcaa | taaaccagcc | agccggaagg | gccgagcgca | gaagtggtcc | tgcaacttta | 7680 |
| tccgcctcca | tccagtctat | taattgttgc | cgggaagcta | gagtaagtag | ttcgccagtt | 7740 |
| aatagtttgc | gcaacgttgt | tgccattgct | acaggcatcg | tggtgtcacg | ctcgtcgttt | 7800 |
| ggtatggctt | cattcagctc | cggttcccaa | cgatcaaggc | gagttacatg | atcccccatg | 7860 |
| ttgtgcaaaa | aagcggttag | ctccttcggt | cctccgatcg | ttgtcagaag | taagttggcc | 7920 |
| gcagtgttat | cactcatggt | tatggcagca | ctgcataatt | ctcttactgt | catgccatcc | 7980 |
| gtaagatgct | tttctgtgac | tggtgagtac | tcaaccaagt | cattctgaga | atagtgtatg | 8040 |
| cggcgaccga | gttgctcttg | cccggcgtca | atacgggata | ataccgcgcc | acatagcaga | 8100 |
| actttaaaag | tgctcatcat | tggaaaacgt | tcttcgggc | gaaaactctc | aaggatctta | 8160 |

| | | |
|---|---|---|
| ccgctgttga gatccagttc gatgtaaccc actcgtgcac ccaactgatc ttcagcatct | | 8220 |
| tttactttca ccagcgtttc tgggtgagca aaaacaggaa ggcaaaatgc cgcaaaaaag | | 8280 |
| ggaataaggg cgacacggaa atgttgaata ctcatactct tcctttttca atattattga | | 8340 |
| agcatttatc agggttattg tctcatgagc ggatacatat ttgaatgtat ttagaaaaat | | 8400 |
| aaacaaatag gggttccgcg cacatttccc cgaaaagtgc cacct | | 8445 |

<210> SEQ ID NO 116
<211> LENGTH: 7011
<212> TYPE: DNA
<213> ORGANISM: Artificial Sequence
<220> FEATURE:
<223> OTHER INFORMATION: pCVL.MND.SceOPT.2A.TagBFP

<400> SEQUENCE: 116

| | | |
|---|---|---|
| gacgtcaatg tagtcttatg caatactctt gtagtcttgc aacatggtaa cgatgagtta | | 60 |
| gcaacatgcc ttacaaggag agaaaaagca ccgtgcatgc cgattggtgg aagtaaggtg | | 120 |
| gtacgatcgt gccttattag gaaggcaaca cgggtctg acatggattg gacgaaccac | | 180 |
| tgaattgccg cattgcagag atattgtatt taagtgccta gctcgataca taaacgggtc | | 240 |
| tctctggtta gaccagatct gagcctggga gctctctggc taactaggga acccactgct | | 300 |
| taagcctcaa taaagcttgc cttgagtgct tcaagtagtg tgtgcccgtc tgttgtgtga | | 360 |
| ctctggtaac tagagatccc tcagaccctt ttagtcagtg tggaaaatct ctagcagtgg | | 420 |
| cgcccgaaca gggacttgaa agcgaaaggg aaaccagagg agctctctcg acgcaggact | | 480 |
| cggcttgctg aagcgcgcac ggcaagaggc gaggggcggc gactggtgag tacgccaaaa | | 540 |
| attttgacta gcggaggcta aaggagaga atgggtgcg agagcgtcag tattaagcgg | | 600 |
| gggagaatta gatcgcgatg ggaaaaaatt cggttaaggc caggggggaaa gaaaaaatat | | 660 |
| aaattaaaac atatagtatg ggcaagcagg gagctagaac gattcgcagt taatcctggc | | 720 |
| ctgttagaaa catcagaagg ctgtagacaa atactgggac agctacaacc atcccttcag | | 780 |
| acaggatcag aagaacttag atcattatat aatacagtag caaccctcta ttgtgtgcat | | 840 |
| caaaggatag agataaaaga caccaaggaa gctttagaca agatagagga agagcaaaac | | 900 |
| aaaagtaaga ccaccgcaca gcaagcggcc ctgatcttca gacctggagg aggagatatg | | 960 |
| agggacaatt ggagaagtga attatataaa tataaagtag taaaaattga accattagga | | 1020 |
| gtagcaccca ccaaggcaaa gagaagagtg gtgcagagag aaaaaagagc agtgggaata | | 1080 |
| ggagctttgt tccttgggtt cttgggagca gcaggaagca ctatgggcgc agcgtcaatg | | 1140 |
| acgctgacgg tacaggccag acaattattg tctggtatag tgcagcagca gaacaatttg | | 1200 |
| ctgagggcta ttgaggcgca acagcatctg ttgcaactca cagtctgggg catcaagcag | | 1260 |
| ctccaggcaa gaatcctggc tgtggaaaga tacctaaagg atcaacagct cctggggatt | | 1320 |
| tggggttgct ctggaaaact catttgcacc actgctgtgc cttggaatgc tagttggagt | | 1380 |
| aatgaatctc tggaacagat ttggaatcac acgacctgga tggagtggga cagagaaatt | | 1440 |
| aacaattaca caagcttaat acactcctta attgaagaat cgcaaaacca gcaagaaaag | | 1500 |
| aatgaacaag aattattgga attagataaa tgggcaagtt tgtggaattg gtttaacata | | 1560 |
| acaaattggc tgtggtatat aaaattattc ataatgatag taggaggctt ggtaggttta | | 1620 |
| agaatagttt ttgctgtact ttctatagtg aatagagtta ggcagggata ttcaccatta | | 1680 |
| tcgtttcaga cccacctccc aaccccgagg ggacccgaca ggcccgaagg aatagaagaa | | 1740 |

```
gaaggtggag agagagacag agacagatcc attcgattag tgaacggatc tcgacggtat    1800
cggttaactt ttaaaagaaa aggggggatt gggggtaca gtgcagggga aagaatagta    1860
gacataatag caacagacat acaaactaaa gaattacaaa acaaattac aaaaattcaa    1920 aattttatcg attacgcgta ggaacagaga acaggagaa tatgggccaa acaggatatc    1980
tgtggtaagc agttcctgcc ccggctcagg gccaagaaca gttggaacag cagaatatgg    2040
gccaaacagg atatctgtgg taagcagttc ctgccccggc tcaggccaa gaacagatgg    2100 tccccagatg cggtcccgcc ctcagcagtt tctagagaac catcagatgt tccagggtg    2160 ccccaaggac ctgaaatgac cctgtgcctt atttgaacta accaatcagt tcgcttctcg    2220
cttctgttcg cgcgcttctg ctccccgagc tctatataag cagagctcgt ttagtgaacc    2280
gtcagatcgc ctggagacgc catccacgct gttttgactt ccatagaagg atctcgagcc    2340
accatgggcg tataccccta cgacgtgccc gactacgccc ccgggccccc taagaaaaag    2400
aggaaggtga agaacatcaa gaagaaccag gtcatgaacc tgggccccaa cagcaagctg    2460
ctgaaggagt acaagagcca gctgatcgag ctgaacatcg agcagttcga ggccggcatc    2520
ggcctgatcc tgggcgacgc ctacatcagg agcagggacg agggcaagac ctactgcatg    2580
cagttcgagt ggaagaacaa ggcctacatg gaccacgtgt gcctgctgta cgaccagtgg    2640
gtgctgagcc ccccacaa gaaggagagg gtgaaccacc tgggcaacct ggtcatcacc    2700
tggggcgccc agaccttcaa gcaccaggcc ttcaacaagc tggccaacct gttcatcgtg    2760
aacaacaaga gaccatccc caacaacctg gtggagaact acctgacccc catgagcctg    2820
gcctactggt tcatggacga cggcggcaag tgggactaca caagaacag caccaacaag    2880 agcatcgtgc tgaacaccca gagcttcacc ttcgaggagg tggagtacct ggtgaagggc    2940
ctgaggaaca agttccagct gaactgctac gtgaagatca caagaacaa gcccatcatc    3000 tacatcgaca gcatgagcta cctgatcttc tacaacctga tcaagcccta cctgatcccc    3060
cagatgatgt acaagctgcc caacaccatc agcagcgaga ccttcctgaa gggcggcggc    3120
ggatccggtg agggcagagg aagtcttcta acatgcggtg acgtggagga gaatccgggc    3180
cccatgagcg agctgattaa ggagaacatg cacatgaagc tgtacatgga gggcaccgtg    3240
gacaaccatc acttcaagtg cacatccgag ggcgaaggca gccctacga gggcacccag    3300 accatgagaa tcaaggtggt cgagggcggc cctctccct tcgccttcga catcctggct    3360
actagcttcc tctacggcag caagaccttc atcaaccaca cccagggcat ccccgacttc    3420
ttcaagcagt ccttccctga gggcttcaca tgggagagag tcaccacata cgaagacggg    3480
ggcgtgctga ccgctaccca ggacaccagc ctccaggacg gctgcctcat ctacaacgtc    3540
aagatcagag gggtgaactt cacatccaac ggccctgtga tgcagaagaa aacactcggc    3600
tgggaggcct tcaccgagac gctgtacccc gctgacggcg gcctggaagg cagaaacgac    3660
atggccctga gctcgtggg cgggagccat ctgatcgcaa acatcaagac acatatagaa    3720
tccaagaaac ccgctaagaa cctcaagatg cctggcgtct actatgtgga ctacagactg    3780
gaaagaatca aggaggccaa caacgagacc tacgtcgagc agcacgaggt ggcagtggcc    3840
agatactgcg acctccctag caaactgggg cacaagctta attgattcta gagtcgaccg    3900
agcatcttac cgccatttat acccatattt gttctgtttt tcttgatttg ggtatacatt    3960
taaatgttaa tagaacaaaa tggtggggca atcatttaca tttttaggga tatgtaatta    4020
ctagttcagg tgtattgcca caagacaaac atgttaagaa acttccccgt tatttacgct    4080
ctgttcctgt taatcaacct ctggattaca aaatttgtga aagattgact gatattctta    4140
```

```
actatgttgc tccttttacg ctgtgtggat atgctgcttt atagcctctg tatctagcta    4200
ttgcttcccg tacggctttc gttttctcct ccttgtataa atcctggttg ctgtctcttt    4260
tagaggagtt gtggcccgtt gtccgtcaac gtggcgtggt gtgctctgtg tttgctgacg    4320
caaccccac tggctggggc attgccacca cctgtcaact cctttctggg actttcgctt     4380
tcccctccc gatcgccacg gcagaactca tcgccgcctg ccttgcccgc tgctggacag     4440
gggctaggtt gctgggcact gataattccg tggtgttgtc atcggtacct ttttaaaaga    4500
aaagggggga ctggaagggc taattcactc ccaacgaaga caagatatca taacttcgta    4560
tagcatacat tatacgaagt tataatttat tgtgaaatt tgtgatgcta ttgctttatt     4620
tgtaaccata tgtttatttg tgaaatttgt gatgctattg ctttatttgt aaccattgct    4680
ttttgcttgt actgggtctc tctgttaga ccagatctga gcctgggagc tctctggcta     4740
actagggaac ccactgctta agcctcaata aagcttgcct cgaccagcct cgactgtgcc    4800
ttctagttgc cagccatctg ttgtttgccc ctccccgtg ccttccttga ccctggaagg     4860
tgccactccc actgtccttt cctaataaaa tgaggaaatt gcatcgcatt gtctgagtag    4920
gtgtcattct attctggggg gtggggtggg gcaggacagc aaggggggagg attgggaaga   4980
caatagcagg catgctgggg atgcggtggg ctctatggcc tgcagctgca ttaatgaatc    5040
ggccaacgcg cggggagagg cggtttgcgt attgggcgct cttccgcttc ctcgctcact    5100
gactcgctgc gctcggtcgt tcggctgcgg cgagcggtat cagctcactc aaaggcggta    5160
atacggttat ccacagaatc aggggataac gcaggaaaga acatgtgagc aaaaggccag    5220
caaaaggcca ggaaccgtaa aaaggccgcg ttgctggcgt ttttccatag gctccgcccc    5280
cctgacgagc atcacaaaaa tcgacgctca agtcagaggt ggcgaaaccc gacaggacta    5340
taaagatacc aggcgtttcc ccctggaagc tccctcgtgc gctctcctgt tccgaccctg    5400
ccgcttaccg gatacctgtc cgcctttctc ccttcgggaa gcgtggcgct ttctcatagc    5460
tcacgctgta ggtatctcag ttcggtgtag gtcgttcgct ccaagctggg ctgtgtgcac    5520
gaaccccccg ttcagcccga ccgctgcgcc ttatccggta actatcgtct tgagtccaac    5580
ccggtaagac acgacttatc gccactggca gcagccactg gtaacaggat tagcagagcg    5640
aggtatgtag gcggtgctac agagttcttg aagtggtggc ctaactacgg ctacactaga    5700
aggacagtat ttggtatctg cgctctgctg aagccagtta ccttcggaaa aagagttggt    5760
agctcttgat ccggcaaaca aaccaccgct ggtagcggtg gtttttttgt ttgcaagcag    5820
cagattacgc gcagaaaaaa aggatctcaa gaagatcctt tgatcttttc tacgggtct    5880
gacgctcagt ggaacgaaaa ctcacgttaa gggattttgg tcatgagatt atcaaaaagg    5940
atcttcacct agatcctttt aaattaaaaa tgaagtttta aatcaatcta agtatatat     6000
gagtaaactt ggtctgacag ttaccaatgc ttaatcagtg aggcacctat ctcagcgatc    6060
tgtctatttc gttcatccat agttgcctga ctccccgtcg tgtagataac tacgatacgg    6120
gagggcttac catctggccc cagtgctgca atgataccgc gagacccacg ctcaccggct    6180
ccagatttat cagcaataaa ccagccagcc ggaagggccg agcgcagaag tggtcctgca    6240
actttatccg cctccatcca gtctattaat tgttgccggg aagctagagt aagtagttcg    6300
ccagttaata gtttgcgcaa cgttgttgcc attgctacag gcatcgtggt gtcacgctcg    6360
tcgtttggta tggcttcatt cagctccggt tcccaacgat caaggcgagt tacatgatcc    6420
cccatgttgt gcaaaaaagc ggttagctcc ttcggtcctc cgatcgttgt cagaagtaag    6480
```

-continued

```
ttggccgcag tgttatcact catggttatg gcagcactgc ataattctct tactgtcatg    6540
ccatccgtaa gatgcttttc tgtgactggt gagtactcaa ccaagtcatt ctgagaatag    6600
tgtatgcggc gaccgagttg ctcttgcccg gcgtcaatac gggataatac cgcgccacat    6660
agcagaactt taaaagtgct catcattgga aaacgttctt cggggcgaaa actctcaagg    6720
atcttaccgc tgttgagatc cagttcgatg taacccactc gtgcacccaa ctgatcttca    6780
gcatctttta ctttcaccag cgtttctggg tgagcaaaaa caggaaggca aaatgccgca    6840
aaaaagggaa taagggcgac acggaaatgt tgaatactca tactcttcct ttttcaatat    6900
tattgaagca tttatcaggg ttattgtctc atgagcggat acatatttga atgtatttag    6960
aaaaataaac aatagggggt tccgcgcaca tttccccgaa aagtgccacc t             7011

<210> SEQ ID NO 117
<211> LENGTH: 7968
<212> TYPE: DNA
<213> ORGANISM: Artificial Sequence
<220> FEATURE:
<223> OTHER INFORMATION: Plasmid pCVL.SFFV.HA.NLS.CLS4617..IRES.mTagBFP

<400> SEQUENCE: 117
gacgtcaatg tagtcttatg caatactctt gtagtcttgc aacatggtaa cgatgagtta     60
gcaacatgcc ttacaaggag agaaaaagca ccgtgcatgc cgattggtgg aagtaaggtg    120
gtacgatcgt gccttattag gaaggcaaca cgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagagag atgggtgcg agagcgtcag tattaagcgg    600
gggagaatta gatcgcgatg gaaaaaatt cggttaaggc caggggggaaa gaaaaatat    660 aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctgggatt    1320 tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
```

-continued

```
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800
cggttaactt ttaaaagaaa aggggggatt gggggtaca gtgcagggga aagaatagta    1860
gacataatag caacagacat acaaactaaa gaattacaaa aacaaattac aaaaattcaa    1920
aattttatcg attacgcgtc acgtgctagc tgcagtaacg ccattttgca aggcatggaa    1980
aaataccaaa ccaagaatag agaagttcag atcaagggcg ggtacatgaa aatagctaac    2040
gttgggccaa acaggatatc tgcggtgagc agtttcggcc ccggcccggg gccaagaaca    2100
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
gcttctgctt cccgagctct ataaaagagc tcacaacccc tcactcggcg cgccagtcct    2340
ccgacagact gagtcgcccg ctcgagccgc caccatggga tatccatacg atgtcccaga    2400
ttatgcgcca cctaagaaga aacgcaaagt cgaattcgcc aataccaaat ataacgaaga    2460
gttcctgctg tacctggccg gctttgtgga cggtgacggt agcatcatcg ctcagattaa    2520
accacgtcag acctataagt ttaaacatca gctacgtttg acctttaaag tgggtcaaaa    2580
gacccagcgc cgttggtttc tggacaaact agtggatgaa attggcgttg gttacgtagc    2640
tgattctggt agcatgtccg aatacaactt aagcgaaatc aagccgctgc acaacttcct    2700
gactcaactg cagccgtttc tggaactgaa acagaaacag gcaaacctgg ttctgaaaat    2760
tatcgaacag ctgccgtctg caaaagaatc cccggacaaa ttcctggaag tttgtacctg    2820
ggtggatcag gttgcagctc tgaacgattc taagacgcgt aaaaccactt ctgaaaccgt    2880
tcgtgctgtg ctggacagcc tgagcgagaa gaagaaatcc tccccggcgg ccggtggatc    2940
tgataagtat aatcaggctc tgtctaaata caaccaagca ctgtccaagt acaatcaggc    3000
cctgtctggt ggaggcggtt ccaacaaaaa attcctgctg tatcttgctg gatttgtgga    3060
ttctgatggc tccatcattg ctcagataaa accaggtcaa cgttacaagt tcaaacacca    3120
gctccgtttg acctttttacg tcactcagaa gacacaaaga aggtggttct tggacaaatt    3180
ggttgatcgt attggtgtgg gctatgtcta cgactctggc tctgcttcaa actaccagct    3240
gtctgaaatt aagcctcttc ataacctgct cacccaactg caaccctttct tgaagctcaa    3300
acagaagcaa gcaaatctgg ttttgaaaat catcgagcaa ctgccatctg ccaaggagtc    3360
ccctgacaag tttcttgaag tgtgtacttg ggtggatcag gttgctgcct tgaatgactc    3420
caagaccaga aaaaccacct ctgagactgt gagggcagtt ctggatagcc agtctgagaa    3480
gaaaaagtac tctccttagc ctgcaggtcg agcatgcatc tagggcggcc aattccgccc    3540
ctctccctcc ccccccccta cgttactggc cgaagccgc ttggaataag gccggtgtgc    3600
gtttgtctat atgtgatttt ccaccatatt gccgtctttt ggcaatgtga gggcccggaa    3660
acctggccct gtcttcttga cgagcattcc taggggtctt tccctctcg ccaaaggaat    3720
gcaaggtctg ttgaatgtcg tgaaggaagc agttcctctg gaagcttctt gaagacaaac    3780
aacgtctgta gcgaccctttt gcaggcagcg gaaccccca cctggcgaca ggtgcctctg    3840
cggccaaaag ccacgtgtat aagatacacc tgcaaaggcg gcacaacccc agtgccacgt    3900
```

-continued

```
tgtgagttgg atagttgtgg aaagagtcaa atggctctcc tcaagcgtat tcaacaaggg    3960
gctgaaggat gcccagaagg tacccccattg tatgggatct gatctggggc ctcggtgcac   4020
atgctttaca tgtgtttagt cgaggttaaa aaaacgtcta ggccccccga accacgggga    4080
cgtggttttc ctttgaaaaa cacgatgata agcttgccac aacccttacc ggtcgccacc    4140
atgagcgagc tgattaagga gaacatgcac atgaagctgt acatggaggg caccgtggac    4200
aaccatcact tcaagtgcac atccgagggc gaaggcaagc cctacgaggg cacccagacc    4260
atgagaatca aggtggtcga gggcggccct ctccccttcg ccttcgacat cctggctact    4320
agcttcctct acggcagcaa gaccttcatc aaccacaccc agggcatccc cgacttcttc    4380
aagcagtcct tccctgaggg cttcacatgg gagagagtca ccacatacga agacggggc    4440 gtgctgaccg ctacccagga caccagcctc caggacggct gcctcatcta caacgtcaag    4500
atcagagggg tgaacttcac atccaacggc cctgtgatgc agaagaaaac actcggctgg    4560
gaggccttca ccgagacgct gtaccccgct gacggcggcc tggaaggcag aaacgacatg    4620
gccctgaagc tcgtgggcgg gagccatctg atcgcaaaca tcaagaccac atatagatcc    4680
aagaaacccg ctaagaacct caagatgcct ggcgtctact atgtggacta cagactggaa    4740
agaatcaagg aggccaacaa cgagacctac gtcgagcagc acgaggtggc agtggccaga    4800
tactgcgacc tccctagcaa actggggcac aagcttaatt gattctagag tcgaccgagc    4860
atcttaccgc catttatacc catatttgtt ctgttttct tgatttgggt atacatttaa     4920
atgttaatag aacaaaatgg tggggcaatc atttacattt ttagggatat gtaattacta    4980
gttcaggtgt attgccacaa gacaaacatg ttaagaaact ttcccgttat ttacgctctg    5040
ttcctgttaa tcaacctctg gattacaaaa tttgtgaaag attgactgat attcttaact    5100
atgttgctcc ttttacgctg tgtggatatg ctgctttata gcctctgtat ctagctattg    5160
cttcccgtac ggctttcgtt ttctcctcct tgtataaatc ctggttgctg tctcttttag    5220
aggagttgtg gcccgttgtc cgtcaacgtg gcgtggtgtg ctctgtgttt gctgacgcaa    5280 ccccccactgg ctggggcatt gccaccacct gtcaactcct ttctgggact ttcgctttcc    5340
ccctcccgat cgccacggca gaactcatcg ccgcctgcct tgcccgctgc tggacagggg   5400
ctaggttgct gggcactgat aattccgtgg tgttgtcatc ggtacctttt taaaagaaaa    5460 gggggggactg gaagggctaa ttcactccca acgaagacaa gatatcataa cttcgtatag   5520
catacattat acgaagttat aatttatttg tgaaatttgt gatgctattg ctttatttgt    5580
aaccatatgt ttatttgtga aatttgtgat gctattgctt tatttgtaac cattgctttt    5640
tgcttgtact gggtctctct ggttagacca gatctgagcc tgggagctct ctggctaact    5700
agggaaccca ctgcttaagc ctcaataaag cttgcctcga ccagcctcga ctgtgccttc    5760
tagttgccag ccatctgttg tttgcccctc ccccgtgcct tccttgaccc tggaaggtgc    5820
cactcccact gtcctttcct aataaaatga ggaaattgca tcgcattgtc tgagtaggtg    5880
tcattctatt ctggggggtg gggtggggca ggacagcaag ggggaggatt gggaagacaa    5940
tagcaggcat gctggggatg cggtgggctc tatggcctgc agctgcatta atgaatcggc    6000
caacgcgcgg ggagaggcgg tttgcgtatt gggcgctctt ccgcttcctc gctcactgac    6060
tcgctgcgct cggtcgttcg gctgcggcga gcggtatcag ctcactcaaa ggcggtaata    6120
cggttatcca cagaatcagg ggataacgca ggaaagaaca tgtgagcaaa aggccagcaa    6180
aaggccagga accgtaaaaa ggccgcgttg ctggcgtttt tccataggct ccgcccccct    6240
gacgagcatc acaaaaatcg acgctcaagt cagaggtggc gaaacccgac aggactataa    6300
```

```
agataccagg cgtttccccc tggaagctcc ctcgtgcgct ctcctgttcc gaccctgccg    6360
cttaccggat acctgtccgc ctttctccct tcgggaagcg tggcgctttc tcatagctca    6420
cgctgtaggt atctcagttc ggtgtaggtc gttcgctcca agctgggctg tgtgcacgaa    6480
ccccccgttc agcccgaccg ctgcgcctta tccggtaact atcgtcttga gtccaacccg    6540
gtaagacacg acttatcgcc actggcagca gccactggta acaggattag cagagcgagg    6600
tatgtaggcg gtgctacaga gttcttgaag tggtggccta actacggcta cactagaagg    6660
acagtatttg gtatctgcgc tctgctgaag ccagttacct tcggaaaaag agttggtagc    6720
tcttgatccg gcaaacaaac caccgctggt agcggtggtt tttttgtttg caagcagcag    6780
attacgcgca gaaaaaaagg atctcaagaa gatcctttga tcttttctac ggggtctgac    6840
gctcagtgga acgaaaactc acgttaaggg attttggtca tgagattatc aaaaaggatc    6900
ttcacctaga tccttttaaa ttaaaaatga agttttaaat caatctaaag tatatatgag    6960
taaacttggt ctgacagtta ccaatgctta atcagtgagg cacctatctc agcgatctgt    7020
ctatttcgtt catccatagt tgcctgactc cccgtcgtgt agataactac gatacgggag    7080
ggcttaccat ctggccccag tgctgcaatg ataccgcgag acccacgctc accggctcca    7140
gatttatcag caataaacca gccagccgga agggccgagc gcagaagtgg tcctgcaact    7200
ttatccgcct ccatccagtc tattaattgt tgccgggaag ctagagtaag tagttcgcca    7260
gttaatagtt tgcgcaacgt tgttgccatt gctacaggca tcgtggtgtc acgctcgtcg    7320
tttggtatgg cttcattcag ctccggttcc caacgatcaa ggcgagttac atgatccccc    7380
atgttgtgca aaaaagcggt tagctccttc ggtcctccga tcgttgtcag aagtaagttg    7440
gccgcagtgt tatcactcat ggttatggca gcactgcata attctcttac tgtcatgcca    7500
tccgtaagat gcttttctgt gactggtgag tactcaacca agtcattctg agaatagtgt    7560
atgcggcgac cgagttgctc ttgcccggcg tcaatacggg ataataccgc gccacatagc    7620
agaactttaa aagtgctcat cattggaaaa cgttcttcgg ggcgaaaact ctcaaggatc    7680
ttaccgctgt tgagatccag ttcgatgtaa cccactcgtg cacccaactg atcttcagca    7740
tcttttactt tcaccagcgt ttctgggtga gcaaaaacag gaaggcaaaa tgccgcaaaa    7800
aagggaataa gggcgacacg gaaatgttga atactcatac tcttcctttt tcaatattat    7860
tgaagcattt atcagggtta ttgtctcatg agcggataca tatttgaatg tatttagaaa    7920
aataaacaaa taggggttcc gcgcacattt ccccgaaaag tgccacct                 7968
```

<210> SEQ ID NO 118
<211> LENGTH: 8742
<212> TYPE: DNA
<213> ORGANISM: Artificial Sequence
<220> FEATURE:
<223> OTHER INFORMATION: Plasmid
pCVL.SFFV.HA.NLS.CLS4617.T2A.Trex2.IRES.mTagBFP <400> SEQUENCE: 118

```
gacgtcaatg tagtcttatg caatactctt gtagtcttgc aacatggtaa cgatgagtta      60
gcaacatgcc ttacaaggag agaaaaagca ccgtgcatgc cgattggtgg aagtaaggtg     120
gtacgatcgt gccttattag gaaggcaaca gacgggtctg acatggattg gacgaaccac     180
tgaattgccg cattgcagag atattgtatt taagtgccta gctcgataca taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
```

```
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg    600
gggagaatta gatcgcgatg ggaaaaaatt cggttaaggc caggggaaa gaaaaaatat    660 aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga gagcaaaac    900 aaaagtaaga ccaccgcaca gcaagcggcc ctgatcttca gacctggagg aggagatatg    960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctgggatt    1320 tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800
cggttaactt ttaaaagaaa aggggggatt ggggggtaca gtgcagggga agaatagta    1860 gacataatag caacagacat acaaactaaa gaattacaaa aacaaattac aaaaattcaa    1920
aattttatcg attacgcgtc acgtgctagc tgcagtaacg ccattttgca aggcatggaa    1980
aaataccaaa ccaagaatag agaagttcag atcaagggcg ggtacatgaa aatagctaac    2040
gttgggccaa acaggatatc tgcggtgagc agtttcggcc ccggcccggg gccaagaaca    2100
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
gcttctgctt cccgagctct ataaaagagc tcacaacccc tcactcggcg cgccagtcct    2340
ccgacagact gagtcgcccg ctcgagccgc caccatggga tatccatacg atgtcccaga    2400
ttatgcgcca cctaagaaga aacgcaaagt cgaattcgcc aataccaaat ataacgaaga    2460
gttcctgctg tacctggccg gctttgtgga cggtgacggt agcatcatcg ctcagattaa    2520
accacgtcag acctataagt ttaaacatca gctacgtttg acctttaaag tgggtcaaaa    2580
gacccagcgc cgttggtttc tggacaaact agtggatgaa attggcgttg gttacgtagc    2640
tgattctggt agcatgtccg aatacaactt aagcgaaatc aagccgctgc acaacttcct    2700
```

```
gactcaactg cagccgtttc tggaactgaa acagaaacag gcaaacctgg ttctgaaaat      2760
tatcgaacag ctgccgtctg caaaagaatc cccggacaaa ttcctggaag tttgtacctg      2820
ggtggatcag gttgcagctc tgaacgattc taagacgcgt aaaaccactt ctgaaaccgt      2880
tcgtgctgtg ctggacagcc tgagcgagaa gaagaaatcc tccccggcgg ccggtggatc      2940
tgataagtat aatcaggctc tgtctaaata caaccaagca ctgtccaagt acaatcaggc      3000
cctgtctggt ggaggcggtt ccaacaaaaa attcctgctg tatcttgctg gatttgtgga      3060
ttctgatggc tccatcattg ctcagataaa accaggtcaa cgttacaagt tcaaacacca      3120
gctccgtttg accttttacg tcactcagaa gacacaaaga aggtggttct tggacaaatt      3180
ggttgatcgt attggtgtgg gctatgtcta cgactctggc tctgcttcaa actaccagct      3240
gtctgaaatt aagcctcttc ataacctgct cacccaactg caaccttct tgaagctcaa      3300 acagaagcaa gcaaatctgg ttttgaaaat catcgagcaa ctgccatctg ccaaggagtc      3360
ccctgacaag tttcttgaag tgtgtacttg ggtggatcag gttgctgcct tgaatgactc      3420
caagaccaga aaaaccacct ctgagactgt gagggcagtt ctggatagcc agtctgagaa      3480
gaaaaagtac tctcctggat ccggtgaggg cagaggaagt cttctaacat gcggtgacgt      3540
ggaggagaat ccgggcccct ccggatctga gccacctcgg gctgagacct ttgtattcct      3600
ggacctagaa gccactgggc tcccaaacat ggaccctgag attgcagaga tatcccttt      3660 tgctgttcac cgctcttccc tggagaaccc agaacgggat gattctggtt ccttggtgct      3720
gccccgtgtt ctggacaagc tcacactgtg catgtgcccg gagcgcccct ttactgccaa      3780
ggccagtgag attactggtt tgagcagcga agcctgatg cactgcggga aggctggttt      3840
caatggcgct gtggtaagga cactgcaggg cttcctaagc cgccaggagg gccccatctg      3900
ccttgtggcc cacaatggct tcgattatga cttcccactg ctgtgcacgg agctacaacg      3960
tctgggtgcc catctgcccc aagacactgt ctgcctggac acactgcctg cattgcgggg      4020
cctggaccgt gctcacagcc acggaccag ggctcaaggc cgcaaaagct acagcctggc      4080
cagtctcttc caccgctact ccaggctga acccagtgct gcccattcag cagaaggtga      4140
tgtgcacacc ctgcttctga tcttcctgca tcgtgctcct gagctgctcg cctgggcaga      4200
tgagcaggcc cgcagctggg ctcatattga gcccatgtac gtgccacctg atggtccaag      4260
cctcgaagcc tgacctgcag gtcgagcatg catctagggc ggccaattcc gcccctctcc      4320 ctccccccc cctaacgtta ctggccgaag ccgcttggaa taaggccggt gtgcgtttgt      4380
ctatatgtga ttttccacca tattgccgtc ttttggcaat gtgagggccc ggaaacctgg      4440
ccctgtcttc ttgacgagca ttcctagggg tctttcccct ctcgccaaag gaatgcaagg      4500
tctgttgaat gtcgtgaagg aagcagttcc tctggaagct tcttgaagac aaacaacgtc      4560
tgtagcgacc ctttgcaggc agcggaaccc cccacctggc gacaggtgcc tctgcggcca      4620
aaagccacgt gtataagata cacctgcaaa ggcggcacaa ccccagtgcc acgttgtgag      4680
ttggatagtt gtggaaagag tcaaatggct ctcctcaagc gtattcaaca aggggctgaa      4740
ggatgcccag aagtaccccc attgtatggg atctgatctg gggcctcggt gcacatgctt      4800
tacatgtgtt tagtcgaggt taaaaaaacg tctaggcccc ccgaaccacg ggacgtggt      4860 tttcctttga aaaacacgat gataagcttg ccacaaccct taccggtcgc caccatgagc      4920
gagctgatta aggagaacat gcacatgaag ctgtacatgg agggcaccgt ggacaaccat      4980
cacttcaagt gcacatccga gggcgaaggc aagccctacg agggcaccca gaccatgaga      5040
atcaaggtgg tcgagggcgg ccctctcccc ttcgccttcg acatcctggc tactagcttc      5100
```

```
ctctacggca gcaagacctt catcaaccac acccagggca tccccgactt cttcaagcag    5160
tccttccctg agggcttcac atgggagaga gtcaccacat acgaagacgg gggcgtgctg    5220
accgctaccc aggacaccag cctccaggac ggctgcctca tctacaacgt caagatcaga    5280
ggggtgaact tcacatccaa cggccctgtg atgcagaaga aaacactcgg ctgggaggcc    5340
ttcaccgaga cgctgtaccc cgctgacggc ggcctggaag cagaaacga catggccctg    5400 aagctcgtgg gcgggagcca tctgatcgca aacatcaaga ccacatatag atccaagaaa    5460
cccgctaaga acctcaagat gcctggcgtc tactatgtgg actacagact ggaaagaatc    5520
aaggaggcca caacgagac ctacgtcgag cagcacgagg tggcagtggc cagatactgc    5580
gacctcccta gcaaactggg gcacaagctt aattgattct agagtcgacc gagcatctta    5640
ccgccattta tacccatatt tgttctgttt ttcttgattt gggtatacat ttaaatgtta    5700
atagaacaaa atggtggggc aatcatttac atttttaggg atatgtaatt actagttcag    5760
gtgtattgcc acaagacaaa catgttaaga aactttcccg ttatttacgc tctgttcctg    5820
ttaatcaacc tctggattac aaaatttgtg aaagattgac tgatattctt aactatgttg    5880
ctccttttac gctgtgtgga tatgctgctt tatagcctct gtatctagct attgcttccc    5940
gtacggcttt cgttttctcc tccttgtata atcctggtt gctgtctctt ttagaggagt    6000
tgtggcccgt tgtccgtcaa cgtggcgtgg tgtgctctgt gtttgctgac gcaacccca    6060 ctggctgggg cattgccacc acctgtcaac tcctttctgg gactttcgct ttccccctcc    6120
cgatcgccac ggcagaactc atcgccgcct gccttgcccg ctgctggaca ggggctaggt    6180
tgctgggcac tgataattcc gtggtgttgt catcggtacc tttttaaaag aaaagggggg    6240
actggaaggg ctaattcact cccaacgaag acaagatatc ataacttcgt atagcataca    6300
ttatacgaag ttataattta tttgtgaaat ttgtgatgct attgctttat tgtaaccat    6360 atgtttattt gtgaaatttg tgatgctatt gctttatttg taaccattgc ttttgcttg    6420 tactgggtct ctctggttag accagatctg agcctgggag ctctctggct aactagggaa    6480
cccactgctt aagcctcaat aaagcttgcc tcgaccagcc tcgactgtgc cttctagttg    6540
ccagccatct gttgtttgcc cctcccccgt gccttccttg accctggaag gtgccactcc    6600
cactgtcctt tcctaataaa atgaggaaat tgcatcgcat tgtctgagta ggtgtcattc    6660
tattctgggg ggtggggtgg ggcaggacag caaggggag gattgggaag acaatagcag    6720
gcatgctggg gatgcggtgg gctctatggc ctgcagctgc attaatgaat cggccaacgc    6780
gcggggagag gcggtttgcg tattgggcgc tcttccgctt cctcgctcac tgactcgctg    6840
cgctcggtcg ttcggctgcg gcgagcggta tcagctcact caaaggcggt aatacggtta    6900
tccacagaat caggggataa cgcaggaaag aacatgtgag caaaaggcca gcaaaggcc    6960 aggaaccgta aaaaggccgc gttgctggcg ttttccata ggctccgccc ccctgacgag    7020
catcacaaaa atcgacgctc aagtcagagg tggcgaaacc cgacaggact ataaagatac    7080
caggcgtttc cccctggaag ctccctcgtg cgctctcctg ttccgaccct gccgcttacc    7140
ggatacctgt ccgcctttct cccttcggga agcgtggcgc tttctcatag ctcacgctgt    7200
aggtatctca gttcggtgta ggtcgttcgc tccaagctgg gctgtgtgca cgaaccccc    7260 gttcagcccg accgctgcgc cttatccggt aactatcgtc ttgagtccaa cccggtaaga    7320
cacgacttat cgccactggc agcagccact ggtaacagga ttagcagagc gaggtatgta    7380
ggcggtgcta cagagttctt gaagtggtgg cctaactacg gctacactag aaggacagta    7440
```

| | |
|---|---|
| tttggtatct gcgctctgct gaagccagtt accttcggaa aaagagttgg tagctcttga | 7500 |
| tccggcaaac aaaccaccgc tggtagcggt ggtttttttg tttgcaagca gcagattacg | 7560 |
| cgcagaaaaa aaggatctca agaagatcct ttgatctttt ctacggggtc tgacgctcag | 7620 |
| tggaacgaaa actcacgtta agggattttg gtcatgagat tatcaaaaag gatcttcacc | 7680 |
| tagatccttt taaattaaaa atgaagtttt aaatcaatct aaagtatata tgagtaaact | 7740 |
| tggtctgaca gttaccaatg cttaatcagt gaggcaccta tctcagcgat ctgtctattt | 7800 |
| cgttcatcca tagttgcctg actccccgtc gtgtagataa ctacgatacg ggagggctta | 7860 |
| ccatctggcc ccagtgctgc aatgataccg cgagacccac gctcaccggc tccagattta | 7920 |
| tcagcaataa accagccagc cggaagggcc gagcgcagaa gtggtcctgc aactttatcc | 7980 |
| gcctccatcc agtctattaa ttgttgccgg gaagctagag taagtagttc gccagttaat | 8040 |
| agtttgcgca acgttgttgc cattgctaca ggcatcgtgg tgtcacgctc gtcgtttggt | 8100 |
| atggcttcat tcagctccgg ttcccaacga tcaaggcgag ttacatgatc ccccatgttg | 8160 |
| tgcaaaaaag cggttagctc cttcggtcct ccgatcgttg tcagaagtaa gttggccgca | 8220 |
| gtgttatcac tcatggttat ggcagcactg cataattctc ttactgtcat gccatccgta | 8280 |
| agatgctttt ctgtgactgg tgagtactca accaagtcat tctgagaata gtgtatgcgg | 8340 |
| cgaccgagtt gctcttgccc ggcgtcaata cgggataata ccgcgccaca tagcagaact | 8400 |
| ttaaaagtgc tcatcattgg aaaacgttct tcggggcgaa aactctcaag gatcttaccg | 8460 |
| ctgttgagat ccagttcgat gtaacccact cgtgcaccca actgatcttc agcatctttt | 8520 |
| actttcacca gcgtttctgg gtgagcaaaa acaggaaggc aaaatgccgc aaaaaaggga | 8580 |
| ataagggcga cacggaaatg ttgaatactc atactcttcc ttttcaata ttattgaagc | 8640 |
| atttatcagg gttattgtct catgagcgga tacatatttg aatgtattta gaaaaataaa | 8700 |
| caaatagggg ttccgcgcac atttccccga aaagtgccac ct | 8742 |

<210> SEQ ID NO 119
<211> LENGTH: 8757
<212> TYPE: DNA
<213> ORGANISM: Artificial Sequence
<220> FEATURE:
<223> OTHER INFORMATION: Plasmid pCVL.SFFV.HA.NLS.mCre
    I.T2A.Trex2.IRES.mTagBFP

<400> SEQUENCE: 119

| | |
|---|---|
| gacgtcaatg tagtcttatg caatactctt gtagtcttgc aacatggtaa cgatgagtta | 60 |
| gcaacatgcc ttacaaggag agaaaaagca ccgtgcatgc cgattggtgg aagtaaggtg | 120 |
| gtacgatcgt gccttattag gaaggcaaca gacgggtctg acatggattg gacgaaccac | 180 |
| tgaattgccg cattgcagag atattgtatt taagtgccta gctcgataca taaacgggtc | 240 |
| tctctggtta gaccagatct gagcctggga gctctctggc taactaggga acccactgct | 300 |
| taagcctcaa taaagcttgc cttgagtgct tcaagtagtg tgtgcccgtc tgttgtgtga | 360 |
| ctctggtaac tagagatccc tcagaccctt ttagtcagtg tggaaaatct ctagcagtgg | 420 |
| cgcccgaaca gggacttgaa agcgaaaggg aaaccagagg agctctctcg acgcaggact | 480 |
| cggcttgctg aagcgcgcac ggcaagaggc gaggggcggc gactggtgag tacgccaaaa | 540 |
| attttgacta gcggaggcta agaggagaga gatgggtgcg agagcgtcag tattaagcgg | 600 |
| gggagaatta gatcgcgatg ggaaaaaatt cggttaaggc cagggggaaa gaaaaaatat | 660 |
| aaattaaaac atatagtatg ggcaagcagg gagctagaac gattcgcagt taatcctggc | 720 |

```
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga agaatagta    1860
gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgac accaagtata caaggagtt    2460
cctgctgtat ctggctggtt tcgtcgatgg cgatggcagc attattgcac agattaagcc   2520
aaaccagtcc tataagttta gcaccagtt gtctctcact tttcaggtga cccaaaaaac    2580
ccaacgccgc tggttcctcg acaagctggt agacgagatc ggtgtgggct acgttcgcga   2640
tcgcggctcc gtttccgact acatcctcag cgagattaaa ccgctgcaca ttttctgac    2700
ccaactgcag ccgtttctga agctcaaaca gaagcaagcg aacctggtgc tgaaaatcat   2760
cgaacagctc ccgtccgcga aggaatctcc ggataagttt ctggaagtgt gcacctgggt   2820
ggaccagatt gctgcactga atgattccaa acccgcaag accacttctg agaccgttcg    2880
cgccgttctg gactctctct ctgaaaaaaa aaaatcttcc ccgaccggta gcggctcagg   2940
atctaaatcc caggctgtgg ctcacccgac agacggccag agggatttcg ggccaaagg    3000
atctgggtcg ggaagcggta ccatgaatac taaatacaat aaagaatttc ttctctacct   3060
cgcgggcttt gtggacggtg acggttccat catcgctcaa atcaaaccta atcaaagcta   3120
```

```
caaattcaaa catcagctgt ccctgacctt ccaagttacg cagaaaacgc agcgtcgttg    3180
gtttctggat aaattggttg atgaaattgg cgtaggttat gtacgtgacc gtggttctgt    3240
gtctgattat attctgtccg aaatcaagcc tctccataac ttcctcacgc agctgcaacc    3300
attcctgaaa ctgaagcaga aacaggctaa tctcgttctg aaaattattg aacagctgcc    3360
atctgctaaa gagtcccctg acaaattcct cgaggtttgt acttggggttg atcaaatcgc    3420
ggcccttaac gacagcaaga ctcgtaaaac taccagcgaa actgtccgtg cagtactcga    3480
ttccctgtcg gagaagaaga agagctctcc aggatccggt gagggcagag aagtcttct     3540
aacatgcggt gacgtggagg agaatccggg cccctccgga tctgagccac tcgggctga    3600
gacctttgta ttcctggacc tagaagccac tgggctccca acatggacc ctgagattgc    3660
agagatatcc cttttttgctg ttcaccgctc ttccctggag aacccagaac gggatgattc   3720
tggttccttg gtgctgcccc gtgttctgga caagctcaca ctgtgcatgt gcccggagcg    3780
ccccttttact gccaaggcca gtgagattac tggtttgagc agcgaaagcc tgatgcactg   3840
cgggaaggct ggtttcaatg cgctgtggt aaggacactg cagggcttcc taagccgcca     3900
ggagggcccc atctgccttg tggcccacaa tggcttcgat tatgacttcc cactgctgtg    3960
cacggagcta caacgtctgg gtgccatct gccccaagac actgtctgcc tggacacact     4020
gcctgcattg cggggcctgg accgtgctca cagccacggc accagggctc aaggccgcaa    4080
aagctacagc ctggccagtc tcttccaccg ctacttccag gctgaaccca gtgctgccca    4140
ttcagcagaa ggtgatgtgc acaccctgct tctgatcttc ctgcatcgtg ctcctgagct    4200
gctcgcctgg gcagatgagc aggcccgcag ctgggctcat attgagccca tgtacgtgcc    4260
acctgatggt ccaagcctcg aagcctgacc tgcaggtcga gcatgcatct agggcggcca   4320
attccgcccc tctccctccc ccccccctaa cgttactggc cgaagccgct tggaataagg    4380
ccggtgtgcg tttgtctata tgtgattttc caccatattg ccgtcttttg gcaatgtgag    4440
ggcccggaaa cctggccctg tcttcttgac gagcattcct aggggtcttt ccctctcgc     4500
caaaggaatg caaggtctgt tgaatgtcgt gaaggaagca gttcctctgg aagcttcttg    4560
aagacaaaca acgtctgtag cgaccctttg caggcagcgg aaccccccac ctggcgacag    4620
gtgcctctgc ggccaaaagc cacgtgtata agatacacct gcaaaggcgg cacaacccca    4680
gtgccacgtt gtgagttgga tagttgtgga agagtcaaa tggctctcct caagcgtatt     4740
caacaagggg ctgaaggatg cccagaaggt acccattgt atgggatctg atctggggcc     4800
tcggtgcaca tgctttacat gtgtttagtc gaggttaaaa aaacgtctag gccccccgaa    4860
ccacggggac gtggttttcc tttgaaaaac acgatgataa gcttgccaca acccttaccg    4920
gtcgccacca tgagcgagct gattaaggag aacatgcaca tgaagctgta catggagggc    4980
accgtggaca accatcactt caagtgcaca tccgagggcg aaggcaagcc ctacgagggc    5040
acccagacca tgagaatcaa ggtggtcgag ggcggccctc tccccttcgc cttcgacatc    5100
ctggctacta gcttcctcta cggcagcaag accttcatca accacaccca gggcatcccc    5160
gacttcttca gcagtccttt ccctgagggc ttcacatggg agagagtcac acatacgaa     5220
gacggggggcg tgctgaccgc tacccaggac accagcctcc aggacggctg cctcatctac    5280
aacgtcaaga tcagagggt gaacttcaca tccaacggcc ctgtgatgca agagaaaaca    5340
ctcggctggg aggccttcac cgagacgctg taccccgctg acggcggcct ggaaggcaga    5400
aacgacatgg ccctgaagct cgtgggcggg agccatctga tcgcaaacat caagaccaca    5460
```

```
tatagatcca agaaacccgc taagaacctc aagatgcctg gcgtctacta tgtggactac    5520
agactggaaa gaatcaagga ggccaacaac gagacctacg tcgagcagca cgaggtggca    5580
gtggccagat actgcgacct ccctagcaaa ctggggcaca agcttaattg attctagagt    5640
cgaccgagca tcttaccgcc atttataccc atatttgttc tgttttcctt gatttgggta    5700
tacatttaaa tgttaataga acaaaatggt ggggcaatca tttacatttt tagggatatg    5760
taattactag ttcaggtgta ttgccacaag acaaacatgt taagaaactt ccccgttatt    5820
tacgctctgt tcctgttaat caacctctgg attacaaaat tgtgaaagat tgactgata    5880
ttcttaacta tgttgctcct tttacgctgt gtggatatgc tgctttatag cctctgtatc    5940
tagctattgc ttcccgtacg gctttcgttt tctcctcctt gtataaatcc tggttgctgt    6000
ctcttttaga ggagttgtgg cccgttgtcc gtcaacgtgg cgtggtgtgc tctgtgtttg    6060
ctgacgcaac ccccactggc tggggcattg ccaccacctg tcaactcctt tctgggactt    6120
tcgctttccc cctcccgatc gccacggcag aactcatcgc cgcctgcctt gcccgctgct    6180
ggacagggc taggttgctg ggcactgata attccgtggt gttgtcatcg gtaccttttt    6240
aaaagaaaag gggggactgg aagggctaat tcactcccaa cgaagacaag atatcataac    6300
ttcgtatagc atacattata cgaagttata atttatttgt gaaatttgtg atgctattgc    6360
tttatttgta accatatgtt tatttgtgaa atttgtgatg ctattgcttt atttgtaacc    6420
attgcttttt gcttgtactg ggtctctctg gttagaccag atctgagcct gggagctctc    6480
tggctaacta gggaacccac tgcttaagcc tcaataaagc ttgcctcgac cagcctcgac    6540
tgtgccttct agttgccagc catctgttgt ttgcccctcc ccgtgccttc cttgaccct    6600
ggaaggtgcc actcccactg tcctttccta ataaaatgag gaaattgcat cgcattgtct    6660
gagtaggtgt cattctattc tggggggtgg ggtggggcag gacagcaagg gggaggattg    6720
ggaagacaat agcaggcatg ctggggatgc ggtgggctct atggcctgca gctgcattaa    6780
tgaatcggcc aacgcgcggg gagaggcggt ttgcgtattg ggcgctcttc cgcttcctcg    6840
ctcactgact cgctgcgctc ggtcgttcgg ctgcggcgag cggtatcagc tcactcaaag    6900
gcggtaatac ggttatccac agaatcaggg gataacgcag gaaagaacat gtgagcaaaa    6960
ggccagcaaa aggccaggaa ccgtaaaaag gccgcgttgc tggcgttttt ccataggctc    7020
cgccccctg acgagcatca caaaaatcga cgctcaagtc agaggtggcg aaacccgaca    7080
ggactataaa gataccaggc gtttccccct ggaagctccc tcgtgcgctc tcctgttccg    7140
accctgccgc ttaccggata cctgtccgcc tttctccctt cgggaagcgt ggcgctttct    7200
catagctcac gctgtaggta tctcagttcg gtgtaggtcg ttcgctccaa gctgggctgt    7260
gtgcacgaac cccccgttca gcccgaccgc tgcgccttat ccggtaacta tcgtcttgag    7320
tccaacccgg taagacacga cttatcgcca ctggcagcag ccactggtaa caggattagc    7380
agagcgaggt atgtaggcgg tgctacagag ttcttgaagt ggtggcctaa ctacggctac    7440
actagaagga cagtatttgg tatctgcgct ctgctgaagc cagttacctt cggaaaaaga    7500
gttggtagct cttgatccgg caaacaaacc accgctggta gcggtggttt ttttgtttgc    7560
aagcagcaga ttacgcgcag aaaaaaagga tctcaagaag atcctttgat cttttctacg    7620
gggtctgacg ctcagtggaa cgaaaactca cgttaaggga ttttggtcat gagattatca    7680
aaaaggatct tcacctagat ccttttaaat taaaaatgaa gttttaaatc aatctaaagt    7740
atatatgagt aaacttggtc tgacagttac caatgcttaa tcagtgaggc acctatctca    7800
gcgatctgtc tatttcgttc atccatagtt gcctgactcc ccgtcgtgta gataactacg    7860
```

```
atacgggagg gcttaccatc tggccccagt gctgcaatga taccgcgaga cccacgctca    7920
ccggctccag atttatcagc aataaaccag ccagccggaa gggccgagcg cagaagtggt    7980
cctgcaactt tatccgcctc catccagtct attaattgtt gccgggaagc tagagtaagt    8040
agttcgccag ttaatagttt gcgcaacgtt gttgccattg ctacaggcat cgtggtgtca    8100
cgctcgtcgt ttggtatggc ttcattcagc tccggttccc aacgatcaag gcgagttaca    8160
tgatccccca tgttgtgcaa aaaagcggtt agctccttcg tcctccgat cgttgtcaga    8220 agtaagttgg ccgcagtgtt atcactcatg gttatggcag cactgcataa ttctcttact    8280
gtcatgccat ccgtaagatg cttttctgtg actggtgagt actcaaccaa gtcattctga    8340
gaatagtgta tgcggcgacc gagttgctct tgcccggcgt caatacggga taataccgcg    8400
ccacatagca gaactttaaa agtgctcatc attggaaaac gttcttcggg gcgaaaactc    8460
tcaaggatct taccgctgtt gagatccagt tcgatgtaac ccactcgtgc acccaactga    8520
tcttcagcat cttttacttt caccagcgtt tctgggtgag caaaaacagg aaggcaaaat    8580
gccgcaaaaa agggaataag ggcgacacgg aaatgttgaa tactcatact cttcctttt    8640 caatattatt gaagcattta tcagggttat tgtctcatga cggatacat atttgaatgt    8700 atttagaaaa ataaacaaat aggggttccg cgcacatttc cccgaaaagt gccacct     8757
```

<210> SEQ ID NO 120
<211> LENGTH: 7986
<212> TYPE: DNA
<213> ORGANISM: Artificial Sequence
<220> FEATURE:
<223> OTHER INFORMATION: Plasmid pCVL.SFFV.HA.NLS.mCre.IRES.mTagBFP

<400> SEQUENCE: 120

```
gacgtcaatg tagtcttatg caatactctt gtagtcttgc aacatggtaa cgatgagtta    60
gcaacatgcc ttacaaggag agaaaaagca ccgtgcatgc cgattggtgg aagtaaggtg   120
gtacgatcgt gccttattag gaaggcaaca gacgggtctg acatggattg gacgaaccac   180
tgaattgccg cattgcagag atattgtatt taagtgccta gctcgataca taaacgggtc   240
tctctggtta gaccagatct gagcctggga gctctctggc taactaggga acccactgct   300
taagcctcaa taaagcttgc cttgagtgct tcaagtagtg tgtgcccgtc tgttgtgtga   360
ctctggtaac tagagatccc tcagaccctt ttagtcagtg tggaaaatct ctagcagtgg   420
cgcccgaaca gggacttgaa agcgaaaggg aaaccagagg agctctctcg acgcaggact   480
cggcttgctg aagcgcgcac ggcaagaggc gaggggcggc gactggtgag tacgccaaaa   540
attttgacta gcggaggcta agaggagaga gatgggtgcg agagcgtcag tattaagcgg   600
gggagaatta gatcgcgatg ggaaaaaatt cggttaaggc caggggggaaa gaaaaaatat   660 aaattaaaac atatagtatg ggcaagcagg gagctagaac gattcgcagt taatcctggc   720
ctgttagaaa catcagaagg ctgtagacaa atactgggac agctacaacc atcccttcag   780
acaggatcag aagaacttag atcattatat aatacagtag caaccctcta ttgtgtgcat   840
caaaggatag agataaaaga caccaaggaa gctttagaca agatagagga agagcaaaac   900
aaaagtaaga ccaccgcaca gcaagcggcc ctgatcttca gacctggagg aggagatatg   960
agggacaatt ggagaagtga attatataaa tataaagtag taaaaattga accattagga  1020
gtagcaccca ccaaggcaaa gagaagagtg gtgcagagag aaaaaagagc agtgggaata  1080
ggagctttgt tccttgggtt cttgggagca gcaggaagca ctatgggcgc agcgtcaatg  1140
```

```
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctggggatt    1320
tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800
cggttaactt ttaaaagaaa aggggggatt ggggggtaca gtgcagggga agaatagta     1860 gacataatag caacagacat acaaactaaa gaattacaaa aacaaattac aaaaattcaa    1920
aattttatcg attacgcgtc acgtgctagc tgcagtaacg ccattttgca aggcatggaa    1980
aaataccaaa ccaagaatag agaagttcag atcaagggcg ggtacatgaa aatagctaac    2040
gttgggccaa acaggatatc tgcggtgagc agtttcggcc ccggcccggg gccaagaaca    2100
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
gcttctgctt cccgagctct ataaagagc tcacaacccc tcactcggcg cgccagtcct    2340
ccgacagact gagtcgcccg ctcgagccgc accatggga tatccatacg atgtcccaga    2400
ttatgcgcca cctaagaaga aacgcaaagt cgaattcgac accaagtata caaggagtt     2460 cctgctgtat ctggctggtt tcgtcgatgg cgatggcagc attattgcac agattaagcc    2520
aaaccagtcc tataagttta agcaccagtt gtctctcact tttcaggtga cccaaaaaac    2580
ccaacgccgc tggttcctcg acaagctggt agacgagatc ggtgtgggct acgttcgcga    2640
tcgcggctcc gtttccgact acatcctcag cgagattaaa ccgctgcaca attttctgac    2700
ccaactgcag ccgtttctga agctcaaaca gaagcaagcg aacctggtgc tgaaaatcat    2760
cgaacagctc ccgtccgcga aggaatctcc ggataagttt ctggaagtgt gcacctgggt    2820
ggaccagatt gctgcactga atgattccaa aacccgcaag accacttctg agaccgttcg    2880
cgccgttctg gactctctct ctgaaaaaaa aaatcttcc ccgaccggta gcggctcagg    2940
atctaaatcc caggctgtgg ctcacccgac agacggccag agggatttcg gggccaaagg    3000
atctgggtcg ggaagcggta ccatgaatac taaatacaat aaagaatttc ttctctacct    3060
cgcgggcttt gtggacggtg acggttccat catcgctcaa atcaaaccta atcaaagcta    3120
caaattcaaa catcagctgt ccctgacctt ccaagttacg cagaaaacgc agcgtcgttg    3180
gtttctggat aaaattggttg atgaaattgg cgtaggttat gtacgtgacc gtggttctgt    3240
gtctgattat attctgtccg aaatcaagcc tctccataac ttcctcacgc agctgcaacc    3300
attcctgaaa ctgaagcaga acaggctaa tctcgttctg aaaattattg aacagctgcc    3360
atctgctaaa gagtcccctg acaaattcct cgaggtttgt acttggttg atcaaatcgc    3420 ggcccttaac gacagcaaga ctcgtaaaac taccagcgaa actgtccgtg cagtactcga    3480
ttccctgtcg gagaagaaga agagctctcc atagtaacct gcaggtcgag catgcatcta    3540
```

```
gggcggccaa ttccgccct ctccctcccc ccccctaac gttactggcc gaagccgctt    3600
ggaataaggc cggtgtgcgt ttgtctatat gtgatttcc accatattgc cgtcttttgg   3660
caatgtgagg gcccggaaac ctggccctgt cttcttgacg agcattccta ggggtctttc   3720
ccctctcgcc aaaggaatgc aaggtctgtt gaatgtcgtg aaggaagcag ttcctctgga   3780
agcttcttga agacaaacaa cgtctgtagc gaccctttgc aggcagcgga acccccacc    3840 tggcgacagg tgcctctgcg gccaaaagcc acgtgtataa gatacacctg caaggcggc    3900 acaaccccag tgccacgttg tgagttggat agttgtggaa agagtcaaat ggctctcctc   3960
aagcgtattc aacaagggc tgaaggatgc ccagaaggta ccccattgta tgggatctga   4020 tctgggcct cggtgcacat gctttacatg tgtttagtcg aggttaaaaa aacgtctagg   4080 cccccgaac cacggggacg tggttttcct ttgaaaaaca cgatgataag cttgccacaa    4140
cccttaccgg tcgccaccat gagcgagctg attaaggaga acatgcacat gaagctgtac   4200
atggagggca ccgtggacaa ccatcacttc aagtgcacat ccgagggcga aggcaagccc   4260
tacgagggca cccagaccat gagaatcaag gtggtcgagg gcggcctct cccttcgcc    4320 ttcgacatcc tggctactag cttcctctac ggcagcaaga ccttcatcaa ccacacccag   4380
ggcatccccg acttcttcaa gcagtccttc cctgagggct tcacatggga gagagtcacc   4440
acatacgaag acgggggcgt gctgaccgct acccaggaca ccagcctcca ggacggctgc   4500
ctcatctaca acgtcaagat cagagggtg aacttcacat ccaacggccc tgtgatgcag   4560
aagaaaacac tcggctggga ggccttcacc gagacgctgt accccgctga cggcggcctg   4620
gaaggcagaa acgacatggc cctgaagctc gtgggcggga gccatctgat cgcaaacatc   4680
aagaccacat atagatccaa gaaacccgct aagaacctca agatgcctgg cgtctactat   4740
gtggactaca gactggaaag aatcaaggag gccaacaacg agacctacgt cgagcagcac   4800
gaggtggcag tggccagata ctgcgacctc cctagcaaac tggggcacaa gcttaattga   4860
ttctagagtc gaccgagcat cttaccgcca tttataccca tatttgttct gttttttcttg   4920 atttgggtat acatttaaat gttaatagaa caaaatggtg gggcaatcat ttacatttt     4980 agggatatgt aattactagt tcaggtgtat tgccacaaga caaacatgtt aagaaacttt   5040
cccgttattt acgctctgtt cctgttaatc aacctctgga ttacaaaatt tgtgaaagat   5100
tgactgatat tcttaactat gttgctcctt ttacgctgtg tggatatgct gctttatagc   5160
ctctgtatct agctattgct tcccgtacgg cttcgtttt ctcctccttg tataaatcct   5220
ggttgctgtc tctttagag gagttgtggc ccgttgtccg tcaacgtggc gtggtgtgct   5280
ctgtgtttgc tgacgcaacc cccactggct ggggcattgc caccacctgt caactccttt   5340
ctgggacttt cgctttcccc ctccccgatcg ccacggcaga actcatcgcc gcctgccttg   5400
cccgctgctg gacagggggct aggttgctgg gcactgataa ttccgtggtg ttgtcatcgg   5460 tacctttta aaagaaaagg ggggactgga agggctaatt cactcccaac gaagacaaga   5520
tatcataact tcgtatagca tacattatac gaagttataa tttatttgtg aaatttgtga   5580
tgctattgct ttatttgtaa ccatatgttt atttgtgaaa tttgtgatgc tattgcttta   5640
tttgtaacca ttgcttttg cttgtactgg gtctctctgg ttagaccaga tctgagcctg   5700
ggagctctct ggctaactag ggaacccact gcttaagcct caataaagct tgcctcgacc   5760
agcctcgact gtgccttcta gttgccagcc atctgttgtt tgcccctccc cgtgccttc    5820 cttgaccctg gaaggtgcca ctcccactgt cctttcctaa taaaatgagg aaattgcatc   5880
```

```
gcattgtctg agtaggtgtc attctattct gggggggtggg gtggggcagg acagcaaggg    5940
ggaggattgg gaagacaata gcaggcatgc tggggatgcg gtgggctcta tggcctgcag    6000
ctgcattaat gaatcggcca acgcgcgggg agaggcggtt tgcgtattgg gcgctcttcc    6060
gcttcctcgc tcactgactc gctgcgctcg gtcgttcggc tgcggcgagc ggtatcagct    6120
cactcaaagg cggtaatacg gttatccaca gaatcagggg ataacgcagg aaagaacatg    6180
tgagcaaaag gccagcaaaa ggccaggaac cgtaaaaagg ccgcgttgct ggcgtttttc    6240
cataggctcc gcccccctga cgagcatcac aaaaatcgac gctcaagtca gaggtggcga    6300
aacccgacag gactataaag ataccaggcg tttccccctg gaagctccct cgtgcgctct    6360
cctgttccga ccctgccgct taccggatac ctgtccgcct ttctcccttc gggaagcgtg    6420
gcgctttctc atagctcacg ctgtaggtat ctcagttcgg tgtaggtcgt tcgctccaag    6480
ctgggctgtg tgcacgaacc ccccgttcag cccgaccgct gcgccttatc cggtaactat    6540
cgtcttgagt ccaacccggt aagacacgac ttatcgccac tggcagcagc cactggtaac    6600
aggattagca gagcgaggta tgtaggcggt gctacagagt tcttgaagtg gtggcctaac    6660
tacggctaca ctagaaggac agtatttggt atctgcgctc tgctgaagcc agttaccttc    6720
ggaaaaagag ttggtagctc ttgatccggc aaacaaacca ccgctggtag cggtggtttt    6780
tttgtttgca agcagcagat tacgcgcaga aaaaaggat ctcaagaaga tcctttgatc    6840
ttttctacgg ggtctgacgc tcagtggaac gaaaactcac gttaagggat tttggtcatg    6900
agattatcaa aaaggatctt cacctagatc cttttaaatt aaaaatgaag ttttaaatca    6960
atctaaagta tatatgagta aacttggtct gacagttacc aatgcttaat cagtgaggca    7020
cctatctcag cgatctgtct atttcgttca tccatagttg cctgactccc cgtcgtgtag    7080
ataactacga tacgggaggg cttaccatct ggccccagtg ctgcaatgat accgcgagac    7140
ccacgctcac cggctccaga tttatcagca ataaaccagc cagccggaag ggccgagcgc    7200
agaagtggtc ctgcaacttt atccgcctcc atccagtcta ttaattgttg ccgggaagct    7260
agagtaagta gttcgccagt taatagtttg cgcaacgttg ttgccattgc tacaggcatc    7320
gtggtgtcac gctcgtcgtt tggtatggct tcattcagct ccggttccca acgatcaagg    7380
cgagttacat gatccccccat gttgtgcaaa aaagcggtta gctccttcgg tcctccgatc    7440
gttgtcagaa gtaagttggc cgcagtgtta tcactcatgg ttatggcagc actgcataat    7500
tctcttactg tcatgccatc cgtaagatgc ttttctgtga ctggtgagta ctcaaccaag    7560
tcattctgag aatagtgtat gcggcgaccg agttgctctt gcccggcgtc aatacgggat    7620
aataccgcgc cacatagcag aactttaaaa gtgctcatca ttggaaaacg ttcttcgggg    7680
cgaaaactct caaggatctt accgctgttg agatccagtt cgatgtaacc cactcgtgca    7740
cccaactgat cttcagcatc ttttactttc accagcgttt ctgggtgagc aaaaacagga    7800
aggcaaaatg ccgcaaaaaa gggaataagg gcgacacgga aatgttgaat actcatactc    7860
ttcctttttc aatattattg aagcatttat cagggttatt gtctcatgag cggatacata    7920
tttgaatgta tttagaaaaa taaacaaata ggggttccgc gcacatttcc ccgaaaagtg    7980
ccacct                                                                7986
```

<210> SEQ ID NO 121
<211> LENGTH: 7665
<212> TYPE: DNA
<213> ORGANISM: Artificial Sequence
<220> FEATURE:
<223> OTHER INFORMATION: Plasmid pCVL.SFFV.HA.NLS.Hje.IRES.mTagBFP

<400> SEQUENCE: 121

```
gacgtcaatg tagtcttatg caatactctt gtagtcttgc aacatggtaa cgatgagtta      60
gcaacatgcc ttacaaggag agaaaaagca ccgtgcatgc cgattggtgg aagtaaggtg     120
gtacgatcgt gccttattag gaaggcaaca gacgggtctg acatggattg gacgaaccac     180
tgaattgccg cattgcagag atattgtatt taagtgccta gctcgataca taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta aaggagaga gatgggtgcg agagcgtcag tattaagcgg     600
gggagaatta gatcgcgatg ggaaaaaatt cggttaaggc caggggggaaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca agatagagga agagcaaaac     900
aaaagtaaga ccaccgcaca gcaagcggcc ctgatcttca gacctggagg aggagatatg     960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctggggatt    1320
tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagacag agacagatcc attcgattga acggatc tcgacggtat    1800
cggttaacttt ttaaaagaaa aggggggatt ggggggtaca gtgcagggga aagaatagta    1860
gacataatag caacagacat acaaactaaa gaattacaaa aacaaattac aaaaattcaa    1920
aatttatcg attacgcgtc acgtgctagc tgcagtaacg ccattttgca aggcatggaa    1980
aaataccaaa ccaagaatag agaagttcag atcaagggcg ggtacatgaa aatagctaac    2040
gttgggccaa acaggatatc tgcggtgagc agtttcggcc ccggcccggg gccaagaaca    2100
gatggtcacc gcagtttcgg ccccggcccg aggccaagaa cagatggtcc ccagatatgg    2160
cccaacctc agcagtttct taagacccat cagatgtttc caggctcccc caaggacctg    2220
aaatgaccct gcgccttatt tgaattaacc aatcagcctg cttctcgctt ctgttcgcgc    2280
```

```
gcttctgctt cccgagctct ataaaagagc tcacaacccc tcactcggcg cgccagtcct    2340
ccgacagact gagtcgcccg ctcgagccgc caccatggga tatccatacg atgtcccaga    2400
ttatgcgcca cctaagaaga aacgcaaagt cgaattcgat cttacgtacg cgtatttagt    2460
tggtctcttc gaaggggatg gatactttag tatcaccaag aaaggcaagt acttgactta    2520
tgaattaggt attgagctga gcatcaaaga cgtccaattg atttacaaga tcaaggacat    2580
cctaggtgtt ggcaaagtaa gcttcaggaa gagaaacgag attgaaatgg tttcattgag    2640
gatccgtgat aagaatcatc taaaaaactt catattgcct atatttgaca agtatccaat    2700
gttatccaac aaacagtacg actatttaag attcaaggat gcattgttat ctaacattat    2760
atactcagat gacttgcctg aatacgctag aagtaacgaa tcgattaatt ctgtagactc    2820
cattatcaac acatcatact tctccgcctg gctagttgga tttatagaag ctgagggctg    2880
tttcagtacg tacaagctga acaaagacga tgactacttg attgcttcat cgacattgc     2940 ccaaaaagat ggtgatatct tgatttcagc aattcacaag tacttaagtt tcactactaa    3000
gatttaccta gacaagacta attgtagcag attgaaggtc accggtgtta gatccgtcaa    3060
gaacgtcgtt aagtttatcc agggtgctcc tgtcaaattg ttaggcaaca agaaactgca    3120
atacaagttg tggataaaac aactaaggaa gatttctagg tattccgaga agatccagct    3180
tccatcaaac tactagcctg caggtcgagc atgcatctag gcggccaat tccgcccctc     3240 tccctccccc cccctaacg ttactggccg aagccgcttg gaataaggcc ggtgtgcgtt    3300
tgtctatatg tgattttcca ccatattgcc gtcttttggc aatgtgaggg cccggaaacc    3360
tggccctgtc ttcttgacga gcattcctag gggtctttcc cctctcgcca aggaatgca     3420 aggtctgttg aatgtcgtga aggaagcagt tcctctggaa gcttcttgaa gacaaacaac    3480
gtctgtagcg accctttgca ggcagcggaa ccccccacct ggcgacaggt gcctctgcgg    3540
ccaaaagcca cgtgtataag atacacctgc aaaggcggca caaccccagt gccacgttgt    3600
gagttggata gttgtggaaa gagtcaaatg gctctcctca agcgtattca acaagggggct   3660 gaaggatgcc cagaaggtac cccattgtat gggatctgat ctggggcctc ggtgcacatg    3720
ctttacatgt gtttagtcga ggttaaaaaa acgtctaggc cccccgaacc acggggacgt    3780
ggttttcctt tgaaaaacac gatgataagc ttgccacaac ccttaccggt cgccaccatg    3840
agcgagctga ttaaggagaa catgcacatg aagctgtaca tggagggcac cgtggacaac    3900
catcacttca gtgcacatc cgagggcgaa ggcaagccct acgagggcac ccagaccatg    3960
agaatcaagg tggtcgaggg cggccctctc cccttcgcct tcgacatcct ggctactagc    4020
ttcctctacg gcagcaagac cttcatcaac cacacccagg gcatccccga cttcttcaag    4080
cagtccttcc ctgagggctt cacatgggag agagtcacca catacgaaga cggggggcgtg    4140 ctgaccgcta cccaggacac cagcctccag gacggctgcc tcatctacaa cgtcaagatc    4200
agaggggtga acttcacatc caacggcccc gtgatgcaga gaaaacact cggctgggag    4260 gccttcaccg agacgctgta ccccgctgac ggcggcctgg aaggcagaaa cgacatggcc    4320
ctgaagctcg tgggcgggag ccatctgatc gcaaacatca gaccacata tagatccaag    4380 aaacccgcta agaacctcaa gatgcctggc gtctactatg tggactacag actgaaaga     4440 atcaaggagg ccaacaacga gacctacgtc gagcagcacg aggtggcagt ggccagatac    4500
tgcgacctcc ctagcaaact ggggcacaag cttaattgat tctagagtcg accgagcatc    4560
ttaccgccat ttatacccat atttgttctg tttttcttga tttgggtata catttaaatg    4620
ttaatagaac aaaatggtgg ggcaatcatt tacatttta gggatatgta attactagtt    4680
```

```
caggtgtatt gccacaagac aaacatgtta agaaactttc ccgttattta cgctctgttc    4740
ctgttaatca acctctggat tacaaaattt gtgaaagatt gactgatatt cttaactatg    4800
ttgctccttt tacgctgtgt ggatatgctg ctttatagcc tctgtatcta gctattgctt    4860
cccgtacggc tttcgttttc tcctccttgt ataaatcctg gttgctgtct cttttagagg    4920
agttgtggcc cgttgtccgt caacgtggcg tggtgtgctc tgtgtttgct gacgcaaccc    4980
ccactggctg gggcattgcc accacctgtc aactcccttc tgggactttc gctttccccc    5040
tcccgatcgc cacggcagaa ctcatcgccg cctgccttgc ccgctgctgg acagggcta    5100 ggttgctggg cactgataat tccgtggtgt tgtcatcggt accttttttaa aagaaaaggg    5160 gggactggaa gggctaattc actcccaacg aagacaagat atcataactt cgtatagcat    5220
acattatacg aagttataat ttatttgtga aatttgtgat gctattgctt tatttgtaac    5280
catatgttta tttgtgaaat ttgtgatgct attgctttat tgtaaccat tgcttttgc     5340 ttgtactggg tctctctggt tagaccagat ctgagcctgg gagctctctg gctaactagg    5400
gaacccactg cttaagcctc aataaagctt gcctcgacca gcctcgactg tgccttctag    5460
ttgccagcca tctgttgttt gcccctcccc cgtgccttcc ttgaccctgg aaggtgccac    5520
tcccactgtc ctttcctaat aaaatgagga aattgcatcg cattgtctga gtaggtgtca    5580
ttctattctg gggggtgggg tggggcagga cagcaagggg gaggattggg aagacaatag    5640
caggcatgct ggggatgcgg tgggctctat ggcctgcagc tgcattaatg aatcggccaa    5700
cgcgcgggga gaggcggttt gcgtattggg cgctcttccg cttcctcgct cactgactcg    5760
ctgcgctcgg tcgttcggct gcggcgagcg gtatcagctc actcaaaggc ggtaatacgg    5820
ttatccacag aatcagggga taacgcagga aagaacatgt gagcaaaagg ccagcaaaag    5880
gccaggaacc gtaaaaaggc cgcgttgctg gcgtttttcc ataggctccg ccccctgac    5940 gagcatcaca aaaatcgacg ctcaagtcag aggtggcgaa acccgacagg actataaaga    6000
taccaggcgt ttccccctgg aagctccctc gtgcgctctc ctgttccgac cctgccgctt    6060
accggatacc tgtccgcctt tctcccttcg ggaagcgtgg cgctttctca tagctcacgc    6120
tgtaggtatc tcagttcggt gtaggtcgtt cgctccaagc tgggctgtgt gcacgaaccc    6180
cccgttcagc ccgaccgctg cgccttatcc ggtaactatc gtcttgagtc aacccggta    6240 agacacgact tatcgccact ggcagcagcc actggtaaca ggattagcag agcgaggtat    6300
gtaggcggtg ctacagagtt cttgaagtgg tggcctaact acggctacac tagaaggaca    6360
gtatttggta tctgcgctct gctgaagcca gttaccttcg gaaaaagagt tggtagctct    6420
tgatccggca acaaaccacc gctggtagc ggtggttttt tgtttgcaa gcagcagatt    6480 acgcgcagaa aaaaggatc tcaagaagat cctttgatct tttctacggg gtctgacgct    6540
cagtggaacg aaaactcacg ttaagggatt ttggtcatga gattatcaaa aaggatcttc    6600
acctagatcc ttttaaatta aaaatgaagt tttaaatcaa tctaaagtat atatgagtaa    6660
acttggtctg acagttacca atgcttaatc agtgaggcac ctatctcagc gatctgtcta    6720
tttcgttcat ccatagttgc ctgactcccc gtcgtgtaga taactacgat acgggagggc    6780
ttaccatctg gccccagtgc tgcaatgata ccgcgagacc cacgctcacc ggctccagat    6840
ttatcagcaa taaaccagcc agccggaagg gccgagcgca gaagtggtcc tgcaacttta    6900
tccgcctcca tccagtctat taattgttgc cgggaagcta gagtaagtag ttcgccagtt    6960
aatagtttgc gcaacgttgt tgccattgct acaggcatcg tggtgtcacg ctcgtcgttt    7020
```

| | | | | | |
|---|---|---|---|---|---|
| ggtatggctt | cattcagctc | cggttcccaa | cgatcaaggc | gagttacatg | atcccccatg | 7080 |
| ttgtgcaaaa | aagcggttag | ctccttcggt | cctccgatcg | ttgtcagaag | taagttggcc | 7140 |
| gcagtgttat | cactcatggt | tatggcagca | ctgcataatt | ctcttactgt | catgccatcc | 7200 |
| gtaagatgct | tttctgtgac | tggtgagtac | tcaaccaagt | cattctgaga | atagtgtatg | 7260 |
| cggcgaccga | gttgctcttg | cccggcgtca | atacgggata | ataccgcgcc | acatagcaga | 7320 |
| actttaaaag | tgctcatcat | tggaaaacgt | tcttcgggc | gaaaactctc | aaggatctta | 7380 |
| ccgctgttga | gatccagttc | gatgtaaccc | actcgtgcac | ccaactgatc | ttcagcatct | 7440 |
| tttactttca | ccagcgtttc | tgggtgagca | aaaacaggaa | ggcaaaatgc | cgcaaaaaag | 7500 |
| ggaataaggg | cgacacggaa | atgttgaata | ctcatactct | tcctttttca | atattattga | 7560 |
| agcatttatc | agggttattg | tctcatgagc | ggatacatat | ttgaatgtat | ttagaaaaat | 7620 |
| aaacaaatag | gggttccgcg | cacatttccc | cgaaaagtgc | cacct | | 7665 |

<210> SEQ ID NO 122
<211> LENGTH: 8439
<212> TYPE: DNA
<213> ORGANISM: Artificial Sequence
<220> FEATURE:
<223> OTHER INFORMATION: Plasmid
    pCVL.SFFV.HA.NLS.ReoHje.T2A.Trex2.IRES.mTagBFP

<400> SEQUENCE: 122

| | | | | | |
|---|---|---|---|---|---|
| gacgtcaatg | tagtcttatg | caatactctt | gtagtcttgc | aacatggtaa | cgatgagtta | 60 |
| gcaacatgcc | ttacaaggag | agaaaaagca | ccgtgcatgc | cgattggtgg | aagtaaggtg | 120 |
| gtacgatcgt | gccttattag | gaaggcaaca | gacgggtctg | acatggattg | gacgaaccac | 180 |
| tgaattgccg | cattgcagag | atattgtatt | taagtgccta | gctcgataca | taaacgggtc | 240 |
| tctctggtta | gaccagatct | gagcctggga | gctctctggc | taactaggga | acccactgct | 300 |
| taagcctcaa | taaagcttgc | cttgagtgct | tcaagtagtg | tgtgcccgtc | tgttgtgtga | 360 |
| ctctggtaac | tagagatccc | tcagaccctt | ttagtcagtg | tggaaaatct | ctagcagtgg | 420 |
| cgcccgaaca | gggacttgaa | agcgaaaggg | aaaccagagg | agctctctcg | acgcaggact | 480 |
| cggcttgctg | aagcgcgcac | ggcaagaggc | gaggggcggc | gactggtgag | tacgccaaaa | 540 |
| attttgacta | gcggaggcta | gaaggagaga | gatgggtgcg | agagcgtcag | tattaagcgg | 600 |
| gggagaatta | gatcgcgatg | ggaaaaaatt | cggttaaggc | caggggggaaa | gaaaaaatat | 660 |
| aaattaaaac | atatagtatg | ggcaagcagg | gagctagaac | gattcgcagt | taatcctggc | 720 |
| ctgttagaaa | catcagaagg | ctgtagacaa | atactgggac | agctacaacc | atcccttcag | 780 |
| acaggatcag | aagaacttag | atcattatat | aatacagtag | caaccctcta | ttgtgtgcat | 840 |
| caaaggatag | agataaaaga | caccaaggaa | gctttagaca | agatagagga | agagcaaaac | 900 |
| aaaagtaaga | ccaccgcaca | gcaagcggcc | ctgatcttca | gacctggagg | aggagatatg | 960 |
| agggacaatt | ggagaagtga | attatataaa | tataaagtag | taaaaattga | accattagga | 1020 |
| gtagcaccca | ccaaggcaaa | gagaagagtg | gtgcagagag | aaaaaagagc | agtgggaata | 1080 |
| ggagcttttgt | tccttgggtt | cttgggagca | gcaggaagca | ctatgggcgc | agcgtcaatg | 1140 |
| acgctgacgg | tacaggccag | acaattattg | tctggtatag | tgcagcagca | gaacaatttg | 1200 |
| ctgagggcta | ttgaggcgca | acagcatctg | ttgcaactca | cagtctgggg | catcaagcag | 1260 |
| ctccaggcaa | gaatcctggc | tgtggaaaga | tacctaaagg | atcaacagct | cctgggatt | 1320 |
| tggggttgct | ctggaaaact | catttgcacc | actgctgtgc | cttggaatgc | tagttggagt | 1380 |

```
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga agaatagta    1860 gacataatag caacagacat acaaactaaa gaattacaaa aacaaattac aaaaattcaa   1920
aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagaccat cagatgtttc caggctcccc caaggacctg    2220
aaatgaccct gcgccttatt tgaattaacc aatcagcctg cttctcgctt ctgttcgcgc   2280
gcttctgctt cccgagctct ataaagagc tcacaacccc tcactcggcg cgccagtcct    2340
ccgacagact gagtcgcccg ctcgagccgc caccatggga tatccatacg atgtcccaga   2400
ttatgcgcca cctaagaaga aacgcaaagt cgaattcgat cttacgtacg cgtatttagt   2460
tggtctcttc gaaggggatg gatactttag tatcaccaag aaaggcaagt acttgactta   2520
tgaattaggt attgagctga gcatcaaaga cgtccaattg atttacaaga tcaaggacat   2580
cctaggtgtt ggcaaagtaa gcttcaggaa gagaaacgag attgaaatgg tttcattgag   2640
gatccgtgat aagaatcatc taaaaaactt catattgcct atatttgaca agtatccaat   2700
gttatccaac aaacagtacg actatttaag attcaaggat gcattgttat ctaacattat   2760
atactcagat gacttgcctg aatacgctag aagtaacgaa tcgattaatt ctgtagactc   2820
cattatcaac acatcatact tctccgcctg gctagttgga tttatagaag ctgagggctg   2880
tttcagtacg tacaagctga acaaagacga tgactacttg attgcttcat cgacattgc    2940 ccaaaaagat ggtgatatct tgatttcagc aattcacaag tacttaagtt tcactactaa   3000
gatttaccta gacaagacta attgtagcag attgaaggtc accggtgtta gatccgtcaa   3060
gaacgtcgtt aagtttatcc agggtgctcc tgtcaaattg ttaggcaaca agaaactgca   3120
atacaagttg tggataaaac aactaaggaa gatttctagg tattccgaga agatccagct   3180
tccatcaaac tacagatccg gtgagggcag aggaagtctt ctaacatgcg gtgacgtgga   3240
ggagaatccg ggcccctccg gatctgagcc acctcgggct gagaccttg tattcctgga    3300 cctagaagcc actgggctcc caaacatgga ccctgagatt gcagagatat ccctttttgc   3360
tgttcaccgc tcttccctgg agaacccaga acgggatgat tctggttcct tggtgctgcc   3420
ccgtgttctg gacaagctca cactgtgcat gtgcccggag cgcccctta ctgccaaggc    3480 cagtgagatt actggtttga gcagcgaaag cctgatgcac tgcgggaagg ctggtttcaa   3540
tggcgctgtg gtaaggacac tgcagggctt cctaagccgc caggagggcc ccatctgcct   3600
tgtggcccac aatggcttcg attatgactt cccactgctg tgcacggagc tacaacgtct   3660
gggtgcccat ctgccccaag acactgtctg cctggacaca ctgcctgcat tgcgggcct    3720 ggaccgtgct cacagccacg gcaccagggc tcaaggccgc aaaagctaca gcctggccag   3780
```

```
tctcttccac cgctacttcc aggctgaacc cagtgctgcc cattcagcag aaggtgatgt   3840
gcacaccctg cttctgatct tcctgcatcg tgctcctgag ctgctcgcct gggcagatga   3900
gcaggcccgc agctgggctc atattgagcc catgtacgtg ccacctgatg gtccaagcct   3960
cgaagcctga cctgcaggtc gagcatgcat ctagggcggc caattccgcc cctctccctc   4020
ccccccccct aacgttactg gccgaagccg cttggaataa ggccggtgtg cgtttgtcta   4080
tatgtgattt tccaccatat tgccgtcttt tggcaatgtg agggcccgga aacctggccc   4140
tgtcttcttg acgagcattc ctaggggtct ttcccctctc gccaaaggaa tgcaaggtct   4200
gttgaatgtc gtgaaggaag cagttcctct ggaagcttct tgaagacaaa caacgtctgt   4260
agcgaccctt tgcaggcagc ggaacccccc acctggcgac aggtgcctct gcggccaaaa   4320
gccacgtgta taagatacac ctgcaaaggc ggcacaaccc cagtgccacg ttgtgagttg   4380
gatagttgtg gaaagagtca aatggctctc ctcaagcgta ttcaacaagg gctgaagga   4440 tgcccagaag gtaccccatt gtatgggatc tgatctgggg cctcggtgca catgctttac   4500
atgtgtttag tcgaggttaa aaaaacgtct aggccccccg aaccacgggg acgtggtttt   4560
cctttgaaaa acacgatgat aagcttgcca caacccttac cggtcgccac catgagcgag   4620
ctgattaagg agaacatgca catgaagctg tacatggagg gcaccgtgga caaccatcac   4680
ttcaagtgca catccgaggg cgaaggcaag ccctacgagg gcacccagac catgagaatc   4740
aaggtggtcg agggcggccc tctccccttc gccttcgaca tcctggctac tagcttcctc   4800
tacggcagca agaccttcat caaccacacc cagggcatcc ccgacttctt caagcagtcc   4860
ttccctgagg gcttcacatg ggagagagtc accacatacg aagacggggg cgtgctgacc   4920
gctacccagg acaccagcct ccaggacggc tgcctcatct acaacgtcaa gatcagaggg   4980
gtgaacttca catccaacgg ccctgtgatg cagaagaaaa cactcggctg ggaggccttc   5040
accgagacgc tgtaccccgc tgacggcggc ctggaaggca gaaacgacat ggcccctgaag   5100 ctcgtgggcg ggagccatct gatcgcaaac atcaagacca catatagatc caagaaaccc   5160
gctaagaacc tcaagatgcc tggcgtctac tatgtggact acagactgga agaatcaag   5220 gaggccaaca acgagaccta cgtcgagcag cacgaggtgg cagtggccag atactgcgac   5280
ctccctagca aactggggca caagcttaat tgattctaga gtcgaccgag catcttaccg   5340
ccatttatac ccatatttgt tctgtttttc ttgatttggg tatacattta aatgttaata   5400
gaacaaaatg gtggggcaat catttacatt tttagggata tgtaattact agttcaggtg   5460
tattgccaca agacaaacat gttaagaaac tttcccgtta tttacgctct gttcctgtta   5520
atcaacctct ggattacaaa atttgtgaaa gattgactga tattcttaac tatgttgctc   5580
cttttacgct gtgtggatat gctgctttat agcctctgta tctagctatt gcttcccgta   5640
cggctttcgt tttctcctcc ttgtataaat cctggttgct gtctctttta gaggagttgt   5700
ggcccgttgt ccgtcaacgt ggcgtggtgt gctctgtgtt tgctgacgca accccactg   5760 gctgggcat tgccaccacc tgtcaactcc tttctgggac tttcgctttc ccctcccga   5820 tcgccacggc agaactcatc gccgcctgcc ttgcccgctg ctggacaggg gctaggttgc   5880
tgggcactga taattccgtg gtgttgtcat cggtaccttt ttaaagaaa agggggact   5940 ggaagggcta attcactccc aacgaagaca agatatcata acttcgtata gcatacatta   6000
tacgaagtta aatttatttt gtgaaatttg tgatgctatt gctttatttg taaccatatg   6060
tttatttgtg aaatttgtga tgctattgct ttatttgtaa ccattgcttt tgcttgtac   6120
```

```
tgggtctctc tggttagacc agatctgagc ctgggagctc tctggctaac tagggaaccc    6180
actgcttaag cctcaataaa gcttgcctcg accagcctcg actgtgcctt ctagttgcca    6240
gccatctgtt gtttgcccct cccccgtgcc ttccttgacc ctggaaggtg ccactcccac    6300
tgtcctttcc taataaaatg aggaaattgc atcgcattgt ctgagtaggt gtcattctat    6360
tctgggggt  ggggtggggc aggacagcaa gggggaggat tgggaagaca atagcaggca    6420
tgctggggat gcggtgggct ctatggcctg cagctgcatt aatgaatcgg ccaacgcgcg    6480
gggagaggcg gtttgcgtat tgggcgctct tccgcttcct cgctcactga ctcgctgcgc    6540
tcggtcgttc ggctgcggcg agcggtatca gctcactcaa aggcggtaat acggttatcc    6600
acagaatcag gggataacgc aggaaagaac atgtgagcaa aaggccagca aaaggccagg    6660
aaccgtaaaa aggccgcgtt gctggcgttt ttccataggc tccgcccccc tgacgagcat    6720
cacaaaaatc gacgctcaag tcagaggtgg cgaaacccga caggactata aagataccag    6780
gcgtttcccc ctggaagctc cctcgtgcgc tctcctgttc cgaccctgcc gcttaccgga    6840
tacctgtccg cctttctccc ttcgggaagc gtggcgcttt ctcatagctc acgctgtagg    6900
tatctcagtt cggtgtaggt cgttcgctcc aagctgggct gtgtgcacga accccccgtt    6960
cagcccgacc gctgcgcctt atccggtaac tatcgtcttg agtccaaccc ggtaagacac    7020
gacttatcgc cactggcagc agccactggt aacaggatta gcagagcgag gtatgtaggc    7080
ggtgctacag agttcttgaa gtggtggcct aactacggct acactagaag acagtattt     7140
ggtatctgcg ctctgctgaa gccagttacc ttcggaaaaa gagttggtag ctcttgatcc    7200
ggcaaacaaa ccaccgctgg tagcggtggt ttttttgttt gcaagcagca gattacgcgc    7260
agaaaaaaag gatctcaaga agatcctttg atcttttcta cggggtctga cgctcagtgg    7320
aacgaaaact cacgttaagg gattttggtc atgagattat caaaaaggat cttcacctag    7380
atccttttaa attaaaaatg aagttttaaa tcaatctaaa gtatatatga gtaaacttgg    7440
tctgacagtt accaatgctt aatcagtgag gcacctatct cagcgatctg tctatttcgt    7500
tcatccatag ttgcctgact ccccgtcgtg tagataacta cgatacggga gggcttacca    7560
tctggcccca gtgctgcaat gataccgcga gacccacgct caccggctcc agatttatca    7620
gcaataaacc agccagccgg aagggccgag cgcagaagtg gtcctgcaac tttatccgcc    7680
tccatccagt ctattaattg ttgccgggaa gctagagtaa gtagttcgcc agttaatagt    7740
ttgcgcaacg ttgttgccat tgctacaggc atcgtggtgt cacgctcgtc gtttggtatg    7800
gcttcattca gctccggttc ccaacgatca aggcgagtta catgatcccc catgttgtgc    7860
aaaaaagcgg ttagctcctt cggtcctccg atcgttgtca gaagtaagtt ggccgcagtg    7920
ttatcactca tggttatggc agcactgcat aattctctta ctgtcatgcc atccgtaaga    7980
tgcttttctg tgactggtga gtactcaacc aagtcattct gagaatagtg tatgcggcga    8040
ccgagttgct cttgcccggc gtcaatacgg gataataccg cgccacatag cagaacttta    8100
aaagtgctca tcattggaaa acgttcttcg ggcgaaaac  tctcaaggat cttaccgctg    8160
ttgagatcca gttcgatgta acccactcgt gcacccaact gatcttcagc atcttttact    8220
ttcaccagcg tttctgggtg agcaaaaaca ggaaggcaaa atgccgcaaa aaagggaata    8280
agggcgacac ggaaatgttg aatactcata ctcttccttt ttcaatatta ttgaagcatt    8340
tatcagggtt attgtctcat gagcggatac atatttgaat gtatttagaa aaataaacaa    8400
ataggggttc cgcgcacatt tccccgaaaa gtgccacct                           8439
```

<210> SEQ ID NO 123
<211> LENGTH: 7803
<212> TYPE: DNA
<213> ORGANISM: Artificial Sequence
<220> FEATURE:
<223> OTHER INFORMATION: Plasmid pCVL.SFFV.HA.NLS.sPan2.IRES.mTagBFP

<400> SEQUENCE: 123

```
gacgtcaatg tagtcttatg caatactctt gtagtcttgc aacatggtaa cgatgagtta      60
gcaacatgcc ttacaaggag agaaaaagca ccgtgcatgc cgattggtgg aagtaaggtg     120
gtacgatcgt gccttattag gaaggcaaca gacgggtctg acatggattg gacgaaccac     180
tgaattgccg cattgcagag atattgtatt taagtgccta gctcgataca taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta agaaggagaga atgggtgcg agagcgtcag tattaagcgg     600
gggagaatta gatcgcgatg ggaaaaaatt cggttaaggc caggggggaaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca atagagga agagcaaaac     900
aaaagtaaga ccaccgcaca gcaagcggcc ctgatcttca gacctggagg aggagatatg     960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctggggatt    1320
tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccaccctcc caaccccgag ggacccgaca ggcccgaagg aatagaagaa    1740
gaaggtggag agagagacag agacagatcc attcgattag tgaacggatc tcgacggtat    1800
cggttaactt ttaaaagaaa aggggggatt ggggggtaca gtgcagggga agaatagta    1860
gacataaatag caacagacat acaaactaaa gaattacaaa aacaaattac aaaaattcaa    1920
aattttatcg attacgcgtc acgtgctagc tgcagtaacg ccattttgca aggcatggaa    1980
aaataccaaa ccaagaatag agaagttcag atcaagggcg gtacatgaa aatagctaac    2040
gttgggccaa acaggatatc tgcggtgagc agtttcggcc ccggcccggg gccaagaaca    2100
```

```
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
gcttctgctt cccgagctct ataaaagagc tcacaacccc tcactcggcg cgccagtcct    2340
ccgacagact gagtcgcccg ctcgagccgc caccatggga tatccatacg atgtcccaga    2400
ttatgcgcca cctaagaaga aacgcaaagt cgaattctct actttggaat ctaagttgaa    2460
cccatcttac atctctggtt tcgtcgacgg tgaaggttct ttcatgttga ctatcatcaa    2520
ggacaacaag tacaagttgg gttggagagt tgtttgtaga ttcgttatct ctttgcacaa    2580
gaaggacttg tctttgttga acaagatcaa ggaatttttc gacgtcggta acgttttctt    2640
gatgactaag gactctgctc aatacagagt tgaatctttg aagggtttgg acttgatcat    2700
caaccacttc gacaagtacc cattgatcac taagaagcaa gctgactaca agttgttcaa    2760
gatggctcac aacttaatta agaacaagtc tcacttgact aaggaaggtt tgttggaatt    2820
ggttgctatc aaggctgtta tcaacaacgg tttgaacaac gacttgtcta tcgctttccc    2880
aggtatcaac actatcttga ggcctgacac ttctttgcca caaatcttga acccattctg    2940
gttgtctggt ttcgttgacg ctgaaggttg ttttctctgt tgtgttttca gtctaagac     3000 ttctaagttg ggtgaagctg ttaagttgtc tttcatcttg actcaatcta acagagacga    3060
atacttgatc aagtctttga tcgaatacct aggttgtggt aacacttctt tggacccaag    3120
aggtactatc gacttcaagg ttactaactt ctcttctatc aaggacatca tcgttccatt    3180
cttcatcaag tacccattga agggtaacaa gaacttggac ttcactgact ctgtgaagt    3240 tgttagattg atggaaaaca agtctcactt gactaaggaa ggtttggacc aaatcaagaa    3300
gatcagaaac agaatgaaca ctaacagaaa gtagcctgca ggtcgagcat gcatctaggg    3360
cggccaattc cgcccctctc cctcccccc cctaacgtt actggccgaa gccgcttgga     3420
ataaggccgg tgtgcgtttg tctatatgtg attttccacc atattgccgt cttttggcaa    3480
tgtgagggcc cggaaacctg gccctgtctt cttgacgagc attcctaggg gtctttcccc    3540
tctcgccaaa ggaatgcaag gtctgttgaa tgtcgtgaag aagcagttc ctctggaagc    3600 ttcttgaaga caaacaacgt ctgtagcgac cctttgcagg cagcggaacc ccccacctgg    3660
cgacaggtgc ctctgcggcc aaaagccacg tgtataagat acacctgcaa aggcggcaca    3720
accccagtgc cacgttgtga gttggatagt tgtggaaaga gtcaaatggc tctcctcaag    3780
cgtattcaac aaggggctga aggatgccca gaaggtaccc cattgtatgg gatctgatct    3840
ggggcctcgg tgcacatgct ttacatgtgt ttagtcgagg ttaaaaaaac gtctaggccc    3900
cccgaaccac ggggacgtgg ttttcctttg aaaaacacga tgataagctt gccacaaccc    3960
ttaccggtcg ccaccatgag cgagctgatt aaggagaaca tgcacatgaa gctgtacatg    4020
gagggcaccg tggacaacca tcacttcaag tgcacatccg agggcgaagg caagccctac    4080
gagggcaccc agaccatgag aatcaaggtg gtcgagggcg gccctctccc cttcgccttc    4140
gacatcctgg ctactagctt cctctacggc agcaagacct tcatcaacca cacccagggc    4200
atccccgact tcttcaagca gtccttccct gagggcttca catgggagag agtcaccaca    4260
tacgaagacg ggggcgtgct gaccgctacc caggacacca gcctccagga cggctgcctc    4320
atctacaacg tcaagatcag aggggtgaac ttcacatcca acggccctgt gatgcagaag    4380
aaaacactcg gctgggaggc cttcaccgag acgctgtacc ccgctgacgg cggcctggaa    4440
ggcagaaacg acatggccct gaagctcgtg ggcgggagcc atctgatcgc aaacatcaag    4500
```

```
accacatata gatccaagaa acccgctaag aacctcaaga tgcctggcgt ctactatgtg   4560
gactacagac tggaaagaat caaggaggcc aacaacgaga cctacgtcga gcagcacgag   4620
gtggcagtgg ccagatactg cgacctccct agcaaactgg ggcacaagct taattgattc   4680
tagagtcgac cgagcatctt accgccattt atacccatat ttgttctgtt tttcttgatt   4740
tgggtataca tttaaatgtt aatagaacaa aatggtgggg caatcattta cattttttagg  4800
gatatgtaat tactagttca ggtgtattgc cacaagacaa acatgttaag aaactttccc   4860
gttatttacg ctctgttcct gttaatcaac ctctggatta caaaatttgt gaaagattga   4920
ctgatattct taactatgtt gctccttta cgctgtgtgg atatgctgct ttatagcctc    4980
tgtatctagc tattgcttcc cgtacggctt tcgttttctc ctccttgtat aaatcctggt   5040
tgctgtctct tttagaggag ttgtggcccg ttgtccgtca acgtggcgtg gtgtgctctg   5100
tgtttgctga cgcaaccccc actggctggg gcattgccac cacctgtcaa ctcctttctg   5160
ggactttcgc tttccccctc ccgatcgcca cggcagaact catcgccgcc tgccttgccc   5220
gctgctggac aggggctagg ttgctgggca ctgataattc cgtggtgttg tcatcggtac   5280
cttttttaaaa gaaaagggg gactggaagg gctaattcac tcccaacgaa gacaagatat    5340
cataacttcg tatagcatac attatacgaa gttataattt atttgtgaaa tttgtgatgc    5400
tattgctttta tttgtaacca tatgtttatt tgtgaaattt gtgatgctat tgctttattt    5460
gtaaccattg cttttttgctt gtactgggtc tctctggtta gaccagatct gagcctggga    5520
gctctctggc taactaggga acccactgct taagcctcaa taaagcttgc ctcgaccagc    5580
ctcgactgtg ccttctagtt gccagccatc tgttgtttgc ccctcccccg tgccttcctt    5640
gaccctggaa ggtgccactc ccactgtcct ttcctaataa aatgaggaaa ttgcatcgca    5700
ttgtctgagt aggtgtcatt ctattctggg gggtggggtg gggcaggaca gcaaggggga    5760
ggattgggaa gacaatagca ggcatgctgg ggatgcggtg ggctctatgg cctgcagctg    5820
cattaatgaa tcggccaacg cgcggggaga ggcggtttgc gtattgggcg ctcttccgct    5880
tcctcgctca ctgactcgct gcgctcggtc gttcggctgc ggcgagcggt atcagctcac    5940
tcaaaggcgg taatacggtt atccacagaa tcagggggata acgcaggaaa gaacatgtga    6000
gcaaaaggcc agcaaaaggc caggaaccgt aaaaaggccg cgttgctggc gttttttccat    6060
aggctccgcc ccctgacga gcatcacaaa aatcgacgct caagtcagag gtggcgaaac      6120
ccgacaggac tataaagata ccaggcgttt ccccctggaa gctccctcgt gcgctctcct    6180
gttccgaccc tgccgcttac cggatacctg tccgcctttc tcccttcggg aagcgtggcg    6240
ctttctcata gctcacgctg taggtatctc agttcggtgt aggtcgttcg ctccaagctg    6300
ggctgtgtgc acgaaccccc cgttcagccc gaccgctgcg ccttatccgg taactatcgt    6360
cttgagtcca acccggtaag acacgactta tcgccactgg cagcagccac tggtaacagg    6420
attagcagag cgaggtatgt aggcggtgct acagagttct tgaagtggtg gcctaactac    6480
ggctacacta gaaggacagt atttggtatc tgcgctctgc tgaagccagt taccttcgga    6540
aaaagagttg gtagctcttg atccggcaaa caaaccaccg ctggtagcgg tggtttttttt    6600
gtttgcaagc agcagattac gcgcagaaaa aaaggatctc aagaagatcc tttgatcttt    6660
tctacggggt ctgacgctca gtggaacgaa aactcacgtt aagggatttt ggtcatgaga    6720
ttatcaaaaa ggatcttcac ctagatcctt ttaaattaaa aatgaagttt taaatcaatc    6780
taaagtatat atgagtaaac ttggtctgac agttaccaat gcttaatcag tgaggcacct    6840
```

| | |
|---|---|
| atctcagcga tctgtctatt tcgttcatcc atagttgcct gactccccgt cgtgtagata | 6900 |
| actacgatac gggagggctt accatctggc cccagtgctg caatgatacc gcgagaccca | 6960 |
| cgctcaccgg ctccagattt atcagcaata aaccagccag ccggaagggc cgagcgcaga | 7020 |
| agtggtcctg caactttatc cgcctccatc cagtctatta attgttgccg ggaagctaga | 7080 |
| gtaagtagtt cgccagttaa tagtttgcgc aacgttgttg ccattgctac aggcatcgtg | 7140 |
| gtgtcacgct cgtcgtttgg tatggcttca ttcagctccg gttcccaacg atcaaggcga | 7200 |
| gttacatgat cccccatgtt gtgcaaaaaa gcggttagct ccttcggtcc tccgatcgtt | 7260 |
| gtcagaagta agttggccgc agtgttatca ctcatggtta tggcagcact gcataattct | 7320 |
| cttactgtca tgccatccgt aagatgcttt tctgtgactg gtgagtactc aaccaagtca | 7380 |
| ttctgagaat agtgtatgcg gcgaccgagt tgctcttgcc cggcgtcaat acgggataat | 7440 |
| accgcgccac atagcagaac tttaaaagtg ctcatcattg gaaaacgttc ttcggggcga | 7500 |
| aaactctcaa ggatcttacc gctgttgaga tccagttcga tgtaacccac tcgtgcaccc | 7560 |
| aactgatctt cagcatcttt tactttcacc agcgtttctg ggtgagcaaa aacaggaagg | 7620 |
| caaaatgccg caaaaaaggg aataagggcg acacggaaat gttgaatact catactcttc | 7680 |
| ctttttcaat attattgaag catttatcag ggttattgtc tcatgagcgg atacatattt | 7740 |
| gaatgtattt agaaaaataa acaaataggg gttccgcgca catttccccg aaaagtgcca | 7800 |
| cct | 7803 |

<210> SEQ ID NO 124
<211> LENGTH: 8577
<212> TYPE: DNA
<213> ORGANISM: Artificial Sequence
<220> FEATURE:
<223> OTHER INFORMATION: Plasmid
    pCVL.SFFV.HA.NLS.sPan2.T2A.Trex2.IRES.mTagBFP

<400> SEQUENCE: 124

| | |
|---|---|
| gacgtcaatg tagtcttatg caatactctt gtagtcttgc aacatggtaa cgatgagtta | 60 |
| gcaacatgcc ttacaaggag agaaaaagca ccgtgcatgc cgattggtgg aagtaaggtg | 120 |
| gtacgatcgt gccttattag gaaggcaaca gacgggtctg acatggattg gacgaaccac | 180 |
| tgaattgccg cattgcagag atattgtatt taagtgccta gctcgataca taaacgggtc | 240 |
| tctctggtta gaccagatct gagcctggga gctctctggc taactaggga acccactgct | 300 |
| taagcctcaa taaagcttgc cttgagtgct tcaagtagtg tgtgcccgtc tgttgtgtga | 360 |
| ctctggtaac tagagatccc tcagaccctt ttagtcagtg tggaaaatct ctagcagtgg | 420 |
| cgcccgaaca gggacttgaa agcgaaaggg aaaccagagg agctctctcg acgcaggact | 480 |
| cggcttgctg aagcgcgcac ggcaagaggc gaggggcggc gactggtgag tacgccaaaa | 540 |
| attttgacta gcggaggcta agaggagaga gatgggtgcg agagcgtcag tattaagcgg | 600 |
| gggagaatta gatcgcgatg ggaaaaaatt cggttaaggc caggggggaaa gaaaaaatat | 660 |
| aaattaaaac atatagtatg ggcaagcagg gagctagaac gattcgcagt taatcctggc | 720 |
| ctgttagaaa catcagaagg ctgtagacaa atactgggac agctacaacc atcccttcag | 780 |
| acaggatcag aagaacttag atcattatat aatacagtag caaccctcta ttgtgtgcat | 840 |
| caaaggatag agataaaaga caccaaggaa gctttagaca agatagagga agagcaaaac | 900 |
| aaaagtaaga ccaccgcaca gcaagcggcc ctgatcttca gacctggagg aggagatatg | 960 |
| agggacaatt ggagaagtga attatataaa tataaagtag taaaaattga accattagga | 1020 |

-continued

```
gtagcaccca ccaaggcaaa gagaagagtg gtgcagagag aaaaaagagc agtgggaata      1080
ggagctttgt tccttgggtt cttgggagca gcaggaagca ctatgggcgc agcgtcaatg      1140
acgctgacgg tacaggccag acaattattg tctggtatag tgcagcagca gaacaatttg      1200
ctgagggcta ttgaggcgca acagcatctg ttgcaactca cagtctgggg catcaagcag      1260
ctccaggcaa gaatcctggc tgtggaaaga tacctaaagg atcaacagct cctgggatt       1320 tggggttgct ctggaaaact catttgcacc actgctgtgc cttggaatgc tagttggagt      1380
aatgaatctc tggaacagat tggaatcac acgacctgga tggagtggga cagagaaatt       1440
aacaattaca caagcttaat acactcctta attgaagaat cgcaaaacca gcaagaaaag      1500
aatgaacaag aattattgga attagataaa tgggcaagtt tgtggaattg gtttaacata      1560
acaaattggc tgtggtatat aaaattattc ataatgatag taggaggctt ggtaggttta      1620
agaatagttt ttgctgtact ttctatagtg aatagagtta ggcagggata ttcaccatta      1680
tcgtttcaga cccacctccc aaccccgagg ggacccgaca ggcccgaagg aatagaagaa      1740
gaaggtggag agagagacag agacagatcc attcgattag tgaacggatc tcgacggtat      1800
cggttaactt ttaaaagaaa agggggatt gggggtaca gtgcagggga aagaatagta       1860
gacataatag caacagacat acaaactaaa gaattacaaa aacaaattac aaaaattcaa      1920
aattttatcg attacgcgtc acgtgctagc tgcagtaacg ccattttgca aggcatggaa      1980
aaataccaaa ccaagaatag agaagttcag atcaagggcg ggtacatgaa aatagctaac      2040
gttgggccaa acaggatatc tgcggtgagc agtttcggcc ccggcccggg gccaagaaca      2100
gatggtcacc gcagtttcgg ccccggcccg aggccaagaa cagatggtcc ccagatatgg      2160
cccaaccctc agcagtttct taagacccat cagatgtttc caggctcccc caaggacctg      2220
aaatgaccct gcgccttatt tgaattaacc aatcagcctg cttctcgctt ctgttcgcgc      2280
gcttctgctt cccgagctct ataaaagagc tcacaacccc tcactcggcg cgccagtcct      2340
ccgacagact gagtcgcccg ctcgagccgc caccatggga tatccatacg atgtcccaga      2400
ttatgcgcca cctaagaaga acgcaaagt cgaattctct actttggaat ctaagttgaa       2460
cccatcttac atctctggtt tcgtcgacgg tgaaggttct ttcatgttga ctatcatcaa      2520
ggacaacaag tacaagttgg gttggagagt tgtttgtaga ttcgttatct cttttgcacaa     2580 gaaggacttg tctttgttga acaagatcaa ggaattttc gacgtcggta acgttttctt       2640
gatgactaag gactctgctc aatacagagt tgaatctttg aagggtttgg acttgatcat      2700
caaccacttc gacaagtacc cattgatcac taagaagcaa gctgactaca gttgttcaa       2760 gatggctcac aacttaatta agaacaagtc tcacttgact aaggaaggtt tgttggaatt      2820
ggttgctatc aaggctgtta tcaacaacgg tttgaacaac gacttgtcta tcgctttccc      2880
aggtatcaac actatcttga ggcctgacac ttctttgcca caaatcttga acccattctg      2940
gttgtctggt ttcgttgacg ctgaaggttg tttctctgtt gttgttttca agtctaagac      3000
ttctaagttg ggtgaagctg ttaagttgtc tttcatcttg actcaatcta acagagacga     3060
atacttgatc aagtctttga tcgaatacct aggttgtggt aacacttctt tggacccaag     3120
aggtactatc gacttcaagg ttactaactt ctcttctatc aaggacatca tcgttccatt      3180
cttcatcaag tacccattga agggtaacaa gaacttggac ttcactgact ctgtgaagt      3240 tgttagattg atggaaaaca agtctccactt gactaaggaa ggtttggacc aaatcaagaa      3300
gatcagaaac agaatgaaca ctaacagaaa gggatccggt gagggcagag aagtcttct       3360 aacatgcggt gacgtggagg agaatcccggg ccctccgga tctgagccac ctcgggctga      3420
```

```
gacctttgta ttcctggacc tagaagccac tgggctccca acatggaccc ctgagattgc    3480
agagatatcc cttttgctg ttcaccgctc ttccctggag aacccagaac gggatgattc    3540
tggttccttg gtgctgcccc gtgttctgga caagctcaca ctgtgcatgt gcccggagcg    3600
cccctttact gccaaggcca gtgagattac tggtttgagc agcgaaagcc tgatgcactg    3660
cgggaaggct ggtttcaatg gcgctgtggt aaggacactg cagggcttcc taagccgcca    3720
ggagggcccc atctgccttg tggcccacaa tggcttcgat tatgacttcc cactgctgtg    3780
cacggagcta caacgtctgg gtgcccatct gccccaagac actgtctgcc tggacacact    3840
gcctgcattg cggggcctgg accgtgctca cagccacggc accagggctc aaggccgcaa    3900
aagctacagc ctggccagtc tcttccaccg ctacttccag gctgaaccca gtgctgccca    3960
ttcagcagaa ggtgatgtgc acaccctgct tctgatcttc ctgcatcgtg ctcctgagct    4020
gctcgcctgg gcagatgagc aggcccgcag ctgggctcat attgagccca tgtacgtgcc    4080
acctgatggt ccaagcctcg aagcctgacc tgcaggtcga gcatgcatct agggcggcca    4140
attccgcccc tctccctccc cccccctaa cgttactggc cgaagccgct tggaataagg    4200
ccggtgtgcg tttgtctata tgtgattttc caccatattg ccgtcttttg gcaatgtgag    4260
ggcccggaaa cctggccctg tcttcttgac gagcattcct aggggtcttt cccctctcgc    4320
caaaggaatg caaggtctgt tgaatgtcgt gaaggaagca gttcctctgg aagcttcttg    4380
aagacaaaca acgtctgtag cgaccctttg caggcagcgg aacccccac ctggcgacag    4440 gtgcctctgc ggccaaaagc cacgtgtata agatacacct gcaaaggcgg cacaacccca    4500
gtgccacgtt gtgagttgga tagttgtgga aagagtcaaa tggctctcct caagcgtatt    4560
caacaagggg ctgaaggatg cccagaaggt accccattgt atgggatctg atctggggcc    4620
tcggtgcaca tgctttacat gtgtttagtc gaggttaaaa aaacgtctag gccccccgaa    4680
ccacggggac gtggttttcc tttgaaaaac acgatgataa gcttgccaca acccttaccg    4740
gtcgccacca tgagcgagct gattaaggag aacatgcaca tgaagctgta catggagggc    4800
accgtggaca accatcactt caagtgcaca tccgagggcg aaggcaagcc ctacgagggc    4860
acccagacca tgagaatcaa ggtggtcgag ggcggccctc tccccttcgc cttcgacatc    4920
ctggctacta gcttcctcta cggcagcaag accttcatca accacaccca gggcatcccc    4980
gacttcttca gcagtccttt ccctgagggc ttcacatggg agagagtcac cacatacgaa    5040
gacgggggcg tgctgaccgc tacccaggac accagcctcc aggacggctg cctcatctac    5100
aacgtcaaga tcgagggggt gaacttcaca tccaacggcc ctgtgatgca aagaaaaca    5160 ctcggctggg aggccttcac cgagacgctg taccccgctg acggcggcct ggaaggcaga    5220
aacgacatgg ccctgaagct cgtgggcggg agccatctga tcgcaaacat caagaccaca    5280
tatagatcca agaaacccgc taagaacctc aagatgcctg gcgtctacta tgtggactac    5340
agactggaaa gaatcaagga ggccaacaac gagacctacg tcgagcagca cgaggtggca    5400
gtggccagat actgcgacct ccctagcaaa ctggggcaca agcttaattg attctagagt    5460
cgaccgagca tcttaccgcc atttataccc atatttgttc tgttttcttt gatttgggta    5520
tacatttaaa tgttaataga acaaaatggt ggggcaatca tttacatttt tagggatatg    5580
taattactag ttcaggtgta ttgccacaag acaaacatgt taagaaactt tcccgttatt    5640
tacgctctgt tcctgttaat caacctctgg attacaaaat tgtgaaaga ttgactgata    5700 ttcttaacta tgttgctcct tttacgctgt gtggatatgc tgctttatag cctctgtatc    5760
```

```
tagctattgc ttcccgtacg gctttcgttt tctcctcctt gtataaatcc tggttgctgt      5820
ctctttttaga ggagttgtgg cccgttgtcc gtcaacgtgg cgtggtgtgc tctgtgtttg     5880
ctgacgcaac ccccactggc tggggcattg ccaccacctg tcaactcctt tctgggactt     5940
tcgctttccc cctcccgatc gccacggcag aactcatcgc cgcctgcctt gcccgctgct     6000
ggacagggc taggttgctg ggcactgata attccgtggt gttgtcatcg gtacctttt      6060
aaaagaaaag gggggactgg aagggctaat tcactcccaa cgaagacaag atatcataac     6120
ttcgtatagc atacattata cgaagttata atttatttgt gaaatttgtg atgctattgc     6180
tttatttgta accatatgtt tatttgtgaa atttgtgatg ctattgcttt atttgtaacc     6240
attgcttttt gcttgtactg ggtctctctg gttagaccag atctgagcct gggagctctc     6300
tggctaacta gggaacccac tgcttaagcc tcaataaagc ttgcctcgac cagcctcgac     6360
tgtgccttct agttgccagc catctgttgt ttgcccctcc cccgtgcctt ccttgaccct     6420
ggaaggtgcc actcccactg tcctttccta taaaatgag gaaattgcat cgcattgtct     6480
gagtaggtgt cattctattc tgggggtgg ggtggggcag acagcaagg gggaggattg      6540
ggaagacaat agcaggcatg ctggggatgc ggtgggctct atggcctgca gctgcattaa     6600
tgaatcggcc aacgcgcggg gagaggcggt ttgcgtattg ggcgctcttc cgcttcctcg     6660
ctcactgact cgctgcgctc ggtcgttcgg ctgcggcgag cggtatcagc tcactcaaag     6720
gcggtaatac ggttatccac agaatcaggg gataacgcag gaaagaacat gtgagcaaaa     6780
ggccagcaaa aggccaggaa ccgtaaaaag gccgcgttgc tggcgttttt ccataggctc     6840
cgcccccctg acgagcatca caaaaatcga cgctcaagtc agaggtggcg aaacccgaca     6900
ggactataaa gataccaggc gtttccccct ggaagctccc tcgtgcgctc tcctgttccg     6960
accctgccgc ttaccggata cctgtccgcc tttctccctt cgggaagcgt ggcgctttct     7020
catagctcac gctgtaggta tctcagttcg gtgtaggtcg ttcgctccaa gctgggctgt     7080
gtgcacgaac ccccgttca gcccgaccgc tgcgccttat ccggtaacta tcgtcttgag     7140
tccaacccgg taagacacga cttatcgcca ctggcagcag ccactggtaa caggattagc     7200
agagcgaggt atgtaggcgg tgctacagag ttcttgaagt ggtggcctaa ctacggctac     7260
actagaagga cagtatttgg tatctgcgct ctgctgaagc cagttacctt cggaaaaaga     7320
gttggtagct cttgatccgg caaacaaacc accgctggta gcggtggttt ttttgtttgc     7380
aagcagcaga ttacgcgcag aaaaaaagga tctcaagaag atcctttgat cttttctacg     7440
gggtctgacg ctcagtggaa cgaaaactca cgttaaggga ttttggtcat gagattatca     7500
aaaaggatct tcacctagat ccttttaaat taaaaatgaa gttttaaatc aatctaaagt     7560
atatatgagt aaacttggtc tgacagttac caatgcttaa tcagtgaggc acctatctca     7620
gcgatctgtc tatttcgttc atccatagtt gcctgactcc ccgtcgtgta gataactacg     7680
atacgggagg gcttaccatc tggccccagt gctgcaatga taccgcgaga cccacgctca     7740
ccggctccag atttatcagc aataaaccag ccagccggaa gggccgagcg cagaagtggt     7800
cctgcaactt tatccgcctc catccagtct attaattgtt gccgggaagc tagagtaagt     7860
agttcgccag ttaatagttt gcgcaacgtt gttgccattg ctacaggcat cgtggtgtca     7920
cgctcgtcgt ttggtatggc ttcattcagc tccggttccc aacgatcaag gcgagttaca     7980
tgatccccca tgttgtgcaa aaaagcggtt agctccttcg gtcctccgat cgttgtcaga     8040
agtaagttgg ccgcagtgtt atcactcatg gttatggcag cactgcataa ttctcttact     8100
gtcatgccat ccgtaagatg cttttctgtg actggtgagt actcaaccaa gtcattctga     8160
```

-continued

```
gaatagtgta tgcggcgacc gagttgctct tgcccggcgt caatacggga taataccgcg    8220
ccacatagca gaactttaaa agtgctcatc attggaaaac gttcttcggg gcgaaaactc    8280
tcaaggatct taccgctgtt gagatccagt tcgatgtaac ccactcgtgc acccaactga    8340
tcttcagcat cttttacttt caccagcgtt tctgggtgag caaaaacagg aaggcaaaat    8400
gccgcaaaaa agggaataag ggcgacacgg aaatgttgaa tactcatact cttcctttttt   8460 caatattatt gaagcattta tcagggttat tgtctcatga cggatacat atttgaatgt    8520 atttagaaaa ataaacaaat aggggttccg cgcacatttc cccgaaaagt gccacct       8577
```

<210> SEQ ID NO 125
<211> LENGTH: 7806
<212> TYPE: DNA
<213> ORGANISM: Artificial Sequence
<220> FEATURE:
<223> OTHER INFORMATION: Plasmid pCVL.SFFV.HA.NLS.I-OnuOpt.IRES.mTagBFP

<400> SEQUENCE: 125

```
gacgtcaatg tagtcttatg caatactctt gtagtcttgc aacatggtaa cgatgagtta     60
gcaacatgcc ttacaaggag agaaaaagca ccgtgcatgc cgattggtgg aagtaaggtg    120
gtacgatcgt gccttattag gaaggcaaca gacgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg    600
gggagaatta gatcgcgatg ggaaaaaatt cggttaaggc caggggggaaa gaaaaaatat    660 aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca atagagga agagcaaaac    900 aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380 aatgatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
```

-continued

```
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800
cggttaactt ttaaaagaaa aggggggatt ggggggtaca gtgcagggga aagaatagta    1860
gacataatag caacagacat acaaactaaa gaattacaaa aacaaattac aaaaattcaa    1920
aattttatcg attacgcgtc acgtgctagc tgcagtaacg ccattttgca aggcatggaa    1980
aaataccaaa ccaagaatag agaagttcag atcaagggcg ggtacatgaa aatagctaac    2040
gttgggccaa acaggatatc tgcggtgagc agtttcggcc ccggcccggg ccaagaaca    2100
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
gcttctgctt cccgagctct ataaagagc tcacaacccc tcactcggcg cgccagtcct    2340
ccgacagact gagtcgcccg ctcgagccgc caccatggga tatccatacg atgtcccaga    2400
ttatgcgcca cctaagaaga aacgcaaagt cgaattcagc cgccgcgaga gcatcaaccc    2460
ctggattctg accggcttcg ccgacgccga gggcagcttc ctgctgcgca tccgcaacaa    2520
caacaagagc agcgtgggct acagcaccga gctgggcttc cagatcaccc tgcacaacaa    2580
ggacaagagc atcctggaga acatccagag catctggaag gtgggcgtga tcgccaacag    2640
cggcgacaac gccgtgagcc tgaaggtgac ccgcttcgag gacctgaagg tgatcatcga    2700
ccacttcgag aagtaccccc tgatcaccca gaagctgggc gactacatgc tgttcaagca    2760
ggccttctgc gtgatggaga acaaggagca cctgaagatc aacggcatca aggagctggt    2820
gcgcatcaag gccaagctga actggggcct gaccgacgag ctgaagaagg ccttccccga    2880
gatcatcagc aaggagcgca gcctgatcaa caagaacatc cccaacttca gtggctggc    2940
cggcttcacc agcggcgagg gctgcttctt cgtgaacctg atcaagagca gagcaagct    3000
gggcgtgcag gtgcagctgg tgttcagcat cacccagcac atcaaggaca gaacctgat    3060
gaacagcctg atcacctacc tgggctgcgg ctacatcaag gagaagaaca gagcgagtt    3120
cagctggctg gacttcgtgg tgaccaagtt cagcgacatc aacgacaaga tcatccccgt    3180
gttccaggag aacaccctga tcggcgtgaa gctggaggac ttcgaggact ggtgcaaggt    3240
ggccaagctg atcgaggaga agaagcacct gaccgagagc ggcctggacg agatcaagaa    3300
gatcaagctg aacatgaaca agggccgcgt gttctagcct gcaggtcgag catgcatcta    3360
gggcggccaa ttccgcccct ctccctcccc cccccctaac gttactggcc gaagccgctt    3420
ggaataaggc cggtgtgcgt ttgtctatat gtgattttcc accatattgc cgtcttttgg    3480
caatgtgagg gcccggaaac ctggccctgt cttcttgacg agcattccta gggtctttc    3540
ccctctcgcc aaaggaatgc aaggtctgtt gaatgtcgtg aaggaagcag ttcctctgga    3600
agcttcttga agacaaacaa cgtctgtagc gaccctttgc aggcagcgga accccccacc    3660
tggcgacagg tgcctctgcg gccaaaagcc acgtgtataa gatacacctg caaggcggc    3720
acaaccccag tgcacgttg tgagttggat agttgtggaa agagtcaaat ggctctcctc    3780
aagcgtattc aacaagggc tgaaggatgc ccagaaggta ccccattgta tgggatctga    3840
tctgggcct cggtgcacat gctttacatg tgtttagtcg aggttaaaaa aacgtctagg    3900
ccccccgaac cacggggacg tggttttcct ttgaaaaaca cgatgataag cttgccacaa    3960
cccttaccgg tcgccaccat gagcgagctg attaaggaga acatgcacat gaagctgtac    4020
```

```
atggagggca ccgtggacaa ccatcacttc aagtgcacat ccgagggcga aggcaagccc    4080
tacgagggca cccagaccat gagaatcaag gtggtcgagg gcggccctct ccccttcgcc    4140
ttcgacatcc tggctactag cttcctctac ggcagcaaga ccttcatcaa ccacacccag    4200
ggcatccccg acttcttcaa gcagtccttc cctgagggct tcacatggga gagagtcacc    4260
acatacgaag acggggggcgt gctgaccgct acccaggaca ccagcctcca ggacggctgc    4320
ctcatctaca acgtcaagat cagagggggtg aacttcacat ccaacggccc tgtgatgcag    4380
aagaaaacac tcggctggga ggccttcacc gagacgctgt accccgctga cggcggcctg    4440
gaaggcagaa acgacatggc cctgaagctc gtgggcggga gccatctgat cgcaaacatc    4500
aagaccacat atagatccaa gaaacccgct aagaacctca agatgcctgg cgtctactat    4560
gtggactaca gactggaaag aatcaaggag gccaacaacg agacctacgt cgagcagcac    4620
gaggtggcag tggccagata ctgcgacctc cctagcaaac tggggcacaa gcttaattga    4680
ttctagagtc gaccgagcat cttaccgcca tttataccca tatttgttct gttttcttg    4740 atttgggtat acatttaaat gttaatagaa caaaatggtg gggcaatcat ttacattttt    4800
agggatatgt aattactagt tcaggtgtat tgccacaaga caaacatgtt aagaaacttt    4860
cccgttattt acgctctgtt cctgttaatc aacctctgga ttacaaaatt tgtgaaagat    4920
tgactgatat tcttaactat gttgctcctt ttacgctgtg tggatatgct gctttatagc    4980
ctctgtatct agctattgct tcccgtacgg cttttcgttt ctcctccttg tataaatcct    5040
ggttgctgtc tcttttagag gagttgtggc ccgttgtccg tcaacgtggc gtggtgtgct    5100
ctgtgtttgc tgacgcaacc cccactggct ggggcattgc caccacctgt caactccttt    5160
ctgggacttt cgctttcccc ctcccgatcg ccacggcaga actcatcgcc gcctgccttg    5220
cccgctgctg gacaggggct aggttgctgg gcactgataa ttccgtggtg ttgtcatcgg    5280 tacctttta aaagaaaagg ggggactgga agggctaatt cactcccaac gaagacaaga    5340
tatcataact tcgtatagca tacattatac gaagttataa tttatttgtg aaatttgtga    5400
tgctattgct ttatttgtaa ccatatgttt atttgtgaaa tttgtgatgc tattgcttta    5460
tttgtaacca ttgcttttg cttgtactgg gtctctctgg ttagaccaga tctgagcctg    5520
ggagctctct ggctaactag ggaacccact gcttaagcct caataaagct tgcctcgacc    5580
agcctcgact gtgccttcta gttgccagcc atctgttgtt tgcccctccc ccgtgccttc    5640
cttgaccctg gaaggtgcca ctcccactgt cctttcctaa taaaatgagg aaattgcatc    5700
gcattgtctg agtaggtgtc attctattct ggggggtggg gtgggcagg acagcaaggg    5760 ggaggattgg gaagacaata gcaggcatgc tggggatgcg gtgggctcta tggcctgcag    5820
ctgcattaat gaatcggcca acgcgcgggg agaggcggtt tgcgtattgg gcgctcttcc    5880
gcttcctcgc tcactgactc gctgcgctcg tcgttcggc tgcggcgagc ggtatcagct    5940
cactcaaagg cggtaatacg ttatccaca gaatcagggg ataacgcagg aaagaacatg    6000
tgagcaaaag gccagcaaaa ggccaggaac cgtaaaaagg ccgcgttgct ggcgtttttc    6060
cataggctcc gccccctga cgagcatcac aaaaatcgac gctcaagtca gaggtggcga    6120
aacccgacag gactataaag ataccaggcg tttccccctg gaagctccct cgtgcgctct    6180
cctgttccga ccctgccgct taccggatac ctgtccgcct ttctcccttc gggaagcgtg    6240
gcgctttctc atagctcacg ctgtaggtat ctcagttcgg tgtaggtcgt tcgctccaag    6300
ctgggctgtg tgcacgaacc cccgttcag cccgaccgct gcgccttatc cggtaactat    6360
```

-continued

```
cgtcttgagt ccaacccggt aagacacgac ttatcgccac tggcagcagc cactggtaac    6420
aggattagca gagcgaggta tgtaggcggt gctacagagt tcttgaagtg gtggcctaac    6480
tacggctaca ctagaaggac agtatttggt atctgcgctc tgctgaagcc agttaccttc    6540
ggaaaaagag ttggtagctc ttgatccggc aaacaaacca ccgctggtag cggtggtttt    6600
tttgtttgca agcagcagat tacgcgcaga aaaaaggat ctcaagaaga tcctttgatc    6660
ttttctacgg ggtctgacgc tcagtggaac gaaaactcac gttaagggat tttggtcatg    6720
agattatcaa aaaggatctt cacctagatc cttttaaatt aaaaatgaag ttttaaatca    6780
atctaaagta tatatgagta aacttggtct gacagttacc aatgcttaat cagtgaggca    6840
cctatctcag cgatctgtct atttcgttca tccatagttg cctgactccc cgtcgtgtag    6900
ataactacga tacgggaggg cttaccatct ggccccagtg ctgcaatgat accgcgagac    6960
ccacgctcac cggctccaga tttatcagca ataaaccagc cagccggaag ggccgagcgc    7020
agaagtggtc ctgcaacttt atccgcctcc atccagtcta ttaattgttg ccgggaagct    7080
agagtaagta gttcgccagt taatagtttg cgcaacgttg ttgccattgc tacaggcatc    7140
gtggtgtcac gctcgtcgtt tggtatggct tcattcagct ccggttccca acgatcaagg    7200
cgagttacat gatcccccat gttgtgcaaa aaagcggtta gctccttcgg tcctccgatc    7260
gttgtcagaa gtaagttggc cgcagtgtta tcactcatgg ttatggcagc actgcataat    7320
tctcttactg tcatgccatc cgtaagatgc ttttctgtga ctggtgagta ctcaaccaag    7380
tcattctgag aatagtgtat gcggcgaccg agttgctctt gcccggcgtc aatacgggat    7440
aataccgcgc cacatagcag aactttaaaa gtgctcatca ttggaaaacg ttcttcgggg    7500
cgaaaactct caaggatctt accgctgttg agatccagtt cgatgtaacc cactcgtgca    7560
cccaactgat cttcagcatc ttttactttc accagcgttt ctgggtgagc aaaaacagga    7620
aggcaaaatg ccgcaaaaaa gggaataagg gcgacacgga aatgttgaat actcatactc    7680 ttccttttc aatattattg aagcatttat cagggttatt gtctcatgag cggatacata    7740
tttgaatgta tttagaaaaa taaacaaata ggggttccgc gcacatttcc ccgaaaagtg    7800
ccacct                                                              7806
```

<210> SEQ ID NO 126
<211> LENGTH: 8580
<212> TYPE: DNA
<213> ORGANISM: Artificial Sequence
<220> FEATURE:
<223> OTHER INFORMATION: Plasmid
       pCVL.SFFV.HA.NLS.I-OnuOpt.T2A.Trex2.IRES.mTagBFP

<400> SEQUENCE: 126

```
gacgtcaatg tagtcttatg caatactctt gtagtcttgc aacatggtaa cgatgagtta     60
gcaacatgcc ttacaaggag agaaaaagca ccgtgcatgc cgattggtgg aagtaaggtg    120
gtacgatcgt gccttattag gaaggcaaca cgggtctg acatggattg gacgaaccac     180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
```

-continued

| | |
|---|---|
| attttgacta gcggaggcta gaaggagaga gatgggtgcg agagcgtcag tattaagcgg | 600 |
| gggagaatta gatcgcgatg ggaaaaaatt cggttaaggc caggggggaaa gaaaaaatat | 660 |
| aaattaaaac atatagtatg ggcaagcagg gagctagaac gattcgcagt taatcctggc | 720 |
| ctgttagaaa catcagaagg ctgtagacaa atactgggac agctacaacc atcccttcag | 780 |
| acaggatcag aagaacttag atcattatat aatacagtag caaccctcta ttgtgtgcat | 840 |
| caaaggatag agataaaaga caccaaggaa gctttagaca agatagagga agagcaaaac | 900 |
| aaaagtaaga ccaccgcaca gcaagcggcc ctgatcttca gacctggagg aggagatatg | 960 |
| agggacaatt ggagaagtga attatataaa tataaagtag taaaaattga accattagga | 1020 |
| gtagcaccca ccaaggcaaa gagaagagtg gtgcagagag aaaaaagagc agtgggaata | 1080 |
| ggagctttgt tccttgggtt cttgggagca gcaggaagca ctatgggcgc agcgtcaatg | 1140 |
| acgctgacgg tacaggccag acaattattg tctggtatag tgcagcagca gaacaatttg | 1200 |
| ctgagggcta ttgaggcgca acagcatctg ttgcaactca cagtctgggg catcaagcag | 1260 |
| ctccaggcaa gaatcctggc tgtggaaaga tacctaaagg atcaacagct cctggggatt | 1320 |
| tggggttgct ctggaaaact catttgcacc actgctgtgc cttggaatgc tagttggagt | 1380 |
| aatgaatctc tggaacagat ttggaatcac acgacctgga tggagtggga cagagaaatt | 1440 |
| aacaattaca caagcttaat acactcctta attgaagaat cgcaaaacca gcaagaaaag | 1500 |
| aatgaacaag aattattgga attagataaa tgggcaagtt tgtggaattg gtttaacata | 1560 |
| acaaattggc tgtggtatat aaaattattc ataatgatag taggaggctt ggtaggttta | 1620 |
| agaatagttt ttgctgtact ttctatagtg aatagagtta ggcagggata ttcaccatta | 1680 |
| tcgtttcaga cccacctccc aaccccgagg ggacccgaca ggcccgaagg aatagaagaa | 1740 |
| gaaggtggag agagagacag agacagatcc attcgattag tgaacggatc tcgacggtat | 1800 |
| cggttaactt ttaaaagaaa aggggggatt ggggggtaca gtgcagggga agaatagta | 1860 |
| gacataatag caacagacat acaaactaaa gaattacaaa aacaaattac aaaaattcaa | 1920 |
| aattttatcg attacgcgtc acgtgctagc tgcagtaacg ccattttgca aggcatggaa | 1980 |
| aaataccaaa ccaagaatag agaagttcag atcaagggcg ggtacatgaa aatagctaac | 2040 |
| gttgggccaa acaggatatc tgcggtgagc agtttcggcc ccggcccggg gccaagaaca | 2100 |
| gatggtcacc gcagtttcgg ccccggcccg aggccaagaa cagatggtcc ccagatatgg | 2160 |
| cccaaccctc agcagtttct taagacccat cagatgtttc caggctcccc caaggacctg | 2220 |
| aaatgaccct gcgccttatt tgaattaacc aatcagcctg cttctcgctt ctgttcgcgc | 2280 |
| gcttctgctt cccgagctct ataaaagagc tcacaacccc tcactcggcg cgccagtcct | 2340 |
| ccgacagact gagtcgcccg ctcgagccgc caccatggga tatccatacg atgtcccaga | 2400 |
| ttatgcgcca cctaagaaga aacgcaaagt cgaattcagc cgccgcgaga gcatcaaccc | 2460 |
| ctggattctg accggcttcg ccgacgccga gggcagcttc ctgctgcgca tccgcaacaa | 2520 |
| caacaagagc agcgtgggct acagcaccga gctgggcttc cagatcaccc tgcacaacaa | 2580 |
| ggacaagagc atcctggaga acatccagag catctggaag gtgggcgtga tcgccaacag | 2640 |
| cggcgacaac gccgtgagcc tgaaggtgac ccgcttcgag gacctgaagg tgatcatcga | 2700 |
| ccacttcgag aagtaccccc tgatcaccca gaagctgggc gactacatgc tgttcaagca | 2760 |
| ggccttctgc gtgatggaga acaaggagca cctgaagatc aacggcatca aggagctggt | 2820 |
| gcgcatcaag gccaagctga actggggcct gaccgacgag ctgaagaagg ccttccccga | 2880 |
| gatcatcagc aaggagcgca gcctgatcaa caagaacatc cccaacttca gtggctggc | 2940 |

```
cggcttcacc agcggcgagg gctgcttctt cgtgaacctg atcaagagca agagcaagct    3000
gggcgtgcag gtgcagctgg tgttcagcat cacccagcac atcaaggaca agaacctgat    3060
gaacagcctg atcacctacc tgggctgcgg ctacatcaag gagaagaaca agagcgagtt    3120
cagctggctg gacttcgtgg tgaccaagtt cagcgacatc aacgacaaga tcatccccgt    3180
gttccaggag aacaccctga tcggcgtgaa gctggaggac ttcgaggact ggtgcaaggt    3240
ggccaagctg atcgaggaga agaagcacct gaccgagagc ggcctggacg agatcaagaa    3300
gatcaagctg aacatgaaca agggccgcgt gttcggatcc ggtgagggca gggaagtct    3360 tctaacatgc ggtgacgtgg aggagaatcc gggcccctcc ggatctgagc cacctcgggc    3420
tgagaccttt gtattcctgg acctagaagc cactgggctc ccaaacatgg accctgagat    3480
tgcagagata tccctttttg ctgttcaccg ctcttccctg gagaacccag aacgggatga    3540
ttctggttcc ttggtgctgc cccgtgttct ggacaagctc acactgtgca tgtgcccgga    3600 gcgcccttt actgccaagg ccagtgagat tactggtttg agcagcgaaa gcctgatgca    3660
ctgcgggaag gctggtttca tggcgctgt ggtaaggaca ctgcagggct tcctaagccg    3720
ccaggagggc cccatctgcc ttgtggccca aatggcttc gattatgact tcccactgct    3780
gtgcacggag ctacaacgtc tgggtgccca tctgccccaa gacactgtct gcctggacac    3840
actgcctgca ttgcggggcc tggaccgtgc tcacagccac ggcaccaggg ctcaaggccg    3900
caaaagctac agcctggcca gtctcttcca ccgctacttc aggctgaac ccagtgctgc    3960 ccattcagca gaaggtgatg tgcacaccct gcttctgatc ttcctgcatc gtgctcctga    4020
gctgctcgcc tgggcagatg agcaggcccg cagctgggct catattgagc ccatgtacgt    4080
gccacctgat ggtccaagcc tcgaagcctg acctgcaggt cgagcatgca tctagggcgg    4140
ccaattccgc ccctctccct cccccccccc taacgttact ggccgaagcc gcttggaata    4200
aggccggtgt gcgtttgtct atatgtgatt ttccaccata ttgccgtctt ttggcaatgt    4260
gagggcccgg aaacctggcc ctgtcttctt gacgagcatt cctaggggtc tttcccctct    4320
cgccaaagga atgcaaggtc tgttgaatgt cgtgaaggaa gcagttcctc tggaagcttc    4380
ttgaagacaa acaacgtctg tagcgaccct ttgcaggcag cggaaccccc cacctggcga    4440
caggtgcctc tgcggccaaa agccacgtgt ataagataca cctgcaaagg cggcacaacc    4500
ccagtgccac gttgtgagtt ggatagttgt ggaaagagtc aaatggctct cctcaagcgt    4560
attcaacaag ggctgaagg atgcccagaa ggtaccccat tgtatgggat ctgatctggg    4620
gcctcggtgc acatgcttta catgtgttta gtcgaggtta aaaaaacgtc taggcccccc    4680
gaaccacggg gacgtggttt ccttgaaa acacgatga taagcttgcc acaacccta    4740 ccggtcgcca ccatgagcga gctgattaag gagaacatgc acatgaagct gtacatggag    4800 gcaccgtgg acaaccatca cttcaagtgc acatccgagg gcgaaggcaa gccctacgag    4860
ggcacccaga ccatgagaat caaggtggtc gagggcggcc ctctcccctt cgccttcgac    4920
atcctggcta ctagcttcct ctacggcagc aagaccttca tcaaccacac ccagggcatc    4980
cccgacttct tcaagcagtc cttccctgag ggcttcacat gggagagagt caccacatac    5040
gaagacgggg gcgtgctgac cgctacccag gacaccagcc tccaggacgg ctgcctcatc    5100
tacaacgtca agatcagagg ggtgaacttc acatccaacg ccctgtgat gcagaagaaa    5160 acactcggct gggaggcctt caccgagacg ctgtaccccg ctgacggcgg cctggaaggc    5220
agaaacgaca tggccctgaa gctcgtgggc gggagccatc tgatcgcaaa catcaagacc    5280
```

```
acatatagat ccaagaaacc cgctaagaac ctcaagatgc ctggcgtcta ctatgtggac    5340
tacagactgg aaagaatcaa ggaggccaac aacgagacct acgtcgagca gcacgaggtg    5400
gcagtggcca gatactgcga cctccctagc aaactggggc acaagcttaa ttgattctag    5460
agtcgaccga gcatcttacc gccatttata cccatatttg ttctgttttt cttgatttgg    5520
gtatacattt aaatgttaat agaacaaaat ggtggggcaa tcatttacat ttttagggat    5580
atgtaattac tagttcaggt gtattgccac aagacaaaca tgttaagaaa ctttcccgtt    5640
atttacgctc tgttcctgtt aatcaacctc tggattacaa aatttgtgaa agattgactg    5700
atattcttaa ctatgttgct ccttttacgc tgtgtggata tgctgcttta tagcctctgt    5760
atctagctat tgcttcccgt acggctttcg ttttctcctc cttgtataaa tcctggttgc    5820
tgtctctttt agaggagttg tggcccgttg tccgtcaacg tggcgtggtg tgctctgtgt    5880
ttgctgacgc aaccccccact ggctggggca ttgccaccac ctgtcaactc ctttctggga    5940
ctttcgcttt cccctcccg atcgccacgg cagaactcat cgccgcctgc cttgcccgct    6000
gctggacagg ggctaggttg ctgggcactg ataattccgt ggtgttgtca tcggtacctt    6060
tttaaaagaa aagggggggac tggaagggct aattcactcc caacgaagac aagatatcat    6120
aacttcgtat agcatacatt atacgaagtt ataatttatt tgtgaaattt gtgatgctat    6180
tgctttattt gtaaccatat gtttatttgt gaaatttgtg atgctattgc tttatttgta    6240
accattgctt tttgcttgta ctgggtctct ctggttagac cagatctgag cctgggagct    6300
ctctggctaa ctagggaacc cactgcttaa gcctcaataa agcttgcctc gaccagcctc    6360
gactgtgcct tctagttgcc agccatcgt tgtttgcccc tcccccgtgc cttccttgac    6420
cctggaaggt gccactccca ctgtcctttc ctaataaaat gaggaaattg catcgcattg    6480
tctgagtagg tgtcattcta ttctgggggg tggggtgggg caggacagca aggggggagga    6540 ttgggaagac aatagcaggc atgctgggga tgcggtgggc tctatggcct gcagctgcat    6600
taatgaatcg gccaacgcgc ggggagaggc ggtttgcgta ttgggcgctc ttccgcttcc    6660
tcgctcactg actcgctgcg ctcggtcgtt cggctgcggc gagcggtatc agctcactca    6720
aaggcggtaa tacggttatc cacagaatca ggggataacg caggaaagaa catgtgagca    6780
aaaggccagc aaaaggccag gaaccgtaaa aaggccgcgt tgctggcgtt tttccatagg    6840
ctccgccccc ctgacgagca tcacaaaaat cgacgctcaa gtcagaggtg gcgaaacccg    6900
acaggactat aaagatacca ggcgtttccc cctggaagct ccctcgtgcg ctctcctgtt    6960
ccgaccctgc cgcttaccgg atacctgtcc gcctttctcc cttcgggaag cgtggcgctt    7020
tctcatagct cacgctgtag gtatctcagt tcggtgtagg tcgttcgctc caagctgggc    7080
tgtgtgcacg aaccccccgt tcagcccgac cgctgcgcct tatccggtaa ctatcgtctt    7140
gagtccaacc cggtaagaca cgacttatcg ccactggcag cagccactgg taacaggatt    7200
agcagagcga ggtatgtagg cggtgctaca gagttcttga agtggtggcc taactacggc    7260
tacactagaa ggacagtatt tggtatctgc gctctgctga agccagttac cttcggaaaa    7320
agagttggta gctcttgatc cggcaaacaa accaccgctg gtagcggtgg tttttttgtt    7380
tgcaagcagc agattacgcg cagaaaaaaa ggatctcaag aagatccttt gatcttttct    7440
acggggtctg acgctcagtg gaacgaaaac tcacgttaag ggattttggt catgagatta    7500
tcaaaaagga tcttcaccta gatccttta aattaaaaat gaagttttaa atcaatctaa    7560
agtatatatg agtaaacttg gtctgacagt taccaatgct taatcagtga ggcacctatc    7620
tcagcgatct gtctatttcg ttcatccata gttgcctgac tccccgtcgt gtagataact    7680
```

```
acgatacggg agggcttacc atctggcccc agtgctgcaa tgataccgcg agacccacgc    7740
tcaccggctc cagatttatc agcaataaac cagccagccg aagggccga gcgcagaagt    7800 ggtcctgcaa ctttatccgc ctccatccag tctattaatt gttgccggga agctagagta    7860
agtagttcgc cagttaatag tttgcgcaac gttgttgcca ttgctacagg catcgtggtg    7920
tcacgctcgt cgtttggtat ggcttcattc agctccggtt cccaacgatc aaggcgagtt    7980
acatgatccc ccatgttgtg caaaaaagcg gttagctcct tcggtcctcc gatcgttgtc    8040
agaagtaagt tggccgcagt gttatcactc atggttatgg cagcactgca taattctctt    8100
actgtcatgc catccgtaag atgcttttct gtgactggtg agtactcaac caagtcattc    8160
tgagaatagt gtatgcggcg accgagttgc tcttgcccgg cgtcaatacg gataatacc    8220 gcgccacata gcagaacttt aaaagtgctc atcattggaa aacgttcttc ggggcgaaaa    8280
ctctcaagga tcttaccgct gttgagatcc agttcgatgt aacccactcg tgcacccaac    8340
tgatcttcag catcttttac tttcaccagc gtttctgggt gagcaaaaac aggaaggcaa    8400
aatgccgcaa aaagggaat aagggcgaca cggaaatgtt gaatactcat actcttcctt    8460
tttcaatatt attgaagcat ttatcagggt tattgtctca tgagcggata catatttgaa    8520
tgtatttaga aaataaaca ataggggtt ccgcgcacat ttccccgaaa agtgccacct    8580
```

<210> SEQ ID NO 127
<211> LENGTH: 7833
<212> TYPE: DNA
<213> ORGANISM: Artificial Sequence
<220> FEATURE:
<223> OTHER INFORMATION: Plasmid pCVL.SFFV.HA.NLS.I-LTR I.IRES.mTagBFP

<400> SEQUENCE: 127

```
gacgtcaatg tagtcttatg caatactctt gtagtcttgc aacatggtaa cgatgagtta      60
gcaacatgcc ttacaaggag agaaaaagca ccgtgcatgc cgattggtgg aagtaaggtg     120
gtacgatcgt gccttattag gaaggcaaca gacgggtctg acatggattg gacgaaccac     180
tgaattgccg cattgcagag atattgtatt taagtgccta gctcgataca taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta aaggagaga gatgggtgcg agagcgtcag tattaagcgg     600
gggagaatta gatcgcgatg gaaaaaatt cggttaaggc cagggggaaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca agatagagga gagcaaaaac     900
aaaagtaaga ccaccgcaca gcaagcggcc ctgatcttca gacctggagg aggagatatg     960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
```

```
acgctgacgg tacaggccag acaattattg tctggtatag tgcagcagca gaacaatttg     1200
ctgagggcta ttgaggcgca acagcatctg ttgcaactca cagtctgggg catcaagcag     1260
ctccaggcaa gaatcctggc tgtggaaaga tacctaaagg atcaacagct cctggggatt     1320
tggggttgct ctggaaaact catttgcacc actgctgtgc cttggaatgc tagttggagt     1380
aatgaatctc tggaacagat ttggaatcac acgacctgga tggagtggga cagagaaatt     1440
aacaattaca caagcttaat acactcctta attgaagaat cgcaaaacca gcaagaaaag     1500
aatgaacaag aattattgga attagataaa tgggcaagtt tgtggaattg gtttaacata     1560
acaaattggc tgtggtatat aaaattattc ataatgatag taggaggctt ggtaggttta     1620
agaatagttt ttgctgtact ttctatagtg aatagagtta ggcagggata ttcaccatta     1680
tcgtttcaga cccacctccc aaccccgagg ggacccgaca ggcccgaagg aatagaagaa     1740
gaaggtggag agagagacag agacagatcc attcgattag tgaacggatc tcgacggtat     1800
cggttaactt ttaaaagaaa aggggggatt gggggtaca gtgcagggga aagaatagta     1860
gacataatag caacagacat acaaactaaa gaattacaaa aacaaattac aaaaattcaa     1920
aattttatcg attacgcgtc acgtgctagc tgcagtaacg ccattttgca aggcatggaa     1980
aaataccaaa ccaagaatag agaagttcag atcaagggcg ggtacatgaa aatagctaac     2040
gttgggccaa acaggatatc tgcggtgagc agtttcggcc ccggcccggg gccaagaaca     2100
gatggtcacc gcagtttcgg ccccggcccg aggccaagaa cagatggtcc ccagatatgg     2160
cccaaccctc agcagtttct taagacccat cagatgtttc caggctcccc caaggacctg     2220
aaatgaccct gcgccttatt tgaattaacc aatcagcctg cttctcgctt ctgttcgcgc     2280
gcttctgctt cccgagctct ataaaagagc tcacaacccc tcactcggcg cgccagtcct     2340
ccgacagact gagtcgcccg ctcgagccgc caccatggga tatccatacg atgtcccaga     2400
ttatgcgcca cctaagaaga acgcaaagt cgaattcttc ccagttcaag ctagaaacga     2460
caacatctct ccatggacta tcactggttt cgctgacgct gaatcttctt tcatgttgac     2520
tgtttctaag gactctaaga gaaacactgg ttggtctgtt agaccaagat tcagaatcgg     2580
tttgcacaac aaggacgtga ctatcttgaa gtctatcaga gaatacttgg gcgccggtat     2640
catcacttct gacaaggacg ctagaatcag attcgaatct ttgaaggaat tggaagttgt     2700
tatcaaccac ttcgacaagt acccattgat cactcaaaag agagctgact acttgttgtt     2760
caagaaggct ttctacttaa ttaagaacaa ggaacacttg actgaagaag gtttgaacca     2820
aatcttgact ttgaaggctt cttttgaactt gggtttgtct gaagaattga aggaagcatt     2880
cccaaacact atcccagctg aaaagttact agttactggt caagaaatcc cagactctaa     2940
ctgggttgct ggtttcactg ctggtgaagg ttctttctac atcagaatcg ctaagaactc     3000
tactttgaag actggttacc aagttcaatc tgttttccaa atcactcaag acacgcgtga     3060
catcgaattg atgaagaact tgatctctta cttgaactgt ggtaacatca gaatcagaaa     3120
gtacaagggt tctgaaggta tccacgacac ttgtgttgac ttggttgtta ctaacttgaa     3180
cgacatcaag gaaagatca tcccattctt caacaagaac cacatcatcg gtgttaagtt     3240
gcaagactac agagactggt gtaaggttgt tactttgatc gacaacaagg aacacttgac     3300
ttctgaaggt ttggaaaaga tccaaaagat caaggaaggt atgaacagag gtagatcttt     3360
gtagcctgca ggtcgagcat gcatctaggg cggccaattc cgcccctctc cctcccccc     3420
ccctaacgtt actggccgaa gccgcttgga ataaggccgg tgtgcgtttg tctatatgtg     3480
attttccacc atattgccgt cttttggcaa tgtgagggcc cggaaacctg gccctgtctt     3540
```

```
cttgacgagc attcctaggg gtctttcccc tctcgccaaa ggaatgcaag gtctgttgaa    3600
tgtcgtgaag gaagcagttc ctctggaagc ttcttgaaga caaacaacgt ctgtagcgac    3660
cctttgcagg cagcggaacc ccccacctgg cgacaggtgc ctctgcggcc aaaagccacg    3720
tgtataagat acacctgcaa aggcggcaca accccagtgc cacgttgtga gttggatagt    3780
tgtggaaaga gtcaaatggc tctcctcaag cgtattcaac aaggggctga aggatgccca    3840
gaaggtaccc cattgtatgg gatctgatct ggggcctcgg tgcacatgct ttacatgtgt    3900
ttagtcgagg ttaaaaaaac gtctaggccc cccgaaccac ggggacgtgg ttttcctttg    3960
aaaaacacga tgataagctt gccacaaccc ttaccggtcg ccaccatgag cgagctgatt    4020
aaggagaaca tgcacatgaa gctgtacatg gagggcaccg tggacaacca tcacttcaag    4080
tgcacatccg agggcgaagg caagccctac gagggcaccc agaccatgag aatcaaggtg    4140
gtcgagggcg gccctctccc cttcgccttc gacatcctgg ctactagctt cctctacggc    4200
agcaagacct tcatcaacca cacccagggc atccccgact tcttcaagca gtccttccct    4260
gagggcttca catgggagag agtcaccaca tacgaagacg gggcgtgct gaccgctacc    4320
caggacacca gcctccagga cggctgcctc atctacaacg tcaagatcag agggtgaac    4380
ttcacatcca acggccctgt gatgcagaag aaaacactcg gctgggaggc cttcaccgag    4440
acgctgtacc ccgctgacgg cggcctggaa ggcagaaacg acatggccct gaagctcgtg    4500
ggcgggagcc atctgatcgc aaacatcaag accacatata gatccaagaa acccgctaag    4560
aacctcaaga tgcctggcgt ctactatgtg gactacagac tggaaagaat caaggaggcc    4620
aacaacgaga cctacgtcga gcagcacgag gtggcagtgg ccagatactg cgacctccct    4680
agcaaactgg ggcacaagct taattgattc tagagtcgac cgagcatctt accgccattt    4740
atacccatat ttgttctgtt tttcttgatt tgggtataca tttaaatgtt aatagaacaa    4800
aatggtgggg caatcattta cattttagg gatatgtaat tactagttca ggtgtattgc    4860
cacaagacaa acatgttaag aaactttccc gttatttacg ctctgttcct gttaatcaac    4920
ctctggatta caaaatttgt gaaagattga ctgatattct taactatgtt gctccttta    4980
cgctgtgtgg atatgctgct ttatagcctc tgtatctagc tattgcttcc cgtacggctt    5040
tcgtttctc ctccttgtat aaatcctggt tgctgtctct tttagaggag ttgtggcccg    5100
ttgtccgtca acgtggcgtg gtgtgctctg tgtttgctga cgcaaccccc actggctggg    5160
gcattgccac cacctgtcaa ctcctttctg ggactttcgc ttccccctc ccgatcgcca    5220
cggcagaact catcgccgcc tgccttgccc gctgctggac aggggctagg ttgctgggca    5280
ctgataattc cgtggtgttg tcatcggtac cttttaaaa gaaaggggg gactggaagg    5340
gctaattcac tcccaacgaa gacaagatat cataacttcg tatagcatac attatacgaa    5400
gttataattt atttgtgaaa tttgtgatgc tattgcttta tttgtaacca tatgtttatt    5460
tgtgaaattt gtgatgctat tgctttattt gtaaccattg cttttgctt gtactgggtc    5520
tctctggtta gaccagatct gagcctggga gctctctggc taactaggga acccactgct    5580
taagcctcaa taaagcttgc ctcgaccagc ctcgactgtg ccttctagtt gccagccatc    5640
tgttgtttgc ccctccccg tgccttcctt gaccctggaa ggtgccactc ccactgtcct    5700
ttcctaataa aatgaggaaa ttgcatcgca ttgtctgagt aggtgtcatt ctattctggg    5760
gggtggggtg gggcaggaca gcaagggga ggattgggaa gacaatagca ggcatgctgg    5820
ggatgcggtg ggctctatgg cctgcagctg cattaatgaa tcggccaacg cgcggggaga    5880
```

| | |
|---|---|
| ggcggtttgc gtattgggcg ctcttccgct tcctcgctca ctgactcgct gcgctcggtc | 5940 |
| gttcggctgc ggcgagcggt atcagctcac tcaaaggcgg taatacggtt atccacagaa | 6000 |
| tcagggggata acgcaggaaa gaacatgtga gcaaaaggcc agcaaaaggc caggaaccgt | 6060 |
| aaaaaggccg cgttgctggc gttttttccat aggctccgcc ccctgacga gcatcacaaa | 6120 |
| aatcgacgct caagtcagag gtggcgaaac ccgacaggac tataaagata ccaggcgttt | 6180 |
| ccccctggaa gctccctcgt gcgctctcct gttccgaccc tgccgcttac cggatacctg | 6240 |
| tccgcctttc tcccttcggg aagcgtggcg ctttctcata gctcacgctg taggtatctc | 6300 |
| agttcggtgt aggtcgttcg ctccaagctg ggctgtgtgc acgaaccccc cgttcagccc | 6360 |
| gaccgctgcg ccttatccgg taactatcgt cttgagtcca acccggtaag acacgactta | 6420 |
| tcgccactgg cagcagccac tggtaacagg attagcagag cgaggtatgt aggcggtgct | 6480 |
| acagagttct tgaagtggtg gcctaactac ggctacacta aaggacagt atttggtatc | 6540 |
| tgcgctctgc tgaagccagt taccttcgga aaaagagttg gtagctcttg atccggcaaa | 6600 |
| caaaccaccg ctggtagcgg tggtttttttt gtttgcaagc agcagattac gcgcagaaaa | 6660 |
| aaaggatctc aagaagatcc tttgatcttt tctacggggt ctgacgctca gtggaacgaa | 6720 |
| aactcacgtt aagggatttt ggtcatgaga ttatcaaaaa ggatcttcac ctagatcctt | 6780 |
| ttaaattaaa aatgaagttt taaatcaatc taaagtatat atgagtaaac ttggtctgac | 6840 |
| agttaccaat gcttaatcag tgaggcacct atctcagcga tctgtctatt tcgttcatcc | 6900 |
| atagttgcct gactccccgt cgtgtagata actacgatac gggagggctt accatctggc | 6960 |
| cccagtgctg caatgatacc gcgagaccca cgctcaccgg ctccagattt atcagcaata | 7020 |
| aaccagccag ccggaagggc cgagcgcaga agtggtcctg caactttatc cgcctccatc | 7080 |
| cagtctatta attgttgccg ggaagctaga gtaagtagtt cgccagttaa tagtttttgcgc | 7140 |
| aacgttgttg ccattgctac aggcatcgtg gtgtcacgct cgtcgtttgg tatggcttca | 7200 |
| ttcagctccg gttcccaacg atcaaggcga gttacatgat ccccccatgtt gtgcaaaaaa | 7260 |
| gcggttagct ccttcggtcc tccgatcgtt gtcagaagta agttggccgc agtgttatca | 7320 |
| ctcatggtta tggcagcact gcataattct cttactgtca tgccatccgt aagatgcttt | 7380 |
| tctgtgactg gtgagtactc aaccaagtca ttctgagaat agtgtatgcg gcgaccgagt | 7440 |
| tgctcttgcc cggcgtcaat acgggataat accgcgccac atagcagaac tttaaaagtg | 7500 |
| ctcatcattg gaaaacgttc ttcggggcga aaactctcaa ggatcttacc gctgttgaga | 7560 |
| tccagttcga tgtaacccac tcgtgcaccc aactgatctt cagcatcttt tactttcacc | 7620 |
| agcgtttctg ggtgagcaaa aacaggaagg caaaatgccg caaaaaaggg aataagggcg | 7680 |
| acacggaaat gttgaatact catactcttc cttttttcaat attattgaag catttatcag | 7740 |
| ggttattgtc tcatgagcgg atacatattt gaatgtattt agaaaaataa acaaataggg | 7800 |
| gttccgcgca catttccccg aaaagtgcca cct | 7833 |

<210> SEQ ID NO 128
<211> LENGTH: 8607
<212> TYPE: DNA
<213> ORGANISM: Artificial Sequence
<220> FEATURE:
<223> OTHER INFORMATION: Plasmid pCVL.SFFV.HA.NLS.I-LTR
      I.T2A.Trex2.IRES.mTagBFP

<400> SEQUENCE: 128
gacgtcaatg tagtcttatg caatactctt gtagtcttgc aacatggtaa cgatgagtta    60

```
gcaacatgcc ttacaaggag agaaaaagca ccgtgcatgc cgattggtgg aagtaaggtg    120
gtacgatcgt gccttattag gaaggcaaca gacgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagacccct ttagtcagtg tggaaaatct ctagcagtgg    420
cgcccgaaca gggacttgaa agcgaagggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg    600
gggagaatta gatcgcgatg ggaaaaaatt cggttaaggc caggggggaaa gaaaaaatat   660 aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagacag agacagatcc attcgattag tgaacggatc tcgacggtat   1800
cggttaactt ttaaagaaa aggggggatt ggggggtaca gtgcagggga agaatagta    1860 gacataatag caacagacat acaaactaaa gaattacaaa acaaattac aaaaattcaa    1920 aatttttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcttc ccagttcaag ctagaaacga   2460
```

```
caacatctct ccatggacta tcactggttt cgctgacgct gaatcttctt tcatgttgac   2520
tgtttctaag gactctaaga gaaacactgg ttggtctgtt agaccaagat tcagaatcgg   2580
tttgcacaac aaggacgtga ctatcttgaa gtctatcaga gaatacttgg gcgccggtat   2640
catcacttct gacaaggacg ctagaatcag attcgaatct ttgaaggaat tggaagttgt   2700
tatcaaccac ttcgacaagt acccattgat cactcaaaag agagctgact acttgttgtt   2760
caagaaggct ttctacttaa ttaagaacaa ggaacacttg actgaagaag gtttgaacca   2820
aatcttgact ttgaaggctt ctttgaactt gggtttgtct gaagaattga aggaagcatt   2880
cccaaacact atcccagctg aaaagttact agttactggt caagaaatcc cagactctaa   2940
ctgggttgct ggtttcactg ctggtgaagg ttctttctac atcagaatcg ctaagaactc   3000
tactttgaag actggttacc aagttcaatc tgttttccaa atcactcaag acacgcgtga   3060
catcgaattg atgaagaact tgatctctta cttgaactgt ggtaacatca gaatcagaaa   3120
gtacaagggt tctgaaggta tccacgacac ttgtgttgac ttggttgtta ctaacttgaa   3180
cgacatcaag gaaaagatca tcccattctt caacaagaac cacatcatcg gtgttaagtt   3240
gcaagactac agagactggt gtaaggttgt tactttgatc gacaacaagg aacacttgac   3300
ttctgaaggt ttggaaaaga tccaaaagat caaggaaggt atgaacagag gtagatcttt   3360
gggatccggt gagggcagag gaagtcttct aacatgcggt gacgtggagg agaatccggg   3420
cccctccgga tctgagccac ctcgggctga ccctttgta ttcctggacc tagaagccac   3480
tgggctccca acatggacc ctgagattgc agagatatcc ctttttgctg ttcaccgctc   3540
ttccctggag aacccagaac gggatgattc tggttccttg gtgctgcccc gtgttctgga   3600
caagctcaca ctgtgcatgt gcccggagcg cccctttact gccaaggcca gtgagattac   3660
tggtttgagc agcgaaagcc tgatgcactg cgggaaggct ggtttcaatg cgctgtggt   3720 aaggacactg cagggcttcc taagccgcca ggagggcccc atctgccttg tgcccacaa   3780 tggcttcgat tatgacttcc cactgctgtg cacggagcta caacgtctgg gtgcccatct   3840
gccccaagac actgtctgcc tggacacact gcctgcattg cggggcctgg accgtgctca   3900
cagccacggc accagggctc aaggccgcaa aagctacagc ctggccagtc tcttccaccg   3960
ctacttccag gctgaaccca gtgctgccca ttcagcagaa ggtgatgtgc acaccctgct   4020
tctgatcttc ctgcatcgtg ctcctgagct gctcgcctgg gcagatgagc aggcccgcag   4080
ctgggctcat attgagccca tgtacgtgcc acctgatggt ccaagcctcg aagcctgacc   4140
tgcaggtcga gcatgcatct agggcggcca attccgcccc tcccctccc ccccctaa   4200 cgttactggc cgaagccgct tggaataagg ccggtgtgcg tttgtctata tgtgattttc   4260
caccatattg ccgtcttttg gcaatgtgag ggcccggaaa cctggccctg tcttcttgac   4320
gagcattcct aggggtcttt ccctctcgc caaaggaatg caaggtctgt tgaatgtcgt   4380
gaaggaagca gttcctctgg aagcttcttg aagacaaaca acgtctgtag cgacccttg   4440 caggcagcgg aaccccccac ctggcgacag gtgcctctgc ggccaaaagc cacgtgtata   4500
agatacacct gcaaaggcgg cacaaccca gtgccacgtt gtgagttgga tagttgtgga   4560
aagagtcaaa tggctctcct caagcgtatt caacaagggg ctgaaggatg cccagaaggt   4620
accccattgt atgggatctg atctggggcc tcggtgcaca tgctttacat gtgtttagtc   4680
gaggttaaaa aaacgtctag gccccccgaa ccacggggac gtggttttcc tttgaaaaac   4740
acgatgataa gcttgcccaca acccttaccg gtcgccacca tgagcgagct gattaaggag   4800
```

```
aacatgcaca tgaagctgta catggagggc accgtggaca ccatcactt caagtgcaca    4860 tccgagggcg aaggcaagcc ctacgagggc acccagacca tgagaatcaa ggtggtcgag    4920
ggcggccctc tccccttcgc cttcgacatc ctggctacta gcttcctcta cggcagcaag    4980
accttcatca accacaccca gggcatcccc gacttcttca gcagtccttc cctgagggc    5040 ttcacatggg agagagtcac cacatacgaa gacgggggcg tgctgaccgc tacccaggac    5100
accagcctcc aggacggctg cctcatctac aacgtcaaga tcagagtggt gaacttcaca    5160
tccaacggcc ctgtgatgca gaagaaaaca ctcggctggg aggccttcac cgagacgctg    5220
taccccgctg acggcggcct ggaaggcaga acgacatgg ccctgaagct cgtgggcggg    5280
agccatctga tcgcaaacat caagaccaca tatagatcca agaaacccgc taagaacctc    5340
aagatgcctg gcgtctacta tgtggactac agactggaaa gaatcaagga ggccaacaac    5400
gagacctacg tcgagcagca cgaggtggca gtggccagat actgcgacct ccctagcaaa    5460
ctggggcaca agcttaattg attctagagt cgaccgagca tcttaccgcc atttataccc    5520
atatttgttc tgttttctt gatttgggta tacatttaaa tgttaataga acaaaatggt    5580
ggggcaatca tttacatttt tagggatatg taattactag ttcaggtgta ttgccacaag    5640
acaaacatgt taagaaactt tcccgttatt tacgctctgt tcctgttaat caacctctgg    5700
attacaaaat ttgtgaaaga ttgactgata ttcttaacta tgttgctcct tttacgctgt    5760
gtggatatgc tgctttatag cctctgtatc tagctattgc ttcccgtacg gcttcgttt    5820 tctcctcctt gtataaatcc tggttgctgt ctctttaga ggagttgtgg cccgttgtcc    5880
gtcaacgtgg cgtggtgtgc tctgtgtttg ctgacgcaac cccactggc tggggcattg    5940 ccaccacctg tcaactcctt tctgggactt cgctttccc cctcccgatc gccacggcag    6000
aactcatcgc cgcctgcctt gcccgctgct ggacaggggc taggttgctg ggcactgata    6060
attccgtggt gttgtcatcg gtaccttttt aaaagaaaag ggggactgg aagggctaat    6120 tcactcccaa cgaagacaag atatcataac ttcgtatagc atacattata cgaagttata    6180
atttatttgt gaaatttgtg atgctattgc tttatttgta accatatgtt tatttgtgaa    6240
atttgtgatg ctattgcttt atttgtaacc attgcttttt gcttgtactg ggtctctctg    6300
gttagaccag atctgagcct gggagctctc tggctaacta gggaacccac tgcttaagcc    6360
tcaataaagc ttgcctcgac cagcctcgac tgtgccttct agttgccagc catctgttgt    6420
ttgcccctcc cccgtgcctt ccttgaccct ggaaggtgcc actcccactg tccttttccta    6480 ataaaatgag gaaattgcat cgcattgtct gagtaggtgt cattctattc tggggggtgg    6540
ggtggggcag gacagcaagg gggaggattg ggaagacaat agcaggcatg ctggggatgc    6600
ggtgggctct atggcctgca gctgcattaa tgaatcggcc aacgcgcggg gagaggcggt    6660
ttgcgtattg ggcgctcttc cgcttcctcg ctcactgact cgctgcgctc ggtcgttcgg    6720
ctgcggcgag cggtatcagc tcactcaaag gcggtaatac ggttatccac agaatcaggg    6780
gataacgcag gaaagaacat gtgagcaaaa ggccagcaaa aggccaggaa ccgtaaaaag    6840
gccgcgttgc tggcgttttt ccataggctc cgcccccctg acgagcatca caaaaatcga    6900
cgctcaagtc agaggtggcg aaacccgaca ggactataaa gataccaggc gtttccccct    6960
ggaagctccc tcgtgcgctc tcctgttccg accctgccgc ttaccggata cctgtccgcc    7020
tttctccctt cgggaagcgt ggcgctttct catagctcac gctgtaggta tctcagttcg    7080
gtgtaggtcg ttcgctccaa gctgggctgt gtgcacgaac cccccgttca gcccgaccgc    7140
tgcgccttat ccggtaacta tcgtcttgag tccaacccgg taagacacga cttatcgcca    7200
```

```
ctggcagcag ccactggtaa caggattagc agagcgaggt atgtaggcgg tgctacagag      7260
ttcttgaagt ggtggcctaa ctacggctac actagaagga cagtatttgg tatctgcgct      7320
ctgctgaagc cagttacctt cggaaaaaga gttggtagct cttgatccgg caaacaaacc      7380
accgctggta gcggtggttt ttttgtttgc aagcagcaga ttacgcgcag aaaaaaagga      7440
tctcaagaag atcctttgat cttttctacg gggtctgacg ctcagtggaa cgaaaactca      7500
cgttaaggga ttttggtcat gagattatca aaaaggatct tcacctagat ccttttaaat      7560
taaaaatgaa gttttaaatc aatctaaagt atatatgagt aaacttggtc tgacagttac      7620
caatgcttaa tcagtgaggc acctatctca gcgatctgtc tatttcgttc atccatagtt      7680
gcctgactcc ccgtcgtgta gataactacg atacgggagg gcttaccatc tggccccagt      7740
gctgcaatga taccgcgaga cccacgctca ccggctccag atttatcagc aataaaccag      7800
ccagccggaa gggccgagcg cagaagtggt cctgcaactt tatccgcctc catccagtct      7860
attaattgtt gccgggaagc tagagtaagt agttcgccag ttaatagttt gcgcaacgtt      7920
gttgccattg ctacaggcat cgtggtgtca cgctcgtcgt ttggtatggc ttcattcagc      7980
tccggttccc aacgatcaag gcgagttaca tgatccccca tgttgtgcaa aaaagcggtt      8040
agctccttcg gtcctccgat cgttgtcaga agtaagttgg ccgcagtgtt atcactcatg      8100
gttatggcag cactgcataa ttctcttact gtcatgccat ccgtaagatg cttttctgtg      8160
actggtgagt actcaaccaa gtcattctga gaatagtgta tgcggcgacc gagttgctct      8220
tgcccggcgt caatacggga taataccgcg ccacatagca gaactttaaa agtgctcatc      8280
attggaaaac gttcttcggg gcgaaaactc tcaaggatct taccgctgtt gagatccagt      8340
tcgatgtaac ccactcgtgc acccaactga tcttcagcat cttttacttt caccagcgtt      8400
tctgggtgag caaaaacagg aaggcaaaat gccgcaaaaa agggaataag ggcgacacgg      8460
aaatgttgaa tactcatact cttccttttt caatattatt gaagcattta tcagggttat      8520
tgtctcatga gcggatacat atttgaatgt atttagaaaa ataaacaaat aggggttccg      8580
cgcacatttc cccgaaaagt gccacct                                          8607
```

<210> SEQ ID NO 129
<211> LENGTH: 7818
<212> TYPE: DNA
<213> ORGANISM: Artificial Sequence
<220> FEATURE:
<223> OTHER INFORMATION: Plasmid pCVL.SFFV.HA.NLS.I-GPI I.IRES.mTagBFP

<400> SEQUENCE: 129

```
gacgtcaatg tagtcttatg caatactctt gtagtcttgc aacatggtaa cgatgagtta       60
gcaacatgcc ttacaaggag agaaaaagca ccgtgcatgc cgattggtgg aagtaaggtg      120
gtacgatcgt gccttattag gaaggcaaca cgggtctg acatggattg gacgaaccac      180
tgaattgccg cattgcagag atattgtatt taagtgccta gctcgataca taaacgggtc      240
tctctggtta gaccagatct gagcctggga gctctctggc taactaggga acccactgct      300
taagcctcaa taaagcttgc cttgagtgct tcaagtagtg tgtgcccgtc tgttgtgtga      360
ctctggtaac tagagatccc tcagaccctt ttagtcagtg tggaaaatct ctagcagtgg      420
cgcccgaaca gggacttgaa agcgaaaggg aaaccagagg agctctctcg acgcaggact      480
cggcttgctg aagcgcgcac ggcaagaggc gaggggcggc gactggtgag tacgccaaaa      540
attttgacta gcggaggcta gaaggagaga gatgggtgcg agagcgtcag tattaagcgg      600
```

```
gggagaatta gatcgcgatg ggaaaaaatt cggttaaggc caggggggaaa gaaaaaatat    660 aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagagacag agacagatcc attcgattag tgaacggatc tcgacggtat   1800
cggttaactt ttaaaagaaa aggggggatt ggggggtaca gtgcagggga agaatagta   1860 gacataatag caacagacat acaaactaaa gaattacaaa acaaattac aaaaattcaa   1920 aattttatcg attacgcgtc acgtgctagc tgcagtaacg ccattttgca aggcatggaa   1980
aaataccaaa ccaagaatag agaagttcag atcaagggcg ggtacatgaa aatagctaac   2040
gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccgagctct ataaaagagc tcacaacccc tcactcggcg cgccagtcct   2340
ccgacagact gagtcgcccg ctcgagccgc caccatggga tatccatacg atgtcccaga   2400
ttatgcgcca cctaagaaga aacgcaaagt cgaattcgct actgttactc cattgatcga   2460
cccatggttc atcactggtt tcgctgacgc tgaatcttct ttcgttgttt ctatcaagag   2520
aaacaagaag atcaagtgtg gttggaacgt tgttactaga ttccaaatcg ccttaagtca   2580
aaaggacttg gctttgttgg aaagaatcaa gtcttacttc aaggacgctg gtaacatcta   2640
catcaagtct gacaaggttt ctgttgactg gcacgttact tctgttaagg acttgaagat   2700
catccttgat cacttcgaca agtacccatt gaagactgaa aagttggctg actacatctt   2760
gttcaaggaa gttttcaaca tcatcttgac taagcaacac ttgactgttg aaggtatcca   2820
aaagatcgtt gctatcagag cttctatcaa caagggtttg tacggtgaat gaaggctgc   2880 attcccaaac atcatcccag ttcaaaggcc taagatcgac gacagattca tcatcgatat   2940
ccaaccatgg tgggttgctg gtttcactga aggtgaaggt tgtttctctg ttgttgttac   3000
```

```
taactctcca tctactaagt ctggtttctc tgcttctttg atcttccaaa tcactcaaca    3060
ctctcgtgac atcgttttga tgcaaaacat catcaagttc ctaggttgtg gtagaatcca    3120
caagagatct aaggaagaag ctgttgacat cttggttact aagttctctg acttgactga    3180
aaaggttatc ccattcttcg aatctatccc attgcaaggt ttgaagttga agaacttcac    3240
tgacttctct aaggctgctg acatcatcaa ggttaagggt cacttgactc caaagggttt    3300
ggacaagatc ttgcaaatca agttgggtat gaacactaga agaatctagc ctgcaggtcg    3360
agcatgcatc tagggcggcc aattccgccc ctctccctcc ccccccccta acgttactgg    3420
ccgaagccgc ttggaataag gccggtgtgc gtttgtctat atgtgatttt ccaccatatt    3480
gccgtctttt ggcaatgtga gggcccggaa acctggccct gtcttcttga cgagcattcc    3540
taggggtctt tcccctctcg ccaaaggaat gcaaggtctg ttgaatgtcg tgaaggaagc    3600
agttcctctg gaagcttctt gaagacaaac aacgtctgta gcgacccttt gcaggcagcg    3660
gaaccccca cctggcgaca ggtgcctctg cggccaaaag ccacgtgtat aagatacacc    3720
tgcaaaggcg gcacaaccc agtgccacgt tgtgagttgg atagttgtgg aaagagtcaa    3780
atggctctcc tcaagcgtat tcaacaaggg gctgaaggat gcccagaagg tacccattg    3840
tatgggatct gatctggggc ctcggtgcac atgctttaca tgtgtttagt cgaggttaaa    3900
aaaacgtcta ggccccccga accacgggga cgtggttttc ctttgaaaaa cacgatgata    3960
agcttgccac aacccttacc ggtcgccacc atgagcgagc tgattaagga gaacatgcac    4020
atgaagctgt acatggaggg caccgtggac aaccatcact tcaagtgcac atccgagggc    4080
gaaggcaagc cctacgaggg cacccagacc atgagaatca aggtggtcga gggcggccct    4140
ctccccttcg ccttcgacat cctggctact agcttcctct acggcagcaa gaccttcatc    4200
aaccacaccc agggcatccc cgacttcttc aagcagtcct cccctgaggg cttcacatgg    4260
gagagagtca ccacatacga agacgggggc gtgctgaccg ctacccagga caccagcctc    4320
caggacggct gcctcatcta caacgtcaag atcagagggg tgaacttcac atccaacggc    4380
cctgtgatgc agaagaaaac actcggctgg gaggccttca ccgagacgct gtaccccgct    4440
gacggcggcc tggaaggcag aaacgacatg gccctgaagc tcgtgggcgg gagccatctg    4500
atcgcaaaca tcaagaccac atatagatcc aagaaacccg ctaagaacct caagatgcct    4560
ggcgtctact atgtggacta cagactggaa agaatcaagg aggccaacaa cgagacctac    4620
gtcgagcagc acgaggtggc agtggccaga tactgcgacc tccctagcaa actggggcac    4680
aagcttaatt gattctagag tcgaccgagc atcttaccgc catttatacc catatttgtt    4740
ctgtttttct tgatttgggt atacatttaa atgttaatag aacaaaatgg tggggcaatc    4800
atttacattt ttagggatat gtaattacta gttcaggtgt attgccacaa acaaacatg    4860
ttaagaaact ttcccgttat ttacgctctg ttcctgttaa tcaacctctg gattacaaaa    4920
tttgtgaaag attgactgat attcttaact atgttgctcc ttttacgctg tgtggatatg    4980
ctgctttata gcctctgtat ctagctattg cttcccgtac ggctttcgtt ttctcctcct    5040
tgtataaatc ctggttgctg tctcttttag aggagttgtg gcccgttgtc cgtcaacgtg    5100
gcgtggtgtg ctctgtgttt gctgacgcaa ccccactgg ctggggcatt gccaccacct    5160
gtcaactcct ttctgggact ttcgctttcc cctcccgat cgccacggca gaactcatcg    5220
ccgcctgcct tgcccgctgc tggacagggg ctaggttgct gggcactgat aattccgtgg    5280
tgttgtcatc ggtaccttt taaaagaaaa gggggactg gaagggctaa ttcactccca    5340
```

```
acgaagacaa gatatcataa cttcgtatag catacattat acgaagttat aatttatttg    5400
tgaaatttgt gatgctattg ctttatttgt aaccatatgt ttatttgtga aatttgtgat    5460
gctattgctt tatttgtaac cattgctttt tgcttgtact gggtctctct ggttagacca    5520
gatctgagcc tgggagctct ctggctaact agggaaccca ctgcttaagc ctcaataaag    5580
cttgcctcga ccagcctcga ctgtgccttc tagttgccag ccatctgttg tttgcccctc    5640
ccccgtgcct tccttgaccc tggaaggtgc cactcccact gtcctttcct aataaaatga    5700
ggaaattgca tcgcattgtc tgagtaggtg tcattctatt ctgggggtg gggtggggca     5760 ggacagcaag ggggaggatt gggaagacaa tagcaggcat gctggggatg cggtgggctc    5820
tatggcctgc agctgcatta atgaatcggc caacgcgcgg ggagaggcgg tttgcgtatt    5880
gggcgctctt ccgcttcctc gctcactgac tcgctgcgct cggtcgttcg gctgcggcga    5940
gcggtatcag ctcactcaaa ggcggtaata cggttatcca cagaatcagg ggataacgca    6000
ggaaagaaca tgtgagcaaa aggccagcaa aaggccagga accgtaaaaa ggccgcgttg    6060
ctggcgtttt tccataggct ccgccccct gacgagcatc acaaaaatcg acgctcaagt     6120
cagaggtggc gaaacccgac aggactataa agataccagg cgtttccccc tggaagctcc    6180
ctcgtgcgct ctcctgttcc gaccctgccg cttaccggat acctgtccgc ctttctccct    6240
tcgggaagcg tggcgctttc tcatagctca cgctgtaggt atctcagttc ggtgtaggtc    6300
gttcgctcca agctgggctg tgtgcacgaa ccccccgttc agcccgaccg ctgcgcctta    6360
tccggtaact atcgtcttga gtccaacccg gtaagacacg acttatcgcc actggcagca    6420
gccactggta acaggattag cagagcgagg tatgtaggcg gtgctacaga gttcttgaag    6480
tggtggccta actacggcta cactagaagg acagtatttg gtatctgcgc tctgctgaag    6540
ccagttacct tcggaaaaag agttggtagc tcttgatccg gcaaacaaac caccgctggt    6600
agcggtggtt ttttgtttg caagcagcag attacgcgca gaaaaaaagg atctcaagaa     6660
gatcctttga tcttttctac ggggtctgac gctcagtgga acgaaaactc acgttaaggg    6720
attttggtca tgagattatc aaaaaggatc ttcacctaga tccttttaaa ttaaaaatga    6780
agttttaaat caatctaaag tatatatgag taaacttggt ctgacagtta ccaatgctta    6840
atcagtgagg cacctatctc agcgatctgt ctatttcgtt catccatagt tgcctgactc    6900
cccgtcgtgt agataactac gatacgggag ggcttaccat ctggccccag tgctgcaatg    6960
ataccgcgag acccacgctc accggctcca gatttatcag caataaacca gccagccgga    7020
agggccgagc gcagaagtgg tcctgcaact ttatccgcct ccatccagtc tattaattgt    7080
tgccgggaag ctagagtaag tagttcgcca gttaatagtt tgcgcaacgt tgttgccatt    7140
gctacaggca tcgtggtgtc acgctcgtcg tttggtatgg cttcattcag ctccggttcc    7200
caacgatcaa ggcgagttac atgatccccc atgttgtgca aaaaagcggt tagctccttc    7260
ggtcctccga tcgttgtcag aagtaagttg gccgcagtgt tatcactcat ggttatggca    7320
gcactgcata attctcttac tgtcatgcca tccgtaagat gcttttctgt gactggtgag    7380
tactcaacca agtcattctg agaatagtgt atgcggcgac cgagttgctc ttgcccggcg    7440
tcaatacggg ataataccgc gccacatagc agaactttaa aagtgctcat cattggaaaa    7500
cgttcttcgg ggcgaaaact ctcaaggatc ttaccgctgt tgagatccag ttcgatgtaa    7560
cccactcgtg cacccaactg atcttcagca tcttttactt tcaccagcgt ttctgggtga    7620
gcaaaaacag gaaggcaaaa tgccgcaaaa aaggaataa gggcgacacg gaaatgttga     7680
atactcatac tcttcctttt tcaatattat tgaagcattt atcagggtta ttgtctcatg    7740
```
agcggataca tatttgaatg tatttagaaa aataaacaaa tagggggttcc gcgcacattt    7800 ccccgaaaag tgccacct    7818

<210> SEQ ID NO 130
<211> LENGTH: 8592
<212> TYPE: DNA
<213> ORGANISM: Artificial Sequence
<220> FEATURE:
<223> OTHER INFORMATION: Plasmid pCVL.SFFV.HA.NLS.I-GPI
     I.T2A.Trex2.IRES.mTagBFP

<400> SEQUENCE: 130
gacgtcaatg tagtcttatg caatactctt gtagtcttgc aacatggtaa cgatgagtta    60
gcaacatgcc ttacaaggag agaaaaagca ccgtgcatgc cgattggtgg aagtaaggtg    120
gtacgatcgt gccttattag aaggcaaca gacgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg    600
gggagaatta gatcgcgatg gaaaaaaatt cggttaaggc caggggggaaa gaaaaaatat    660 aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca atagagga agagcaaaac    900 aaaagtaaga ccaccgcaca gcaagcggcc ctgatcttca gacctggagg aggagatatg    960
agggacaatt ggagaagtga attatataaa tataaagtag taaaaattga accattagga    1020
gtagcaccca ccaaggcaaa gagaagagtg gtgcagagag aaaaaagagc agtgggaata    1080
ggagctttgt tccttgggtt cttgggagca gcaggaagca ctatgggcgc agcgtcaatg    1140
acgctgacgg tacaggccag acaattattg tctggtatag tgcagcagca gaacaatttg    1200
ctgagggcta ttgaggcgca acagcatctg ttgcaactca cagtctgggg catcaagcag    1260
ctccaggcaa gaatcctggc tgtggaaaga tacctaaagg atcaacagct cctggggatt    1320
tggggttgct ctggaaaact catttgcacc actgctgtgc cttggaatgc tagttggagt    1380
aatgaatctc tggaacagat ttggaatcac acgacctgga tggagtggga cagagaaatt    1440
aacaattaca caagcttaat acactcctta attgaagaat cgcaaaacca gcaagaaaag    1500
aatgaacaag aattattgga attagataaa tgggcaagtt tgtggaattg gtttaacata    1560
acaaattggc tgtggtatat aaaattattc ataatgatag taggaggctt ggtaggttta    1620
agaatagttt ttgctgtact ttctatagtg aatagagtta ggcagggata ttcaccatta    1680
tcgtttcaga cccacctccc aaccccgagg ggacccgaca ggcccgaagg aatagaagaa    1740
gaaggtggag agagagacag agacagatcc attcgattag tgaacggatc tcgacggtat    1800 cggttaacctt ttaaagaaa agggggggatt ggggggtaca gtgcagggga agaatagta    1860 gacataatag caacagacat acaaactaaa gaattacaaa aacaaattac aaaaattcaa    1920

```
aattttatcg attacgcgtc acgtgctagc tgcagtaacg ccattttgca aggcatggaa    1980
aaataccaaa ccaagaatag agaagttcag atcaagggcg ggtacatgaa aatagctaac    2040
gttgggccaa acaggatatc tgcggtgagc agtttcggcc ccggcccggg gccaagaaca    2100
gatggtcacc gcagtttcgg ccccggcccg aggccaagaa cagatggtcc ccagatatgg    2160
cccaaccctc agcagtttct taagacccat cagatgtttc caggctcccc caaggacctg    2220
aaatgaccct gcgccttatt tgaattaacc aatcagcctg cttctcgctt ctgttcgcgc    2280
gcttctgctt cccgagctct ataaagagc tcacaacccc tcactcggcg cgccagtcct    2340
ccgacagact gagtcgcccg ctcgagccgc caccatggga tatccatacg atgtcccaga    2400
ttatgcgcca cctaagaaga aacgcaaagt cgaattcgct actgttactc cattgatcga    2460
cccatggttc atcactggtt tcgctgacgc tgaatcttct ttcgttgttt ctatcaagag    2520
aaacaagaag atcaagtgtg gttggaacgt tgttactaga ttccaaatcg ccttaagtca    2580
aaaggacttg gctttgttgg aaagaatcaa gtcttacttc aaggacgctg gtaacatcta    2640
catcaagtct gacaaggttt ctgttgactg gcacgttact tctgttaagg acttgaagat    2700
catccttgat cacttcgaca agtacccatt gaagactgaa aagttggctg actacatctt    2760
gttcaaggaa gttttcaaca tcatcttgac taagcaacac ttgactgttg aaggtatcca    2820
aaagatcgtt gctatcagag cttctatcaa caagggtttg tacggtgaat tgaaggctgc    2880
attcccaaac atcatcccag ttcaaaggcc taagatcgac gacagattca tcatcgatat    2940
ccaaccatgg tgggttgctg gtttcactga aggtgaaggt tgtttctctg ttgttgttac    3000
taactctcca tctactaagt ctggttttctc tgcttctttg atcttccaaa tcactcaaca    3060
ctctcgtgac atcgttttga tgcaaaacat catcaagttc ctaggttgtg gtagaatcca    3120
caagagatct aaggaagaag ctgttgacat cttggttact aagttctctg acttgactga    3180
aaaggttatc ccattcttcg aatctatccc attgcaaggt ttgaagttga agaacttcac    3240
tgacttctct aaggctgctg acatcatcaa ggttaagggt cacttgactc caaagggttt    3300
ggacaagatc ttgcaaatca gttgggtat gaacactaga agaatcggat ccggtgaggg    3360
cagaggaagt cttctaacat gcggtgacgt ggaggagaat ccgggcccct ccggatctga    3420
gccacctcgg gctgagacct ttgtattcct ggacctagaa gccactgggc tcccaaacat    3480
ggaccctgag attgcagaga tatcccttt tgctgttcac cgctcttccc tggagaaccc    3540
agaacgggat gattctggtt ccttggtgct gccccgtgtt ctggacaagc tcacactgtg    3600
catgtgcccg gagcgcccct ttactgccaa ggccagtgag attactggtt tgagcagcga    3660
aagcctgatg cactgcggga aggctggttt caatggcgct gtggtaagga cactgcaggg    3720
cttcctaagc cgccaggagg gccccatctg ccttgtggcc cacaatggct tcgattatga    3780
cttcccactg ctgtgcacgg agctacaacg tctgggtgcc catctgcccc aagacactgt    3840
ctgcctggac acactgcctg cattgcgggg cctggaccgt gctcacagcc acggcaccag    3900
ggctcaaggc cgcaaaagct acagcctggc cagtctcttc caccgctact ccaggctga    3960 acccagtgct gcccattcag cagaaggtga tgtgcacacc ctgcttctga tcttcctgca    4020
tcgtgctcct gagctgctcg cctgggcaga tgagcaggcc gcagctggg ctcatattga    4080 gcccatgtac gtgccacctg atggtccaag cctcgaagcc tgacctgcag gtcgagcatg    4140
catctagggc ggccaattcc gcccctctcc ctcccccccc cctaacgtta ctggccgaag    4200
ccgcttggaa taaggccggt gtgcgtttgt ctatatgtga ttttccacca tattgccgtc    4260
```

```
ttttggcaat gtgagggccc ggaaacctgg ccctgtcttc ttgacgagca ttcctagggg    4320
tctttcccct ctcgccaaag gaatgcaagg tctgttgaat gtcgtgaagg aagcagttcc    4380
tctggaagct tcttgaagac aaacaacgtc tgtagcgacc ctttgcaggc agcggaaccc    4440
cccacctggc gacaggtgcc tctgcggcca aaagccacgt gtataagata cacctgcaaa    4500
ggcggcacaa ccccagtgcc acgttgtgag ttggatagtt gtggaaagag tcaaatggct    4560
ctcctcaagc gtattcaaca aggggctgaa ggatgcccag aaggtacccc attgtatggg    4620
atctgatctg gggcctcggt gcacatgctt tacatgtgtt tagtcgaggt taaaaaaacg    4680
tctaggcccc ccgaaccacg gggacgtggt tttcctttga aaaacacgat gataagcttg    4740
ccacaaccct taccggtcgc caccatgagc gagctgatta aggagaacat gcacatgaag    4800
ctgtacatgg agggcaccgt ggacaaccat cacttcaagt gcacatccga ggcgaaggc     4860
aagccctacg agggcaccca gaccatgaga atcaaggtgg tcgagggcgg ccctctcccc    4920
ttcgccttcg acatcctggc tactagcttc ctctacggca gcaagacctt catcaaccac    4980
acccagggca tccccgactt cttcaagcag tccttccctg agggcttcac atgggagaga    5040
gtcaccacat acgaagacgg gggcgtgctg accgctaccc aggacaccag cctccaggac    5100
ggctgcctca tctacaacgt caagatcaga ggggtgaact tcacatccaa cggccctgtg    5160
atgcagaaga aaacactcgg ctgggaggcc ttcaccgaga cgctgtaccc cgctgacggc    5220
ggcctggaag gcagaaacga catggccctg aagctcgtgg gcgggagcca tctgatcgca    5280
aacatcaaga ccacatatag atccaagaaa cccgctaaga acctcaagat gcctggcgtc    5340
tactatgtgg actacagact ggaaagaatc aaggaggcca caacgagac ctacgtcgag     5400
cagcacgagg tggcagtggc cagatactgc gacctcccta gcaaactggg gcacaagctt    5460
aattgattct agagtcgacc gagcatctta ccgccattta tacccatatt tgttctgttt    5520
ttcttgattt gggtatacat ttaaatgtta atagaacaaa atggtggggc aatcatttac    5580
atttttaggg atatgtaatt actagttcag gtgtattgcc acaagacaaa catgttaaga    5640
aactttcccg ttatttacgc tctgttcctg ttaatcaacc tctggattac aaaatttgtg    5700
aaagattgac tgatattctt aactatgttg ctccttttac gctgtgtgga tatgctgctt    5760
tatagcctct gtatctagct attgcttccc gtacggcttt cgttttctcc tccttgtata    5820
aatcctggtt gctgtctctt ttagaggagt tgtggcccgt tgtccgtcaa cgtggcgtgg    5880
tgtgctctgt gtttgctgac gcaacccca ctggctgggg cattgccacc acctgtcaac     5940
tcctttctgg gactttcgct ttcccccctcc cgatcgccac ggcagaactc atcgccgcct    6000
gccttgcccg ctgctggaca ggggctaggt tgctgggcac tgataattcc gtggtgttgt    6060
catcggtacc tttttaaaag aaaggggggg actggaaggg ctaattcact cccaacgaag    6120
acaagatatc ataacttcgt atagcataca ttatacgaag ttataattta tttgtgaaat    6180
ttgtgatgct attgctttat ttgtaaccat atgtttattt gtgaaatttg tgatgctatt    6240
gctttatttg taaccattgc ttttgcttg tactgggtct ctctggttag accagatctg     6300
agcctgggag ctctctggct aactagggaa cccactgctt aagcctcaat aaagcttgcc    6360
tcgaccagcc tcgactgtgc cttcagttg ccagccatct gttgtttgcc cctccccgt      6420
gccttccttg accctggaag gtgccactcc cactgtcctt tcctaataaa atgaggaaat    6480
tgcatcgcat tgtctgagta ggtgtcattc tattctgggg gtgggtgg ggcaggacag      6540
caagggggag gattggaag acaatagcag gcatgctggg gatgcggtgg gctctatggc     6600
ctgcagctgc attaatgaat cggccaacgc gcggggagag gcggtttgcg tattgggcgc    6660
```

```
tcttccgctt cctcgctcac tgactcgctg cgctcggtcg ttcggctgcg gcgagcggta    6720
tcagctcact caaaggcggt aatacggtta tccacagaat caggggataa cgcaggaaag    6780
aacatgtgag caaaaggcca gcaaaaggcc aggaaccgta aaaaggccgc gttgctggcg    6840 ttttccata ggctccgccc ccctgacgag catcacaaaa atcgacgctc aagtcagagg    6900
tggcgaaacc cgacaggact ataaagatac caggcgtttc ccctggaag ctccctcgtg    6960 cgctctcctg ttccgaccct gccgcttacc ggatacctgt ccgcctttct cccttcggga    7020
agcgtggcgc tttctcatag ctcacgctgt aggtatctca gttcggtgta ggtcgttcgc    7080
tccaagctgg gctgtgtgca cgaaccccc gttcagcccg accgctgcgc cttatccggt    7140
aactatcgtc ttgagtccaa cccggtaaga cacgacttat cgccactggc agcagccact    7200
ggtaacagga ttagcagagc gaggtatgta ggcggtgcta cagagttctt gaagtggtgg    7260
cctaactacg gctacactag aaggacagta tttggtatct gcgctctgct gaagccagtt    7320
accttcggaa aaagagttgg tagctcttga tccggcaaac aaaccaccgc tggtagcggt    7380
ggtttttttg tttgcaagca gcagattacg cgcagaaaaa aaggatctca agaagatcct    7440
ttgatctttt ctacggggtc tgacgctcag tggaacgaaa actcacgtta agggattttg    7500
gtcatgagat tatcaaaaag gatcttcacc tagatccttt taaattaaaa atgaagtttt    7560
aaatcaatct aaagtatata tgagtaaact tggtctgaca gttaccaatg cttaatcagt    7620
gaggcaccta tctcagcgat ctgtctattt cgttcatcca tagttgcctg actccccgtc    7680
gtgtagataa ctacgatacg ggagggctta ccatctggcc ccagtgctgc aatgataccg    7740
cgagacccac gctcaccggc tccagattta tcagcaataa accagccagc cggaagggcc    7800
gagcgcagaa gtggtcctgc aactttatcc gcctccatcc agtctattaa ttgttgccgg    7860
gaagctagag taagtagttc gccagttaat agtttgcgca acgttgttgc cattgctaca    7920
ggcatcgtgg tgtcacgctc gtcgtttggt atggcttcat tcagctccgg ttcccaacga    7980
tcaaggcgag ttacatgatc ccccatgttg tgcaaaaaag cggttagctc cttcggtcct    8040
ccgatcgttg tcagaagtaa gttggccgca gtgttatcac tcatggttat ggcagcactg    8100
cataattctc ttactgtcat gccatccgta agatgctttt ctgtgactgg tgagtactca    8160
accaagtcat tctgagaata gtgtatgcgg cgaccgagtt gctcttgccc ggcgtcaata    8220
cgggataata ccgcgccaca tagcagaact ttaaaagtgc tcatcattgg aaaacgttct    8280
tcggggcgaa aactctcaag gatcttaccg ctgttgagat ccagttcgat gtaacccact    8340
cgtgcaccca actgatcttc agcatctttt actttcacca gcgtttctgg gtgagcaaaa    8400
acaggaaggc aaaatgccgc aaaaaaggga ataagggcga cacggaaatg ttgaatactc    8460
atactcttcc ttttcaata ttattgaagc atttatcagg gttattgtct catgagcgga    8520
tacatatttg aatgtattta gaaaaataaa caaatagggg ttccgcgcac atttccccga    8580
aaagtgccac ct                                                       8592
```

<210> SEQ ID NO 131
<211> LENGTH: 7818
<212> TYPE: DNA
<213> ORGANISM: Artificial Sequence
<220> FEATURE:
<223> OTHER INFORMATION: Plasmid pCVL.SFFV.HA.NLS.I-GZE I.IRES.mTagBFP

<400> SEQUENCE: 131

```
gacgtcaatg tagtcttatg caatactctt gtagtcttgc aacatggtaa cgatgagtta    60
```

```
gcaacatgcc ttacaaggag agaaaaagca ccgtgcatgc cgattggtgg aagtaaggtg    120
gtacgatcgt gccttattag gaaggcaaca gacgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagacccct ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg    600
gggagaatta gatcgcgatg ggaaaaaatt cggttaaggc cagggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga gagcaaaaac    900
aaaagtaaga ccaccgcaca gcaagcggcc ctgatcttca gacctggagg aggagatatg    960
agggacaatt ggagaagtga attatataaa tataaagtag taaaaattga accattagga   1020
gtagcaccca ccaaggcaaa gagaagagtg gtgcagagag aaaaaagagc agtgggaata   1080
ggagctttgt tccttgggtt cttgggagca gcaggaagca ctatgggcgc agcgtcaatg   1140
acgctgacgg tacaggccag acaattattg tctggtatag tgcagcagca gaacaatttg   1200
ctgagggcta ttgaggcgca acagcatctg ttgcaactca cagtctgggg catcaagcag   1260
ctccaggcaa gaatcctggc tgtggaaaga tacctaaagg atcaacagct cctggggatt   1320
tggggttgct ctggaaaact catttgcacc actgctgtgc cttggaatgc tagttggagt   1380
aatgaatctc tggaacagat ttggaatcac acgacctgga tggagtggga cagagaaatt   1440
aacaattaca caagcttaat acactcctta attgaagaat cgcaaaacca gcaagaaaag   1500
aatgaacaag aattattgga attagataaa tgggcaagtt tgtggaattg gtttaacata   1560
acaaattggc tgtggtatat aaaattattc ataatgatag taggaggctt ggtaggttta   1620
agaatagttt ttgctgtact ttctatagtg aatagagtta ggcagggata ttcaccatta   1680
tcgtttcaga cccacctccc aaccccgagg ggacccgaca ggcccgaagg aatagaagaa   1740
gaaggtggag agagacag agacagatcc attcgattag tgaacggatc tcgacggtat   1800
cggttaactt ttaaaagaaa aggggggatt ggggggtaca gtgcagggga agaatagta   1860 gacataatag caacagacat acaaactaaa gaattacaaa acaaattac aaaaattcaa   1920 aattttatcg attacgcgtc acgtgctagc tgcagtaacg ccattttgca aggcatggaa   1980
aaataccaaa ccaagaatag agaagttcag atcaagggcg gtacatgaa aatagctaac   2040 gttgggccaa acaggatatc tgcggtgagc agtttcggcc ccggcccggg gccaagaaca   2100
gatggtcacc gcagtttcgg ccccggcccg aggccaagaa cagatggtcc ccagatatgg   2160
cccaaccctc agcagtttct taagacccat cagatgtttc caggctcccc caaggacctg   2220
aaatgaccct gcgccttatt tgaattaacc aatcagcctg cttctcgctt ctgttcgcgc   2280
gcttctgctt cccagctctc taaaagagc tcacaacccc tcactcggcg cgccagtcct   2340
ccgacagact gagtcgcccg ctcgagccgc caccatggga tatccatacg atgtcccaga   2400
ttatgcgcca cctaagaaga acgcaaagt cgaattcgct agctctttgg aacaatcttc   2460
```

```
tttgccacca aagttggacc catcttacgt tactggtttc actgacggtg aaggttcttt    2520
catcttgact atcatcaagg acaacaagta caagttgggt tggagagttg catgcagatt    2580
cgttatctct ttgcacaaga aggacttggt tttgttgaac tctttgaaga acttcttcaa    2640
cactggttct gttttcttga tgggtaaggg cgccgctcaa tacagagttg aatctttgac    2700
tggtttgtct atcatcatca accacttcga cagatacccca ttgaacacta agaagcaagc    2760
tgactacatg ttgttcaagt tggcttacaa cttgatcatc aacaagtctc acttgactga    2820
aaagggtttg tctgaactag tttctttgaa ggctgttatg aacaacggtt tgaaggacga    2880
attgaagatc gcttacccaa acatcactcc agttttgagg cctgaaatcc cattgtcttt    2940
gaacatcgat ccattgtggt tggctggttt cactgacgct gaaggttgtt tctctgttgt    3000
tgttttcaag tctaagactt ctaagatcgg tgaagctgtt aagttgtctt tcatcatcac    3060
tcaatctgtt agagacgaat ttttaattaa gtctttgatc gaatacttgg gttgtggtta    3120
cacttctttg gacggtagag gtgctatcga cttcaaggtt tctgacttct cttctcttaa    3180
gaacatcatc atcccattct acgacaagta ctacatccac ggtaacaagt ctttggactt    3240
caaggacttc tctcgtgttg ttactttgat ggaaaacaag aagcacttga ctaagcaagg    3300
tttggacgaa atcaagaaga tcagaaacgc tatgaacact aacagatagc ctgcaggtcg    3360
agcatgcatc tagggcggcc aattccgccc ctctccctcc cccccccta acgttactgg    3420 ccgaagccgc ttggaataag gccggtgtgc gtttgtctat atgtgatttt ccaccatatt    3480
gccgtctttt ggcaatgtga gggcccggaa acctggccct gtcttcttga cgagcattcc    3540
taggggtctt tcccctctcg ccaaaggaat gcaaggtctg ttgaatgtcg tgaaggaagc    3600
agttcctctg gaagcttctt gaagacaaac aacgtctgta cgaccctttt gcaggcagcg    3660 gaaccccccca cctggcgaca ggtgcctctg cggccaaaag ccacgtgtat aagatacacc    3720
tgcaaaggcg gcacaacccc agtgccacgt tgtgagttgg atagttgtgg aaagagtcaa    3780
atggctctcc tcaagcgtat tcaacaaggg gctgaaggat gcccagaagg taccccattg    3840
tatgggatct gatctggggc ctcggtgcac atgctttaca tgtgtttagt cgaggttaaa    3900
aaaacgtcta ggccccccga accacgggga cgtggttttc ctttgaaaaa cacgatgata    3960
agcttgccac aacccttacc ggtcgccacc atgagcgagc tgattaagga gaacatgcac    4020
atgaagctgt acatggaggg caccgtggac aaccatcact caagtgcac atccgagggc    4080 gaaggcaagc cctacgaggg cacccagacc atgagaatca aggtggtcga gggcggccct    4140 ctcccccttcg ccttcgacat cctggctact agcttcctct acggcagcaa gaccttcatc    4200
aaccacaccc agggcatccc cgacttcttc aagcagtcct cccctgaggg cttcacatgg    4260
gagagagtca ccacatacga agacgggggc gtgctgaccg ctacccagga caccagcctc    4320
caggacggct gcctcatcta caacgtcaag atcagagggg tgaacttcac atccaacggc    4380
cctgtgatgc agaagaaaac actcggctgg gaggccttca ccgagacgct gtaccccgct    4440
gacggcggcc tggaaggcag aaacgacatg gccctgaagc tcgtgggcgg gagccatctg    4500
atcgcaaaca tcaagaccac atatagatcc aagaaacccg ctaagaacct caagatgcct    4560
ggcgtctact atgtggacta cagactggaa agaatcaagg aggccaacaa cgagacctac    4620
gtcgagcagc acgaggtggc agtggccaga tactgcgacc tccctagcaa actggggcac    4680
aagcttaatt gattctagag tcgaccgagc atcttaccgc catttatacc catatttgtt    4740 ctgttttttct tgatttgggt atacatttaa atgttaatag aacaaaatgg tggggcaatc    4800
```

```
atttacattt ttagggatat gtaattacta gttcaggtgt attgccacaa gacaaacatg    4860
ttaagaaact ttcccgttat ttacgctctg ttcctgttaa tcaacctctg gattacaaaa    4920
tttgtgaaag attgactgat attcttaact atgttgctcc ttttacgctg tgtggatatg    4980
ctgctttata gcctctgtat ctagctattg cttcccgtac ggctttcgtt ttctcctcct    5040
tgtataaatc ctggttgctg tctcttttag aggagttgtg gcccgttgtc cgtcaacgtg    5100
gcgtggtgtg ctctgtgttt gctgacgcaa cccccactgg ctggggcatt gccaccacct    5160
gtcaactcct ttctgggact ttcgctttcc ccctcccgat cgccacggca gaactcatcg    5220
ccgcctgcct tgcccgctgc tggacagggg ctaggttgct gggcactgat aattccgtgg    5280
tgttgtcatc ggtacctttt taaaagaaaa gggggggactg gaagggctaa ttcactccca    5340
acgaagacaa gatatcataa cttcgtatag catacattat acgaagttat aatttatttg    5400
tgaaatttgt gatgctattg ctttatttgt aaccatatgt ttatttgtga aatttgtgat    5460
gctattgctt tatttgtaac cattgctttt tgcttgtact gggtctctct ggttagacca    5520
gatctgagcc tgggagctct ctggctaact agggaaccca ctgcttaagc ctcaataaag    5580
cttgcctcga ccagcctcga ctgtgccttc tagttgccag ccatctgttg tttgcccctc    5640
ccccgtgcct tccttgaccc tggaaggtgc cactcccact gtccttttcct aataaaatga    5700 ggaaattgca tcgcattgtc tgagtaggtg tcattctatt ctggggggtg ggtggggca    5760 ggacagcaag ggggaggatt gggaagacaa tagcaggcat gctggggatg cggtgggctc    5820
tatggcctgc agctgcatta atgaatcggc caacgcgcgg ggagaggcgg tttgcgtatt    5880
gggcgctctt ccgcttcctc gctcactgac tcgctgcgct cggtcgttcg gctgcggcga    5940
gcggtatcag ctcactcaaa ggcggtaata cggttatcca cagaatcagg ggataacgca    6000
ggaaagaaca tgtgagcaaa aggccagcaa aaggccagga accgtaaaaa ggccgcgttg    6060
ctggcgtttt tccataggct ccgcccccct gacgagcatc acaaaaatcg acgctcaagt    6120
cagaggtggc gaaacccgac aggactataa agataccagg cgtttccccc tggaagctcc    6180
ctcgtgcgct ctcctgttcc gaccctgccg cttaccggat acctgtccgc ctttctccct    6240
tcgggaagcg tggcgctttc tcatagctca cgctgtaggt atctcagttc ggtgtaggtc    6300
gttcgctcca agctgggctg tgtgcacgaa ccccccgttc agcccgaccg ctgcgcctta    6360
tccggtaact atcgtcttga gtccaacccg gtaagacacg acttatcgcc actggcagca    6420
gccactggta acaggattag cagagcgagg tatgtaggcg gtgctacaga gttcttgaag    6480
tggtggccta actacggcta cactagaagg acagtatttg gtatctgcgc tctgctgaag    6540
ccagttacct tcggaaaaag agttggtagc tcttgatccg gcaaacaaac caccgctggt    6600
agcggtggtt tttttgtttg caagcagcag attacgcgca gaaaaaaagg atctcaagaa    6660
gatcctttga tcttttctac ggggtctgac gctcagtgga acgaaaactc acgttaaggg    6720
attttggtca tgagattatc aaaaaggatc ttcacctaga tccttttaaa ttaaaaatga    6780
agttttaaat caatctaaag tatatatgag taaacttggt ctgacagtta ccaatgctta    6840
atcagtgagg cacctatctc agcgatctgt ctatttcgtt catccatagt tgcctgactc    6900
cccgtcgtgt agataactac gatacgggag ggcttaccat ctggccccag tgctgcaatg    6960
ataccgcgag acccacgctc accggctcca gatttatcag caataaacca gccagccgga    7020
agggccgagc gcagaagtgg tcctgcaact ttatccgcct ccatccagtc tattaattgt    7080
tgccgggaag ctagagtaag tagttcgcca gttaatagtt tgcgcaacgt tgttgccatt    7140
gctacaggca tcgtggtgtc acgctcgtcg tttggtatgg cttcattcag ctccggttcc    7200
```

```
caacgatcaa ggcgagttac atgatccccc atgttgtgca aaaaagcggt tagctccttc   7260
ggtcctccga tcgttgtcag aagtaagttg gccgcagtgt tatcactcat ggttatggca   7320
gcactgcata attctcttac tgtcatgcca tccgtaagat gcttttctgt gactggtgag   7380
tactcaacca agtcattctg agaatagtgt atgcggcgac cgagttgctc ttgcccggcg   7440
tcaatacggg ataataccgc gccacatagc agaactttaa aagtgctcat cattggaaaa   7500
cgttcttcgg ggcgaaaact ctcaaggatc ttaccgctgt tgagatccag ttcgatgtaa   7560
cccactcgtg cacccaactg atcttcagca tcttttactt tcaccagcgt ttctgggtga   7620
gcaaaaacag gaaggcaaaa tgccgcaaaa aagggaataa gggcgacacg gaaatgttga   7680
atactcatac tcttcctttt tcaatattat tgaagcattt atcagggtta ttgtctcatg   7740
agcggataca tatttgaatg tatttagaaa aataaacaaa tagggg ttcc gcgcacattt   7800 ccccgaaaag tgccacct                                                7818
```

```
<210> SEQ ID NO 132
<211> LENGTH: 8592
<212> TYPE: DNA
<213> ORGANISM: Artificial Sequence
<220> FEATURE:
<223> OTHER INFORMATION: Plasmid pCVL.SFFV.HA.NLS.I-GZE
      I.T2A.Trex2.IRES.mTagBFP

<400> SEQUENCE: 132
```

```
gacgtcaatg tagtcttatg caatactctt gtagtcttgc aacatggtaa cgatgagtta    60
gcaacatgcc ttacaaggag agaaaaagca ccgtgcatgc cgattggtgg aagtaaggtg   120
gtacgatcgt gccttattag gaaggcaaca gacgggtctg acatggattg gacgaaccac   180
tgaattgccg cattgcagag atattgtatt taagtgccta gctcgataca taaacgggtc   240
tctctggtta gaccagatct gagcctggga gctctctggc taactaggga acccactgct   300
taagcctcaa taaagcttgc cttgagtgct tcaagtagtg tgtgcccgtc tgttgtgtga   360
ctctggtaac tagagatccc tcagaccctt ttagtcagtg tggaaaatct ctagcagtgg   420
cgcccgaaca gggacttgaa agcgaaaggg aaaccagagg agctctctcg acgcaggact   480
cggcttgctg aagcgcgcac ggcaagaggc gaggggcggc gactggtgag tacgccaaaa   540
attttgacta gcggaggcta gaaggagaga tgggtgcg agagcgtcag tattaagcgg   600
gggagaatta gatcgcgatg ggaaaaaatt cggttaaggc caggggg aaa gaaaaaatat   660 aaattaaaac atatagtatg ggcaagcagg gagctagaac gattcgcagt taatcctggc   720
ctgttagaaa catcagaagg ctgtagacaa atactgggac agctacaacc atcccttcag   780
acaggatcag aagaacttag atcattatat aatacagtag caaccctcta ttgtgtgcat   840
caaaggatag agataaaaga caccaaggaa gctttagaca agatagagga gagcaaaac   900 aaaagtaaga ccaccgcaca gcaagcggcc ctgatcttca gacctggagg aggagatatg   960
agggacaatt ggagaagtga attatataaa tataaagtag taaaaattga accattagga  1020
gtagcaccca ccaaggcaaa gagaagagtg gtgcagagag aaaaaagagc agtgggaata  1080 ggagcttt gt tccttgggtt cttgggagca gcaggaagca ctatgggcgc agcgtcaatg  1140
acgctgacgg tacaggccag acaattattg tctggtatag tgcagcagca gaacaatttg  1200
ctgagggcta ttgaggcgca acagcatctg ttgcaactca cagtctgggg catcaagcag  1260
ctccaggcaa gaatcctggc tgtggaaaga tacctaaagg atcaacagct cctgggg att  1320 tggggttgct ctggaaaact catttgcacc actgctgtgc cttggaatgc tagttggagt  1380
```

```
aatgaatctc tggaacagat ttggaatcac acgacctgga tggagtggga cagagaaatt      1440
aacaattaca caagcttaat acactcctta attgaagaat cgcaaaacca gcaagaaaag      1500
aatgaacaag aattattgga attagataaa tgggcaagtt tgtggaattg gtttaacata      1560
acaaattggc tgtggtatat aaaattattc ataatgatag taggaggctt ggtaggttta      1620
agaatagttt ttgctgtact ttctatagtg aatagagtta ggcagggata ttcaccatta      1680
tcgtttcaga cccacctccc aaccccgagg ggacccgaca ggcccgaagg aatagaagaa      1740
gaaggtggag agagagacag agacagatcc attcgattag tgaacggatc tcgacggtat      1800
cggttaactt ttaaaagaaa aggggggatt gggggggtaca gtgcagggga aagaatagta      1860
gacataatag caacagacat acaaactaaa gaattacaaa acaaattac aaaaattcaa       1920 aattttatcg attacgcgtc acgtgctagc tgcagtaacg ccattttgca aggcatggaa      1980
aaataccaaa ccaagaatag agaagttcag atcaagggcg ggtacatgaa aatagctaac      2040
gttgggccaa acaggatatc tgcggtgagc agtttcggcc ccggcccggg gccaagaaca      2100
gatggtcacc gcagtttcgg ccccggcccg aggccaagaa cagatggtcc ccagatatgg      2160
cccaaccctc agcagtttct taagacccat cagatgtttc caggctcccc caaggacctg      2220
aaatgaccct gcgccttatt tgaattaacc aatcagcctg cttctcgctt ctgttcgcgc      2280
gcttctgctt cccgagctct ataaaagagc tcacaacccc tcactcggcg cgccagtcct      2340
ccgacagact gagtcgcccg ctcgagccgc caccatggga tatccatacg atgtcccaga      2400
ttatgcgcca cctaagaaga aacgcaaagt cgaattcgct agctctttgg aacaatcttc      2460
tttgccacca aagttggacc catcttacgt tactggtttc actgacggtg aaggttcttt      2520
catcttgact atcatcaagg acaacaagta caagttgggt tggagagttg catgcagatt      2580
cgttatctct ttgcacaaga aggacttggt tttgttgaac tctttgaaga acttcttcaa      2640
cactggttct gttttcttga tgggtaaggg cgccgctcaa tacagagttg aatctttgac      2700
tggtttgtct atcatcatca accacttcga cagatatccca ttgaacacta agaagcaagc      2760
tgactacatg ttgttcaagt tggcttacaa cttgatcatc aacaagtctc acttgactga      2820
aaagggtttg tctgaactag tttctttgaa ggctgttatg aacaacggtt tgaaggacga      2880
attgaagatc gcttacccaa acatcactcc agttttgagg cctgaaatcc cattgtcttt      2940
gaacatcgat ccattgtggt tggctggttt cactgacgct gaaggttgtt tctctgttgt      3000
tgttttcaag tctaagactt ctaagatcgg tgaagctgtt aagttgtctt tcatcatcac      3060
tcaatctgtt agagacgaat ttttaattaa gtctttgatc gaatacttgg ttgtggtta       3120 cacttctttg gacggtagag gtgctatcga cttcaaggtt tctgacttct cttctcttaa      3180
gaacatcatc atcccattct acgacaagta ctacatccac ggtaacaagt ctttggactt      3240
caaggacttc tctcgtgttg ttactttgat ggaaaacaag aagcacttga ctaagcaagg      3300
tttggacgaa atcaagaaga tcagaaacgc tatgaacact aacagaggat ccggtgaggg      3360
cagaggaagt cttctaacat gcggtgacgt ggaggagaat ccgggccct  ccggatctga      3420 gccacctcgg gctgagacct ttgtattcct ggacctagaa gccactgggc tcccaaacat      3480
ggaccctgag attgcagaga tatcccttt tgctgttcac cgctcttccc tggagaaccc      3540
agaacgggat gattctggtt ccttggtgct gccccgtgtt ctggacaagc tcacactgtg      3600
catgtgcccg gagcgcccct ttactgccaa ggccagtgag attactggtt tgagcagcga      3660
aagcctgatg cactgcggga aggctggttt caatggcgct gtggtaagga cactgcaggg      3720
```

```
cttcctaagc cgccaggagg gccccatctg ccttgtggcc cacaatggct tcgattatga    3780
cttcccactg ctgtgcacgg agctacaacg tctgggtgcc catctgcccc aagacactgt    3840
ctgcctggac acactgcctg cattgcgggg cctggaccgt gctcacagcc acggcaccag    3900
ggctcaaggc cgcaaaagct acagcctggc cagtctcttc caccgctact tccaggctga    3960
acccagtgct gcccattcag cagaaggtga tgtgcacacc ctgcttctga tcttcctgca    4020
tcgtgctcct gagctgctcg cctgggcaga tgagcaggcc cgcagctggg ctcatattga    4080
gcccatgtac gtgccacctg atggtccaag cctcgaagcc tgacctgcag gtcgagcatg    4140
catctagggc ggccaattcc gcccctctcc ctccccccc cctaacgtta ctggccgaag     4200
ccgcttggaa taaggccggt gtgcgtttgt ctatatgtga ttttccacca tattgccgtc    4260
ttttggcaat gtgagggccc ggaaacctgg ccctgtcttc ttgacgagca ttcctagggg    4320
tctttcccct ctcgccaaag gaatgcaagg tctgttgaat gtcgtgaagg aagcagttcc    4380
tctggaagct tcttgaagac aaacaacgtc tgtagcgacc ctttgcaggc agcggaaccc    4440
cccacctggc gacaggtgcc tctgcggcca aaagccacgt gtataagata cacctgcaaa    4500
ggcggcacaa ccccagtgcc acgttgtgag ttggatagtt gtggaaagag tcaaatggct    4560
ctcctcaagc gtattcaaca aggggctgaa ggatgcccag aaggtacccc attgtatggg    4620
atctgatctg gggcctcggt gcacatgctt tacatgtgtt tagtcgaggt taaaaaaacg    4680
tctaggcccc ccgaaccacg gggacgtggt tttcctttga aaaacacgat gataagcttg    4740
ccacaaccct taccggtcgc caccatgagc gagctgatta aggagaacat gcacatgaag    4800
ctgtacatgg agggcaccgt ggacaaccat cacttcaagt gcacatccga gggcgaaggc    4860
aagccctacg agggcaccca gaccatgaga atcaaggtgg tcgagggcgg ccctctcccc    4920
ttcgccttcg acatcctggc tactagcttc ctctacggca gcaagacctt catcaaccac    4980
acccagggca tccccgactt cttcaagcag tccttccctg agggcttcac atgggagaga    5040
gtcaccacat acgaagacgg gggcgtgctg accgctaccc aggacaccag cctccaggac    5100
ggctgcctca tctacaacgt caagatcaga ggggtgaact tcacatccaa cggccctgtg    5160
atgcagaaga aaacactcgg ctgggaggcc ttcaccgaga cgctgtaccc cgctgacggc    5220
ggcctggaag gcagaaacga catggccctg aagctcgtgg gcgggagcca tctgatcgca    5280
aacatcaaga ccatatag atccaagaaa cccgctaaga acctcaagat gcctggcgtc     5340
tactatgtgg actacagact ggaaagaatc aaggaggcca caacgagac ctacgtcgag    5400
cagcacgagg tggcagtggc cagatactgc gacctcccta gcaaactggg gcacaagctt    5460
aattgattct agagtcgacc gagcatctta ccgccattta tacccatatt tgttctgttt    5520
ttcttgattt gggtatacat ttaaatgtta atagaacaaa atggtgggc aatcatttac     5580
attttaggg atatgtaatt actagttcag gtgtattgcc acaagacaaa catgttaaga    5640
aactttcccg ttatttacgc tctgttcctg ttaatcaacc tctggattac aaaatttgtg    5700
aaagattgac tgatattctt aactatgttg ctccttttac gctgtgtgga tatgctgctt    5760
tatagcctct gtatctagct attgcttccc gtacggcttt cgttttctcc tccttgtata    5820
aatcctggtt gctgtctctt ttagaggagt gtggcccgt tgtccgtcaa cgtgcgtgg     5880
tgtgctctgt gtttgctgac gcaacccca ctggctgggg cattgccacc acctgtcaac    5940
tcctttctgg gactttcgct ttcccctcc cgatcgccac ggcagaactc atcgccgcct    6000
gccttgcccg ctgctggaca ggggctaggt tgctgggcac tgataattcc gtggtgttgt    6060
catcggtacc tttttaaaag aaaagggggg actggaaggg ctaattcact cccaacgaag    6120
```

```
acaagatatc ataacttcgt atagcataca ttatacgaag ttataattta tttgtgaaat    6180
ttgtgatgct attgctttat ttgtaaccat atgtttattt gtgaaatttg tgatgctatt    6240
gctttatttg taaccattgc tttttgcttg tactgggtct ctctggttag accagatctg    6300
agcctgggag ctctctggct aactagggaa cccactgctt aagcctcaat aaagcttgcc    6360
tcgaccagcc tcgactgtgc cttctagttg ccagccatct gttgtttgcc cctcccccgt    6420
gccttccttg accctggaag gtgccactcc cactgtcctt tcctaataaa atgaggaaat    6480
tgcatcgcat tgtctgagta ggtgtcattc tattctgggg ggtggggtgg ggcaggacag    6540 caaggggag gattgggaag acaatagcag gcatgctggg gatgcggtgg gctctatggc    6600
ctgcagctgc attaatgaat cggccaacgc gcggggagag gcggtttgcg tattgggcgc    6660
tcttccgctt cctcgctcac tgactcgctg cgctcggtcg ttcggctgcg gcgagcggta    6720
tcagctcact caaaggcggt aatacggtta tccacagaat caggggataa cgcaggaaag    6780
aacatgtgag caaaaggcca gcaaaaggcc aggaaccgta aaaaggccgc gttgctggcg    6840 ttttccata ggctccgccc ccctgacgag catcacaaaa atcgacgctc aagtcagagg    6900
tggcgaaacc cgacaggact ataaagatac caggcgtttc ccctggaag ctccctcgtg    6960 cgctctcctg ttccgaccct gccgcttacc ggatacctgt ccgcctttct cccttcggga    7020
agcgtggcgc tttctcatag ctcacgctgt aggtatctca gttcggtgta ggtcgttcgc    7080
tccaagctgg gctgtgtgca cgaaccccc gttcagcccg accgctgcgc cttatccggt    7140
aactatcgtc ttgagtccaa cccggtaaga cacgacttat cgccactggc agcagccact    7200
ggtaacagga ttagcagagc gaggtatgta ggcggtgcta cagagttctt gaagtggtgg    7260
cctaactacg gctacactag aaggacagta tttggtatct gcgctctgct gaagccagtt    7320
accttcggaa aaagagttgg tagctcttga tccggcaaac aaaccaccgc tggtagcggt    7380 ggttttttg tttgcaagca gcagattacg cgcagaaaaa aaggatctca agaagatcct    7440
ttgatctttt ctacggggtc tgacgctcag tggaacgaaa actcacgtta agggattttg    7500
gtcatgagat tatcaaaaag gatcttcacc tagatccttt taaattaaaa atgaagtttt    7560
aaatcaatct aaagtatata tgagtaaact tggtctgaca gttaccaatg cttaatcagt    7620
gaggcaccta tctcagcgat ctgtctattt cgttcatcca tagttgcctg actccccgtc    7680
gtgtagataa ctacgatacg ggagggctta ccatctggcc ccagtgctgc aatgataccg    7740
cgagacccac gctcaccggc tccagattta tcagcaataa accagccagc cggaagggcc    7800
gagcgcagaa gtggtcctgc aactttatcc gcctccatcc agtctattaa ttgttgccgg    7860
gaagctagag taagtagttc gccagttaat agtttgcgca acgttgttgc cattgctaca    7920
ggcatcgtgg tgtcacgctc gtcgtttggt atggcttcat tcagctccgg ttcccaacga    7980
tcaaggcgag ttacatgatc ccccatgttg tgcaaaaaag cggttagctc cttcggtcct    8040
ccgatcgttg tcagaagtaa gttggccgca gtgttatcac tcatggttat ggcagcactg    8100
cataattctc ttactgtcat gccatccgta agatgctttt ctgtgactgg tgagtactca    8160
accaagtcat tctgagaata gtgtatgcgg cgaccgagtt gctcttgccc ggcgtcaata    8220
cgggataata ccgcgccaca tagcagaact ttaaaagtgc tcatcattgg aaaacgttct    8280
tcggggcgaa aactctcaag gatcttaccg ctgttgagat ccagttcgat gtaacccact    8340
cgtgcaccca actgatcttc agcatctttt actttcacca gcgtttctgg gtgagcaaaa    8400
acaggaaggc aaaatgccgc aaaaaaggga ataagggcga cacggaaatg ttgaatactc    8460
```

```
atactcttcc tttttcaata ttattgaagc atttatcagg gttattgtct catgagcgga    8520
tacatatttg aatgtattta gaaaaataaa caaatagggg ttccgcgcac atttccccga    8580
aaagtgccac ct                                                        8592
```

<210> SEQ ID NO 133
<211> LENGTH: 6955
<212> TYPE: DNA
<213> ORGANISM: Artificial Sequence
<220> FEATURE:
<223> OTHER INFORMATION: pExodus ExoI

<400> SEQUENCE: 133

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
atggggatac agggattgct acaatttatc aaagaagctt cagaacccat ccatgtgagg     960
aagtataaag gcaggtagt agctgtggat acatattgct ggcttcacaa aggagctatt    1020
gcttgtgctg aaaaactagc caaaggtgaa cctactgata ggtatgtagg attttgtatg    1080
aaatttgtaa atatgttact atctcatggg atcaagccta ttctcgtatt tgatggatgt    1140
actttacctt ctaaaaagga agtagagaga tctagaagag aaagacgaca agccaatctt    1200
cttaagggaa agcaacttct tcgtgagggg aaagtctcgg aagctcgaga gtgtttcacc    1260
cggtctatca atatcacaca tgccatggcc cacaaagtaa ttaaagctgc ccggtctcag    1320
ggggtagatt gcctcgtggc tccctatgaa gctgatgcgc agttggccta tcttaacaaa    1380
gcgggaattg tgcaagccat aattacagag gactcggatc tcctagcttt tggctgtaaa    1440
aaggtaattt taaagatgga ccagtttgga aatggacttg aaattgatca agctcggcta    1500
ggaatgtgca gacagcttgg ggatgtattc acgaagaga agtttcgtta catgtgtatt    1560
ctttcaggtt gtgactacct gtcatcactg cgtgggattg gattagcaaa ggcatgcaaa    1620
gtcctaagac tagccaataa tccagatata gtaaaggtta tcaagaaaat tggacattat    1680
ctcaagatga atatcacggt accagaggat tacatcaacg gtttattcg ggccaacaat    1740 accttcctct atcagctagt ttttgatccc atcaaaagga aacttattcc tctgaacgcc    1800
tatgaagatg atgttgatcc tgaaacacta agctacgctg gcaatatgt tgatgattcc    1860 atagctcttc aaatagcact tggaaataaa gatataaata cttttgaaca gatcgatgac    1920
```

```
tacaatccag acactgctat gcctgcccat tcaagaagtc atagttggga tgacaaaaca    1980
tgtcaaaagt cagctaatgt tagcagcatt tggcatagga attactctcc cagaccagag    2040
tcgggtactg tttcagatgc cccacaattg aaggaaaatc caagtactgt gggagtggaa    2100
cgagtgatta gtactaaagg gttaaatctc ccaaggaaat catccattgt gaaaagacca    2160
agaagtgcag agctgtcaga agatgacctg ttgagtcagt attctctttc atttacgaag    2220
aagaccaaga aaaatagctc tgaaggcaat aaatcattga gcttttctga agtgtttgtg    2280
cctgacctgg taaatggacc tactaacaaa aagagtgtaa gcactccacc taggacgaga    2340
aataaatttg caacattttt acaaggaaa atgaagaaa gtggtgcagt tgtggttcca    2400
gggaccagaa gcaggttttt ttgcagttca gattctactg actgtgtatc aaacaaagtg    2460
agcatccagc tctggatga aactgctgtc acagataaag agaacaatct gcatgaatca    2520
gagtatggag accaagaagg caagagactg gttgacacag atgtagcacg taattcaagt    2580
gatgacattc cgaataatca tattccaggt gatcatattc cagacaaggc aacagtgttt    2640
acagatgaag agtcctactc ttttgagagc agcaaattta caaggaccat ttcaccaccc    2700
actttgggaa cactaagaag ttgttttagt tggtctggag gtcttggaga tttttcaaga    2760
acgccgagcc cctctccaag cacagcattg cagcagttcc gaagaaagag cgattccccc    2820
acctcttttgc ctgagaataa tatgtctgat gtgtcgcagt taaagagcga ggagtccagt    2880
gacgatgagt ctcatccctt acgagaaggg gcatgttctt cacagtccca ggaaagtgga    2940
gaattctcac tgcagagttc aaatgcatca aagctttctc agtgctctag taaggactct    3000
gattcagagg aatctgattg caatattaag ttacttgaca gtcaaagtga ccagacctcc    3060
aagctatgtt tatctcattt ctcaaaaaaa gacacacctc taaggaacaa ggttcctggg    3120
ctatataagt ccagttctgc agactctctt tctacaacca agatcaaacc tctaggacct    3180
gccagagcca gtgggctgag caagaagccg gcaagcatcc agaagagaaa gcatcataat    3240
gccgagaaca agccggggtt acagatcaaa ctcaatgagc tctggaaaaa ctttggattt    3300
aaaaaagatt ctgaaaagct tcctccttgt aagaaacccc tgtccccagt cagagataac    3360
atccaactaa ctccagaagc ggaagaggat atatttaaca aacctgaatg tggccgtgtt    3420
caaagagcaa tattccagtg aggatccact agtccagtgt ggtggaattc tgcagatatc    3480
cagcacagtg gcggccgctc gagtctagag ggcccgttta acccgctga tcagcctcga    3540
ctgtgccttc tagttgccag ccatctgttg tttgcccctc cccgtgcctt ccttgaccc    3600
tggaaggtgc cactcccact gtcctttcct aataaaatga ggaaattgca tcgcattgtc    3660
tgagtaggtg tcattctatt ctggggggtg gggtggggca ggacagcaag ggggaggatt    3720
gggaagacaa tagcaggcat gctggggatg cggtgggctc tatggcttct gaggcggaaa    3780
gaaccagctg gggctctagg gggtatcccc acgcgccctg tagcggcgca ttaagcgcgg    3840
cgggtgtggt ggttacgcgc agcgtgaccg ctacacttgc cagcgcccta gcgcccgctc    3900
ctttcgcttt cttcccttcc tttctcgcca cgttcgccgg ctttccccgt caagctctaa    3960
atcgggggct ccctttaggg ttccgattta gtgctttacg gcacctcgac cccaaaaaac    4020
ttgattaggg tgatggttca cgtagtgggc catcgccctg atagacggtt tttcgccctt    4080
tgacgttgga gtccacgttc tttaatagtg gactcttgtt ccaaactgga acaacactca    4140
accctatctc ggtctattct tttgatttat aagggatttt gccgatttcg gcctattggt    4200
taaaaaatga gctgatttaa caaaaattta acgcgaatta attctgtgga atgtgtgtca    4260
```

```
gttagggtgt ggaaagtccc caggctcccc agcaggcaga agtatgcaaa gcctatcagg    4320
acatagcgtt ggctacccgt gatattgctg aagagcttgg cggcgaatgg gctgaccgct    4380
tcctcgtgct ttacggtatc gccgctcccg attcgcagcg catcgccttc tatcgccttc    4440
ttgacgagtt cttctgagcg ggactctggg gttcgaaatg accgaccaag cgacgcccaa    4500
cctgccatca cgagatttcg attccaccgc cgccttctat gaaaggttgg gcttcggaat    4560
cgttttccgg gacgccggct ggatgatcct ccagcgcggg gatctcatgc tggagttctt    4620
cgcccacccc aacttgttta ttgcagctta taatggttac aaataaagca atagcatcac    4680
aaatttcaca aataaagcat tttttcact gcattctagt tgtggtttgt ccaaactcat    4740
caatgtatct tatcatgtct gtataccgtc gacctctagc tagagcttgg cgtaatcatg    4800
gtcatagctg tttcctgtgt gaaattgtta tccgctcaca attccacaca acatacgagc    4860
cggaagcata aagtgtaaag cctggggtgc ctaatgagtg agctaactca cattaattgc    4920
gttgcgctca ctgcccgctt tccagtcggg aaacctgtcg tgccagctgc attaatgaat    4980
cggccaacgc gcgggagag gcggtttgcg tattgggcgc tcttccgctt cctcgctcac    5040
tgactcgctg cgctcggtcg ttcggctgcg gcgagcggta tcagctcact caaaggcggt    5100
aatacggtta tccacagaat caggggataa cgcaggaaag aacatgtgag caaaaggcca    5160
gcaaaaggcc aggaaccgta aaaaggccgc gttgctggcg ttttttccata ggctccgccc    5220 ccctgacgag catcacaaaa atcgacgctc aagtcagagg tggcgaaacc cgacaggact    5280
ataaagatac caggcgtttc ccctggaag ctccctcgtg cgctctcctg ttccgaccct    5340
gccgcttacc ggatacctgt ccgcctttct cccttcggga agcgtggcgc tttctcatag    5400
ctcacgctgt aggtatctca gttcggtgta ggtcgttcgc tccaagctgg gctgtgtgca    5460
cgaacccccc gttcagcccg accgctgcgc cttatccggt aactatcgtc ttgagtccaa    5520
cccggtaaga cacgacttat cgccactggc agcagccact ggtaacagga ttagcagagc    5580
gaggtatgta ggcggtgcta cagagttctt gaagtggtgg cctaactacg gctacactag    5640
aagaacagta tttggtatct gcgctctgct gaagccagtt accttcggaa aaagagttgg    5700
tagctcttga tccggcaaac aaaccaccgc tggtagcggt tttttttgttt gcaagcagca    5760 gattacgcgc agaaaaaag gatctcaaga agatcctttg atcttttcta cggggtctga    5820
cgctcagtgg aacgaaaact cacgttaagg gattttggtc atgagattat caaaaaggat    5880
cttcacctag atccttttaa attaaaaatg aagttttaaa tcaatctaaa gtatatatga    5940
gtaaacttgg tctgacagtt accaatgctt aatcagtgag gcacctatct cagcgatctg    6000
tctatttcgt tcatccatag ttgcctgact ccccgtcgtg tagataacta cgatacggga    6060
gggcttacca tctggcccca gtgctgcaat gataccgcga gacccacgct caccggctcc    6120
agatttatca gcaataaacc agccagccgg aagggccgag cgcagaagtg gtcctgcaac    6180
tttatccgcc tccatccagt ctattaattg ttgccgggaa gctagagtaa gtagttcgcc    6240
agttaatagt ttgcgcaacg ttgttgccat tgctacaggc atcgtggtgt cacgctcgtc    6300
gtttggtatg gcttcattca gctccggttc ccaacgatca aggcgagtta catgatcccc    6360
catgttgtgc aaaaaagcgg ttagctcctt cggtcctccg atcgttgtca gaagtaagtt    6420
ggccgcagtg ttatcactca tggttatggc agcactgcat aattctctta ctgtcatgcc    6480
atccgtaaga tgcttttctg tgactggtga gtactcaacc aagtcattct gagaatagtg    6540
tatgcggcga ccgagttgct cttgcccggc gtcaatacgg gataataccg cgccacatag    6600
cagaacttta aaagtgctca tcattggaaa acgttcttcg gggcgaaaac tctcaaggat    6660
```

```
cttaccgctg ttgagatcca gttcgatgta acccactcgt gcacccaact gatcttcagc    6720
atcttttact ttcaccagcg tttctgggtg agcaaaaaca ggaaggcaaa atgccgcaaa    6780
aaagggaata agggcgacac ggaaatgttg aatactcata ctcttccttt ttcaatatta    6840
ttgaagcatt tatcagggtt attgtctcat gagcggatac atatttgaat gtatttagaa    6900
aaataaacaa atagggggttc cgcgcacatt tccccgaaaa gtgccacctg acgtc        6955
```

<210> SEQ ID NO 134
<211> LENGTH: 5036
<212> TYPE: DNA
<213> ORGANISM: Artificial Sequence
<220> FEATURE:
<223> OTHER INFORMATION: pExodus Lambda exonuclease

<400> SEQUENCE: 134

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
atgacacccg acattattct ccagcggaca ggtattgacg tgagggccgt ggaacagggg     960
gatgatgctt ggcacaaact gaggctcggc gtgatcaccg catctgaggt gcacaacgtc    1020
attgccaaac cccgctctgg aaagaaatgg cctgacatga agatgagtta cttccatact    1080
ctgctcgccg aggtgtgcac cggagtcgct cccgaagtga cgccaaggc tctggcatgg    1140 ggtaaacagt acgagaatga cgctcgaacc ctcttcgagt tcaccagtgg ggtgaacgtc    1200
acagagtcac caatcatcta ccgggatgaa agcatgcgca ctgcatgctc ccccgacggt    1260
ctgtgttctg atgggaatgg tctggagctc aagtgtcctt tcacctcccg agatttcatg    1320
aagttcaggc tcggcggatt tgaagctatc aagagcgcat acatgcccca ggtccagtat    1380
tccatgtggg tgacaagaaa aaacgcttgg tactttgcaa attatgaccc taggatgaag    1440
agagagggcc tgcactacgt ggtcatcgag cgggacgaaa aatatatggc cagcttcgat    1500
gaaatcgtgc cagagtttat tgaaaagatg gatgaggccc tggctgaaat tggcttcgtg    1560
tttggagagc agtggcggct cgagtctaga gggcccgttt aaacccgctg atcagcctcg    1620
actgtgcctt ctagttgcca gccatctgtt gtttgcccct cccccgtgcc ttccttgacc    1680
ctggaaggtg ccactcccac tgtcctttcc taataaaatg aggaaattgc atcgcattgt    1740
```

```
ctgagtaggt gtcattctat tctgggggt ggggtggggc aggacagcaa gggggaggat    1800
tgggaagaca atagcaggca tgctggggat gcggtgggct ctatggcttc tgaggcggaa    1860
agaaccagct ggggctctag ggggtatccc cacgcgccct gtagcggcgc attaagcgcg    1920
gcgggtgtgg tggttacgcg cagcgtgacc gctacacttg ccagcgccct agcgcccgct    1980
cctttcgctt tcttcccttc ctttctcgcc acgttcgccg gctttccccg tcaagctcta    2040
aatcgggggc tccctttagg gttccgattt agtgctttac ggcacctcga ccccaaaaaa    2100
cttgattagg gtgatggttc acgtagtggg ccatcgccct gatagacggt ttttcgccct    2160
ttgacgttgg agtccacgtt ctttaatagt ggactcttgt tccaaactgg aacaacactc    2220
aaccctatct cggtctattc ttttgattta aagggatttt gccgatttc ggcctattgg    2280
ttaaaaatg agctgattta acaaaaattt aacgcgaatt aattctgtgg aatgtgtgtc    2340
agttagggtg tggaaagtcc ccaggctccc cagcaggcag aagtatgcaa agcctatcag    2400
gacatagcgt tggctacccg tgatattgct gaagagcttg gcggcgaatg ggctgaccgc    2460
ttcctcgtgc tttacggtat cgccgctccc gattcgcagc gcatcgcctt ctatcgcctt    2520
cttgacgagt tcttctgagc gggactctgg ggttcgaaat gaccgaccaa gcgacgccca    2580
acctgccatc acgagatttc gattccaccg ccgccttcta tgaaaggttg gcttcggaa    2640
tcgtttccg ggacgccggc tggatgatcc tccagcgcgg ggatctcatg ctggagttct    2700
tcgcccaccc caacttgttt attgcagctt ataatggtta caaataaagc aatagcatca    2760
caaatttcac aaataaagca ttttttttcac tgcattctag ttgtggtttg tccaaactca    2820
tcaatgtatc ttatcatgtc tgtataccgt cgacctctag ctagagcttg gcgtaatcat    2880
ggtcatagct gtttcctgtg tgaaattgtt atccgctcac aattccacac aacatacgag    2940
ccggaagcat aaagtgtaaa gcctggggtg cctaatgagt gagctaactc acattaattg    3000
cgttgcgctc actgcccgct ttccagtcgg gaaacctgtc gtgccagctg cattaatgaa    3060
tcggccaacg cgcggggaga ggcggtttgc gtattgggcg ctcttccgct tcctcgctca    3120
ctgactcgct gcgctcggtc gttcggctgc ggcgagcggt atcagctcac tcaaaggcgg    3180
taatacggtt atccacagaa tcaggggata acgcaggaaa gaacatgtga gcaaaaggcc    3240
agcaaaaggc caggaaccgt aaaaaggccg cgttgctggc gtttttccat aggctccgcc    3300
cccctgacga gcatcacaaa aatcgacgct caagtcagag gtggcgaaac ccgacaggac    3360
tataaagata ccaggcgttt ccccctggaa gctccctcgt gcgctctcct gttccgaccc    3420
tgccgcttac cggatacctg tccgcctttc tcccttcggg aagcgtggcg ctttctcata    3480
gctcacgctg taggtatctc agttcggtgt aggtcgttcg ctccaagctg ggctgtgtgc    3540
acgaacccc cgttcagccc gaccgctgcg ccttatccgg taactatcgt cttgagtcca    3600
acccggtaag acacgactta tcgccactgg cagcagccac tggtaacagg attagcagag    3660
cgaggtatgt aggcggtgct acagagttct tgaagtggtg gcctaactac ggctacacta    3720
gaagaacagt atttggtatc tgcgctctgc tgaagccagt taccttcgga aaaagagttg    3780
gtagctcttg atccggcaaa caaaccaccg ctggtagcgg ttttttttgtt tgcaagcagc    3840
agattacgcg cagaaaaaaa ggatctcaag aagatccttt gatcttttct acggggtctg    3900
acgctcagtg gaacgaaaac tcacgttaag ggattttggt catgagatta tcaaaaagga    3960
tcttcaccta gatcctttta aattaaaaat gaagttttaa atcaatctaa agtatatatg    4020
agtaaacttg gtctgacagt taccaatgct taatcagtga ggcacctatc tcagcgatct    4080
gtctatttcg ttcatccata gttgcctgac tccccgtcgt gtagataact acgatacggg    4140
```

```
agggcttacc atctggcccc agtgctgcaa tgataccgcg agaccacgc tcaccggctc    4200 cagatttatc agcaataaac cagccagccg aagggccga cgcagaagt ggtcctgcaa    4260 ctttatccgc ctccatccag tctattaatt gttgccggga agctagagta agtagttcgc    4320
cagttaatag tttgcgcaac gttgttgcca ttgctacagg catcgtggtg tcacgctcgt    4380
cgtttggtat ggcttcattc agctccggtt cccaacgatc aaggcgagtt acatgatccc    4440
ccatgttgtg caaaaaagcg gttagctcct tcggtcctcc gatcgttgtc agaagtaagt    4500
tggccgcagt gttatcactc atggttatgg cagcactgca taattctctt actgtcatgc    4560
catccgtaag atgcttttct gtgactggtg agtactcaac caagtcattc tgagaatagt    4620
gtatgcggcg accgagttgc tcttgcccgg cgtcaatacg ggataatacc gcgccacata    4680
gcagaacttt aaaagtgctc atcattggaa aacgttcttc ggggcgaaaa ctctcaagga    4740
tcttaccgct gttgagatcc agttcgatgt aacccactcg tgcacccaac tgatcttcag    4800
catcttttac tttcaccagc gtttctgggt gagcaaaaac aggaaggcaa aatgccgcaa    4860
aaaagggaat aagggcgaca cggaaatgtt gaatactcat actcttcctt tttcaatatt    4920
attgaagcat ttatcagggt tattgtctca tgagcggata catatttgaa tgtatttaga    4980
aaaataaaca ataggggtt ccgcgcacat ttccccgaaa agtgccacct gacgtc        5036
```

<210> SEQ ID NO 135
<211> LENGTH: 5816
<212> TYPE: DNA
<213> ORGANISM: Artificial Sequence
<220> FEATURE:
<223> OTHER INFORMATION: pExodus Sox

<400> SEQUENCE: 135

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca tgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
atggaagcaa cccctacacc cgccgacctg tttagcgaag attacctcgt ggatacctc     960 gacggactga ttgtggatga ccagcaggct gtgctggcat ctctcagttt ctcaaagttt    1020
ctgaaacacg ccaaggtgcg agattggtgc gcacaggcca agatccagcc aagcatgccc    1080
gccctcagga tggcttacaa ttatttcctg ttttccaaag tgggcgagtt cattggatct    1140
```

```
gaagacgtct gcaacttctt tgtggataga gtctttggag gagtgcggct gctcgacgtg    1200
gcctctgtct acgccgcttg tagtcagatg aatgctcatc agaggcacca tatctgctgt    1260
ctggtggaga gagcaacaag ctcccagtcc ctcaacccag tctgggacgc actgcgagat    1320
gggatcattt ctagttcaaa attccactgg gccgtgaagc agcagaatac aagcaagaaa    1380
atctttcccc cctggcctat tactaacaat catttcgtgg caggacccct cgcctttgga    1440
ctgcgatgcg aggaagtggt caagacactg ctcgctactc tgctccaccc cgacgaggca    1500
aactgtctgg attacggctt catgcagagt cctcagaatg ggatcttcgg tgtgtccctg    1560
gactttgcag ccaacgtcaa aactgatacc gagggacggc tgcagttcga ccccaactgc    1620
aaggtgtacg aaatcaaatg tcgcttcaag tatacttttg ctaaaatgga gtgcgatcct    1680
atctacgctg catatcagag gctgtatgaa gccccaggaa aactggctct caaggacttc    1740
ttttacagca tctccaaacc agccgtggag tatgtcggcc tgggaaagct ccctctgaa     1800 agtgactacc tggtggccta cgaccaggag tgggaagcct gccccggaa gaaacgcaag     1860 ctgaccccctc tccacaacct gatcagagag tgtattctgc ataatagtac cacagaatca   1920
gacgtgtacg tcctgaccga ccctcaggat acacgcgggc agatcagcat caaggctcga    1980
ttcaaggcaa acctgtttgt gaatgtcaga cacagctact tctatcaggt gctgctccag    2040
agctccatcg tcgaggaata cattgggctc gattcaggta tcccacggct gggtagcccc    2100
aaatactata ttgctaccgg gttcttcagg aagagaggtt atcaggaccc tgtgaactgt    2160
acaatcggag gtgacgccct ggaccccac gtcgagatcc caactctgct cattgtgacc     2220
cccgtctact tccccagggg cgctaagcac aggctgctcc atcaggccgc taattttggg    2280
tcacggagcg caaaagatac cttcccatac attaagtggg acttttccta tctgtctgcc    2340
aacgtgcctc attctccact cgagtctaga gggcccgttt aaacccgctg atcagcctcg    2400
actgtgcctt ctagttgcca gccatctgtt gtttgcccct cccccgtgcc ttccttgacc    2460
ctggaaggtg ccactcccac tgtccttttcc taataaaatg aggaaattgc atcgcattgt    2520
ctgagtaggt gtcattctat tctggggggt ggggtggggc aggacagcaa gggggaggat    2580
tgggaagaca atagcaggca tgctggggat gcggtgggc ctatggcttc tgaggcggaa     2640
agaaccagct ggggctctag ggggtatccc cacgcgccct gtagcggcgc attaagcgcg    2700
gcgggtgtgg tggttacgcg cagcgtgacc gctacacttg ccagcgccct agcgcccgct    2760
cctttcgctt tcttcccttc ctttctcgcc acgttcgccg gctttccccg tcaagctcta    2820 aatcggggggc tccctttagg gttccgattt agtgctttac ggcacctcga ccccaaaaaa   2880
cttgattagg gtgatggttc acgtagtggg ccatcgccct gatagacggt ttttcgccct    2940
ttgacgttgg agtccacgtt ctttaatagt ggactcttgt tccaaactgg aacaacactc    3000
aaccctatct cggtctattc ttttgattta agggatttt gccgatttc ggcctattgg      3060 ttaaaaaatg agctgattta acaaaaattt aacgcgaatt aattctgtgg aatgtgtgtc    3120
agttagggtg tggaaagtcc caggctccc cagcaggcag aagtatgcaa agcctatcag     3180
gacatagcgt tggctacccg tgatattgct gaagagcttg gcggcgaatg ggctgaccgc    3240
ttcctcgtgc tttacggtat cgccgctccc gattcgcagc gcatcgcctt ctatcgcctt    3300
cttgacgagt tcttctgagc gggactctgg ggttcgaaat gaccgaccaa gcgacgccca    3360
acctgccatc acgagatttc gattccaccg ccgccttcta tgaaaggttg gcttcggaa     3420 tcgttttccg ggacgccggc tggatgatcc tccagcgcgg ggatctcatg ctggagttct    3480
tcgcccaccc caacttgttt attgcagctt ataatggtta caaataaagc aatagcatca    3540
```

```
caaatttcac aaataaagca ttttttttcac tgcattctag ttgtggtttg tccaaactca   3600
tcaatgtatc ttatcatgtc tgtataccgt cgacctctag ctagagcttg gcgtaatcat   3660
ggtcatagct gtttcctgtg tgaaattgtt atccgctcac aattccacac aacatacgag   3720
ccggaagcat aaagtgtaaa gcctggggtg cctaatgagt gagctaactc acattaattg   3780
cgttgcgctc actgcccgct ttccagtcgg gaaacctgtc gtgccagctg cattaatgaa   3840
tcggccaacg cgcggggaga ggcggtttgc gtattgggcg ctcttccgct tcctcgctca   3900
ctgactcgct gcgctcggtc gttcggctgc ggcgagcggt atcagctcac tcaaaggcgg   3960
taatacggtt atccacagaa tcaggggata acgcaggaaa gaacatgtga gcaaaaggcc   4020
agcaaaaggc caggaaccgt aaaaaggccg cgttgctggc gtttttccat aggctccgcc   4080
cccctgacga gcatcacaaa aatcgacgct caagtcagag gtggcgaaac ccgacaggac   4140
tataaagata ccaggcgttt ccccctggaa gctccctcgt gcgctctcct gttccgaccc   4200
tgccgcttac cggatacctg tccgcctttc tcccttcggg aagcgtggcg ctttctcata   4260
gctcacgctg taggtatctc agttcggtgt aggtcgttcg ctccaagctg gctgtgtgc   4320 acgaaccccc cgttcagccc gaccgctgcg ccttatccgg taactatcgt cttgagtcca   4380
acccggtaag acacgactta tcgccactgg cagcagccac tggtaacagg attagcagag   4440
cgaggtatgt aggcggtgct acagagttct tgaagtggtg gcctaactac ggctacacta   4500
gaagaacagt atttggtatc tgcgctctgc tgaagccagt taccttcgga aaaagagttg   4560
gtagctcttg atccggcaaa caaaccaccg ctggtagcgg ttttttttgtt tgcaagcagc   4620 agattacgcg cagaaaaaaa ggatctcaag aagatccttt gatcttttct acggggtctg   4680
acgctcagtg gaacgaaaac tcacgttaag ggattttggt catgagatta tcaaaaagga   4740
tcttcaccta gatcctttta aattaaaaat gaagttttaa atcaatctaa agtatatatg   4800
agtaaacttg gtctgacagt taccaatgct taatcagtga ggcacctatc tcagcgatct   4860
gtctatttcg ttcatccata gttgcctgac tccccgtcgt gtagataact acgatacggg   4920
agggcttacc atctggcccc agtgctgcaa tgataccgcg agaccacgc tcaccggctc   4980 cagatttatc agcaataaac cagccagccg gaagggccga gcgcagaagt ggtcctgcaa   5040
ctttatccgc ctccatccag tctattaatt gttgccggga agctagagta agtagttcgc   5100
cagttaatag tttgcgcaac gttgttgcca ttgctacagg catcgtggtg tcacgctcgt   5160
cgtttggtat ggcttcattc agctccggtt cccaacgatc aaggcgagtt acatgatccc   5220
ccatgttgtg caaaaaagcg gttagctcct tcggtcctcc gatcgttgtc agaagtaagt   5280
tggccgcagt gttatcactc atggttatgg cagcactgca taattctctt actgtcatgc   5340
catccgtaag atgcttttct gtgactggtg agtactcaac caagtcattc tgagaatagt   5400
gtatgcggcg accgagttgc tcttgcccgg cgtcaatacg ggataatacc gcgccacata   5460
gcagaacttt aaaagtgctc atcattggaa aacgttcttc ggggcgaaaa ctctcaagga   5520
tcttaccgct gttgagatcc agttcgatgt aacccactcg tgcacccaac tgatcttcag   5580
catcttttac tttcaccagc gtttctgggt gagcaaaaac aggaaggcaa aatgccgcaa   5640
aaaagggaat aagggcgaca cggaaatgtt gaatactcat actcttcctt tttcaatatt   5700
attgaagcat ttatcagggt tattgtctca tgagcggata catatttgaa tgtatttaga   5760
aaaataaaca ataggggtt ccgcgcacat ttccccgaaa agtgccacct gacgtc      5816
```

<210> SEQ ID NO 136

<211> LENGTH: 6236
<212> TYPE: DNA
<213> ORGANISM: Artificial Sequence
<220> FEATURE:
<223> OTHER INFORMATION: pExodus UL12

<400> SEQUENCE: 136

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
atggaaagca ctgggggtcc tgcctgtcct cctgggcgaa ccgtgactaa aaggtcctgg     960
gctctggctg aagatacacc aagggggcct gacagccccc ctaagaggcc aagacccaac    1020
tccctgccac tcaccacaac tttcaggcca ctgccaccac ctccacagac cacaagtgcc    1080
gtcgatccaa gctcccactc acccgtgaat cccccaggg accagcatgc cactgacacc    1140
gctgatgaga aacctcgcgc cgcttcacca gcactgtctg atgccagtgg accacccacc    1200
cccgacattc ctctgagccc aggcggaaca cacgcaagag acccagatgc cgaccccgat    1260
agccctgacc tggattccat gtggagtgct tcagtgattc ccaacgcact ccctagccac    1320
atcctggccg agaccttcga cgacatctg aggggactgc tcagagggt gcgggcaccc    1380
ctcgctatcg gacctctgtg ggcccggctg gattacctct gctccctggc cgtggtgctg    1440
gaggaagctg gaatggtgga ccgaggactg gacgccacc tctggcgact gaccaggaga    1500
gcacctccag cagccgctga tgcagtggca cctcggccac tgatgggttt ctatgaggca    1560
gccactcaga tcaggcaga ctgccagctg tgggcactgc tccgacgagg actcactacc    1620
gcctctaccc tgcgatgggg accacagggt ccctgttttt ctccccagtg gctcaagcat    1680
aacgctagtc tgcggcctga cgtgcagtct agtgcagtca tgttcggacg agtgaatgag    1740
ccaacagcac ggagcctgct ctttcgctac tgcgtgggtc gagctgacga tgggggcgag    1800
gctggcgcag atactcgaag gttcatcttt cacgaaccta gtgacctggc cgaggaaaac    1860
gtccacacat gcggggtgct gatggatggc catactggaa tggtcggggc ttctctcgat    1920
attctggtgt gtccaaggga catccacggc tacctggcac ccgtgcctaa aactcccctg    1980
gctttctacg aggtcaagtg tagagcaaaa tatgcctttg acctatgga ccctctgac    2040
cccacagcca gtgcttacga ggacctgatg gcccacagat cccctgaggc cttcagggcc    2100
ttcatcagat caattccaaa gcccagcgtc aggtatttcg ctccaggtag agtgcctggc    2160
```

```
ccagaggaag ctctggtcac ccaggatcag gcatggtccg aggcacacgc ctctggtgaa    2220
aaaagacgat gcagcgctgc agaccgagca ctcgtggagc tgaacagtgg cgtggtctca    2280
gaagtgctgc tctttggagc tcctgatctg gggcgccata caatctcacc agtgagctgg    2340
tcaagcggcg acctggtccg ccgagagcca gtgttcgcca ccctcggca cccaaatttt     2400 aagcagattc tcgtgcaggg atacgtcctg gattcccatt tccccgactg tccccctcac    2460
cctcatctgg tgaccttcat cggacggcac cgcacttctg ccgaggaagg ggtgaccttc    2520
aggctggagg atggagctgg tgcactgggt gcagctggac catccaaggc ttctattctc    2580
ccaaatcagg ctgtgcccat cgcactgatc attacccctg tcaggatcga cccagaaatc    2640
tacaaagcaa tccagcgctc ctctcgactg gcctttgacg atacactcgc cgagctgtgg    2700
gccagcagga gccaggcccc tggaccagca gccgctgaaa caactagttc aagccctacc    2760
acaggaagga gcagcaggct cgagtctaga gggcccgttt aaacccgctg atcagcctcg    2820
actgtgcctt ctagttgcca gccatctgtt gtttgcccct cccccgtgcc ttccttgacc    2880
ctggaaggtg ccactcccac tgtcctttcc taataaaatg aggaaattgc atcgcattgt    2940
ctgagtaggt gtcattctat tctgggggt ggggtgggc aggacagcaa ggggaggat      3000 tgggaagaca atagcaggca tgctggggat gcggtgggct ctatggcttc tgaggcggaa    3060
agaaccagct ggggctctag ggggtatccc cacgcgccct gtagcggcgc attaagcgcg    3120
gcgggtgtgg tggttacgcg cagcgtgacc gctacacttg ccagcgccct agcgcccgct    3180
cctttcgctt tcttcccttc ctttctcgcc acgttcgccg gctttccccg tcaagctcta    3240 aatcggggc tccctttagg gttccgattt agtgctttac ggcacctcga ccccaaaaaa    3300
cttgattagg gtgatggttc acgtagtggg ccatcgccct gatagacggt ttttcgccct    3360
ttgacgttgg agtccacgtt ctttaatagt ggactcttgt tccaaactgg aacaacactc    3420
aaccctatct cggtctattc ttttgattta aagggatttt gccgatttc ggcctattgg     3480 ttaaaaaatg agctgattta acaaaaattt aacgcgaatt aattctgtgg aatgtgtgtc    3540
agttagggtg tggaaagtcc ccaggctccc cagcaggcag aagtatgcaa agccatcag    3600 gacatagcgt tggctacccg tgatattgct gaagagcttg gcggcgaatg ggctgaccgc    3660
ttcctcgtgc tttacggtat cgccgctccc gattcgcagc gcatcgcctt ctatcgcctt    3720
cttgacgagt tcttctgagc gggactctgg ggttcgaaat gaccgaccaa gcgacgccca    3780
acctgccatc acgagatttc gattccaccg ccgccttcta tgaaaggttg gcttcggaa     3840 tcgtttttccg gacgccggc tggatgatcc tccagcgcgg ggatctcatg ctggagttct    3900
tcgcccaccc caacttgttt attgcagctt ataatggtta caaataaagc aatagcatca    3960
caaatttcac aaataaagca tttttttcac tgcattctag ttgtggtttg tccaaactca    4020
tcaatgtatc ttatcatgtc tgtataccgt cgacctctag ctagagcttg gcgtaatcat    4080
ggtcatagct gtttcctgtg tgaaattgtt atccgctcac aattccacac aacatacgag    4140
ccggaagcat aaagtgtaaa gcctggggtg cctaatgagt gagctaactc acattaattg    4200
cgttgcgctc actgcccgct ttccagtcgg gaaacctgtc gtgccagctg cattaatgaa    4260
tcggccaacg cgcggggaga ggcggtttgc gtattgggcg ctcttccgct tcctcgctca    4320
ctgactcgct gcgctcggtc gttcggctgc ggcgagcggt atcagctcac tcaaaggcgg    4380
taatacggtt atccacagaa tcaggggata acgcaggaaa gaacatgtga gcaaaaggcc    4440
agcaaaaggc caggaaccgt aaaaaggccg cgttgctggc gtttttccat aggctccgcc    4500
```

```
cccctgacga gcatcacaaa aatcgacgct caagtcagag gtggcgaaac ccgacaggac   4560
tataaagata ccaggcgttt ccccctggaa gctccctcgt gcgctctcct gttccgaccc   4620
tgccgcttac cggatacctg tccgcctttc tcccttcggg aagcgtggcg ctttctcata   4680
gctcacgctg taggtatctc agttcggtgt aggtcgttcg ctccaagctg gctgtgtgc   4740 acgaaccccc cgttcagccc gaccgctgcg ccttatccgg taactatcgt cttgagtcca   4800
acccggtaag acacgactta tcgccactgg cagcagccac tggtaacagg attagcagag   4860
cgaggtatgt aggcggtgct acagagttct tgaagtggtg gcctaactac ggctacacta   4920
gaagaacagt atttggtatc tgcgctctgc tgaagccagt taccttcgga aaaagagttg   4980
gtagctcttg atccggcaaa caaccaccg ctggtagcgg ttttttttgtt tgcaagcagc   5040 agattacgcg cagaaaaaaa ggatctcaag aagatccttt gatcttttct acggggtctg   5100
acgctcagtg aacgaaaac tcacgttaag ggattttggt catgagatta tcaaaaagga   5160
tcttcaccta gatccttta aattaaaaat gaagttttaa atcaatctaa agtatatatg   5220
agtaaacttg gtctgacagt taccaatgct taatcagtga ggcacctatc tcagcgatct   5280
gtctatttcg ttcatccata gttgcctgac tccccgtcgt gtagataact acgatacggg   5340
agggcttacc atctggcccc agtgctgcaa tgataccgcg agaccacgc tcaccggctc   5400 cagatttatc agcaataaac cagccagccg aagggccga gcgcagaagt ggtcctgcaa   5460
ctttatccgc ctccatccag tctattaatt gttgccggga agctagagta agtagttcgc   5520
cagttaatag tttgcgcaac gttgttgcca ttgctacagg catcgtggtg tcacgctcgt   5580
cgtttggtat ggcttcattc agctccggtt cccaacgatc aaggcgagtt acatgatccc   5640
ccatgttgtg caaaaaagcg gttagctcct tcggtcctcc gatcgttgtc agaagtaagt   5700
tggccgcagt gttatcactc atggttatgg cagcactgca taattctctt actgtcatgc   5760
catccgtaag atgcttttct gtgactggtg agtactcaac caagtcattc tgagaatagt   5820
gtatgcggcg accgagttgc tcttgcccgg cgtcaatacg ggataatacc gcgccacata   5880
gcagaacttt aaaagtgctc atcattggaa aacgttcttc ggggcgaaaa ctctcaagga   5940
tcttaccgct gttgagatcc agttcgatgt aacccactcg tgcacccaac tgatcttcag   6000
catcttttac tttcaccagc gtttctgggt gagcaaaaac aggaaggcaa aatgccgcaa   6060
aaaagggaat aagggcgaca cggaaatgtt gaatactcat actcttcctt tttcaatatt   6120
attgaagcat ttatcagggt tattgtctca tgagcggata catatttgaa tgtatttaga   6180
aaaataaaca aataggggtt ccgcgcacat ttccccgaaa agtgccacct gacgtc       6236
```

<210> SEQ ID NO 137
<211> LENGTH: 5954
<212> TYPE: DNA
<213> ORGANISM: Artificial Sequence
<220> FEATURE:
<223> OTHER INFORMATION: pExodus Apollo

<400> SEQUENCE: 137

```
gacggatcgg gagatctccc gatccccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
```

```
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
atgaacggcg tgctgattcc tcacactcct attgctgtgg acttctggtc tctccggcga    960
gctgggactg cccgactctt ctttctgagt cacatgcatt cagatcacac tgtgggactg   1020
agctccacct gggcccgacc actgtactgc tcccccatca cagctcatct gctccacagg   1080
catctgcagg tgagcaagca gtggattcag gccctggagg tcggcgaatc ccacgtcctg   1140
cctctcgatg agatcggaca ggaaaccatg acagtgactc tgctcgacgc taatcattgc   1200
ccagggtccg tcatgttcct gtttgagggc tacttcggaa caattctgta tactggcgat   1260
tttcggtaca ctccatctat gctgaaggaa cccgccctga ccctcggaaa acagatccac   1320
acactgtacc tcgacaacac taattgtaac cctgctctgg tgctcccatc caggcaggag   1380
gccgctcacc agatcgtcca gctgattaga aagcacccac agcataacat caaaattggg   1440
ctgtatagtc tcggcaagga gtcactgctc gaacagctgg ccctggagtt ccagacatgg   1500
gtggtcctgt ctcccaggag actggaactc gtgcagctgc tcgggctggc tgatgtgttt   1560
actgtcgagg aaaaggctgg tagaatccac gcagtggacc acatggagat tgtcacagc    1620
aatatgctga gatggaacca gacccatcct acaatcgcca ttctgccaac tagccggaag   1680
atccactcta gtcatcccga tatccacgtg attccttatt ctgaccattc aagctacagt   1740
gagctgcgag cattcgtggc agccctcaag ccatgccagg tggtccctat cgtcagccgg   1800
cgcccttgtg gaggatttca ggattcactg agcccacgca tctcagtgcc actgattccc   1860
gacagcgtcc agcagtacat gtcctctagt tcacgaaagc ccagcctgct ctggctgctg   1920
gagcgaaggc tgaaacgccc ccgaacccag ggagtggtct tcgaaagccc tgaggaatcc   1980
gccgatcagt ctcaggctga tagggactcc aagaaagcaa agaaagagaa gctgtctccc   2040
tggcctgccg atctcgaaaa acagcccagc caccatcctc tgaggatcaa gaaacagctg   2100
ttcccagacc tctattctaa ggagtggaac aaggctgtgc ccttttgcga aagtcagaag   2160
agagtcacta tgctgaccgc acctctcggc ttcagcgtgc acctgcggtc caccgacgag   2220
gagttcatca gtcagaaaac acgcgaggaa attggcctgg atcacctct cgtgccaatg    2280
ggcgacgatg acggggggtcc agaggcaacc ggaaatcaga gcgcctggat ggggcacggt   2340
tccccactgt ctcatagctc caaggggacc cccctgctcg ctacagagtt cagggtctg    2400
gcactcaaat atctgctcac acccgtgaac ttctttcagg ccggctactc tagtagacgg   2460
tttgaccagc aggtcgagaa gtatcacaaa ccttgtctcg agtctagagg gcccgtttaa   2520
acccgctgat cagcctcgac tgtgccttct agttgccagc catctgttgt ttgcccctcc   2580
cccgtgcctt ccttgaccct ggaaggtgcc actcccactg tcctttccta ataaaatgag   2640
gaaattgcat cgcattgtct gagtaggtgt cattctattc tggggggtgg ggtggggcag   2700
```

```
gacagcaagg gggaggattg ggaagacaat agcaggcatg ctggggatgc ggtgggctct    2760
atggcttctg aggcggaaag aaccagctgg ggctctaggg ggtatcccca cgcgccctgt    2820
agcggcgcat taagcgcggc gggtgtggtg gttacgcgca gcgtgaccgc tacacttgcc    2880
agcgccctag cgcccgctcc tttcgctttc ttcccttcct ttctcgccac gttcgccggc    2940
tttccccgtc aagctctaaa tcgggggctc cctttagggt tccgatttag tgctttacgg    3000
cacctcgacc ccaaaaaact tgattagggt gatggttcac gtagtgggcc atcgccctga    3060
tagacggttt ttcgcccttt gacgttggag tccacgttct ttaatagtgg actcttgttc    3120
caaactggaa caacactcaa ccctatctcg gtctattctt ttgatttata agggattttg    3180
ccgatttcgg cctattggtt aaaaaatgag ctgatttaac aaaaatttaa cgcgaattaa    3240
ttctgtggaa tgtgtgtcag ttagggtgtg gaaagtcccc aggctcccca gcaggcagaa    3300
gtatgcaaag cctatcagga catagcgttg gctacccgtg atattgctga agagcttggc    3360
ggcgaatggg ctgaccgctt cctcgtgctt tacggtatcg ccgctcccga ttcgcagcgc    3420
atcgccttct atcgccttct tgacgagttc ttctgagcgg gactctgggg ttcgaaatga    3480
ccgaccaagc gacgcccaac ctgccatcac gagatttcga ttccaccgcc gccttctatg    3540
aaaggttggg cttcggaatc gttttccggg acgccggctg gatgatcctc cagcgcgggg    3600
atctcatgct ggagttcttc gcccacccca acttgtttat tgcagcttat aatggttaca    3660
aataaagcaa tagcatcaca aatttcacaa ataaagcatt ttttttcactg cattctagtt    3720 gtggtttgtc caaactcatc aatgtatctt atcatgtctg tataccgtcg acctctagct    3780
agagcttggc gtaatcatgg tcatagctgt ttcctgtgtg aaattgttat ccgctcacaa    3840
ttccacacaa catacgagcc ggaagcataa agtgtaaagc ctggggtgcc taatgagtga    3900
gctaactcac attaattgcg ttgcgctcac tgcccgcttt ccagtcggga aacctgtcgt    3960
gccagctgca ttaatgaatc ggccaacgcg cggggagagg cggtttgcgt attgggcgct    4020
cttccgcttc ctcgctcact gactcgctgc gctcggtcgt tcggctgcgg cgagcggtat    4080
cagctcactc aaaggcggta atacggttat ccacagaatc aggggataac gcaggaaaga    4140
acatgtgagc aaaaggccag caaaaggcca ggaaccgtaa aaaggccgcg ttgctggcgt    4200
ttttccatag gctccgcccc cctgacgagc atcacaaaaa tcgacgctca agtcagaggt    4260
ggcgaaaccc gacaggacta taaagatacc aggcgtttcc ccctggaagc tccctcgtgc    4320
gctctcctgt tccgaccctg ccgcttaccg gatacctgtc cgcctttctc ccttcgggaa    4380
gcgtggcgct ttctcatagc tcacgctgta ggtatctcag ttcggtgtag gtcgttcgct    4440
ccaagctggg ctgtgtgcac gaaccccccg ttcagcccga ccgctgcgcc ttatccggta    4500
actatcgtct tgagtccaac ccggtaagac acgacttatc gccactggca gcagccactg    4560
gtaacaggat tagcagagcg aggtatgtag gcggtgctac agagttcttg aagtggtggc    4620
ctaactacgg ctacactaga agaacagtat ttggtatctg cgctctgctg aagccagtta    4680
ccttcggaaa aagagttggt agctcttgat ccggcaaaca aaccaccgct ggtagcggtt    4740 ttttgtttg caagcagcag attacgcgca gaaaaaaagg atctcaagaa gatcctttga    4800
tcttttctac ggggtctgac gctcagtgga acgaaaactc acgttaaggg attttggtca    4860
tgagattatc aaaaaggatc ttcacctaga tccttttaaa ttaaaaatga agttttaaat    4920
caatctaaag tatatatgag taaacttggt ctgacagtta ccaatgctta atcagtgagg    4980
cacctatctc agcgatctgt ctatttcgtt catccatagt tgcctgactc cccgtcgtgt    5040
agataactac gatacgggag ggcttaccat ctggccccag tgctgcaatg ataccgcgag    5100
```

```
acccacgctc accggctcca gatttatcag caataaacca gccagccgga agggccgagc    5160
gcagaagtgg tcctgcaact ttatccgcct ccatccagtc tattaattgt tgccgggaag    5220
ctagagtaag tagttcgcca gttaatagtt tgcgcaacgt tgttgccatt gctacaggca    5280
tcgtggtgtc acgctcgtcg tttggtatgg cttcattcag ctccggttcc caacgatcaa    5340
ggcgagttac atgatccccc atgttgtgca aaaaagcggt tagctccttc ggtcctccga    5400
tcgttgtcag aagtaagttg gccgcagtgt tatcactcat ggttatggca gcactgcata    5460
attctcttac tgtcatgcca tccgtaagat gcttttctgt gactggtgag tactcaacca    5520
agtcattctg agaatagtgt atgcggcgac cgagttgctc ttgcccggcg tcaatacggg    5580
ataataccgc gccacatagc agaactttaa aagtgctcat cattggaaaa cgttcttcgg    5640
ggcgaaaact ctcaaggatc ttaccgctgt tgagatccag ttcgatgtaa cccactcgtg    5700
cacccaactg atcttcagca tcttttactt tcaccagcgt ttctgggtga gcaaaaacag    5760
gaaggcaaaa tgccgcaaaa aagggaataa gggcgacacg gaaatgttga atactcatac    5820
tcttcctttt tcaatattat tgaagcattt atcagggtta ttgtctcatg agcggataca    5880
tatttgaatg tatttagaaa aataaacaaa taggggttcc gcgcacattt ccccgaaaag    5940
tgccacctga cgtc                                                      5954
```

<210> SEQ ID NO 138
<211> LENGTH: 5498
<212> TYPE: DNA
<213> ORGANISM: Artificial Sequence
<220> FEATURE:
<223> OTHER INFORMATION: pExodus FenI

<400> SEQUENCE: 138

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
atgggcatcc aggggctcgc aaaactcatc gcagacgtgg ctccttccgc aattagagag     960
aacgacatca gtcctatttt cggcagaaag gtggctatcg acgcatctat gagtatctac    1020
cagttcctga ttgccgtgag gcagggcgga gatgtcctcc agaacgagga aggcgagacc    1080
acaagccacc tgatgggaat gttctacaga acaatccgga tgatggagaa tggcattaag    1140
```

```
ccagtgtatg tctttgacgg gaaaccccct cagctgaagt caggcgagct cgccaaaaga    1200
agcgaaagga gagccgaagc tgagaagcag ctgcagcagg cacaggcagc tggagccgaa    1260
caggaggtgg aaaaattcac aaagcggctg gtgaaagtca ctaagcagca caacgacgag    1320
tgcaagcatc tgctcagcct gatgggaatc ccctacctcg atgctccttc cgaggcagaa    1380
gcctcttgcg cagccctggt gaaagcaggg aaggtctatg ctgcagccac cgaggacatg    1440
gattgtctga catttggttc ccctgtgctg atgcgacacc tcaccgcctc tgaggctaag    1500
aaactgccaa tccaggagtt ccatctgtcc cgcattctcc aggagctggg gctcaatcag    1560
gaacagtttg tggacctgtg catcctgctc ggtagtgatt actgtgagtc aatcagggggg    1620
attggtccca agagagctgt ggacctgatt cagaaacata agtctatcga ggaaattgtg    1680
aggaggctgg accccaacaa atatccagtc cccgagaatt ggctccacaa ggaagcccat    1740
cagctgttcc tggagccaga agtgctggac cccgagagcg tcgaactcaa gtggtccgag    1800
cccaacgagg aagagctgat caaattcatg tgtggcgaga agcagttttc tgaagagcga    1860
attaggagtg gagtgaaacg cctgtcaaag agccgacagg ggagtactca gggtcggctg    1920
gacgatttct ttaaggtcac cggcagcctc agctccgcta aacgcaagga gcctgaacca    1980
aaaggaagca ctaagaaaaa ggccaagacc ggcgctgccg gcaagttcaa gagaggaaag    2040
ctcgagtcta gagggcccgt ttaaacccgc tgatcagcct cgactgtgcc ttctagttgc    2100
cagccatctg ttgtttgccc ctcccccgtg ccttccttga ccctggaagg tgccactccc    2160
actgtccttt cctaataaaa tgaggaaatt gcatcgcatt gtctgagtag gtgtcattct    2220
attctggggg gtggggtggg gcaggacagc aaggggggagg attgggaaga caatagcagg    2280
catgctgggg atgcggtggg ctctatggct tctgaggcgg aaagaaccag ctggggctct    2340
agggggtatc cccacgcgcc ctgtagcggc gcattaagcg cggcgggtgt ggtggttacg    2400
cgcagcgtga ccgctacact tgccagcgcc ctagcgcccg ctcctttcgc tttcttccct    2460
tcctttctcg ccacgttcgc cggctttccc cgtcaagctc taaatcgggg gctcccttta    2520
gggttccgat ttagtgcttt acggcacctc gaccccaaaa aacttgatta gggtgatggt    2580
tcacgtagtg gccatcgcc ctgatagacg gttttcgcc ctttgacgtt ggagtccacg    2640
ttctttaata gtggactctt gttccaaact ggaacaacac tcaaccctat ctcggtctat    2700
tcttttgatt tataagggat tttgccgatt tcggcctatt ggttaaaaaa tgagctgatt    2760
taacaaaaat ttaacgcgaa ttaattctgt ggaatgtgtg tcagttaggg tgtggaaagt    2820
ccccaggctc cccagcaggc agaagtatgc aaagcctatc aggacatagc gttggctacc    2880
cgtgatattg ctgaagagct tggcggcgaa tgggctgacc gcttcctcgt gctttacggt    2940
atcgccgctc ccgattcgca gcgcatcgcc ttctatcgcc ttcttgacga gttcttctga    3000
gcgggactct ggggttcgaa atgaccgacc aagcgacgcc caacctgcca tcacgagatt    3060
tcgattccac cgccgccttc tatgaaaggt tgggcttcgg aatcgttttc cgggacgccg    3120
gctggatgat cctccagcgc ggggatctca tgctggagtt cttcgcccac cccaacttgt    3180
ttattgcagc ttataatggt tacaaataaa gcaatagcat cacaaatttc acaaataaag    3240
cattttttc actgcattct agttgtggtt tgtccaaact catcaatgta tcttatcatg    3300
tctgtatacc gtcgacctct agctagagct tggcgtaatc atggtcatag ctgtttcctg    3360
tgtgaaattg ttatccgctc acaattccac acaacatacg agccggaagc ataaagtgta    3420
aagcctgggg tgcctaatga gtgagctaac tcacattaat tgcgttgcgc tcactgcccg    3480
ctttccagtc gggaaacctg tcgtgccagc tgcattaatg aatcggccaa cgcgcgggga    3540
```

```
gaggcggttt gcgtattggg cgctcttccg cttcctcgct cactgactcg ctgcgctcgg      3600
tcgttcggct gcggcgagcg gtatcagctc actcaaaggc ggtaatacgg ttatccacag      3660
aatcagggga taacgcagga aagaacatgt gagcaaaagg ccagcaaaag gccaggaacc      3720
gtaaaaaggc cgcgttgctg gcgttttttcc ataggctccg ccccccctgac gagcatcaca    3780 aaaatcgacg ctcaagtcag aggtggcgaa acccgacagg actataaaga taccaggcgt      3840
ttccccctgg aagctccctc gtgcgctctc ctgttccgac cctgccgctt accggatacc      3900
tgtccgcctt tctcccttcg ggaagcgtgg cgctttctca tagctcacgc tgtaggtatc      3960
tcagttcggt gtaggtcgtt cgctccaagc tgggctgtgt gcacgaaccc cccgttcagc      4020
ccgaccgctg cgccttatcc ggtaactatc gtcttgagtc aacccggta agacacgact       4080 tatcgccact ggcagcagcc actggtaaca ggattagcag agcgaggtat gtaggcggtg      4140
ctacagagtt cttgaagtgg tggcctaact acggctacac tagaagaaca gtatttggta     4200
tctgcgctct gctgaagcca gttaccttcg gaaaaagagt tggtagctct tgatccggca     4260
aacaaaccac cgctggtagc ggttttttttg tttgcaagca gcagattacg cgcagaaaaa    4320
aaggatctca agaagatcct ttgatctttt ctacggggtc tgacgctcag tggaacgaaa     4380
actcacgtta agggattttg gtcatgagat tatcaaaaag gatcttcacc tagatccttt     4440
taaattaaaa atgaagtttt aaatcaatct aaagtatata tgagtaaact tggtctgaca    4500
gttaccaatg cttaatcagt gaggcaccta tctcagcgat ctgtctattt cgttcatcca    4560
tagttgcctg actccccgtc gtgtagataa ctacgatacg ggagggctta ccatctggcc    4620
ccagtgctgc aatgataccg cgagacccac gctcaccggc tccagattta tcagcaataa    4680
accagccagc cggaagggcc gagcgcagaa gtggtcctgc aactttatcc gcctccatcc    4740
agtctattaa ttgttgccgg gaagctagag taagtagttc gccagttaat agtttgcgca    4800
acgttgttgc cattgctaca ggcatcgtgg tgtcacgctc gtcgtttggt atggcttcat    4860
tcagctccgg ttcccaacga tcaaggcgag ttacatgatc ccccatgttg tgcaaaaaag    4920
cggttagctc cttcggtcct ccgatcgttg tcagaagtaa gttggccgca gtgttatcac    4980
tcatggttat ggcagcactg cataattctc ttactgtcat gccatccgta agatgctttt    5040
ctgtgactgg tgagtactca accaagtcat tctgagaata gtgtatgcgg cgaccgagtt    5100
gctcttgccc ggcgtcaata cgggataata ccgcgccaca gcagaact ttaaaagtgc      5160 tcatcattgg aaaacgttct cggggcgaa aactctcaag gatcttaccg ctgttgagat     5220
ccagttcgat gtaaccact cgtgcaccca actgatcttc agcatctttt actttcacca     5280
gcgtttctgg gtgagcaaaa acaggaaggc aaaatgccgc aaaaaaggga taagggcga    5340 cacggaaatg ttgaatactc atactcttcc ttttttcaata ttattgaagc atttatcagg  5400
gttattgtct catgagcgga tacatatttg aatgtattta gaaaaataaa caaatagggg    5460
ttccgcgcac atttccccga aaagtgccac ctgacgtc                             5498
```

<210> SEQ ID NO 139
<211> LENGTH: 6341
<212> TYPE: DNA
<213> ORGANISM: Artificial Sequence
<220> FEATURE:
<223> OTHER INFORMATION: pExodus RecE

<400> SEQUENCE: 139

```
gacggatcgg gagatctccc gatcccctat ggtgcactct cagtacaatc tgctctgatg       60
```

```
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
atgtccacta aaccctcttt cctcctgaga aaagccaaaa aatcaagcgg cgaacccgat      960
gtcgtcctct gggcaagcaa tgacttcgag tctacatgcg ctactctgga ctacctcatc     1020
gtgaagagtg ggaagaaact gagctcctat ttcaaagctg tcgcaacaaa ttttccagtg     1080
gtcaacgacc tgcctgcaga gggagaaatt gatttcacct ggtccgagag ataccagctg     1140
tccaaggact ctatgacatg ggaactgaaa ccaggagccg ctcccgataa tgctcactat     1200
cagggaaaca ccaatgtgaa cggggaggac atgacagaaa tcgaggaaaa catgctgctc     1260
ccaatctctg acaggagct gcccattaga tggctcgccc agcacgggag tgaaaagcct     1320
gtgacccatg tctcaaggga cggtctgcag gctctccata ttgccagagc tgaggaactg     1380
ccagcagtga ctgcactggc cgtcagtcac aagacctcac tgctcgatcc cctggagatc     1440
cgggaactgc ataagctcgt gcgcgatact gacaaagtct ttccaaaccc cggaaatagc     1500
aacctggggt cattaccgc tttctttgag gcatacctga atgccgatta tagaccgc      1560 ggactgctca ctaaggaatg gatgaaaggg aacagggtgt ctcacatcac aagaactgcc     1620 agtgggcta atgcaggcgg agggaacctg acagaccgag gcgagggctt cgtgcatgac     1680
ctgacatcac tcgctcgcga tgtggcaact ggcgtcctgg ctcgaagcat ggatctggac     1740
atctacaatc tccaccccgc ccatgctaag cggattgagg aaatcattgc cgagaacaag     1800
ccccctttct ccgtgtttcg ggacaagttc atcaccatgc ctggtggcct ggattactca     1860
cgcgccattg tggtcgccag cgtgaaggag gcccctatcg aattgaagt gatcccagct     1920 cacgtcacag agtatctgaa caaggtgctc accgaaacag atcatgcaaa ccctgaccca     1980
gagatcgtcg atattggatg cggcaggagc agcgcaccaa tgcctcagcg ggtgaccgag     2040
gaaggcaagc aggacgatga ggaaaaacca cagccctctg gcaccacagc agtggagcag     2100
ggagaggcag aaacaatgga gcccgacgcc acagaacacc atcaggacac tcagcctctg     2160
gatgcacaga gccaggtgaa cagcgtcgat gccaagtacc aggagctgcg agctgagctc     2220
cacgaagcaa ggaagaatat ccctagcaaa aacccagtgg acgatgacaa actgctcgca     2280
gccagccgag gtgagttcgt ggacggcatc tccgatccca acgacctaa gtgggtgaaa     2340 ggcatccaga ctagggactg tgtctaccag aatcagcccg agaccgaaaa gacaagtcct     2400
gatatgaacc agcctgagcc agtggtccag caggagcctg aaatcgcatg caatgcctgt     2460
```

```
gggcagaccg gaggggataa ctgcccagac tgtggagccg tgatggggga cgctacttat   2520
caggagacct tgatgagga atcccaggtc gaggccaagg aaaacgaccc tgaggaaatg    2580
gagggtgctg aacacccaca taatgagaac gcaggctccg atccccacag ggattgctct   2640
gacgagaccg gagaagtggc tgacccagtg atcgtcgagg atattgaacc cggtatctac   2700
tatggcattt ctaatgagaa ctaccatgcc ggtccaggca tctcaaagag ccagctggat   2760
gacattgcag acacacctgc cctgtatctc tggagaaaaa acgccccagt ggacactacc   2820
aagactaaaa ccctggatct cggcactgct ttccactgtc gggtgctgga gcccgaggaa   2880
tttctcgagt ctagagggcc cgtttaaacc cgctgatcag cctcgactgt gccttctagt   2940
tgccagccat ctgttgtttg cccctccccc gtgccttcct tgaccctgga aggtgccact   3000
cccactgtcc tttcctaata aaatgaggaa attgcatcgc attgtctgag taggtgtcat   3060
tctattctgg ggggtggggt ggggcaggac agcaagggg aggattggga agacaatagc    3120
aggcatgctg gggatgcggt gggctctatg gcttctgagg cggaaagaac cagctggggc   3180 tctaggggt atccccacgc gccctgtagc ggcgcattaa gcgcggcggg tgtggtggtt    3240
acgcgcagcg tgaccgctac acttgccagc gccctagcgc ccgctccttt cgctttcttc   3300
ccttcctttc tcgccacgtt cgccggcttt ccccgtcaag ctctaaatcg ggggctccct   3360
ttagggttcc gatttagtgc tttacggcac ctcgacccca aaaaacttga ttagggtgat   3420
ggttcacgta gtgggccatc gccctgatag acggtttttc gccctttgac gttggagtcc   3480
acgttcttta atagtggact cttgttccaa actggaacaa cactcaaccc tatctcggtc   3540
tattcttttg atttataagg gattttgccg atttcggcct attggttaaa aaatgagctg   3600
atttaacaaa aatttaacgc gaattaattc tgtggaatgt gtgtcagtta gggtgtggaa   3660
agtccccagg ctccccagca ggcagaagta tgcaaagcct atcaggacat agcgttggct   3720
acccgtgata ttgctgaaga gcttggcggc gaatgggctg accgcttcct cgtgctttac   3780
ggtatcgccg ctcccgattc gcagcgcatc gccttctatc gccttcttga cgagttcttc   3840
tgagcgggac tctggggttc gaaatgaccg accaagcgac gcccaacctg ccatcacgag   3900
atttcgattc caccgccgcc ttctatgaaa ggttgggctt cggaatcgtt ttccgggacg   3960
ccggctggat gatcctccag cgcggggatc tcatgctgga gttcttcgcc cacccccaact  4020 tgtttattgc agcttataat ggttacaaat aaagcaatag catcacaaat ttcacaaata   4080
aagcattttt ttcactgcat tctagttgtg gtttgtccaa actcatcaat gtatcttatc   4140
atgtctgtat accgtcgacc tctagctaga gcttggcgta atcatggtca tagctgtttc   4200
ctgtgtgaaa ttgttatccg ctcacaattc cacacaacat acgagccgga agcataaagt   4260
gtaaagcctg gggtgcctaa tgagtgagct aactcacatt aattgcgttg cgctcactgc   4320
ccgctttcca gtcgggaaac ctgtcgtgcc agctgcatta tgaatcggc caacgcgcgg    4380 ggagaggcgg tttgcgtatt gggcgctctt ccgcttcctc gctcactgac tcgctgcgct   4440
cggtcgttcg gctgcggcga gcggtatcag ctcactcaaa ggcggtaata cggttatcca   4500
cagaatcagg ggataacgca ggaaagaaca tgtgagcaaa aggccagcaa aaggccagga   4560
accgtaaaaa ggccgcgttg ctggcgtttt tccataggct ccgcccccct gacgagcatc   4620
acaaaaatcg acgctcaagt cagaggtggc gaaacccgac aggactataa agataccagg   4680
cgtttccccc tggaagctcc ctcgtgcgct ctcctgttcc gaccctgccg cttaccggat   4740
acctgtccgc ctttctccct tcgggaagcg tggcgctttc tcatagctca cgctgtaggt   4800
```

| atctcagttc ggtgtaggtc gttcgctcca agctgggctg tgtgcacgaa ccccccgttc | 4860 |
|---|---|
| agcccgaccg ctgcgcctta tccggtaact atcgtcttga gtccaacccg gtaagacacg | 4920 |
| acttatcgcc actggcagca gccactggta acaggattag cagagcgagg tatgtaggcg | 4980 |
| gtgctacaga gttcttgaag tggtggccta actacggcta cactagaaga acagtatttg | 5040 |
| gtatctgcgc tctgctgaag ccagttacct tcggaaaaag agttggtagc tcttgatccg | 5100 |
| gcaaacaaac caccgctggt agcggttttt ttgtttgcaa gcagcagatt acgcgcagaa | 5160 |
| aaaaggatc tcaagaagat cctttgatct tttctacggg gtctgacgct cagtggaacg | 5220 |
| aaaactcacg ttaagggatt ttggtcatga gattatcaaa aaggatcttc acctagatcc | 5280 |
| ttttaaatta aaaatgaagt tttaaatcaa tctaaagtat atatgagtaa acttggtctg | 5340 |
| acagttacca atgcttaatc agtgaggcac ctatctcagc gatctgtcta tttcgttcat | 5400 |
| ccatagttgc ctgactcccc gtcgtgtaga taactacgat acgggagggc ttaccatctg | 5460 |
| gccccagtgc tgcaatgata ccgcgagacc cacgctcacc ggctccagat ttatcagcaa | 5520 |
| taaaccagcc agccggaagg gccgagcgca gaagtggtcc tgcaacttta tccgcctcca | 5580 |
| tccagtctat taattgttgc cgggaagcta gagtaagtag ttcgccagtt aatagtttgc | 5640 |
| gcaacgttgt tgccattgct acaggcatcg tggtgtcacg ctcgtcgttt ggtatggctt | 5700 |
| cattcagctc cggttcccaa cgatcaaggc gagttacatg atcccccatg ttgtgcaaaa | 5760 |
| aagcggttag ctccttcggt cctccgatcg ttgtcagaag taagttggcc gcagtgttat | 5820 |
| cactcatggt tatggcagca ctgcataatt ctcttactgt catgccatcc gtaagatgct | 5880 |
| tttctgtgac tggtgagtac tcaaccaagt cattctgaga atagtgtatg cggcgaccga | 5940 |
| gttgctcttg cccggcgtca atacgggata ataccgcgcc acatagcaga actttaaaag | 6000 |
| tgctcatcat tggaaaacgt tcttcggggc gaaaactctc aaggatctta ccgctgttga | 6060 |
| gatccagttc gatgtaaccc actcgtgcac ccaactgatc ttcagcatct tttactttca | 6120 |
| ccagcgtttc tgggtgagca aaaacaggaa ggcaaaatgc cgcaaaaaag gaataagggg | 6180 |
| cgacacggaa atgttgaata ctcatactct tcctttttca atattattga agcatttatc | 6240 |
| agggttattg tctcatgagc ggatacatat ttgaatgtat ttagaaaaat aaacaaatag | 6300 |
| gggttccgcg cacatttccc cgaaaagtgc cacctgacgt c | 6341 |

<210> SEQ ID NO 140
<211> LENGTH: 6434
<212> TYPE: DNA
<213> ORGANISM: Artificial Sequence
<220> FEATURE:
<223> OTHER INFORMATION: pExodus Artemis

<400> SEQUENCE: 140

| gacggatcgg gagatctccc gatccccctat ggtgcactct cagtacaatc tgctctgatg | 60 |
|---|---|
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |

```
atgcccagta catgaccttta tgggactttc tacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
atgtcctcat ttgaagggca gatggcagaa taccccacca ttagcattga tagatttgat    960
agggaaaacc tcagggcacg ggcttatttc ctgagccact gccataagga ccacatgaaa   1020
gggctcaggg cacctaccct caagaggaga ctggagtgct ccctcaaagt ctacctgtat   1080
tgttctccag tgacaaagga gctgctcctg acttccccca atatcgctt ttggaagaaa   1140
cgaatcattt ctatcgagat tgaaactcca acccagatca gtctggtgga tgaggcttca   1200
ggcgaaaagg aggaaattgt ggtcaccctc ctgccagcag gacactgtcc aggtagcgtc   1260
atgttcctgt ttcagggcaa caatggaacc gtgctgtaca caggcgactt ccgcctcgct   1320
cagggagagg cagctcgaat ggaactcctg cattctggcg gacgggtcaa ggatatccag   1380
agtgtgtatc tggacaccac attctgcgat ccccggtttt accagattcc tagccgcgag   1440
gaatgtctgt ccggagtgct ggagctggtg aggtcatgga tcaccagaag cccatatcac   1500
gtggtctggc tgaactgcaa ggcagcctac gggtatgagt acctcttcac aaatctgtcc   1560
gaggaactcg gtgtgcaggt ccatgtgaac aaactggaca tgtttcgcaa tatgcccgag   1620
atcctccacc atctgactac cgataggaac acccagattc acgcttgcag acatcccaag   1680
gcagaggaat acttccagtg gagtaaactg ccttgtggca tcacttcacg gaaccgcatt   1740
cccctccaca tcattagcat caagccttcc accatgtggt ttggcgagcg atccaggaaa   1800
accaatgtca ttgtgcgaac aggagaaagc tcctataggg cctgcttctc ttttcattct   1860
agttacagtg agatcaagga cttcctctct tatctgtgtc ctgtgaacgc ttaccctaat   1920
gtcatcccag tgggcacaac tatggataag gtggtcgaga ttctcaaacc actgtgtcgg   1980
tcaagccaga gcacagaacc caagtacaaa cctctcggaa agctgaaaag agcccggact   2040
gtgcaccgag acagcgagga agaggacgat tatctgtttg acgatcccct gcctatccca   2100
ctcagacaca aggtgcccta ccctgagact ttccatcccg aagtcttttc catgaccgct   2160
gtgtctgaga agcagccaga aaaactgaga cagaccccag gatgctgtcg agcagagtgc   2220
atgcagtcct ctaggttcac aaactttgtg gactgtgaag agtccaattc tgagagtgaa   2280
gaggaagtgg gcatccccgc ctcactgcag ggggatctcg gtagcgtgct ccacctgcag   2340
aaggctgacg gcgacgtccc acagtgggag gtgttcttta aagaaacga cgaaatcacc   2400
gatgagtccc tggaaaattt ccctagttca acagtggccg ggggttcaca gagcccaaag   2460
ctgtttttccg actctgatgg ggagtctact cacatcagct cccagaactc tagtcagagc   2520
acacatatta ctgagcaggg ctcccaggga tgggacagtc agtcagatac agtcctggtg   2580
tcaagccagg agcggaacag tgtgacatc acatcactgg acaaggcaga ttatcgccct   2640
actatcaaag agaacattcc agccagcctg atggaacaga atgtgatttg ccctaaggac   2700
acctactctg atctgaagag tagagacaaa gatgtcacta tcgtgcctag caccggcgag   2760
ccaaccacac tgtcctctga aactcacatt cccgaggaaa agagcctcct gaacctgtcc   2820
accaatgcag actctcagag ttcaagcgat ttcgaggtgc catctacacc cgaggccgaa   2880
```

```
ctgcctaagc gggaacatct ccagtatctg tacgagaaac tggccacagg agaaagcatc   2940
gctgtgaaga aacgcaagtg tagcctcctg gacactctcg agtctagagg gcccgtttaa   3000
acccgctgat cagcctcgac tgtgccttct agttgccagc catctgttgt ttgcccctcc   3060
cccgtgcctt ccttgaccct ggaaggtgcc actcccactg tccttcccta ataaaatgag   3120
gaaattgcat cgcattgtct gagtaggtgt cattctattc tggggggtgg ggtggggcag   3180
gacagcaagg gggaggattg ggaagacaat agcaggcatg ctggggatgc ggtgggctct   3240
atggcttctg aggcggaaag aaccagctgg ggctctaggg ggtatcccca cgcgccctgt   3300
agcggcgcat taagcgcggc gggtgtggtg gttacgcgca gcgtgaccgc tacacttgcc   3360
agcgccctag cgcccgctcc tttcgctttc ttcccttcct ttctcgccac gttcgccggc   3420
tttccccgtc aagctctaaa tcggggggctc cctttagggt tccgatttag tgctttacgg   3480
cacctcgacc ccaaaaaact tgattagggt gatggttcac gtagtgggcc atcgccctga   3540
tagacggttt ttcgcccttt gacgttggag tccacgttct ttaatagtgg actcttgttc   3600
caaactggaa caacactcaa ccctatctcg gtctattctt ttgatttata agggattttg   3660
ccgatttcgg cctattggtt aaaaaatgag ctgatttaac aaaaatttaa cgcgaattaa   3720
ttctgtggaa tgtgtgtcag ttagggtgtg aaagtccccc aggctcccca gcaggcagaa   3780
gtatgcaaag cctatcagga catagcgttg gctacccgtg atattgctga agagcttggc   3840
ggcgaatggg ctgaccgctt cctcgtgctt tacggtatcg ccgctcccga ttcgcagcgc   3900
atcgccttct atcgccttct tgacgagttc ttctgagcgg gactctgggg ttcgaaatga   3960
ccgaccaagc gacgcccaac ctgccatcac gagatttcga ttccaccgcc gccttctatg   4020
aaaggttggg cttcggaatc gttttccggg acgccggctg gatgatcctc cagcgcgggg   4080
atctcatgct ggagttcttc gcccacccca acttgtttat tgcagcttat aatggttaca   4140
aataaagcaa tagcatcaca aatttcacaa ataaagcatt ttttttcactg cattctagtt   4200 gtggtttgtc caaactcatc aatgtatctt atcatgtctg tataccgtcg acctctagct   4260
agagcttggc gtaatcatgg tcatagctgt ttcctgtgtg aaattgttat ccgctcacaa   4320
ttccacacaa catacgagcc ggaagcataa agtgtaaagc ctggggtgcc taatgagtga   4380
gctaactcac attaattgcg ttgcgctcac tgcccgcttt ccagtcggga aacctgtcgt   4440
gccagctgca ttaatgaatc ggccaacgcg cggggagagg cggtttgcgt attgggcgct   4500
cttccgcttc ctcgctcact gactcgctgc gctcggtcgt tcggctgcgg cgagcggtat   4560
cagctcactc aaaggcggta atacggttat ccacagaatc aggggataac gcaggaaaga   4620
acatgtgagc aaaaggccag caaaaggcca ggaaccgtaa aaaggccgcg ttgctggcgt   4680
ttttccatag gctccgcccc cctgacgagc atcacaaaaa tcgacgctca agtcagaggt   4740
ggcgaaaccc gacaggacta taaagatacc aggcgtttcc ccctggaagc tccctcgtgc   4800
gctctcctgt tccgaccctg ccgcttaccg gatacctgtc cgcctttctc ccttcgggaa   4860
gcgtggcgct ttctcatagc tcacgctgta ggtatctcag ttcggtgtag gtcgttcgct   4920
ccaagctggg ctgtgtgcac gaaccccccg ttcagcccga ccgctgcgcc ttatccggta   4980
actatcgtct tgagtccaac ccggtaagac acgacttatc gccactggca gcagccactg   5040
gtaacaggat tagcagagcg aggtatgtag gcggtgctac agagttcttg aagtggtggc   5100
ctaactacgg ctacactaga agaacagtat ttggtatctg cgctctgctg aagccagtta   5160
ccttcggaaa aagagttggt agctcttgat ccggcaaaca aaccaccgct ggtagcggt    5220 ttttttgtttg caagcagcag attacgcgca gaaaaaaagg atctcaagaa gatcctttga   5280
```

```
tcttttctac ggggtctgac gctcagtgga acgaaaactc acgttaaggg attttggtca    5340
tgagattatc aaaaaggatc ttcacctaga tccttttaaa ttaaaaatga agttttaaat    5400
caatctaaag tatatatgag taaacttggt ctgacagtta ccaatgctta atcagtgagg    5460
cacctatctc agcgatctgt ctatttcgtt catccatagt tgcctgactc cccgtcgtgt    5520
agataactac gatacgggag ggcttaccat ctggccccag tgctgcaatg ataccgcgag    5580
acccacgctc accggctcca gatttatcag caataaacca gccagccgga agggccgagc    5640
gcagaagtgg tcctgcaact ttatccgcct ccatccagtc tattaattgt tgccgggaag    5700
ctagagtaag tagttcgcca gttaatagtt tgcgcaacgt tgttgccatt gctacaggca    5760
tcgtggtgtc acgctcgtcg tttggtatgg cttcattcag ctccggttcc caacgatcaa    5820
ggcgagttac atgatccccc atgttgtgca aaaaagcggt tagctccttc ggtcctccga    5880
tcgttgtcag aagtaagttg gccgcagtgt tatcactcat ggttatggca gcactgcata    5940
attctcttac tgtcatgcca tccgtaagat gcttttctgt gactggtgag tactcaacca    6000
agtcattctg agaatagtgt atgcggcgac cgagttgctc ttgcccggcg tcaatacggg    6060
ataataccgc gccacatagc agaactttaa aagtgctcat cattggaaaa cgttcttcgg    6120
ggcgaaaact ctcaaggatc ttaccgctgt tgagatccag ttcgatgtaa cccactcgtg    6180
cacccaactg atcttcagca tcttttactt tcaccagcgt ttctgggtga gcaaaaacag    6240
gaaggcaaaa tgccgcaaaa aagggaataa gggcgacacg gaaatgttga atactcatac    6300
tcttcctttt tcaatattat tgaagcattt atcagggtta ttgtctcatg agcggataca    6360
tatttgaatg tatttagaaa aataaacaaa taggggttcc gcgcacattt ccccgaaaag    6420
tgccacctga cgtc                                                      6434

<210> SEQ ID NO 141
<211> LENGTH: 6419
<212> TYPE: DNA
<213> ORGANISM: Artificial Sequence
<220> FEATURE:
<223> OTHER INFORMATION: pExodus Dna2

<400> SEQUENCE: 141
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
```

```
ctgcttactg gcttatcgaa attaatacga ctcactatag ggagacccaa gctggctagc      900
atggaacagc tcaacgaact ggaactcctc atggagaagt ccttttggga agaagccgaa      960
ctgcctgccg aactgtttca gaagaaggtg gtcgcttctt tcccccgcac cgtgctgagt     1020
acagggatgg acaaccgata cctcgtcctg gcagtgaata ccgtccagaa caaagagggt     1080
aattgcgaaa agcgactggt catcacagcc agccagtccc tggagaataa ggaactgtgc     1140
attctcagaa acgactggtg ttccgtgcca gtcgagcccg cgatatcat tcacctggaa      1200
ggagactgca catctgatac ttggatcatt gacaaggatt tcggctacct catcctgtat     1260
cctgacatgc tgattagcgg aacttccatc gccagctcca ttaggtgtat gaggagagct     1320
gtgctgagcg agacctttcg ctctagtgat cccgctaccc gacagatgct catcggcaca     1380
gtgctgcacg aggtcttcca gaaagccatt aacaatagct tgctcctga aagctgcag      1440
gaactcgcat ttcagacaat ccaggagatt aggcatctga agaaatgta cagactcaat      1500
ctgtctcagg acgagatcaa gcaggaggtg aagattatc tgccaagttt ctgcaaatgg     1560
gccggagact ttatgcataa gaacactagc accgatttcc cacagatgca gctctctctg     1620
cccagtgaca actcaaaaga taattccacc tgtaacatcg aggtggtcaa gcctatggac     1680
atcgaggaaa gcatttggtc cccacggttt gggctgaagg gtaaaatcga tgtgactgtc     1740
ggggtgaaga ttcaccgcgg ttacaagacc aaatataaga tcatgcccct ggagctgaag     1800
acaggcaagg agtctaacag tattgaacat cggtcccagg tggtcctgta cacactgctc     1860
tctcaggagc gacgagccga ccccgaagct ggactgctcc tgtacctgaa gactggacag     1920
atgtatcccg tgcctgcaaa tcacctggat aaaagagagc tcctgaagct gcggaaccag     1980
atggccttca gcctgtttca tcggatctca aaaagcgcaa ctcgccagaa gacccagctg     2040
gccagcctcc ctcagatcat tgaggaagag aaaacatgca agtactgtag tcagatcgga     2100
aattgcgcac tgtattcaag agccgtggag cagcagatgg actgttcaag cgtgcccatc     2160
gtcatgctgc taaaattga agaggaaaca cagcacctca gcagactca tctgagtat       2220
ttctccctct ggtgcctcat gctgacccct gaatcccagt ctaaggacaa caagaaaaat     2280
caccagaaca tctggctgat gcctgcttct gagatggaaa agagtggctc atgtatcgga     2340
aacctgatta ggatggagca tgtgaagatt gtctgcgacg ggcagtacct gcacaatttc     2400
cagtgtaagc atggtgctat cccagtgacc aacctgatgg cagggataga gtcattgtg      2460
tctggcgagg aacgaagtct gtttgccctc tcaagggat atgtgaagga gatcaatatg      2520
accacagtca catgcctcct ggacaggaac ctgagcgtgc tcccagaatc cactctgttc     2580
agactcgatc aggaggagaa gaactgtgac atcgatactc ccctggggaa tctcagcaag    2640
ctgatggaga cacctttgt gtccaagaaa ctcagagacc tgatcattga tttccgggaa     2700
cccagtttta tctcctacct ctcctctgtg ctgcctcacg acgctaagga taccgtcgca    2760
tgcattctca aagggctgaa caagcctcag cggcaggcta tgaagaaagt gctcctgtct    2820
aaagactata ctctgatcgt cggcatgcca ggcaccggaa agactaccac aatctgtaca    2880
ctggtgcgct tccgaaggtt tattcagctc agttcaaatc tgcagtcaaa gaaattcgcc    2940
gatcagagcc ctctgaaccc actcgagtct agagggccct tttaaacccg ctgatcagcc    3000
tcgactgtgc cttctagttg ccagccatct gttgtttgcc cctcccccgt gccttccttg    3060
accctggaag gtgccactcc cactgtcctt tcctaataaa atgaggaaat tgcatcgcat    3120
tgtctgagta ggtgtcattc tattctgggg ggtggggtgg gcaggacag caaggggag     3180
gattgggaag acaatagcag gcatgctggg gatgcggtgg gctctatggc ttctgaggcg    3240
```

```
gaaagaacca gctggggctc tagggggtat ccccacgcgc cctgtagcgg cgcattaagc   3300
gcggcgggtg tggtggttac gcgcagcgtg accgctacac ttgccagcgc cctagcgccc   3360
gctcctttcg ctttcttccc ttcctttctc gccacgttcg ccggctttcc ccgtcaagct   3420
ctaaatcggg ggctcccttt agggttccga tttagtgctt tacggcacct cgaccccaaa   3480
aaacttgatt agggtgatgg ttcacgtagt gggccatcgc cctgatagac ggttttcgc    3540 cctttgacgt tggagtccac gttctttaat agtggactct tgttccaaac tggaacaaca   3600
ctcaacccta tctcggtcta ttcttttgat ttataaggga ttttgccgat tcggcctat    3660 tggttaaaaa atgagctgat ttaacaaaaa tttaacgcga attaattctg tggaatgtgt   3720
gtcagttagg gtgtggaaag tccccaggct ccccagcagg cagaagtatg caaagcctat   3780
caggacatag cgttggctac ccgtgatatt gctgaagagc ttggcggcga atgggctgac   3840
cgcttcctcg tgctttacgg tatcgccgct cccgattcgc agcgcatcgc cttctatcgc   3900
cttcttgacg agttcttctg agcgggactc tggggttcga atgaccgac caagcgacgc    3960 ccaacctgcc atcacgagat ttcgattcca ccgccgcctt ctatgaaagg ttgggcttcg   4020
gaatcgtttt ccgggacgcc ggctggatga tcctccagcg cggggatctc atgctggagt   4080
tcttcgccca ccccaacttg tttattgcag cttataatgg ttacaaataa agcaatagca   4140
tcacaaattt cacaaataaa gcatttttt cactgcattc tagttgtggt ttgtccaaac    4200
tcatcaatgt atcttatcat gtctgtatac cgtcgacctc tagctagagc ttggcgtaat   4260
catggtcata gctgtttcct gtgtgaaatt gttatccgct cacaattcca cacaacatac   4320
gagccggaag cataaagtgt aaagcctggg gtgcctaatg agtgagctaa ctcacattaa   4380
ttgcgttgcg ctcactgccc gctttccagt cgggaaacct gtcgtgccag ctgcattaat   4440
gaatcggcca acgcgcgggg agaggcggtt tgcgtattgg gcgctcttcc gcttcctcgc   4500
tcactgactc gctgcgctcg tcgttcggc tgcggcgagc ggtatcagct cactcaaagg    4560
cggtaatacg gttatccaca gaatcagggg ataacgcagg aaagaacatg tgagcaaaag   4620
gccagcaaaa ggccaggaac cgtaaaaagg ccgcgttgct ggcgtttttc cataggctcc   4680
gcccccctga cgagcatcac aaaaatcgac gctcaagtca gaggtggcga aacccgacag   4740
gactataaag ataccaggcg tttccccctg gaagctccct cgtgcgctct cctgttccga   4800
ccctgccgct taccggatac ctgtccgcct ttctcccttc gggaagcgtg gcgctttctc   4860
atagctcacg ctgtaggtat ctcagttcgg tgtaggtcgt tcgctccaag ctgggctgtg   4920
tgcacgaacc ccccgttcag cccgaccgct gcgccttatc cggtaactat cgtcttgagt   4980
ccaacccggt aagacacgac ttatcgccac tggcagcagc cactggtaac aggattagca   5040
gagcgaggta tgtaggcggt gctacagagt tcttgaagtg gtggcctaac tacggctaca   5100
ctagaagaac agtatttggt atctgcgctc tgctgaagcc agttaccttc ggaaaaagag   5160
ttggtagctc ttgatccggc aaacaaacca ccgctggtag cggtttttt gtttgcaagc    5220 agcagattac gcgcagaaaa aaaggatctc aagaagatcc tttgatcttt tctacggggt   5280
ctgacgctca gtggaacgaa aactcacgtt aagggatttt ggtcatgaga ttatcaaaaa   5340
ggatcttcac ctagatcctt ttaaattaaa aatgaagttt aaatcaatc taaagtatat    5400 atgagtaaac ttggtctgac agttaccaat gcttaatcag tgaggcacct atctcagcga   5460
tctgtctatt tcgttcatcc atagttgcct gactccccgt cgtgtagata actacgatac   5520
gggagggctt accatctggc cccagtgctg caatgatacc gcgagaccca cgctcaccgg   5580
```

```
ctccagattt atcagcaata aaccagccag ccggaagggc cgagcgcaga agtggtcctg    5640
caactttatc cgcctccatc cagtctatta attgttgccg ggaagctaga gtaagtagtt    5700
cgccagttaa tagtttgcgc aacgttgttg ccattgctac aggcatcgtg gtgtcacgct    5760
cgtcgtttgg tatggcttca ttcagctccg gttcccaacg atcaaggcga gttacatgat    5820
cccccatgtt gtgcaaaaaa gcggttagct ccttcggtcc tccgatcgtt gtcagaagta    5880
agttggccgc agtgttatca ctcatggtta tggcagcact gcataattct cttactgtca    5940
tgccatccgt aagatgcttt tctgtgactg gtgagtactc aaccaagtca ttctgagaat    6000
agtgtatgcg cgaccgagt tgctcttgcc cggcgtcaat acgggataat accgcgccac    6060
atagcagaac tttaaaagtg ctcatcattg gaaaacgttc ttcggggcga aaactctcaa    6120
ggatcttacc gctgttgaga tccagttcga tgtaacccac tcgtgcaccc aactgatctt    6180
cagcatcttt tactttcacc agcgtttctg ggtgagcaaa aacaggaagg caaaatgccg    6240
caaaaaaggg aataagggcg acacggaaat gttgaatact catactcttc ctttttcaat    6300
attattgaag catttatcag ggttattgtc tcatgagcgg atacatattt gaatgtattt    6360
agaaaaataa acaaataggg gttccgcgca catttccccg aaaagtgcca cctgacgtc    6419
```

<210> SEQ ID NO 142
<211> LENGTH: 6482
<212> TYPE: DNA
<213> ORGANISM: Artificial Sequence
<220> FEATURE:
<223> OTHER INFORMATION: pExodus MreII

<400> SEQUENCE: 142

```
gacggatcgg agatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
atgagcaccg cagacgccct ggacgatgag aacacattca aaatcctggt cgcaacagac     960
attcacctcg ggtttatgga gaaagacgcc gtgagggga acgatacttt cgtcaccctg    1020
gacgagatcc tgcggctcgc tcaggagaac gaagtggatt tcattctgct cggcggagac    1080
ctgtttcacg aaaataagcc aagcagaaaa acactccata cttgcctgga gctgctccgc    1140
aagtactgta tgggcgatcg accagtgcag ttcgagatcc tgtctgacca gagtgtcaac    1200
ttcggatttt ccaagttccc ctgggtgaat tatcaggatg ggaacctgaa tatctcaatt    1260
```

```
cccgtgttca gcatccacgg caaccatgac gatcctaccg gagcagatgc cctgtgcgcc    1320
ctcgacatcc tgagctgtgc tgggttcgtg aatcactttg gcaggtccat gtctgtggag    1380
aagatcgaca tttctcccgt cctgctccag aagggcagta ccaaaatcgc cctctacggc    1440
ctgggaagca ttcctgatga gcgcctctat cgaatgtttg tgaacaagaa agtcacaatg    1500
ctgcgcccaa aggaggacga aaactcctgg ttcaatctct tgtgatcca ccagaaccgg     1560
tctaaacatg gcagtacaaa tttcattcct gagcagttcc tcgacgattt tatcgacctg    1620
gtcatctggg gacacgagca tgaatgcaag atcgctccaa caaaaaacga acagcagctg    1680
tttacatttt ctcagcctgg gagctccgtg gtcactagtc tgtcaccagg cgaggcagtg    1740
aagaaacacg tcggcctgct ccggatcaag ggacgcaaaa tgaacatgca caagattccc    1800
ctgcatactg tgagacagtt ctttatggag gatatcgtcc tggccaatca tcctgatatt    1860
ttcaaccccg acaatcctaa ggtgacccag gctatccaga gcttttgtct cgaaaaaatt    1920
gaggaaatgc tggagaacgc agagcgcgaa cgactgggaa attcccacca gccagaaaag    1980
cccctcgtga ggctgagagt ggactattct gggggtttcg agccattttc cgtgctgaga    2040
ttctctcaga agtttgtgga tcgggtcgct aacccccaaag acatcattca cttctttcgg    2100
catcgcgagc agaaggaaaa aacaggggag gaaatcaatt tcggcaagct gattactaaa    2160
ccttctgaag gaccacact cagggtggag gacctggtca agcagtactt tcagaccgcc     2220
gagaagaacg tgcagctgag cctgctcaca gagagaggga tgggtgaagc tgtgcaggag    2280
ttcgtcgata ggaggaaaa agacgcaatc gaggaactcg tgaagtatca gctggagaaa    2340
acccagcgat tcctcaagga aaggcacatc gacgctctgg aggataaaat tgacgaggaa    2400
gtcaggaggt tcagggagac cagacagaag aacacaaatg aggaagacga tgaggtgcgc    2460
gaagcaatga cacgagctag ggcactgagg agccagtccg aggaatctgc cagtgctttc    2520
agtgccgacg atctcatgtc aatcgatctg gctgagcaga tggcaaacga ctccgacgat    2580
tcaatcagcg ccgctactaa taagggcaga ggacgggggc gcggtcggcg cggcggacgc    2640
ggacagaact ccgcatctag gggggttct cagcgaggca gggcagatac tggactggag     2700
acctcaacaa gaagccggaa ctccaagacc gcagtgagtg cctcacggaa tatgagcatc    2760
attgacgcct tcaagagcac cagacagcag ccctcccgga acgtcactac caaaaattac    2820
tcagaagtga tcgaagtcga tgagagcgac gtggaggaag atatttttcc tacaactagt    2880
aagactgacc agaggtggtc tagtacctca agctccaaga tcatgagcca gtcccaggtg    2940
tccaaaggag tggacttcga atctagtgag gacgatgacg atgacccctt catgaacaca    3000
tcaagcctgc gaaggaatag acggctcgag tctagagggc ccgtttaaac ccgctgatca    3060
gcctcgactg tgccttctag ttgccagcca tctgttgttt gccctccccc cgtgccttcc    3120
ttgaccctgg aaggtgccac tcccactgtc cttttctaat aaaatgagga aattgcatcg    3180
cattgtctga gtaggtgtca ttctattctg ggggtgggg tggggcagga cagcaagggg     3240
gaggattggg aagacaatag caggcatgct ggggatgcgg tgggctctat ggcttctgag    3300
gcggaaagaa ccagctgggg ctctagggggg tatccccacg cgccctgtag cggcgcatta   3360
agcgcggcgg gtgtggtggt tacgcgcagc gtgaccgcta cacttgccag cgccctagcg    3420
cccgctcctt tcgctttctt cccttccttt ctcgccacgt tcgccggctt tccccgtcaa    3480
gctctaaatc gggggctccc tttagggttc cgatttagtg ctttacgca cctcgacccc     3540
aaaaaacttg attagggtga tggttcacgt agtgggccat cgccctgata gacggttttt    3600
```

```
cgcccttcga cgttggagtc cacgttcttt aatagtggac tcttgttcca aactggaaca      3660
acactcaacc ctatctcggt ctattctttt gatttataag ggattttgcc gatttcggcc      3720
tattggttaa aaaatgagct gatttaacaa aaatttaacg cgaattaatt ctgtggaatg      3780
tgtgtcagtt agggtgtgga aagtcccag gctcccagc aggcagaagt atgcaaagcc        3840
tatcaggaca tagcgttggc tacccgtgat attgctgaag agcttggcgg cgaatgggct      3900
gaccgcttcc tcgtgcttta cggtatcgcc gctcccgatt cgcagcgcat cgccttctat      3960
cgccttcttg acgagttctt ctgagcggga ctctggggtt cgaaatgacc gaccaagcga      4020
cgcccaacct gccatcacga gatttcgatt ccaccgccgc cttctatgaa aggttgggct      4080
tcggaatcgt tttccgggac gccggctgga tgatcctcca gcgcgggat ctcatgctgg       4140 agttcttcgc ccaccccaac ttgtttattg cagcttataa tggttacaaa taaagcaata     4200
gcatcacaaa tttcacaaat aaagcatttt tttcactgca ttctagttgt ggtttgtcca     4260
aactcatcaa tgtatcttat catgtctgta taccgtcgac ctctagctag agcttggcgt     4320
aatcatggtc atagctgttt cctgtgtgaa attgttatcc gctcacaatt ccacacaaca     4380
tacgagccgg aagcataaag tgtaaagcct ggggtgccta atgagtgagc taactcacat     4440
taattgcgtt gcgctcactg cccgctttcc agtcgggaaa cctgtcgtgc cagctgcatt     4500
aatgaatcgg ccaacgcgcg gggagaggcg gtttgcgtat tgggcgctct tccgcttcct     4560
cgctcactga ctcgctgcgc tcggtcgttc ggctgcggcg agcggtatca gctcactcaa     4620
aggcggtaat acggttatcc acagaatcag gggataacgc aggaaagaac atgtgagcaa     4680
aaggccagca aaaggccagg aaccgtaaaa aggccgcgtt gctggcgttt ttccataggc     4740 tccgccccc tgacgagcat cacaaaaatc gacgctcaag tcagaggtgg cgaaacccga      4800
caggactata aagataccag gcgtttcccc ctggaagctc cctcgtgcgc tctcctgttc     4860
cgaccctgcc gcttaccgga tacctgtccg cctttctccc ttcgggaagc gtggcgcttt    4920
ctcatagctc acgctgtagg tatctcagtt cggtgtaggt cgttcgctcc aagctgggct     4980
gtgtgcacga accccccgtt cagcccgacc gctgcgcctt atccggtaac tatcgtcttg     5040
agtccaaccc ggtaagacac gacttatcgc cactggcagc agccactggt aacaggatta    5100
gcagagcgag gtatgtaggc ggtgctacag agttcttgaa gtggtggcct aactacggct    5160
acactagaag aacagtattt ggtatctgcg ctctgctgaa gccagttacc ttcggaaaaa     5220
gagttggtag ctcttgatcc ggcaaacaaa ccaccgctgg tagcggtttt tttgtttgca    5280
agcagcagat tacgcgcaga aaaaaaggat ctcaagaaga tcctttgatc ttttctacgg    5340
ggtctgacgc tcagtggaac gaaaactcac gttaagggat tttggtcatg agattatcaa    5400
aaaggatctt cacctagatc cttttaaatt aaaaatgaag ttttaaatca atctaaagta    5460
tatatgagta aacttggtct gacagttacc aatgcttaat cagtgaggca cctatctcag    5520
cgatctgtct atttcgttca tccatagttg cctgactccc cgtcgtgtag ataactacga    5580
tacgggaggg cttaccatct ggccccagtg ctgcaatgat accgcgagac ccacgctcac    5640
cggctccaga tttatcagca ataaaccagc cagccggaag ggccgagcgc agaagtggtc    5700
ctgcaacttt atccgcctcc atccagtcta ttaattgttg ccgggaagct agagtaagta    5760
gttcgccagt taatagtttg cgcaacgttg ttgccattgc tacaggcatc gtggtgtcac    5820
gctcgtcgtt tggtatggct tcattcagct ccggttccca acgatcaagg cgagttacat    5880 gatccccat gttgtgcaaa aaagcggtta gctccttcgg tcctccgatc gttgtcagaa     5940
gtaagttggc cgcagtgtta tcactcatgg ttatggcagc actgcataat tctcttactg    6000
```

| | | | |
|---|---|---|---|
| tcatgccatc | cgtaagatgc | ttttctgtga ctggtgagta | ctcaaccaag tcattctgag | 6060 |
| aatagtgtat | gcggcgaccg | agttgctctt gcccggcgtc | aatacgggat aataccgcgc | 6120 |
| cacatagcag | aactttaaaa | gtgctcatca ttggaaaacg | ttcttcgggg cgaaaactct | 6180 |
| caaggatctt | accgctgttg | agatccagtt cgatgtaacc | cactcgtgca cccaactgat | 6240 |
| cttcagcatc | ttttactttc | accagcgttt ctgggtgagc | aaaaacagga aggcaaaatg | 6300 |
| ccgcaaaaaa | gggaataagg | gcgacacgga aatgttgaat | actcatactc ttcctttttc | 6360 |
| aatattattg | aagcatttat | cagggttatt gtctcatgag | cggatacata tttgaatgta | 6420 |
| tttagaaaaa | taaacaaata | ggggttccgc gcacatttcc | ccgaaaagtg ccacctgacg | 6480 |
| tc | | | | 6482 |

<210> SEQ ID NO 143
<211> LENGTH: 5885
<212> TYPE: DNA
<213> ORGANISM: Artificial Sequence
<220> FEATURE:
<223> OTHER INFORMATION: pExodus TdT

<400> SEQUENCE: 143

| | | | | |
|---|---|---|---|---|
| gacggatcgg | gagatctccc | gatcccctat | ggtgcactct cagtacaatc | tgctctgatg | 60 |
| ccgcatagtt | aagccagtat | ctgctccctg | cttgtgtgtt ggaggtcgct | gagtagtgcg | 120 |
| cgagcaaaat | ttaagctaca | acaaggcaag | gcttgaccga caattgcatg | aagaatctgc | 180 |
| ttagggttag | gcgttttgcg | ctgcttcgcg | atgtacgggc cagatatacg | cgttgacatt | 240 |
| gattattgac | tagttattaa | tagtaatcaa | ttacggggtc attagttcat | agcccatata | 300 |
| tggagttccg | cgttacataa | cttacggtaa | atggcccgcc tggctgaccg | cccaacgacc | 360 |
| cccgcccatt | gacgtcaata | atgacgtatg | ttcccatagt aacgccaata | gggactttcc | 420 |
| attgacgtca | atgggtggag | tatttacggt | aaactgccca cttggcagta | catcaagtgt | 480 |
| atcatatgcc | aagtacgccc | cctattgacg | tcaatgacgg taaatggccc | gcctggcatt | 540 |
| atgcccagta | catgacctta | tgggactttc | ctacttggca gtacatctac | gtattagtca | 600 |
| tcgctattac | catggtgatg | cggttttggc | agtacatcaa tgggcgtgga | tagcggtttg | 660 |
| actcacgggg | atttccaagt | ctccacccca | ttgacgtcaa tgggagtttg | ttttggcacc | 720 |
| aaaatcaacg | ggacttttcca | aaatgtcgta | acaactccgc cccattgacg | caaatgggcg | 780 |
| gtaggcgtgt | acggtgggag | gtctatataa | gcagagctct ctggctaact | agagaaccca | 840 |
| ctgcttactg | gcttatcgaa | attaatacga | ctcactatag ggagacccaa | gctggctagc | 900 |
| atggacccac | caagggcatc | acatctctcc | cccaggaaga aaagaccaag | acagacaggc | 960 |
| gctctcatgg | caagttcacc | tcaggatatc | aagttccagg acctcgtggt | ctttattctg | 1020 |
| gaaaagaaaa | tgggaaccac | aaggagagca | ttcctcatgg agctggcccg | gcgcaagggg | 1080 |
| tttagggtgg | aaaacgagct | gtccgactct | gtcacacaca tcgtggctga | aacaatagt | 1140 |
| ggttcagatg | tgctcgaatg | gctgcaggca | cagaaggtgc aggtcagctc | ccagcccgag | 1200 |
| ctgctcgatg | tcagctggct | gatcgaatgc | attagagctg gcaagccgt | ggagatgact | 1260 |
| ggcaaacatc | agctggtggt | ccgaagggac | tacagcgatt ccactaaccc | aggaccacct | 1320 |
| aagacccac | caatcgctgt | gcagaaaatt | agtcagtatg catgccagag | acggactacc | 1380 |
| ctgaacaatt | gtaatcagat | tttcaccgac | gcctttgata ttctggctga | aaactgcgag | 1440 |
| ttccgagaaa | atgaggactc | ctgtgtcacc | ttcatgagag ccgcttccgt | gctcaagtct | 1500 |

```
ctgcctttca caatcatctc aatgaaggat actgagggca tcccatgcct gggaagcaag    1560
gtgaaaggga tcattgagga aatcattgaa gacggagagt ctagtgaagt caaggccgtg    1620
ctgaacgatg agagatacca gagcttcaag ctgttcacct cagtcttcgg ggtgggtctg    1680
aagacatccg agaaatggtt cagaatggga tttcggactc tctctaaggt gcggtctgac    1740
aagagtctga aattcacccg catgcagaaa gcagggtttc tctactatga ggatctggtc    1800
tcttgtgtga cccgcgcaga agccgaggct gtgagtgtcc tcgtgaagga ggctgtctgg    1860
gcattcctgc ctgacgcctt tgtgacaatg actggcggat ccgccgagg gaagaaaatg     1920
ggtcacgacg tggattttct gatcacctca ccaggtagca cagaagacga ggaacagctg    1980
ctccagaaag tgatgaatct gtgggagaag aaaggcctgc tcctgtacta tgatctggtc    2040
gagagcactt tcgaaaagct ccgcctgcca tcccgaaaag tggacgccct ggatcatttt    2100
cagaagtgct tcctcatctt taaactgccc cgacagaggg tggactctga tcagtcaagc    2160
tggcaggaag aaagacctg gaaagctatt cgggtggacc tggtgctgtg tccctacgag     2220
aggagagcat tcgcactcct gggatggaca ggcagcagg agtttgaaag ggacctgcgg     2280
cgctacgcaa ctcacgagcg aagatgatc ctcgacaacc atgccctgta tgataagaca     2340
aaacgcattt tcctgaaggc cgagagcgag gaagaaatct tcgctcacct cggcctggac    2400
tatattgagc cttgggaaag aaatgctctc gagtctagag ggcccgttta aacccgctga    2460
tcagcctcga ctgtgccttc tagttgccag ccatctgttg tttgccctc ccccgtgcct     2520
tccttgaccc tggaaggtgc cactcccact gtccttcct aataaaatga ggaaattgca     2580
tcgcattgtc tgagtaggtg tcattctatt ctggggggtg gggtggggca ggacagcaag    2640
ggggaggatt gggaagacaa tagcaggcat gctgggatg cggtgggctc tatggcttct     2700
gaggcggaaa gaaccagctg gggctctagg gggtatcccc acgcgcctg tagcggcgca     2760
ttaagcgcgg cgggtgtggt ggttacgcgc agcgtgaccg ctacacttgc cagcgcccta    2820
gcgcccgctc ctttcgcttt cttcccttcc tttctcgcca cgttcgccgg ctttccccgt    2880
caagctctaa atcgggggct ccctttaggg ttccgattta gtgctttacg gcacctcgac    2940
cccaaaaaac ttgattaggg tgatggttca cgtagtgggc catcgccctg atagacggtt    3000
tttcgccctt tgacgttgga gtccacgttc tttaatagtg gactcttgtt ccaaactgga    3060
acaacactca accctatctc ggtctattct tttgatttat aagggatttt gccgatttcg    3120
gcctattggt taaaaaatga gctgatttaa caaaaattta acgcgaatta attctgtgga    3180
atgtgtgtca gttagggtgt ggaaagtccc caggctcccc agcaggcaga agtatgcaaa    3240
gcctatcagg acatagcgtt ggctacccgt gatattgctg aagagcttgg cggcgaatgg    3300
gctgaccgct tcctcgtgct ttacggtatc gccgctcccg attcgcagcg catcgccttc    3360
tatcgccttc ttgacgagtt cttctgagcg ggactctggg gttcgaaatg accgaccaag    3420
cgacgcccaa cctgccatca cgagatttcg attccaccgc cgccttctat gaaaggttgg    3480
gcttcggaat cgttttccgg gacgccggct ggatgatcct ccagcgcggg gatctcatgc    3540
tggagttctt cgcccacccc aacttgttta ttgcagctta atggttac aaataaagca      3600
atagcatcac aaatttcaca aataaagcat ttttttcact gcattctagt tgtggtttgt    3660
ccaaactcat caatgtatct tatcatgtct gtataccgtc gacctctagc tagagcttgg    3720
cgtaatcatg gtcatagctg tttcctgtgt gaaattgtta tccgctcaca attccacaca    3780
acatacgagc cggaagcata aagtgtaaag cctggggtgc ctaatgagtg agctaactca    3840
cattaattgc gttgcgctca ctgcccgctt tccagtcggg aaacctgtcg tgccagctgc    3900
```

```
attaatgaat cggccaacgc gcggggagag gcggtttgcg tattgggcgc tcttccgctt    3960
cctcgctcac tgactcgctg cgctcggtcg ttcggctgcg gcgagcggta tcagctcact    4020
caaaggcggt aatacggtta tccacagaat caggggataa cgcaggaaag aacatgtgag    4080
caaaaggcca gcaaaggcca ggaaccgta  aaaaggccgc gttgctggcg ttttccata     4140 ggctccgccc ccctgacgag catcacaaaa atcgacgctc aagtcagagg tggcgaaacc    4200
cgacaggact ataaagatac caggcgtttc ccctggaag  ctcccgtg  cgctctcctg     4260 ttccgaccct gccgcttacc ggatacctgt ccgcctttct cccttcggga agcgtggcgc    4320
tttctcatag ctcacgctgt aggtatctca gttcggtgta ggtcgttcgc tccaagctgg    4380
gctgtgtgca cgaaccccc  gttcagcccg accgctgcgc cttatccggt aactatcgtc    4440
ttgagtccaa cccggtaaga cacgacttat cgccactggc agcagccact ggtaacagga    4500
ttagcagagc gaggtatgta ggcggtgcta cagagttctt gaagtggtgg cctaactacg    4560
gctacactag aagaacagta tttggtatct gcgctctgct gaagccagtt accttcggaa    4620
aaagagttgg tagctcttga tccggcaaac aaaccaccgc tggtagcggt ttttttgttt    4680
gcaagcagca gattacgcgc agaaaaaaag gatctcaaga agatcctttg atcttttcta    4740
cggggtctga cgctcagtgg aacgaaaact cacgttaagg gattttggtc atgagattat    4800
caaaaaggat cttcacctag atccttttaa attaaaaatg aagttttaaa tcaatctaaa    4860
gtatatatga gtaaacttgg tctgacagtt accaatgctt aatcagtgag gcacctatct    4920
cagcgatctg tctatttcgt tcatccatag ttgcctgact ccccgtcgtg tagataacta    4980
cgatacggga gggcttacca tctggcccca gtgctgcaat gataccgcga acccacgct     5040 caccggctcc agatttatca gcaataaacc agccagccgg aagggccgag cgcagaagtg    5100
gtcctgcaac tttatccgcc tccatccagt ctattaattg ttgccgggaa gctagagtaa    5160
gtagttcgcc agttaatagt ttgcgcaacg ttgttgccat tgctacaggc atcgtggtgt    5220
cacgctcgtc gtttggtatg gcttcattca gctccggttc ccaacgatca aggcgagtta    5280
catgatcccc catgttgtgc aaaaaagcgg ttagctcctt cggtcctccg atcgttgtca    5340
gaagtaagtt ggccgcagtg ttatcactca tggttatggc agcactgcat aattctctta    5400
ctgtcatgcc atccgtaaga tgcttttctg tgactggtga gtactcaacc aagtcattct    5460
gagaatagtg tatgcggcga ccgagttgct cttgcccggc gtcaatacgg gataataccg    5520
cgccacatag cagaacttta aaagtgctca tcattggaaa acgttcttcg ggcgaaaac    5580 tctcaaggat cttaccgctg ttgagatcca gttcgatgta acccactcgt gcacccaact    5640
gatcttcagc atcttttact ttcaccagcg tttctgggtg agcaaaaaca ggaaggcaaa    5700
atgccgcaaa aaagggaata agggcgacac ggaaatgttg aatactcata ctcttccttt    5760
ttcaatatta ttgaagcatt tatcagggtt attgtctcat gagcggatac atatttgaat    5820
gtatttagaa aaataaacaa ataggggttc cgcgcacatt tccccgaaaa gtgccacctg    5880
acgtc                                                                5885
```

<210> SEQ ID NO 144
<211> LENGTH: 7412
<212> TYPE: DNA
<213> ORGANISM: Artificial Sequence
<220> FEATURE:
<223> OTHER INFORMATION: pExodus Vaccinia Polymerase

<400> SEQUENCE: 144

```
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca caaggcaag gcttgaccga caattgcatg aagaatctgc    180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccaccca ttgacgtcaa tgggagtttg ttttggcacc    720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
atggatgtcc gctgtattaa ctggtttgaa tctcatggtg aaaatcggtt cctgtatctg   960
aaaagtcggt gtagaaatgg cgagaccgtg ttcatcaggt ttcctcacta cttttactat  1020
gtggtcactg acgaaatcta ccagtctctg agtccccctc cattcaatgc tcgcccactc  1080
gggaagatgc gaactatcga cattgatgag accatcagtt acaacctgga cattaaggat  1140
cgaaaatgct cagtggcaga catgtggctg atcgaggaac caaagaaacg cagcattcag  1200
aacgccacaa tggatgaatt tctgaatatc tcctggttct atatcagtaa cgggatttca  1260
cccgacggtt gctacagcct ggatgagcag tatctcacta agatcaacaa tggatgctac  1320
cattgtgacg atcctagaaa ctgttttgca aagaaaatcc cccgattcga cattcctagg  1380
agctatctgt tcctcgacat cgagtgccac ttcgataaga aatttccaag cgtgttcatc  1440
aatcccatct cccatacatc ttactgttac attgatctga gcggcaagcg gctgctcttc  1500
actctgatca acgaggaaat gctcaccgag caggaaattc aggaggcagt ggaccgagga  1560
tgcctgcgca tccagtctct catggagatg gattacgaga gggaactggt gctctgtagt  1620
gaaatcgtcc tgctcagaat tgccaagcag ctgctggagc tgacatttga ctacgtggtc  1680
acttttaacg ggacacaattt cgatctgaga tatatcacca caggctgga gctgctcaca  1740 ggtgaaaaga tcattttccg gtcccccgac aagaagagg ctgtgtacct gtgcatctat  1800
gaacgcaatc agagctccca caaggcgtg gcggaatgg caaacaccac atttcatgtc  1860
aacaataaca atggaaccat cttctttgac ctgtacagct tcattcagaa gtccgaaaaa  1920
ctggactctt ataagctcga ttcaatcagc aagaacgctt tttcttgtat gggcaaggtg  1980
ctgaacaggg gagtcagaga gatgacattc attgggacg atactaccga cgccaagggt  2040
aaagccgctg catttgccaa agtgctgaca actggcgctg ataacaattt cacccaggag  2100
acagctactg gtaactacgt gactgtggac gaggacatta tctgtaaagt gattagaaag  2160
gacatttggg agaacggctt caaggtggtg ctcctgtgcc ccactctccc taacgacacc  2220
tacaaactca gcttcggaaa ggacgatgtg gacctggccc agatgtacaa ggattataac  2280
ctgaatatcg ccctcgacat ggctaggtac tgtattcacg atgcttgcct gtgtcagtat  2340
ctctgggagt actatgggt ggaaactaag accgatgccg gtgcttctac ctacgtcctg  2400
```

```
cctcagagta tggtgtttga gtatcgagca tccacagtca tcaaagggcc actgctcaag    2460
ctgctcctgg agacaaagac tattctggtg aggagcgaga ccaaacagaa gttcccttac    2520
gaaggcggaa aggtcttcgc tccaaaacag aagatgtttt caaacaatgt gctcatcttc    2580
gactacaaca gcctgtatcc caatgtctgc atttttggca acctgtcccc tgagactctc    2640
gtgggagtgg tcgtgtctac caataggctg gaggaagaga tcaacaatca gctcctgctc    2700
cagaagtacc cccctccaag gtatatcaca gtgcattgtg agccaagact gcccaacctc    2760
attagtgaaa tcgccatttt tgacagatca atcgagggca ccattccacg actgctcagg    2820
acattcctgg ctgaacgagc aaggtacaag aaaatgctga acaggctac cagctccaca    2880 gagaaggcaa tctacgattc catgcagtac acatataaga ttgtcgcaaa cagtgtgtat    2940
gggctcatgg gcttcaggaa cagcgccctg tacagttatg catcagccaa gagctgcact    3000
tccatcggga ggagaatgat tctgtacctg gagagcgtgc tgaacggcgc cgaactctcc    3060
aatggaatgc tgcggtttgc taaccctctg tctaatccat tctatatgga cgatcgcgac    3120
atcaacccaa ttgtcaagac cagcctgccc atcgattaca gattccggtt tcgctcagtc    3180
tatggtgaca cagatagcgt gtttactgaa atcgacagcc aggacgtgga taaatccatc    3240
gagattgcca aggaactgga gagactcatt aacaatcggg tcctgttcaa caattttaaa    3300
atcgagttcg aggctgtgta caagaacctg attatgcaga gcaagaaaaa gtacaccaca    3360
atgaaatatt ccgcatctag taactccaag tctgtccccg agaggatcaa caaggggact    3420
tccgaaaccc ggcgcgacgt gtctaagttc cacaagaaca tgatcaaaac atataagact    3480
cggctgtctg agatgctcag tgaaggtcgc atgaactcta atcaagtgtg tatcgatatt    3540
ctgaggagcc tggagaccga cctgcgctca gaatttgata gccgatcaag ccctctggag    3600
ctcttcatgc tgagccgcat gcaccattcc aactacaagt ctgccgacaa cccaaatatg    3660
tacctggtga cagagtataa caagaacaat cccgaaacta tcgagctggg cgaacggtac    3720
tattttgcat acatttgccc cgccaacgtc ccttggacaa aaaagctggt gaatatcaag    3780
acctatgaga caatcattga ccgaagtttc aaactgggat cagatcagag gatcttctac    3840
gaagtgtatt ttaagagact gacttccgag atcgtcaacc tgctcgataa caaggtgctg    3900
tgtatttctt tcttttgaacg catgttcgga agtaaaccca ccttttacga ggctctcgag    3960
tctagagggc ccgtttaaac ccgctgatca gcctcgactg tgccttctag ttgccagcca    4020
tctgttgttt gccccctccc cgtgccttcc ttgaccctgg aaggtgccac tcccactgtc    4080
ctttcctaat aaaatgagga attgcatcg cattgtctga gtaggtgtca ttctattctg    4140
gggggtgggg tggggcagga cagcaagggg gaggattggg aagacaatag caggcatgct    4200
ggggatgcgg tgggctctat ggcttctgag gcggaaagaa ccagctgggg ctctagggg    4260 tatccccacg cgccctgtag cggcgcatta agcgcggcgg gtgtggtggt tacgcgcagc    4320
gtgaccgcta cacttgccag cgccctagcg cccgctcctt tcgctttctt cccttccttt    4380
ctcgccacgt tcgccggctt tccccgtcaa gctctaaatc gggggctccc tttagggttc    4440
cgatttagtg ctttacggca cctcgacccc aaaaaacttg attagggtga tggttcacgt    4500
agtgggccat cgccctgata gacggttttt cgccctttga cgttggagtc acgttcttt    4560 aatagtggac tcttgttcca aactggaaca acactcaacc ctatctcggt ctattctttt    4620
gatttataag ggattttgcc gatttcggcc tattggttaa aaaatgagct gatttaacaa    4680
aaatttaacg cgaattaatt ctgtggaatg tgtgtcagtt agggtgtgga aagtccccag    4740
```

```
gctccccagc aggcagaagt atgcaaagcc tatcaggaca tagcgttggc tacccgtgat    4800
attgctgaag agcttggcgg cgaatgggct gaccgcttcc tcgtgcttta cggtatcgcc    4860
gctcccgatt cgcagcgcat cgccttctat cgccttcttg acgagttctt ctgagcggga    4920 ctctgggggtt cgaaatgacc gaccaagcga cgcccaacct gccatcacga gatttcgatt    4980
ccaccgccgc cttctatgaa aggttgggct tcggaatcgt tttccgggac gccggctgga    5040
tgatcctcca gcgcggggat ctcatgctgg agttcttcgc ccaccccaac ttgtttattg    5100
cagcttataa tggttacaaa taaagcaata gcatcacaaa tttcacaaat aaagcatttt    5160
tttcactgca ttctagttgt ggtttgtcca aactcatcaa tgtatcttat catgtctgta    5220
taccgtcgac ctctagctag agcttggcgt aatcatggtc atagctgttt cctgtgtgaa    5280
attgttatcc gctcacaatt ccacacaaca tacgagccgg aagcataaag tgtaaagcct    5340
ggggtgccta atgagtgagc taactcacat taattgcgtt gcgctcactg cccgctttcc    5400
agtcgggaaa cctgtcgtgc cagctgcatt aatgaatcgg ccaacgcgcg gggagaggcg    5460
gtttgcgtat tgggcgctct tccgcttcct cgctcactga ctcgctgcgc tcggtcgttc    5520
ggctgcggcg agcggtatca gctcactcaa aggcggtaat acggttatcc acagaatcag    5580
gggataacgc aggaaagaac atgtgagcaa aaggccagca aaaggccagg aaccgtaaaa    5640
aggccgcgtt gctggcgttt ttccataggc tccgccccccc tgacgagcat cacaaaaatc    5700
gacgctcaag tcagaggtgg cgaaacccga caggactata agataccagg cgtttccccc    5760
ctggaagctc cctcgtgcgc tctcctgttc cgaccctgcc gcttaccgga tacctgtccg    5820
cctttctccc ttcgggaagc gtggcgcttt ctcatagctc acgctgtagg tatctcagtt    5880
cggtgtaggt cgttcgctcc aagctgggct gtgtgcacga acccccccgtt cagcccgacc    5940 gctgcgcctt atccggtaac tatcgtcttg agtccaaccc ggtaagacac gacttatcgc    6000
cactggcagc agccactggt aacaggatta gcagagcgag gtatgtaggc ggtgctacag    6060
agttcttgaa gtggtggcct aactacggct acactagaag aacagtattt ggtatctgcg    6120
ctctgctgaa gccagttacc ttcggaaaaa gagttggtag ctcttgatcc ggcaaacaaa    6180
ccaccgctgg tagcggtttt tttgtttgca agcagcagat tacgcgcaga aaaaaaggat    6240
ctcaagaaga tcctttgatc ttttctacgg ggtctgacgc tcagtggaac gaaaactcac    6300
gttaagggat tttggtcatg agattatcaa aaaggatctt cacctagatc cttttaaatt    6360
aaaaatgaag ttttaaatca atctaaagta tatatgagta aacttggtct gacagttacc    6420
aatgcttaat cagtgaggca cctatctcag cgatctgtct atttcgttca tccatagttg    6480
cctgactccc cgtcgtgtag ataactacga tacgggaggg cttaccatct ggccccagtg    6540
ctgcaatgat accgcgagac ccacgctcac cggctccaga tttatcagca ataaaccagc    6600
cagccggaag ggccgagcgc agaagtggtc ctgcaacttt atccgcctcc atccagtcta    6660
ttaattgttg ccgggaagct agagtaagta gttcgccagt taatagtttg cgcaacgttg    6720
ttgccattgc tacaggcatc gtggtgtcac gctcgtcgtt tggtatggct tcattcagct    6780
ccggttccca acgatcaagg cgagttacat gatcccccat gttgtgcaaa aaagcggtta    6840
gctccttcgg tcctccgatc gttgtcagaa gtaagttggc cgcagtgtta tcactcatgg    6900
ttatggcagc actgcataat tctcttactg tcatgccatc cgtaagatgc ttttctgtga    6960
ctggtgagta ctcaaccaag tcattctgag aatagtgtat gcggcgaccg agttgctctt    7020
gcccggcgtc aatacgggat aataccgcgc cacatagcag aactttaaaa gtgctcatca    7080
ttggaaaacg ttcttcgggg cgaaaactct caaggatctt accgctgttg agatccagtt    7140
```

| | |
|---|---|
| cgatgtaacc cactcgtgca cccaactgat cttcagcatc ttttactttc accagcgttt | 7200 |
| ctgggtgagc aaaaacagga aggcaaaatg ccgcaaaaaa gggaataagg gcgacacgga | 7260 |
| aatgttgaat actcatactc ttccttttc aatattattg aagcatttat cagggttatt | 7320 |
| gtctcatgag cggatacata tttgaatgta tttagaaaaa taaacaaata ggggttccgc | 7380 |
| gcacatttcc ccgaaaagtg ccacctgacg tc | 7412 |

<210> SEQ ID NO 145
<211> LENGTH: 5601
<212> TYPE: DNA
<213> ORGANISM: Artificial Sequence
<220> FEATURE:
<223> OTHER INFORMATION: pExodus Rad2

<400> SEQUENCE: 145

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| atggggatac agggattgct acaatttatc aaagaagctt cagaacccat ccatgtgagg | 960 |
| aagtataaag ggcaggtagt agctgtggat acatattgct ggcttcacaa aggagctatt | 1020 |
| gcttgtgctg aaaaactagc caaaggtgaa cctactgata ggtatgtagg attttgtatg | 1080 |
| aaatttgtaa atatgttact atctcatggg atcaagccta ttctcgtatt tgatggatgt | 1140 |
| actttacctt ctaaaaagga agtagagaga tctagaagag aaagacgaca agccaatctt | 1200 |
| cttaagggaa agcaacttct tcgtgagggg aaagtctcgg aagctcgaga gtgtttcacc | 1260 |
| cggtctatca atatcacaca tgccatggcc cacaaagtaa ttaaagctgc ccggtctcag | 1320 |
| ggggtagatt gcctcgtggc tcctatgaa gctgatgcgc agttggccta tcttaacaaa | 1380 |
| gcgggaattg tgcaagccat aattacagag gactcggatc tcctagcttt tggctgtaaa | 1440 |
| aaggtaattt taaagatgga ccagtttgga aatggacttg aaattgatca agctcggcta | 1500 |
| ggaatgtgca gacagcttgg ggatgtattc acggaagaga gtttcgtta catgtgtatt | 1560 |
| ctttcaggtt gtgactacct gtcatcactg cgtgggattg gattagcaaa ggcatgcaaa | 1620 |
| gtcctaagac tagccaataa tccagatata gtaaaggtta tcaagaaaat tggacattat | 1680 |
| ctcaagatga atatcacggt accagaggat tacatcaacg ggtttattcg ggccaacaat | 1740 |

```
accttcctct atcagctagt ttttgatccc atcaaaagga aacttattcc tctgaacgcc    1800
tatgaagatg atgttgatcc tgaaacacta agctacgctg gcaatatgt tgatgattcc     1860 atagctcttc aaatagcact tggaaataaa gatataaata cttttgaaca gatcgatgac    1920
tacaatccag acactgctat gcctgcccat tcaagaagtc atagttggga tgacaaaaca    1980
tgtcaaaagt cagctaatgt tagcagcatt tggcatagga attactctcc cagaccagag    2040
tcgggtactg tttcagatgc cccacaattg aaggaaaatc caagtgagga tccactagtc    2100
cagtgtggtg gaattctgca gatatccagc acagtggcgg ccgctcgagt ctagagggcc    2160
cgtttaaacc cgctgatcag cctcgactgt gccttctagt tgccagccat ctgttgtttg    2220
cccctccccc gtgccttcct tgaccctgga aggtgccact cccactgtcc tttcctaata    2280
aaatgaggaa attgcatcgc attgtctgag taggtgtcat tctattctgg ggggtggggt    2340
ggggcaggac agcaaggggg aggattggga agacaatagc aggcatgctg gggatgcggt    2400
gggctctatg gcttctgagg cggaaagaac cagctgggc tctagggggt atccccacgc     2460
gccctgtagc ggcgcattaa gcgcggcggg tgtggtggtt acgcgcagcg tgaccgctac    2520
acttgccagc gccctagcgc ccgctccttt cgctttcttc ccttcctttc tcgccacgtt    2580
cgccggcttt cccgtcaag ctctaaatcg ggggctccct ttagggttcc gatttagtgc     2640
tttacggcac ctcgacccca aaaaacttga ttagggtgat ggttcacgta gtgggccatc    2700
gccctgatag acgttttttc gcccttgac gttggagtcc acgttcttta atagtggact     2760
cttgttccaa actggaacaa cactcaaccc tatctcggtc tattcttttg atttataagg    2820
gattttgccg atttcggcct attggttaaa aaatgagctg atttaacaaa aatttaacgc    2880
gaattaattc tgtggaatgt gtgtcagtta gggtgtggaa agtccccagg ctccccagca    2940
ggcagaagta tgcaaagcct atcaggacat agcgttggct acccgtgata ttgctgaaga    3000
gcttggcggc gaatgggctg accgcttcct cgtgctttac ggtatcgccg ctcccgattc    3060
gcagcgcatc gccttctatc gccttcttga cgagttcttc tgagcgggac tctgggttc     3120 gaaatgaccg accaagcgac gcccaacctg ccatcacgag atttcgattc caccgccgcc    3180
ttctatgaaa ggttgggctt cggaatcgtt ttccgggacg ccggctggat gatcctccag    3240
cgcggggatc tcatgctgga gttcttcgcc caccccaact tgtttattgc agcttataat    3300
ggttacaaat aaagcaatag catcacaaat ttcacaaata aagcattttt ttcactgcat    3360
tctagttgtg gtttgtccaa actcatcaat gtatcttatc atgtctgtat accgtcgacc    3420
tctagctaga gcttggcgta atcatggtca tagctgtttc ctgtgtgaaa ttgttatccg    3480
ctcacaattc cacacaacat acgagccgga agcataaagt gtaaagcctg ggtgcctaa     3540 tgagtgagct aactcacatt aattgcgttg cgctcactgc ccgctttcca gtcgggaaac    3600
ctgtcgtgcc agctgcatta atgaatcggc caacgcgcgg ggagaggcgg tttgcgtatt    3660
gggcgctctt ccgcttcctc gctcactgac tcgctgcgct cggtcgttcg gctgcggcga    3720
gcggtatcag ctcactcaaa ggcggtaata cggttatcca cagaatcagg gataacgca     3780 ggaaagaaca tgtgagcaaa aggccagcaa aaggccagga accgtaaaaa ggccgcgttg    3840
ctggcgtttt tccataggct ccgcccccct gacgagcatc acaaaaatcg acgctcaagt    3900
cagaggtggc gaaacccgac aggactataa agataccagg cgtttccccc tggaagctcc    3960
ctcgtgcgct ctcctgttcc gaccctgccg cttaccggat acctgtccgc ctttctccct    4020
tcgggaagcg tggcgctttc tcatagctca cgctgtaggt atctcagttc ggtgtaggtc    4080
gttcgctcca agctgggctg tgtgcacgaa ccccccgttc agcccgaccg ctgcgcctta    4140
```

```
tccggtaact atcgtcttga gtccaacccg gtaagacacg acttatcgcc actggcagca    4200
gccactggta acaggattag cagagcgagg tatgtaggcg gtgctacaga gttcttgaag    4260
tggtggccta actacggcta cactagaaga acagtatttg gtatctgcgc tctgctgaag    4320
ccagttacct tcggaaaaag agttggtagc tcttgatccg gcaaacaaac caccgctggt    4380
agcggttttt ttgtttgcaa gcagcagatt acgcgcagaa aaaaggatc tcaagaagat    4440 cctttgatct tttctacggg gtctgacgct cagtggaacg aaaactcacg ttaagggatt    4500
ttggtcatga gattatcaaa aaggatcttc acctagatcc ttttaaatta aaaatgaagt    4560
tttaaatcaa tctaaagtat atatgagtaa acttggtctg acagttacca atgcttaatc    4620
agtgaggcac ctatctcagc gatctgtcta tttcgttcat ccatagttgc ctgactcccc    4680
gtcgtgtaga taactacgat acgggagggc ttaccatctg gccccagtgc tgcaatgata    4740
ccgcgagacc cacgctcacc ggctccagat ttatcagcaa taaaccagcc agccggaagg    4800
gccgagcgca gaagtggtcc tgcaacttta tccgcctcca tccagtctat taattgttgc    4860
cgggaagcta gagtaagtag ttcgccagtt aatagtttgc gcaacgttgt tgccattgct    4920
acaggcatcg tggtgtcacg ctcgtcgttt ggtatggctt cattcagctc cggttcccaa    4980
cgatcaaggc gagttacatg atcccccatg ttgtgcaaaa aagcggttag ctccttcggt    5040
cctccgatcg ttgtcagaag taagttggcc gcagtgttat cactcatggt tatggcagca    5100
ctgcataatt ctcttactgt catgccatcc gtaagatgct tttctgtgac tggtgagtac    5160
tcaaccaagt cattctgaga atagtgtatg cggcgaccga gttgctcttg cccggcgtca    5220
atacgggata taccgcgcc acatagcaga actttaaaag tgctcatcat tggaaaacgt    5280 tcttcgggc gaaaactctc aaggatctta ccgctgttga gatccagttc gatgtaaccc    5340
actcgtgcac ccaactgatc ttcagcatct tttactttca ccagcgtttc tgggtgagca    5400
aaaacaggaa ggcaaaatgc cgcaaaaaag ggaataaggg cgacacggaa atgttgaata    5460
ctcatactct tcctttttca atattattga agcatttatc agggttattg tctcatgagc    5520
ggatacatat ttgaatgtat ttagaaaaat aaacaaatag gggttccgcg cacatttccc    5580
cgaaaagtgc cacctgacgt c                                              5601

<210> SEQ ID NO 146
<211> LENGTH: 30
<212> TYPE: DNA
<213> ORGANISM: Artificial Sequence
<220> FEATURE:
<223> OTHER INFORMATION: Cleavage site for I-SceI

<400> SEQUENCE: 146
agttacgcta gggataacag ggtaatatag                                        30

<210> SEQ ID NO 147
<211> LENGTH: 24
<212> TYPE: DNA
<213> ORGANISM: Artificial Sequence
<220> FEATURE:
<223> OTHER INFORMATION: Target site for zinc finger nuclease VF2468.

<400> SEQUENCE: 147
accatcttct tcaaggacga cggc                                              24
```